(12) United States Patent
Isshiki et al.

(10) Patent No.: US 7,745,663 B2
(45) Date of Patent: Jun. 29, 2010

(54) 5-SUBSTITUTED-2-PHENYLAMINO BENZAMIDES AS MEK INHIBITORS

(75) Inventors: Yoshiaki Isshiki, Kanagawa (JP); Yasunori Kohchi, Kanagawa (JP); Eisaku Mizuguchi, Kanagawa (JP); Hitoshi Iikura, Kanagawa (JP); Yasuaki Matsubara, Kanagawa (JP); Shinji Tsujii, Kanagawa (JP); Nobuo Shimma, Kanagawa (JP); Masanori Miwa, Kanagawa (JP); Satoshi Aida, Kanagawa (JP); Masami Kohchi, Kanagawa (JP); Takeshi Murata, Kanagawa (JP); Kosuke Aso, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 476 days.

(21) Appl. No.: 11/658,533

(22) PCT Filed: Jul. 26, 2005

(86) PCT No.: PCT/JP2005/013620

§ 371 (c)(1),
(2), (4) Date: Sep. 17, 2007

(87) PCT Pub. No.: WO2006/011466

PCT Pub. Date: Feb. 2, 2006

(65) Prior Publication Data

US 2009/0233915 A1      Sep. 17, 2009

(30) Foreign Application Priority Data

Jul. 26, 2004   (JP) .............................. 2004-218004
Mar. 14, 2005   (JP) .............................. 2005-072093

(51) Int. Cl.
| | | |
|---|---|---|
| C07C 239/00 | (2006.01) |
| C07C 259/00 | (2006.01) |
| C07C 233/00 | (2006.01) |
| C07C 235/00 | (2006.01) |
| C07C 237/00 | (2006.01) |
| C07C 229/00 | (2006.01) |
| C07C 251/00 | (2006.01) |
| C07D 265/00 | (2006.01) |
| A61K 31/535 | (2006.01) |
| A01N 37/18 | (2006.01) |
| A61K 31/16 | (2006.01) |
| A61K 31/165 | (2006.01) |

(52) U.S. Cl. ........................ 564/300; 564/253; 564/167; 514/619; 514/228.8; 544/63; 562/454

(58) Field of Classification Search ........................ None
See application file for complete search history.

(56) References Cited

U.S. PATENT DOCUMENTS

| | | | |
|---|---|---|---|
| 2,967,187 | A | 1/1961 | Serres, Jr. et al. |
| 3,725,417 | A | 4/1973 | Holland |
| 4,001,420 | A | 1/1977 | Malen et al. |
| 4,469,885 | A | 9/1984 | Mueller et al. |
| 4,501,895 | A | 2/1985 | Mueller et al. |
| 6,440,966 | B1 | 8/2002 | Barrett et al. |
| 6,750,217 | B2 | 6/2004 | Barrett et al. |
| 7,001,905 | B2 | 2/2006 | Biwersi et al. |
| 2003/0092748 | A1 | 5/2003 | Barrett et al. |
| 2003/0225076 | A1 | 12/2003 | Biwersi et al. |
| 2007/0105859 | A1 | 5/2007 | Isshiki et al. |

FOREIGN PATENT DOCUMENTS

| | | |
|---|---|---|
| EP | 1 674 452 | 6/2006 |
| EP | 1 780 197 | 5/2007 |
| JP | 48-61448 | 8/1973 |
| JP | 59-210046 | 11/1984 |
| JP | 2003-527379 | 9/2003 |
| WO | WO 99/01426 | 1/1999 |
| WO | WO 00/35436 | 6/2000 |
| WO | WO 01/68619 | 9/2001 |
| WO | WO 02/06213 | 1/2002 |
| WO | WO 03/051877 | 6/2003 |
| WO | WO 2005/028426 | 3/2005 |
| WO | WO 2006/011466 | 2/2006 |

OTHER PUBLICATIONS

Patani et al. Chem. Rev. 1996, 96, 3147-3176.*
Heintz et al., "Electrosynthesis of aryl-carboxylic acids from chlorobenzene derivatives and carbon dioxide," *Tetrahedron*, 44:1631-1636 (1988).
LoRusso et al., "A phase 1 clinical and pharmacokinetic evaluation of the oral MEK inhibitor, CI-1040, administered for 21 consecutive days, repeated every 4 weeks in patients with advanced cancer," *Proc. Am. Soc. Clin. Oncol.* 21: 2002 (*abstr. 321*).
Mitchell et al., "Pharmacokinetics (PK) and pharmacodynamics (PD) of the oral MEK inhibitor, CI-1040, following multiple dose administration to patients with advanced cancer," *Proc. Am. Soc. Clin. Oncol.* 21: 2002 (*abstr. 320*).
Ozaki et al., "Studies on 4(1*H*)-Quinazolinones. 5. Synthesis and Antiinflammatory Activity of 4(1*H*)-Quinazolinone Derivatives," *J. Med. Chem.*, 28:568-576 (1985).
Chardonnens et al., "256. Fluorènacènes et fluorènaphènes. Synthèses dans la série des indèno-fluorènes VIII.¹ ) Méthyl-3-, diméthyl-1,4-, diméthyl-1,3- et triméthyl-1,3,4-*cis*-fluorènacène," *Helv. Chim. Acta*, 41:2436-2440 (1958).
Watson et al., "An Orally Bioavailable Oxime Ether Capsid Binder with Potent Activity against Human Rhinovirus," *J. Med. Chem.*, 46(15):3181-3184 (2003).
USPTO Restriction Requirement in U.S. Appl. No. 10/572,255, mailed May 29, 2009, 10 pages.
Japanese Patent Office, International Search Report for App. Ser. No. PCT/JP2004/013501, mailed Dec. 28, 2004, 4 pages.
Japanese Patent Office, International Preliminary Report on Patentability for App. Ser. No. PCT/JP2004/013501, 6 pages.
European Search Report for App. Ser. No. EP 04 77 3160, dated Sep. 4, 2007 (2 pages).
Japanese Patent Office, International Search Report for App. Ser. No. PCT/JP2005/013620, dated Nov. 22, 2005, 3 pages.
Japanese Patent Office, International Preliminary Report on Patentability for App. Ser. No. PCT/JP2005/013620, 6 pages.
Garcia-Echeverria and Sellers, "Drug discovery approaches targeting the PI3K/Akt pathway in cancer," *Oncogene*, 27:5511-5526 (2008).
Shioi et al., "Akt/Protein Kinase B Promotes Organ Growth in Transgenic Mice," *Mol. Cell. Biol.*, 22(8):2799-2809 (2002).
USPTO Non-Final Office Action in U.S. Appl. No. 10/572,255, mailed Sep. 21, 2009, 26 pages.

* cited by examiner

*Primary Examiner*—Rosalynd Keys
*Assistant Examiner*—Clinton Brooks
(74) *Attorney, Agent, or Firm*—Fish & Richardson P.C.

(57) ABSTRACT

An objective of the present invention is to provide compounds that exhibit strong MEK-inhibiting activity and are stable in vivo and soluble in water, which can be used as preventive or therapeutic agents for proliferative diseases.

The compounds of the present invention and pharmaceutically acceptable salts thereof are represented by the following formula (1):

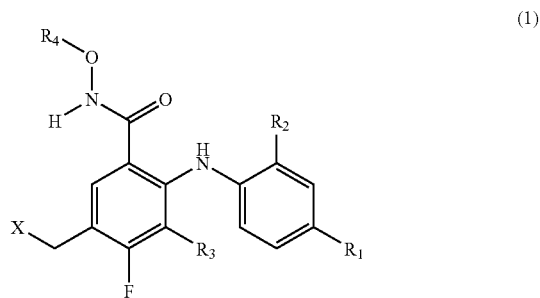

[where $R_1$, $R_2$, $R_3$, $R_4$, and X are the same as defined in the present patent application].

30 Claims, 1 Drawing Sheet

5-SUBSTITUTED-2-PHENYLAMINO BENZAMIDES AS MEK INHIBITORS

CROSS-REFERENCE TO RELATED APPLICATIONS

This application is the National Stage of International Application No. PCT/JP2005/013620, filed on Jul. 26, 2005, which claims the benefit of Japanese Patent Application Serial No. 2004-218004, filed on Jul. 26, 2004, and Japanese Patent Application Serial No. 2005-072093, filed on Mar. 14, 2005. The contents of all foregoing applications are hereby incorporated by reference in their entireties.

TECHNICAL FIELD

The present invention relates to novel compounds having MEK inhibitory activity and pharmaceutically acceptable salts thereof, intermediates for synthesis of the compounds, and pharmaceutical compositions comprising the compounds or pharmaceutically acceptable salts thereof.

The compounds of the present invention can be used as MEK inhibitors. The compounds can be used to treat proliferative diseases, for example, cancers, psoriasis, restenosis, autoimmune diseases, and atherosclerosis, and other diseases such as sequelae of heart failure, heterograft rejection, osteoarthritis, chronic rheumatoid arthritis, asthma, cystic fibrosis, hepatomegalia, cardiac hypertrophy, Alzheimer's disease, diabetes, septic shock, and HIV infection.

BACKGROUND ART

Cell survival is regulated by various extracellular signals, for example, growth factors, cytokines, and extracellular matrices (ECM), via cell surface receptors.

Two major signal transduction pathways regulate the process of signal transduction from the cell surface to the nucleus. One is the Ras signaling pathway, and the other is the PI3K (Phosphatidylinositol 3 kinase) pathway. The PI3K pathway is either activated via cell surface receptors or indirectly by Ras. The present invention focuses on the Ras signaling pathway.

The MAPK (mitogen-activated protein kinase) cascade which comprises three kinases, namely, Raf, MEK (MAPK or ERK kinase), and ERK (extracellular stimulus regulated kinase), is a key component of the Ras signaling pathway. The cascade starts with the activation of Ras and in response to extracellular signals, plays an important role in regulating cell proliferation, differentiation, and transformation (Person, G, F. Robinson, T. Beers Gibson, B. Xu, M. Karandikar, K. Berman, and M. H. Cobb. Endocrine Rev., 22, 153-183 (2001); Bryan A. Ballif and John Blenis, Cell Growth & Differentiation, 12, 397-408 (2001); Cobb M H, Prog. Biophys. Mol. Biol., 71 479-500 (1999); Lewis T S, Shapiro P S and Ahn N G. Adv. Cancer Res., 74 49-139 (1998); Kolch W, Biochem. J., 351, 289-305 (2000); Judith S Sebolt-Leopold, Oncogene, 19, 6594-6599 (2000); Roman Herrera and Judith S. Sebolt-Leopold, Treds in Molecular Medicine, 8, S27-S31 (2002)).

Ras activation is regulated through the interplay between GTP-exchange factors (GEFs) and GTPase-activating proteins (GAPs) (Giorgio Scita, Pierluigi Tenca, Emanuela Frittoli Arianna Tocchetti, Metello Innocenti, Giuseppina Giardina and Pier Paolo Di Fiore, EMBO Journal. 19, 2393-2398 (2000)). GEFs activate Ras through the formation of Ras-GTP complex, and GAPs inactivate Ras through the formation of Ras-GDP complex. Ras activation results from growth factor-mediated extracellular signals to cell surface receptors or from Ras mutations. Ras mutations are found in many human cancer cells. It is known that such Ras mutations result in sustained Ras activation (GTP complex) and play key roles in the proliferation of human cancer cells.

Activated Ras interacts with Raf-1, a serine/threonine protein kinase, to activate Raf-1 (Daum G, Eisenmann-Tappe I, Fries H W, Troppmair J and Rapp U R, Trends Biochem. Sci., 19, 474-480 (1994); Stokoe D, Macdonald S G, Cadwallader K, Symons M and Hacock J F, Science, 264, 1463-1467 (1994)).

Activated Raf-1 then phosphorylates and activates MEK1 and MEK2. MEK is phosphorylated on two serine residues (Ser218 and Ser222) (Dent P, Haser W, Haystead T A, Vincent L A, Roberts T M and Sturgill T W, Science, 257, 1404-1407 (1992); Crews C M, Alessandrini A and Erikson R L, Science, 258, 478-480 (1992); Her J H, Lakhani S, Zu K, Vila J, Dent P, Sturgill T W and Weber M J, Biochem. J., 296, 25-31 (1993); Alessi, D. R., Y. Saito, D. G. Campgell, P. Cohen, G. Sithanandam, U. Rapp, A. Ashworth, C. J. Marshall, and S. Cowley. Trends Biochem. Sci. 21 373-372 (1994); Zheng, C. F., and K. L. Guan. J. Biol. Chem. 268, 23933-23939 (1993)).

MEK is a dual-specificity kinase. Activated MEK phosphorylates ERK1 and ERK2 on tyrosine (185) and threonine (183) residues (Anderson N G, Maller J L, Tonks N K and Sturgill T W, Nature, 343, 651-653 (1990); Seger R and Krebs E G, FASEG J, 9 716-735 (1995)).

The MEK-mediated ERK phosphorylation results in not only ERK activation but also translocation of ERK to the nucleus.

Activated ERK (MAPK) activates various substrates, for example, transcription factors in the cytoplasm and nucleus, and the result is that the activation leads to cellular changes (proliferation, differentiation, and transformation) depending on the extracellular signal.

MEK has a strict substrate specificity. ERK1 and ERK2 are the only substrates of MEK phosphorylation that have been identified (Seger R, Ahn N G, Posada J, Munar E S, Jensen A M, Cooper J A, Cobb M H and Kregs E G, J. Biol. Chem., 267, 14373-14381 (1992)).

Strict substrate specificity (limited substrates: ERK1 and 2) and dual specificity (phosphorylation on both tyrosine and threonine), which are unique properties of MEK bur rarely found in other kinases, are suggested to play a central role in the MEK integration of signals in the MAPK pathway.

Constitutive activation of the MEK/MAPK pathway is shown to be associated with the neoplastic phenotypes of a relatively large number of cancer cell types (Hoshino R, Chatani Y, Yamori T, Tsuruo T, Oka H, Yoshida O, Shimada Y, Ari-I S, Wada H, Fujimoto J, Kohno M, oncogene, 18, 813 (1999); Kim S C, Hahn J S, Min Y H, Yoo N C, Ko Y W, Lee W J, Blood, 93, 3893 (1999); Morgan M A, Dolp O, Reuter C W, Blood, 97, 1823 (2001)).

In addition, constitutive activation of MEK has been reported to result in cellular alteration (transformation or canceration) (Cowley S, Paterson H, Kemp P and Marshall C J, Cell, 77, 841-852 (1994); Mansour S J, Matten W T, Hermann A S, Candia J M, Rong S, Fukasawa K, Vande Woude G F and Ahn N G, Science, 265, 966-970 (1994)).

Furthermore, studies of MEK inhibitors (PD98059 and others) have revealed that MEK inhibition not only results in impaired cell proliferation, but also has impact on various cellular events, including cell differentiation, apoptosis, and angiogenesis (Dudley D T, Pang L, Decker S J, Bridges A J and Saltiel A R, Proc. Natl. Acad. Sci. USA, 92, 7686-7689 (1995); Alessi D R, Cuenda A, Cohen P, Dudley D T and Saltiel A R, J. Biol. Chem., 270, 27489-27494 (1995); Pages G, Lenorman D, L'Allemain G, Chambard J C, Meloche S and Puyssegur J, Proc. Natl. Acad. Sci. USA., 90, 8319-8323 (1993); Pang L, Sawada T, Decker S J and Saltiel A R., J. Biol. Chem., 270, 13585-13588 (1995); Finalay D, Healy V, Furlong F, O'Connell F C, Keon N K and Martin F, Cell Death Differ. 7, 303-313 (2000); Holmstrom T H, Tran S E, Johnson V L, Ahn N G, Chow S C and Eriksson J E, Mol. Cell. Biol., 19, 5991-6002 (1999); Elliceiri B P, Klemke R, Stromblad S and Cherexh D A, J. Cell Biol., 141, 1255-1263 (1998); Milanini J, Vinals F, Pouyssegur J and Pages G, J. Biol. Chem., 273, 18165-18172 (1998)).

The above-described findings suggest that MEK, one of the major mediators in the MAPK cascade, can serves as a potential target for therapeutic agents used in treating diseases caused by aberrant cell proliferation.

There are many previously reported MEK inhibitors including, for example, compounds having the backbone structure of a 2-phenylaminobenzoic acid or a derivative thereof, and which comprise various types of substituents at different positions (U.S. Pat. No. 6,251,943; U.S. Pat. No. 6,310,060; U.S. Pat. No. 6,506,798; International Publication WO 98/37881; WO 99/01421; WO 99/01426; WO 00/35435; WO 00/35436; WO 00/37141; WO 00/40235; WO 00/40237; WO 00/41505; WO 00/41994; WO 00/42002; WO 00/42003; WO 00/42022; WO 00/42029; WO 00/64856; WO 01/05390; WO 01/05391; WO 01/05392; WO 01/05393; WO 01/68619; WO 02/06213; WO 02/18319; WO 03/062189; WO 03/062191; WO 03/077855; WO 03/077914; WO 04/056789; and Japanese Patent Application Kokai Publication No. (JP-A) 2001-55376 (unexamined published Japanese patent application)). The previously reported compounds also include N-alkoxy-2-phenylamino-benzamide derivatives which have an alkoxy residue as the substituent on the amide nitrogen atom. Furthermore, the reported compounds also include compounds which comprise as a substituent, a halogen atom, a carbamoyl group, a sulfamoyl group, or such, at position 5 of the benzamide ring (International Publication WO 98/37881; WO 99/01426; WO 00/42003; WO 01/68619; and WO 02/06213).

Meanwhile, the anti-cancer effect of compounds comprising the feature of an MEK inhibitor, as reported, has been drawing attention. Such compounds include, for example, compound CI-1040 described below (in Example 95 of WO 99/01426). The result of a phase I clinical trial of compound CI-1040 was reported in the American Society of Clinical Oncology Annual Meeting in 2002 (American Society of Clinical Oncology Annual Meeting in 2002 (Abstract Nos. 320 and 321; May, 18-21, 2002)). However, various problems have been pointed out, for example, rapid hydrolysis and inactivation of the compound in vivo; high lipid solubility and low water solubility; and a wide interpatient variability in pharmacokinetic parameters. The clinical trial for CI-1040 was thus terminated. At present, PD0325901 (WO 02/06213) is currently at the stage of a phase II clinical trial in U.S.

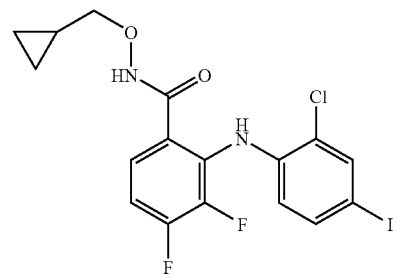

Meanwhile, there are reports on methods of preventing or treating rheumatoid arthritis or osteoarthritis using compounds having MEK-inhibiting activity (International Publication WO 00/35436; WO 01/68619; and JP-A 2001-55376).

DISCLOSURE OF THE INVENTION

An objective of the present invention is to provide preventive or therapeutic agents for proliferative diseases, that have excellent safety, exhibit strong MEK inhibitory effect, and are stable in vivo and soluble in water.

Through various intensive studies, the present inventors discovered that N-alkoxy-2-phenylamino-benzamide derivatives which comprise a substituent at position 5 of the ring have an unexpectedly strong MEK inhibitory effect and high water solubility, and are highly stable in vivo. In addition, the inventors discovered that the compounds of the present invention have effects of suppressing tumor growth and of suppressing the onset of arthritis, and that they could serve as preventive or therapeutic agents for cancers and arthritis with improved biological utility, thereby completing the present invention.

Specifically, the present invention includes:

[1] a compound represented by the following formula (1), or a pharmaceutically acceptable salt thereof,

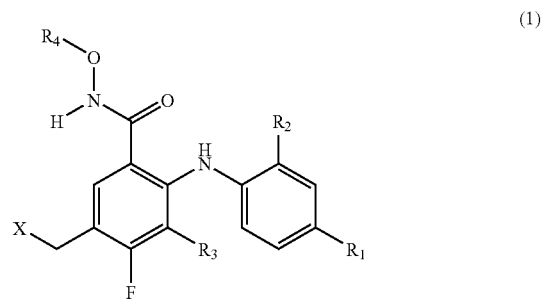

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group; the alkyl group, the alkenyl group, and the alkynyl group may have one to three substituents selected from the group consisting of —ORa, —NRaRb, —NRaCORb, a heterocyclic group, and a heteroaryl group;

the heterocyclic group and the heteroaryl group may have one to three substituents selected from the group consisting of a $C_{1-5}$ alkyl group, —ORa, and —NRaRb;

X represents a group represented by the following formula (i);

wherein
Y represents —O—, —$NR_8$O—, —ON$R_8$—, —$NR_8$CO—, or —$NR_8SO_2$—;
Z represents an $C_{1-8}$ alkylene chain which may be substituted by one to three groups represented by W';
where $R_8$ represents a hydrogen atom, an alkyl group, —ORa, or —CO$R_9$; and the alkyl group may be substituted by a halogen atom, —ORa, or —NRaRb;
$R_9$ represents a hydrogen atom, an alkyl group, or —ORa; and the alkyl group may be substituted by a halogen atom, —ORa, or —NRaRb;
$R_8$ and $R_9$ may be linked to the alkylene chain of Z or form a heterocyclic group through a linkage to the substituent represented by Ra or Rb of W)

or alternatively,

X represents a group represented by the following formula (ii):

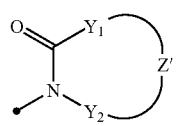

wherein
$Y_1$ and $Y_2$, which may be the same or different, each represent a single bond, —CO—, —COO—, —O—, —OCO—, —NRa—, or —$SO_2$—;
Z' represents a $C_{1-5}$ chain which may be substituted by one to three groups represented by W');
in the above formulae (i) and (ii),
W and W', which may be the same or different, each represent a $C_{1-5}$ alkyl group, a halogen atom, an oxo group, —ORa, —COORa, —COOCORa, —CO-halogen atom, —OCORa, —CONRaRb, —SRa, —SORa, —$SO_2$Ra, —NRaRb, —NRaCORb, —NRa$SO_2$Rb, —$SO_2$NRaRb, a heterocyclic group, or a heteroaryl group; the heterocyclic group and the heteroaryl group may have a substituent selected from the group consisting of a $C_{1-5}$ alkyl group, —ORa, and —NRaRb; the alkyl group may be substituted by a hydroxyl group, a $C_{1-5}$ alkoxy group, or an amino group;
the above substituents except the oxo group and the halogen may be linked to each other to form a cycloalkyl group or a heterocyclic group; the cycloalkyl group or the heterocyclic group may have a substituent selected from the group consisting of, —ORa, —NRaRb, and a $C_{1-5}$ alkyl group that may be substituted with —ORa;
Ra and Rb, which may be the same or different, each represent a hydrogen atom or a $C_{1-5}$ alkyl group; the alkyl group may be substituted by one to three groups selected from the group consisting of a hydroxyl group, a $C_{1-5}$ alkoxy group, and an amino group;
provided that, when X is the group represented by the above formula (i) and Y is not —O—, W may be a hydrogen atom;
Herein, the symbol "●" used in the formulae such as (i), (ii), (iii), and (iv) means the site of bonding.

[2] the compound according to [1], or a pharmaceutically acceptable salt thereof, wherein X represents the group —Y—Z—W of the formula (i) and Z represents a $C_{1-5}$ alkylene chain,
wherein the alkylene chain may have one to three substituents selected from the group consisting of a $C_{1-5}$ alkyl group, a halogen atom, —ORa, —NRaRb, and an oxo group; the above substituents except the oxo group and the halogen atom may be linked to each other to form a cycloalkyl group or a heterocyclic group;
the cycloalkyl group or the heterocyclic group may have a substituent selected from the group consisting of —ORa, —NRaRb, and a $C_{1-5}$ alkyl group that may be substituted with —ORa;
Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

[3] the compound according to [1] or [2], or a pharmaceutically acceptable salt thereof, wherein X represents the group —Y—Z—W of the formula (i), wherein the alkylene chain of Z is any one of the groups represented by the following formulae:

—$CH_2$—, —$(CH_2)_2$—, —$(CH_2)_3$—, —$(CH_2)_4$—, —$CH_2CH(Me)$—, —$CH_2C(Me)_2$-, —$C(Me)_2CH_2$—, —$(CH_2)_2CH(Me)$—, —$(CH_2)_2C(Me)_2$-, —$CH(Me)(CH_2)_2$—, —$C(Me)_2(CH_2)_2$—, —$CH_2CH(Me)CH_2$—, —$CH_2C(Me)_2CH_2$—, —$CH_2C(CH_2CH_2)CH_2$—, —CO—, —$CH_2$CO—, —CO$CH_2$—, —$(CH_2)_2$CO—, —CO$(CH_2)_2$—, —CHOH—, —$CH_2$CH(OH)—, —CH(OH)$CH_2$—, —$CH_2$CH(OH)$CH_2$—, —CH(OH)$CH_2CH_2$—, and —$CH_2CH_2$CH(OH)—;

[4] the compound according to any one of [1] to [3], or a pharmaceutically acceptable salt thereof, wherein X represents —Y—Z—W of the formula (i), wherein $R_8$ represents a hydrogen atom, a hydroxyl group, a $C_{1-5}$ alkyl group, or —CO$R_9$;

$R_9$ represents a hydrogen atom, a hydroxyl group, a $C_{1-5}$ alkyl group, or a $C_{1-5}$ alkoxy group;

the alkyl group and the alkoxy group represented by $R_8$ and $R_9$ may be substituted by one to three hydroxyl groups at arbitrary positions of the hydrocarbon moiety;

[5] the compound according to any one of [1] to [4], or a pharmaceutically acceptable salt thereof, wherein X represents —Y—Z—W of the formula (i), wherein $R_8$ represents a hydrogen atom, a hydroxyl group, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a formyl group, an acetyl group, a 2-methoxyacetyl group, a 2-ethoxyacetyl group, a 2-hydroxyacetyl group, a propionyl group, a 2-methylpropionyl group, a 2-methoxypropionyl group, a 2-ethoxypropionyl group, a 2-hydroxypropionyl group, a 3-methoxypropionyl group, a 3-ethoxypropionyl group, a 3-hydroxypropionyl group, a methoxy group, an ethoxy group, an n-propyloxy group, an i-propyloxy group, a hydroxymethyl group, or a 2-hydroxyethyl group;

[6] the compound according to any one of [1] to [5], or a pharmaceutically acceptable salt thereof, wherein X represents —Y—Z—W of the formula (i), wherein Y represents —O—, —NHO—, —N(COC$H_3$)O—, —N(COC$H_2$OH)O—, —N(COC$H_2$C$H_3$)O—, —N(COCH(OH)C$H_3$)O—, —N(COC$H_2$C$H_2$OH)O—, —N(COCH(OH)C$H_2$OH)O—, —N(COC$H_2$C$H_2$C$H_3$)O—, —N(COC$H_2$C$H_2$C$H_2$OH)O—,

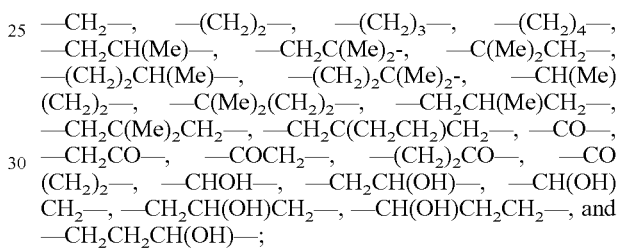

—N(COCH(OH)CH₂CH₃)O—, —N(COCH₂CH(OH)CH₃)
O—, —NHCO—, or —NHSO₂—;

[7] the compound according to [1], or a pharmaceutically acceptable salt thereof, wherein X represents a group represented by the formula (ii) and X is any one of the groups represented by the following formulae:

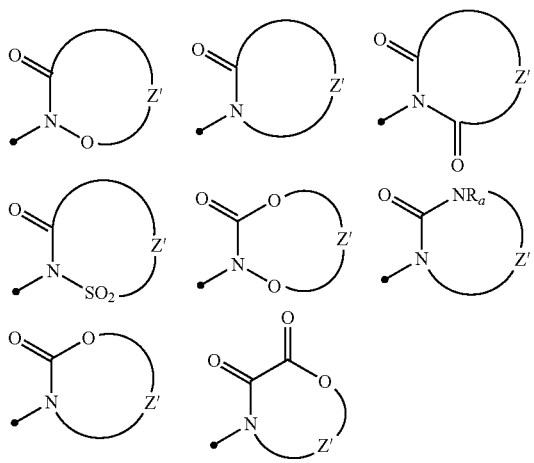

wherein Z' represents a $C_{1-5}$ alkylene chain which may be substituted by one to three groups represented by W';

W' represents a $C_{1-5}$ alkyl group, a halogen atom, an oxo group, —ORa, —CONRaRb, —SRa, —SORa, —SO₂Ra, —NRaRb, —NRaCORb, —NRaSO₂Rb, —SO₂NRaRb, a heterocyclic group, or a heteroaryl group;

the heterocyclic group and the heteroaryl group may have substituents selected from the group consisting of a $C_{1-5}$ alkyl group, —ORa, and —NRaRb; the alkyl group may be substituted by a hydroxyl group, a $C_{1-5}$ alkoxy group, or an amino group;

the above substituents except the oxo group and the halogen may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

[8] the compound according to any one of [1] or [7], or a pharmaceutically acceptable salt thereof, wherein X represents the group represented by the formula (ii), wherein W' represents any one of the groups represented by the formulae:

-Me, -Et, -n-Pr, -i-Pr, —CH₂OH, —CH₂CH₂OH, —CH(OH)CH₃, —OH, —OMe, —OEt, —OCH₂OH, —O(CH₂)₂OH, —O(i-Pr), —O(n-Pr), —CONH₂, —CONHMe, —CONHEt, —CONH(n-Pr), —CONH(i-Pr), —CONMe₂, —CON(Et)Me, —SO₂Me, —SOMe, —SMe, —NH₂, —NHMe, —NHCH₂OH, —NH(CH₂)₂OH, —N(Me)CH₂CH₂OH, —NHEt, —NMe₂, —N(Et)Me, —NHCOMe, —NMeCOMe, —NHCOEt, —NHCO(n-Pr), and —NHCO(i-Pr);

[9] the compound according to any one of [1], [7], and [8], or a pharmaceutically acceptable salt thereof, wherein X represents the group represented by the formula (ii), wherein the alkylene chain of Z' is any one of the groups represented by the following formulae:

—CH₂—, —(CH₂)₂—, —(CH₂)₃—, —(CH₂)₄—, —CH₂CH(Me)—, —CH₂C(Me)₂-, —C(Me)₂CH₂—, —(CH₂)₂CH(Me)—, —(CH₂)₂C(Me)₂-, —CH(Me)(CH₂)₂—, —C(Me)₂(CH₂)₂—, —CH₂CH(Me)CH₂—, —CH₂C(Me)₂CH₂—, —CHOH—, —CH₂CH(OH)—, —CH(OH)CH₂—, —CH₂CH(OH)CH₂—, —CH(OH)CH₂CH₂—, —CH₂CH₂CH(OH)—, —CO—, —CH₂CO—, —COCH₂—, —(CH₂)₂CO—, —CO(CH₂)₂—, and —CH₂CH(OH)CH₂—;

[10] the compound according to any one of [1], [7], [8], and [9], or a pharmaceutically acceptable salt thereof, wherein X represents the group represented by the formula (ii) and X is any one of the groups represented by the following formulae:

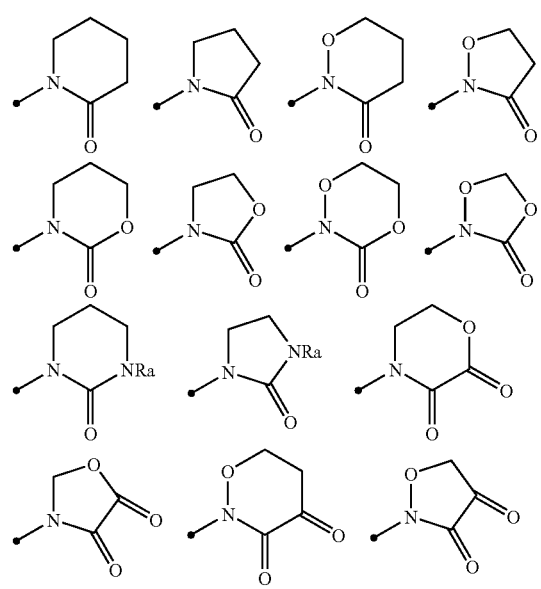

wherein the alkylene chain may be substituted at arbitrary positions by one to three substituents selected from the group consisting of a $C_{1-5}$ alkyl group, a halogen atom, —ORa, —NRaRb, and an oxo group; Ra and Rb, which may be the same or different, each represent a hydrogen atom or a $C_{1-5}$ alkyl group; the alkyl group may be substituted by a hydroxyl group, a $C_{1-5}$ alkoxy group, or an amino group; Ra represents a hydrogen atom or a $C_{1-5}$ alkyl group; and the alkyl group may be substituted by a hydroxyl group, a $C_{1-5}$ alkoxy group, or an amino group;

[11] the compound according to [1], or a pharmaceutically acceptable salt thereof, wherein X represents the group represented by the following formula (iii) or (iv):

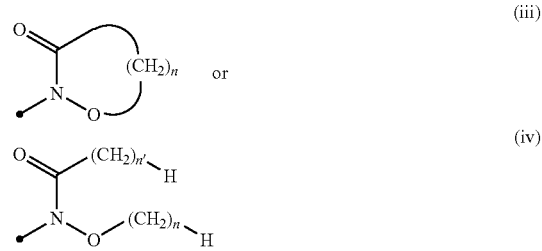

wherein n represents an integer ranging from 1 to 5 and n' represents an integer ranging from 0 to 5; the repeated units represented by —(CH₂)$_n$— or —(CH₂)n'- in the formulae may be substituted at arbitrary positions in the hydrocarbon moiety by one to three substituents selected from the group consisting of a $C_{1-5}$ alkyl group, a halogen atom, —ORa, —NRaRb, and an oxo group; Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

[12] the compound according to [1], or a pharmaceutically acceptable salt thereof, wherein X represents a group selected from the group consisting of a 2-hydroxyethoxy group, a 3-hydroxy-2-dimethylpropoxy group, a 3-hydroxypropoxy group, a 2-carbamoylethoxy group, a 2-methylcarbamoylethoxy group, a 2-methanesulfonyl-ethoxy group, a 2-acetylamino-ethoxy group, a 2-hydroxyethoxyamino group, a 3-hydroxypropionyl amino group, a 2-hydroxyethanesulfonamide group, a 1-hydroxymethyl-cyclopropylmethoxy group, a 2,3-dihydroxy-propoxy group, a 1H-imidazol-2-ylmethoxy group, a 2-methylcarbamoyl-ethoxyamino group, a 2-acetylamino-ethoxyamino group, a 2-methanesulfonyl-ethoxyamino group, a 1H-imidazol-2-yl-methoxyamino group, a 3-hydroxypropoxyamino group, a 2-(2-hydroxyethoxy)-ethoxy group, a 2-methylaminoethoxy group, a 2-(2-hydroxyethylamino)-ethoxy group, a 2-morpholin-4-yl-ethoxy group, a 2-(4-hydroxy-piperidin-1-yl)-ethoxy group, a 2-methylamino-ethoxyamino group, a 2,3-dihydroxy-propoxyamino group, a formyl-methoxyamino group, an acetyl-methoxyamino group, a methoxy-propionylamino group, an isobutyryl-methoxy-amino group, a (2-hydroxy-acetyl)-methoxyamino group, a methoxy-(2-methoxy-acetyl)-amino group, an acetyl-ethoxy-amino group, an ethoxy-propionyl-amino group, an acetyl-isopropoxy-amino group, an acetylhydroxyamino group, an acetoxy-acetyl-amino group, an acetyl-(2-hydroxy-ethoxy)-amino group, an acetyl-(3-hydroxy-propoxy)-amino group, an acetyl-(2-hydroxy-2-methyl-propoxy)-amino group, an acetyl-(2-acetylamino-ethoxy)-amino group, an acetyl-(2-propionylamino-ethoxy)-amino group, an acetyl-(2-isobutyrylamino-ethoxy)-amino group, an acetyl-(2-methylsulfanyl-ethoxy)-amino group, an acetyl-(3-methylsulfanyl-propoxy)-amino group, a 2-hydroxy-1,1-dimethyl-ethoxy group, a methylcarbamoylmethoxyamino group, an ethylcarbamoyl-methoxyamino group, a propylcarbamoylmethoxyamino group, an isopropylcarbamoyl-methoxyamino group, a dimethylcarbamoylmethoxyamino group, a 2-ethylcarbamoyl-ethoxyamino group, a 2-propylcarbamoyl-ethoxyamino group, a 2-isopropylcarbamoyl-ethoxyamino group, a 3-methylcarbamoyl-propoxyamino group, a 2-methoxycarbonyl-ethoxyamino group, a methoxyamino group, a methoxy-methyl-amino group, an ethoxyamino group, an isopropoxyamino group, a 2-hydroxy-2-methyl-propoxyamino group, a 2-methylsulfanyl-ethoxyamino group, a 2-methanesulfinyl-ethoxyamino group, a 3-methylsulfanyl-propoxyamino group, a 3-methanesulfinyl-propoxyamino group, a 2-propionylamino-ethoxyamino group, a 2-isobutyrylamino-ethoxyamino group, a 2-hydroxy-acetylamino group, and an acetyl-(2-hydroxy-ethyl)-amino group;

[13] the compound according to [1], or a pharmaceutically acceptable salt thereof, wherein X represents a group selected from the group consisting of a 3-oxo-[1,2]oxazinan-2-yl group, a 3-oxo-isoxazolidin-2-yl group, a 4,4-dimethyl-3-oxo-isoxazolidin-2-yl group, a 4-hydroxy-3-oxo-[1,2]oxazinan-2-yl group, a 3-oxo-[1,4,2]dioxazinan-2-yl group, a 2-oxo-pyrrolidin-1-yl group, a 2-oxo-piperidin-1-yl group, a 2-oxo-oxazolidin-3-yl group, a 2-oxo-tetrahydro-pyrimidin-1-yl group, and a 2,3-dioxo-morpholin-4-yl group;

[14] the compound according to any one of [1] to [13], or a pharmaceutically acceptable salt thereof, wherein $R_1$ represents an iodine atom, a bromine atom, a vinyl group, or an ethynyl group;

[15] the compound according to any one of [1] to [14], or a pharmaceutically acceptable salt thereof, wherein $R_1$ represents an iodine atom or an ethynyl group;

[16] the compound according to any one of [1] to [15], or a pharmaceutically acceptable salt thereof, wherein $R_2$ represents a chlorine atom, a fluorine atom, a methyl group, or a hydroxymethyl group;

[17] the compound according to any one of [1] to [16], or a pharmaceutically acceptable salt thereof, wherein $R_2$ represents a fluorine atom;

[18] the compound according to any one of [1] to [17], or a pharmaceutically acceptable salt thereof, wherein $R_3$ represents a fluorine atom;

[19] the compound according to any one of [1] to [18], or a pharmaceutically acceptable salt thereof, wherein $R_4$ represents a $C_{1-5}$ alkyl group substituted by one to three hydroxyl groups;

[20] the compound according to any one of [1] to [19], or a pharmaceutically acceptable salt thereof, wherein $R_4$ represents a group selected from the group consisting of the groups represented by the following formulae:

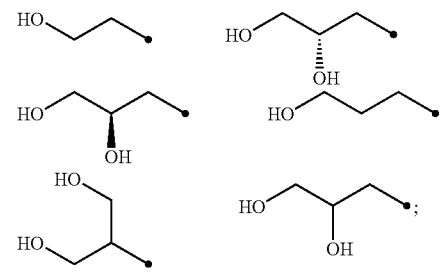

[21] the compound according to [1], or a pharmaceutically acceptable salt thereof, wherein Ra and Rb, which may be the same or different, each represent a group selected from the group consisting of a hydrogen atom, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a hydroxymethyl group, a 1-hydroxyethyl group, a 1-hydroxy-1-methylethyl group, a 2-hydroxy-1-methylethyl group, a 2-hydroxy-1,1-dimethylethyl group, a 2-hydroxyethyl group, a 1-hydroxypropyl group, a 2-hydroxypropyl group, and a 3-hydroxypropyl group;

[22] the compound according to [1] to [6], or a pharmaceutically acceptable salt thereof, wherein X represents —Y—Z—W of the formula (i), wherein W and W', which may be the same or different, each represent a group selected from the group consisting of —OH, —OMe, —OEt, —OCH$_2$OH, —O(CH$_2$)$_2$OH, —O(i-Pr), —O(n-Pr), —COOH, —COOMe, —COOEt, —COOCOMe, —COCl, —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr); and W may be a hydrogen atom when Y is not —O—;

[23] the compound according to [1], or a pharmaceutically acceptable salt thereof, wherein the compound represented by the above formula (1) is any one selected from the group consisting of:

(1) B-1
3,4-difluoro-2-(2-fluoro-4-iodo-phenylamino)-N-(2-hydroxy-ethoxy)-5-(2-hydroxy-ethoxymethyl)-benzamide, (2) B-2
2-(4-ethynyl-2-fluoro-phenylamino)-3,4-difluoro-N-(2-hydroxy-ethoxy)-5-(2-hydroxy-ethoxymethyl)-benzamide, (3) B-3
N-(2,3-dihydroxy-propoxy)-3,4-difluoro-2-(2-fluoro-4-iodo-phenylamino)-5-(2-hydroxy-ethoxymethyl)-benzamide, (4) B-4
2-(2-chloro-4-iodo-phenylamino)-3,4-difluoro-N-(2-hydroxy-ethoxy)-5-(2-hydroxy-ethoxymethyl)-benzamide, (5) B-5
3,4-difluoro-2-(2-fluoro-4-vinyl-phenylamino)-N-(2-hydroxy-ethoxy)-5-(2-hydroxy-ethoxymethyl)-benzamide, (6) B-6
3,4-difluoro-2-(2-fluoro-4-iodo-phenylamino)-N-(2-hydroxy-ethoxy)-5-(3-hydroxypropoxymethyl)-benzamide, (7) B-7
3,4-difluoro-2-(2-fluoro-4-iodo-phenylamino)-5-(3-hydroxy-2,2-dimethyl-propoxymethyl)-N-(2-hydroxy-ethoxy)-benzamide, (8) B-8
3,4-difluoro-2-(2-fluoro-4-iodo-phenylamino)-N-(2-hydroxy-ethoxy)-5-(1-hydroxymethyl-cyclo propylmethoxymethyl)-benzamide, (9) B-9
5-(2,3-dihydroxy-propoxymethyl)-3,4-difluoro-2-(2-fluoro-4-iodo-phenylamino)-N-(2-hydroxy-ethoxy)-benzamide,

(10) B-10
3,4-difluoro-2-(2-fluoro-4-iodo-phenylamino)-N-(2-hydroxy-ethoxy)-5-(2-methylcarbamoyl-ethoxymethyl)-benzamide,

(11) B-11
5-(2-acetylamino-ethoxymethyl)-3,4-difluoro-2-(2-fluoro-4-iodo-phenylamino)-N-(2-hydroxy-ethoxy)-benzamide,

(12) B-12
3,4-difluoro-2-(2-fluoro-4-iodo-phenylamino)-N-(2-hydroxy-ethoxy)-5-(2-methanesulfonyl-ethoxymethyl)-benzamide,

(13) B-13
3,4-difluoro-2-(2-fluoro-4-iodo-phenylamino)-N-(2-hydroxy-ethoxy)-5-(1H-imidazol-2-yl methoxymethyl)-benzamide,

(14) B-14
3,4-difluoro-2-(2-fluoro-4-iodo-phenylamino)-N-(2-hydroxy-ethoxy)-5-[2-(2-hydroxy-ethoxy)-ethoxymethyl]-benzamide,

(15) B-15
3,4-difluoro-2-(2-fluoro-4-iodo-phenylamino)-N-(2-hydroxy-ethoxy)-5-(2-methylamino-ethoxymethyl)-benzamide,

(16) B-16
3,4-difluoro-2-(2-fluoro-4-iodo-phenylamino)-N-(2-hydroxy-ethoxy)-5-[2-(2-hydroxy-ethylamino)-ethoxymethyl]-benzamide,

(17) B-17
3,4-difluoro-2-(2-fluoro-4-iodo-phenylamino)-N-(2-hydroxy-ethoxy)-5-(2-morpholin-4-yl-ethoxymethyl)-benzamide,

(18) B-18
3,4-difluoro-2-(2-fluoro-4-iodo-phenylamino)-N-(2-hydroxy-ethoxy)-5-[2-(4-hydroxy-piperidin-1-yl)-ethoxymethyl]-benzamide, and

(19) B-19
3,4-difluoro-2-(2-fluoro-4-iodo-phenylamino)-5-(2-hydroxy-1,1-dimethyl-ethoxymethyl)-N-(2-hydroxy-ethoxy)-benzamide;

[24] the compound according to [1], or a pharmaceutically acceptable salt thereof, wherein the compound represented by the above formula (1) is any one selected from the group consisting of:

(1) C-1
3,4-difluoro-2-(2-fluoro-4-iodo-phenylamino)-N-(2-hydroxy-ethoxy)-5-[(2-hydroxy-ethoxyamino)-methyl]-benzamide, (2) C-2
2-(4-ethynyl-2-fluoro-phenylamino)-3,4-difluoro-N-(2-hydroxy-ethoxy)-5-[(2-hydroxy-ethoxyamino)-methyl]-benzamide, (3) C-3
N-(2,3-dihydroxy-propoxy)-3,4-difluoro-2-(2-fluoro-4-iodo-phenylamino)-5-[(2-hydroxy-ethoxyamino)-methyl]-benzamide, (4) C-4
2-(2-chloro-4-iodo-phenylamino)-3,4-difluoro-N-(2-hydroxy-ethoxy)-5-[(2-hydroxy-ethoxyamino)-methyl]-benzamide, (5) C-5
3,4-difluoro-2-(2-fluoro-4-vinyl-phenylamino)-N-(2-hydroxy-ethoxy)-5-[(2-hydroxy-ethoxyamino)-methyl]-benzamide, (6) C-6
3,4-difluoro-2-(2-fluoro-4-iodo-phenylamino)-N-(2-hydroxy-ethoxy)-5-[(2-methylcarbamoyl-ethoxyamino)-methyl]-benzamide, (7) C-7
5-[(2-acetylamino-ethoxyamino)-methyl]-3,4-difluoro-2-(2-fluoro-4-iodo-phenylamino)-N-(2-hydroxy-ethoxy)-benzamide, (8) C-8
3,4-difluoro-2-(2-fluoro-4-iodo-phenylamino)-N-(2-hydroxy-ethoxy)-5-[(2-methanesulfonyl-ethoxyamino)-methyl]-benzamide, (9) C-9
3,4-difluoro-2-(2-fluoro-4-iodo-phenylamino)-N-(2-hydroxy-ethoxy)-5-[(1H-imidazol-2-ylmethoxyamino)-methyl]-benzamide,

(10) C-10
3,4-difluoro-2-(2-fluoro-4-iodo-phenylamino)-N-(2-hydroxy-ethoxy)-5-[(3-hydroxy-propoxyamino)-methyl]-benzamide,

(11) C-11
3,4-difluoro-2-(2-fluoro-4-iodo-phenylamino)-N-(2-hydroxy-ethoxy)-5-[(2-methylamino-ethoxyamino)-methyl]-benzamide,

(12) C-12
5-[(2,3-dihydroxy-propoxyamino)-methyl]-3,4-difluoro-2-(2-fluoro-4-iodo-phenylamino)-N-(2-hydroxy-ethoxy)-benzamide,

(13) C-13
3,4-difluoro-2-(2-fluoro-4-iodo-phenylamino)-N-(2-hydroxy-ethoxy)-5-(methylcarbamoylmethoxyamino-methyl)-benzamide,

(14) C-14
5-(ethylcarbamoylmethoxyamino-methyl)-3,4-difluoro-2-(2-fluoro-4-iodo-phenylamino)-N-(2-hydroxy-ethoxy)-benzamide,

(15) C-15
3,4-difluoro-2-(2-fluoro-4-iodo-phenylamino)-N-(2-hydroxy-ethoxy)-5-(propylcarbamoylmethoxyamino-methyl)-benzamide,

(16) C-16
3,4-difluoro-2-(2-fluoro-4-iodo-phenylamino)-N-(2-hydroxy-ethoxy)-5-[(isopropylcarbamoyl-methoxyamino)-methyl]-benzamide,

(17) C-17
5-(dimethylcarbamoylmethoxyamino-methyl)-3,4-difluoro-2-(2-fluoro-4-iodo-phenylamino)-N-(2-hydroxy-ethoxy)-benzamide,

(18) C-18
5-[(2-ethylcarbamoyl-ethoxyamino)-methyl]-3,4-difluoro-2-(2-fluoro-4-iodo-phenylamino)-N-(2-hydroxy-ethoxy)-benzamide,

(19) C-19
5-[(2-propylcarbamoyl-ethoxyamino)-methyl]-3,4-difluoro-2-(2-fluoro-4-iodo-phenylamino)-N-(2-hydroxy-ethoxy)-benzamide,

(20) C-20
5-[(2-isopropylcarbamoyl-ethoxyamino)-methyl]-3,4-difluoro-2-(2-fluoro-4-iodo-phenylamino)-N-(2-hydroxy-ethoxy)-benzamide,

(21) C-21
3,4-difluoro-2-(2-fluoro-4-iodo-phenylamino)-N-(2-hydroxy-ethoxy)-5-[(3-methylcarbamoyl-propoxyamino)-methyl]-benzamide,

(22) C-22
3-[N-[2,3-difluoro-4-(2-fluoro-4-iodo-phenylamino)-5-(2-hydroxyethoxycarbamoyl)benzyl]aminooxy]propionic acid methyl ester,

(24) C-24
3,4-difluoro-2-(2-fluoro-4-iodo-phenylamino)-N-(2-hydroxy-ethoxy)-5-(methoxyamino-methyl)-benzamide,

(25) C-25
3,4-difluoro-2-(2-fluoro-4-iodo-phenylamino)-N-(2-hydroxy-ethoxy)-5-[(methoxy-methyl-amino)-methyl]-benzamide,

(26) C-26
5-(ethoxyamino-methyl)-3,4-difluoro-2-(2-fluoro-4-iodo-phenylamino)-N-(2-hydroxy-ethoxy)-benzamide,

(27) C-27
3,4-difluoro-2-(2-fluoro-4-iodo-phenylamino)-N-(2-hydroxy-ethoxy)-5-(isopropoxyamino-methyl)-benzamide,

(28) C-28
3,4-difluoro-2-(2-fluoro-4-iodo-phenylamino)-N-(2-hydroxy-ethoxy)-5-[(2-hydroxy-2-methyl-propoxyamino)-methyl]-benzamide,

(29) C-29
2-(4-ethynyl-2-fluoro-phenylamino)-3,4-difluoro-N-(2-hydroxy-ethoxy)-5-[(2-hydroxy-2-methyl-propoxyamino)-methyl]-benzamide,

(30) C-30
3,4-difluoro-2-(2-fluoro-4-iodo-phenylamino)-N-(2-hydroxy-ethoxy)-5-[(2-methylsulfanyl-ethoxyamino)-methyl]-benzamide,

(31) C-31
3,4-difluoro-2-(2-fluoro-4-iodo-phenylamino)-N-(2-hydroxy-ethoxy)-5-[(2-methanesulfinyl-ethoxyamino)-methyl]-benzamide,

(32) C-32
3,4-difluoro-2-(2-fluoro-4-iodo-phenylamino)-N-(2-hydroxy-ethoxy)-5-[(3-methylsulfanyl-propoxyamino)-methyl]-benzamide,

(33) C-33
3,4-difluoro-2-(2-fluoro-4-iodo-phenylamino)-N-(2-hydroxy-ethoxy)-5-[(3-methanesulfinyl-propoxyamino)-methyl]-benzamide,

(34) C-34
3,4-difluoro-2-(2-fluoro-4-iodo-phenylamino)-N-(2-hydroxy-ethoxy)-5-[(2-propionylamino-ethoxyamino)-methyl]-benzamide, and

(35) C-35
3,4-difluoro-2-(2-fluoro-4-iodo-phenylamino)-N-(2-hydroxy-ethoxy)-5-[(2-isobutyrylamino-ethoxyamino)-methyl]-benzamide;

[25] the compound according to [1], or a pharmaceutically acceptable salt thereof, wherein the compound represented by the above formula (1) is any one selected from the group consisting of:

(1) E-1
3,4-difluoro-2-(2-fluoro-4-iodo-phenylamino)-N-(2-hydroxy-ethoxy)-5-[(3-hydroxy-propionylamino)-methyl]-benzamide (2) E-2
2-(4-ethynyl-2-fluoro-phenylamino)-3,4-difluoro-N-(2-hydroxy-ethoxy)-5-[(3-hydroxy-propionylamino)-methyl]-benzamide (3) E-3
3,4-difluoro-2-(2-fluoro-4-iodo-phenylamino)-5-[(2-hydroxy-ethanesulfonylamino)-methyl]-N-(2-hydroxy-ethoxy)-benzamide, (4) E-4
2-(4-ethynyl-2-fluoro-phenylamino)-3,4-difluoro-5-[(2-hydroxy-ethanesulfonylamino)-methyl]-N-(2-hydroxy-ethoxy)-benzamide, (5) E-5
3,4-difluoro-2-(2-fluoro-4-iodo-phenylamino)-5-[(2-hydroxy-acetylamino)-methyl]-N-(2-hydroxy-ethoxy)-benzamide, and (6) E-6
5-{[acetyl-(2-hydroxy-ethyl)-amino]-methyl}-3,4-difluoro-2-(2-fluoro-4-iodo-phenylamino)-N-(2-hydroxy-ethoxy)-benzamide;

[26] the compound according to [1], or a pharmaceutically acceptable salt thereof, wherein the compound represented by the above formula (1) is any one selected from the group consisting of:

(1) F-1
3,4-difluoro-2-(2-fluoro-4-iodo-phenylamino)-5-[(formyl-methoxy-amino)-methyl]-N-(2-hydroxy-ethoxy)-benzamide, (2) F-2
5-[acetyl-methoxy-amino-methyl]-3,4-difluoro-2-(2-fluoro-4-iodo-phenylamino)-N-(2-hydroxy-ethoxy)-benzamide, (3) F-3
3,4-difluoro-2-(2-fluoro-4-iodo-phenylamino)-N-(2-hydroxy-ethoxy)-5-[(methoxy-propionyl-amino)-methyl]-benzamide, (4) F-4
3,4-difluoro-2-(2-fluoro-4-iodo-phenylamino)-N-(2-hydroxy-ethoxy)-5-[(isobutyryl-methoxy-amino)-methyl]-benzamide, (5) F-5
3,4-difluoro-2-(2-fluoro-4-iodo-phenylamino)-5-{[(2-hydroxy-acetyl)-methoxy-amino]-methyl}-N-(2-hydroxy-ethoxy)-benzamide, (6) F-6
3,4-difluoro-2-(2-fluoro-4-iodo-phenylamino)-N-(2-hydroxy-ethoxy)-5-{[methoxy-(2-methoxy-acetyl)-amino]-methyl}-benzamide, (7) F-7
5-[(acetyl-methoxy-amino)-methyl]-2-(4-ethynyl-2-fluoro-phenylamino)-3,4-difluoro-N-(2-hydroxy-ethoxy)-benzamide, (8) F-8
2-(4-ethynyl-2-fluoro-phenylamino)-3,4-difluoro-N-(2-hydroxy-ethoxy)-5-[(methoxy-propionyl-amino)-methyl]-benzamide, (9) F-9
2-(4-ethynyl-2-fluoro-phenylamino)-3,4-difluoro-N-(2-hydroxy-ethoxy)-5-[(isobutyryl-methoxy-amino)-methyl]-benzamide,

(10) F-10
5-[(acetyl-ethoxy-amino)-methyl]-3,4-difluoro-2-(2-fluoro-4-iodo-phenylamino)-N-(2-hydroxy-ethoxy)-benzamide,

(11) F-11
5-[(ethoxy-propionyl-amino)-methyl]-3,4-difluoro-2-(2-fluoro-4-iodo-phenylamino)-N-(2-hydroxy-ethoxy)-benzamide,

(12) F-12
5-[(acetyl-isopropoxy-amino)-methyl]-3,4-difluoro-2-(2-fluoro-4-iodo-phenylamino)-N-(2-hydroxy-ethoxy)-benzamide,

(13) F-13
5-[(acetyl-hydroxy-amino)-methyl]-3,4-difluoro-2-(2-fluoro-4-iodo-phenylamino)-N-(2-hydroxy-ethoxy)-benzamide,

(14) F-14
5-[(acetoxy-acetyl-amino)-methyl]-3,4-difluoro-2-(2-fluoro-4-iodo-phenylamino)-N-(2-hydroxy-ethoxy)-benzamide,

(15) F-15
5-{[acetyl-(2-hydroxy-ethoxy)-amino]-methyl}-3,4-difluoro-2-(2-fluoro-4-iodo-phenylamino)-N-(2-hydroxy-ethoxy)-benzamide,

(16) F-16
5-{[acetyl-(3-hydroxy-propoxy)-amino]-methyl}-3,4-difluoro-2-(2-fluoro-4-iodo-phenylamino)-N-(2-hydroxy-ethoxy)-benzamide,

(17) F-17
5-{[acetyl-(2-hydroxy-2-methyl-propoxy)-amino]-methyl}-3,4-difluoro-2-(2-fluoro-4-iodo-phenylamino)-N-(2-hydroxy-ethoxy)-benzamide,

(18) F-18
5-{[acetyl-(2-acetylamino-ethoxy)-amino]-methyl}-3,4-difluoro-2-(2-fluoro-4-iodo-phenylamino)-N-(2-hydroxy-ethoxy)-benzamide,

(19) F-19
5-{[acetyl-(2-propionylamino-ethoxy)-amino]-methyl}-3,4-difluoro-2-(2-fluoro-4-iodo-phenylamino)-N-(2-hydroxy-ethoxy)-benzamide,

(20) F-20
5-{[acetyl-(2-isobutyrylamino-ethoxy)-amino]-methyl}-3,4-difluoro-2-(2-fluoro-4-iodo-phenylamino)-N-(2-hydroxy-ethoxy)-benzamide,

(21) F-21
5-{[acetyl-(2-methylsulfanyl-ethoxy)-amino]-methyl}-3,4-difluoro-2-(2-fluoro-4-iodo-phenylamino)-N-(2-hydroxy-ethoxy)-benzamide,

(22) F-22
5-{[acetyl-(3-methylsulfanyl-propoxy)-amino]-methyl}-3,4-difluoro-2-(2-fluoro-4-iodo-phenylamino)-N-(2-hydroxy-ethoxy)-benzamide,

(23) F-23
5-[(acetyl-ethoxy-amino)-methyl]-2-(4-ethynyl-2-fluoro-phenylamino)-3,4-difluoro-N-(2-hydroxy-ethoxy)-benzamide,

(24) F-24
5-[(ethoxy-propionyl-amino)-methyl]-2-(4-ethynyl-2-fluoro-phenylamino)-3,4-difluoro-N-(2-hydroxy-ethoxy)-benzamide,

(25) F-25
5-{[acetyl-(2-hydroxy-ethoxy)-amino]-methyl}-2-(4-ethynyl-2-fluoro-phenylamino)-3,4-difluoro-N-(2-hydroxy-ethoxy)-benzamide, and

(26) F-26
5-{[acetyl-(2-hydroxy-2-methyl-propoxy)-amino]-methyl}-2-(4-ethynyl-2-fluoro-phenylamino)-3,4-difluoro-N-(2-hydroxy-ethoxy)-benzamide;

[27] the compound according to [1], or a pharmaceutically acceptable salt thereof, wherein the compound represented by the above formula (1) is any one selected from the group consisting of:

(1) G-1
3,4-difluoro-2-(2-fluoro-4-iodo-phenylamino)-N-(2-hydroxy-ethoxy)-5-(3-oxo-[1,2]oxazinan-2-ylmethyl)-benzamide, (2) G-2
3,4-difluoro-2-(2-fluoro-4-iodo-phenylamino)-N-(2-hydroxy-ethoxy)-5-(3-oxo-isoxazolidin-2-yl methyl)-benzamide, (3) G-3
5-(4,4-dimethyl-3-oxo-isoxazolidin-2-ylmethyl)-3,4-difluoro-2-(2-fluoro-4-iodo-phenylamino)-N-(2-hydroxyethoxy)-benzamide, (4) G-4
2-(4-ethynyl-2-fluoro-phenylamino)-3,4-difluoro-N-(2-hydroxy-ethoxy)-5-(3-oxo-[1,2]oxazinan-2-ylmethyl)-benzamide, (5) G-5
2-(4-ethynyl-2-fluoro-phenylamino)-3,4-difluoro-N-(2-hydroxy-ethoxy)-5-(3-oxo-isoxazolidin-2-ylmethyl)-benzamide, (6) G-6
N-(2,3-dihydroxy-propoxy)-3,4-difluoro-2-(2-fluoro-4-iodo-phenylamino)-5-(3-oxo-[1,2]oxazinan-2-ylmethyl)-benzamide, (7) G-7
N-(2,3-dihydroxy-propoxy)-3,4-difluoro-2-(2-fluoro-4-iodo-phenylamino)-5-(3-oxo-isoxazolidin-2-ylmethyl)-benzamide, and (8) G-8
3,4-difluoro-2-(2-fluoro-4-iodo-phenylamino)-N-(2-hydroxy-ethoxy)-5-(4-hydroxy-3-oxo-[1,2]oxazinan-2-ylmethyl)-benzamide;

[28] the compound according to [1], or a pharmaceutically acceptable salt thereof, wherein the compound represented by the above formula (1) is any one selected from the group consisting of:

(1) H-1
3,4-difluoro-2-(2-fluoro-4-iodo-phenylamino)-N-(2-hydroxy-ethoxy)-5-(3-oxo-[1,4,2]dioxazinan-2-ylmethyl)-benzamide, (2) H-2
2-(4-ethynyl-2-fluoro-phenylamino)-3,4-difluoro-N-(2-hydroxy-ethoxy)-5-(3-oxo-[1,4,2]dioxazinan-2-ylmethyl)-benzamide, (3) H-3
3,4-difluoro-2-(2-fluoro-4-iodo-phenylamino)-N-(2-hydroxy-ethoxy)-5-(2-oxo-pyrrolidin-1-ylmethyl)-benzamide, (4) H-4
3,4-difluoro-2-(2-fluoro-4-iodo-phenylamino)-N-(2-hydroxy-ethoxy)-5-(2-oxo-piperidin-1-ylmethyl)-benzamide, (5) H-5
3,4-difluoro-2-(2-fluoro-4-iodo-phenylamino)-N-(2-hydroxy-ethoxy)-5-(2-oxo-oxazolidin-3-ylmethyl)-benzamide, (6) H-6
3,4-difluoro-2-(2-fluoro-4-iodo-phenylamino)-N-(2-hydroxy-ethoxy)-5-(2-oxo-tetrahydro-pyrimidin-1-ylmethyl)-benzamide, and (7) H-7
5-(2,3-dioxo-morpholin-4-ylmethyl)-3,4-difluoro-2-(2-fluoro-4-iodo-phenylamino)-N-(2-hydroxy-ethoxy)-benzamide;

[29] a synthetic intermediate (E) of the compound represented by the formula (1) according to [1], wherein the intermediate is represented by the following formula (6):

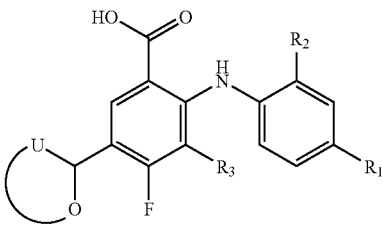

(6)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

in the above formula (6), the group represented by the following formula (a):

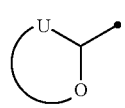

(a)

represents a 3- to 10-membered heterocyclic group that may have one to three substituents selected from the group consisting of a $C_{1-5}$ alkyl group, a halogen atom, —ORa, —NRaRb, and an oxo group;

the above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; the alkyl group may be substituted by a hydroxyl group, a $C_{1-5}$ alkoxy group, or an amino group;

U represents —O—, —CONRd-, —S—, —SO—, —SO$_2$—, —NRd-, —NRdCO—, —NRdSO$_2$—, —SO$_2$NRd-, a divalent heterocyclic group, or a divalent heteroaryl group; Rd represents a hydrogen atom or a $C_{1-5}$ alkyl group; the alkyl group may be substituted by a hydroxyl group, a $C_{1-5}$ alkoxy group, or an amino group;

$R_1$, $R_2$, $R_3$, and U may have protecting group(s) required for the synthesis;

[30] the synthetic intermediate (E) according to [29], wherein $R_1$ represents an iodine atom, a bromine atom, an ethynyl group, or a vinyl group;

$R_2$ represents a chlorine atom or a fluorine atom;

$R_3$ represents a fluorine atom; and

U represents —O—;

[31] the synthetic intermediate (E) according to [29], wherein the heterocyclic group represented by the formula (a)

is a [1,3]dioxoran-2-yl group or a [1,3]dioxan-2-yl group, which may be substituted by a hydroxyl group or a $C_{1-5}$ alkyl group;

[32] a synthetic intermediate (F) of the compound represented by the formula (1) according to [1], wherein the intermediate is represented by the following formula (7):

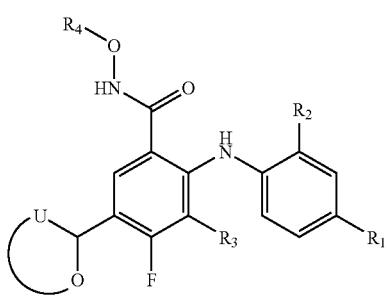

(7)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group; the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb; Ra and Rb, which may be the same or different, each represent a hydrogen atom or a $C_{1-5}$ alkyl group; the alkyl group may be substituted by a hydroxyl group, a $C_{1-5}$ alkoxy group, or an amino group; in the above formula (7), the group represented by the following formula (a):

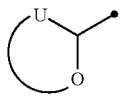

(a)

represents a 3- to 10-membered heterocyclic group that may have one to three substituents selected from the group consisting of a $C_{1-5}$ alkyl group, a halogen atom, —ORa, —NRaRb, and an oxo group;

the above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

U represents —O—, —CONRd-, —S—, —SO—, —SO$_2$—, —NRd-, —NRdCO—, —NRdSO$_2$—, —SO$_2$NRd-, a divalent heterocyclic group, or a divalent heteroaryl group; Rd represents a hydrogen atom or a $C_{1-5}$ alkyl group; the alkyl group may be substituted by a hydroxyl group, a $C_{1-5}$ alkoxy group, or an amino group;

$R_1$, $R_2$, $R_3$, and U may have protecting group(s) required for the synthesis;

[33] the synthetic intermediate (F) according to [32], wherein $R_1$ represents an iodine atom, a bromine atom, an ethynyl group, or a vinyl group;

$R_2$ represents a chlorine atom or a fluorine atom;

$R_3$ represents a fluorine atom;

$R_4$ represents a hydroxy alkyl group, in which the hydroxy moiety may be protected; and U represents —O—;

[34] the synthetic intermediate (F) according to [32], wherein the heterocyclic group represented by the formula (a) is a [1,3]dioxolan-2-yl group or a [1,3]dioxan-2-yl group, which may be substituted by a hydroxyl group or a $C_{1-5}$ alkyl group;

[35] a synthetic intermediate (I) of the compound represented by the formula (1) according to [1], wherein the intermediate is represented by the following formula (10):

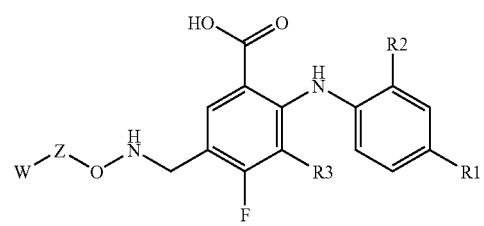

(10)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

Z represents a $C_{1-8}$ alkylene chain which may be substituted by one to three groups represented by W';

W or W', which may be the same or different, each represent a hydrogen atom, a $C_{1-5}$ alkyl group, a halogen atom, an oxo group, —ORa, —COORa, —COOCORa, —CO—[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group;

the heterocyclic group and the heteroaryl group may have a substituent selected from the group consisting of a $C_{1-5}$ alkyl group, —ORa, and —NRaRb; the alkyl group may be substituted by a hydroxyl group, a $C_{1-5}$ alkoxy group, or an amino group;

the above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; and the alkyl group may be substituted a hydroxyl group, a $C_{1-5}$ alkoxy group, or an amino group; and $R_1$, $R_2$, $R_3$, Z, W and W' may have protecting group(s) required for the synthesis;

[36] the synthetic intermediate according to [35], which is a synthetic intermediate (K) represented by the following formula (12):

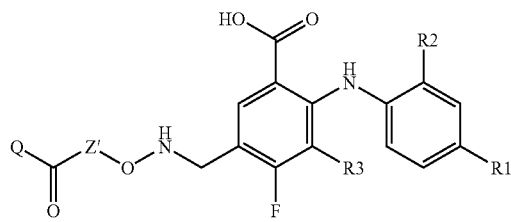

(12)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

Z' represents a $C_{1-5}$ alkylene chain that may be substituted by one to three groups represented by W';

W' represents any one of the groups represented by the formulae:

—OH, —OMe, —OEt, —OCH$_2$OH, —O(CH$_2$)$_2$OH, —O(i-Pr), —O(n-Pr), —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr);

Q represents —ORc, —OCORc, —NRcRd, or a halogen atom; Rc and Rd, which may be the same or different, each represent a hydrogen atom or a $C_{1-5}$ alkyl group;

$R_1$, $R_2$, and $R_3$ are defined herein above; and $R_1$, $R_2$, $R_3$, Z', Q and W' may have protecting group(s) required for the synthesis;

[37] the synthetic intermediate according to [35] or [36], wherein $R_1$ represents an iodine atom, a bromine atom, an ethynyl group, or a vinyl group;

$R_2$ represents a chlorine atom or a fluorine atom; and $R_3$ represents a fluorine atom;

[38] a synthetic intermediate (L) of the compound represented by the formula (1) the according to [1], wherein the intermediate is represented the following formula (13):

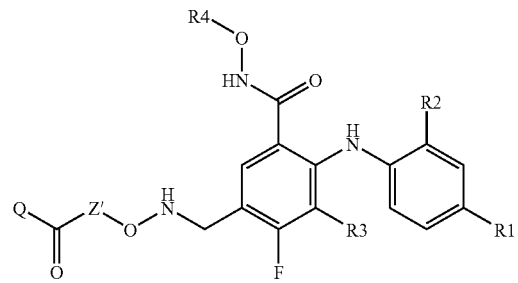

(13)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group; the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb; Ra and Rb, which may be the same or different, each represent a hydrogen atom or a $C_{1-5}$ alkyl group; the alkyl group may be substituted by a hydroxyl group, a $C_{1-5}$ alkoxy group, or an amino group;

Z' represents a $C_{1-5}$ alkylene chain that may have one to three groups represented by W';

W' represents the group represented by any one of the groups represented by the following formulae:

—OH, —OMe, —OEt, —OCH$_2$OH, —O(CH$_2$)$_2$OH, —O(i-Pr), —O(n-Pr), —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr);

Q represents —ORc, —OCORc, —NRcRd, or a halogen atom; Rc and Rd, which may be the same or different, each represent a hydrogen atom or a $C_{1-5}$ alkyl group; and $R_1$, $R_2$, $R_3$, $R_4$, Z', Q, and W' may have protecting group(s) required for the synthesis];

[39] the synthetic intermediate (L) according to [38], wherein $R_1$ represents an iodine atom, a bromine atom, an ethynyl group, or a vinyl group;

$R_2$ represents a chlorine atom or a fluorine atom;

$R_3$ represents a fluorine atom; and $R_4$ represents a hydroxy alkyl group, in which the hydroxy alkyl moiety may be protected;

[40] a method for producing any one of the compounds (M), (N), (M'), and (N'), wherein the method comprises reacting a reducing agent, in a solvent at neutral pH or in the presence of an acid, with a synthetic intermediate (E) represented by the following formula (6) or a synthetic intermediate (F) represented by the following formula (7):

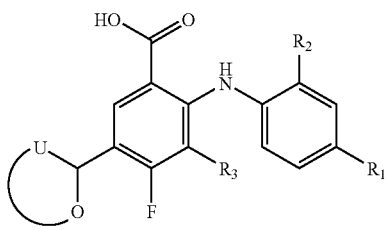

(6)

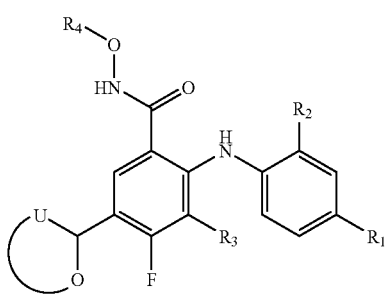

(7)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group;

the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

in the formulae (6) and (7), the group represented by the following formula (a):

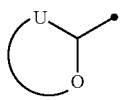

(a)

represents a 3- to 10-membered heterocyclic group that may have one to three substituents selected from the group consisting of a $C_{1-5}$ alkyl group, a halogen atom, —ORa, —NRaRb, and an oxo group;

the above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

U represents —O—, —CONRd-, —S—, —SO—, —SO$_2$—, —NRd-, —NRdCO—, —NRdSO$_2$—, —SO$_2$NRd-, a divalent heterocyclic group, or a divalent heteroaryl group; Rd represents a hydrogen atom or a $C_{1-5}$ alkyl group; the alkyl group may be substituted by a hydroxyl group, a $C_{1-5}$ alkoxy group, or an amino group; and $R_1$, $R_2$, $R_3$, and U may have protecting group(s) required for the synthesis to thereby obtain the compounds (M), (N), (M'), and (N') represented by the formulae (14), (15), (14'), and (15'), respectively:

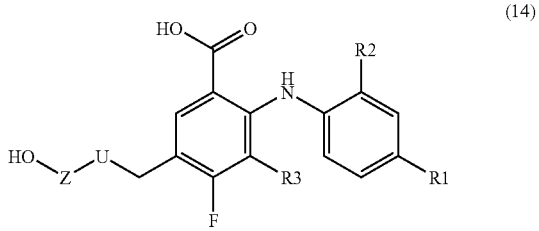

(14)

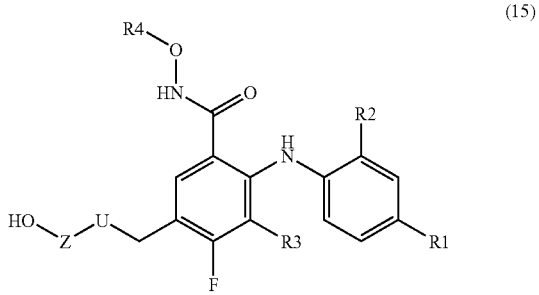

(15)

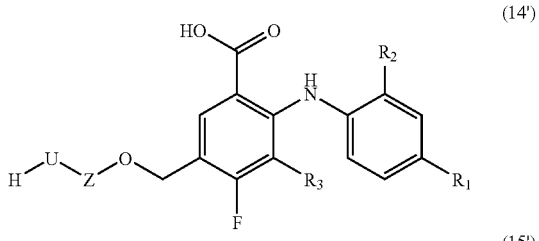

(14')

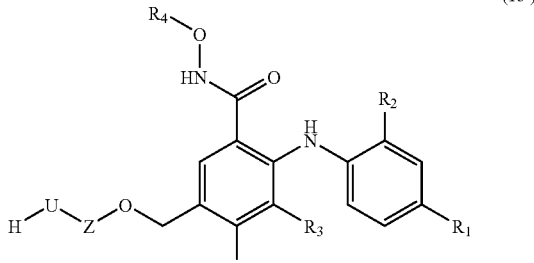

(15')

wherein $R_1$, $R_2$, $R_3$, $R_4$, and U are defined herein above in formulae (6) and (7);

Z corresponds to the alkylene chain constituting the ring in the above formula (a); Z represents a $C_{1-8}$ alkylene chain, which may be substituted by one to three groups represented by W'; W' represents any one of substituents selected from the group consisting of a $C_{1-5}$ alkyl group, a halogen atom, —ORa, —NRaRb, and an oxo group; the above substituents except the oxo group and the halogen atom may be linked to each other to form a cycloalkyl group or a heterocyclic group;

Ra and Rb, which may be the same or different, each represent a hydrogen atom or a $C_{1-5}$ alkyl group; the alkyl group may be substituted by a hydroxyl group, a $C_{1-5}$ alkoxy group, or an amino group;

[41] a method for producing compound (I) or compound (J), wherein the method comprises reacting a reducing agent, in a solvent at neutral pH or in the presence of an acid, with a synthetic intermediate (G) of the compound represented by the formula (1) according to [1], wherein (G) is represented by the following formula (8):

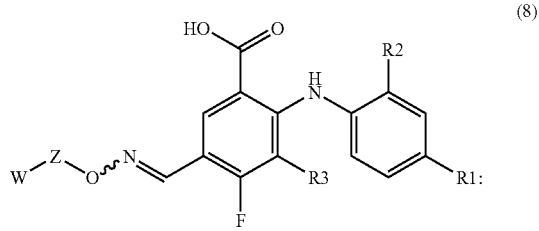

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

Z represents a $C_{1-8}$ alkylene chain that may have one to three groups represented by W';

W or W', which may be the same or different, each represent a hydrogen atom, a $C_{1-5}$ alkyl group, a halogen atom, an oxo group, —ORa, —COORa, —COOCORa, —CO—[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group;

the heterocyclic group and the heteroaryl group may have a substituent selected from the group consisting of a $C_{1-5}$ alkyl group, —ORa, and —NRaRb; the alkyl group may be substituted by a hydroxyl group, a $C_{1-5}$ alkoxy group, or an amino group;

the above substituents except the oxo group and the halogen may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; the alkyl group may be substituted by a hydroxyl group, a $C_{1-5}$ alkoxy group, or an amino group; and $R_1$, $R_2$, $R_3$, Z, W, and W' may have protecting group(s) required for the synthesis, or a synthetic intermediate (H) of the compound represented by the formula (1) according to [1], wherein (H) is represented by the following formula (9):

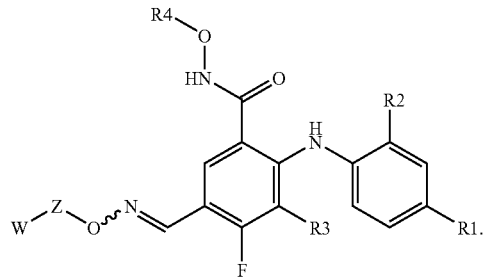

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group;

the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

Z represents a $C_{1-8}$ alkylene chain that may be substituted by one to three groups represented by W';

W or W', which may be the same or different, each represent a hydrogen atom, a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group;

the heterocyclic group and the heteroaryl group may have a substituent selected from the group consisting of a $C_{1-5}$ alkyl group, —ORa, and —NRaRb; the alkyl group may be substituted by a hydroxyl group, a $C_{1-5}$ alkoxy group, or an amino group;

the above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

$R_1$, $R_2$, $R_3$, Z, W, and W' may have protecting group(s) required for the synthesis, to thereby obtain compound (I) represented by the following formula (10):

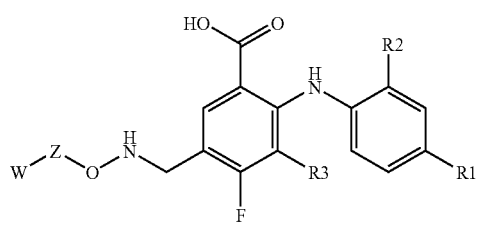

or compound (J) represented by the following formula (11):

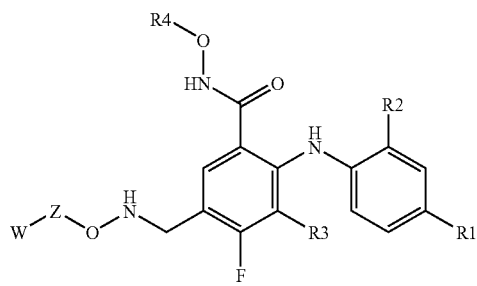

in the formulae (10) and (11), $R_1$, $R_2$, $R_3$, $R_4$, Z, W, and W' are defined herein above in formulae (8) and (9);

[42] a method for producing compound (O) or compound (P), wherein the method comprises allowing a synthetic intermediate (K) or (L) represented by the following formula (13) to intramolecularly cyclize at neutral pH or in the presence of an acid or a base in a solvent that optionally contains a peptide condensing agent, wherein the synthetic intermediates (K) and (L) are represented by the following formulae (12) and (13), respectively:

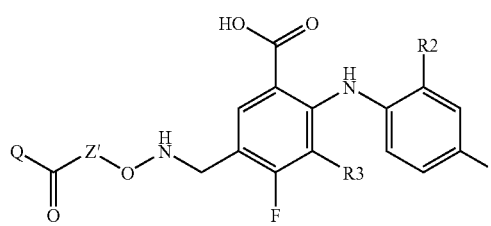

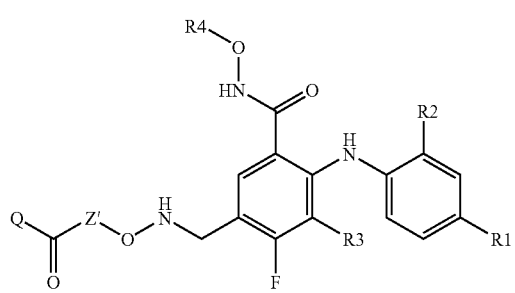

n the above formulae (12) and (13), $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group;

the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

Z' represents a $C_{1-5}$alkylene chain that may be substituted by one to three groups represented by W';

W' represents any one of the groups of —OH, —OMe, —OEt, —OCH$_2$OH, —O(CH$_2$)$_2$OH, —O(i-Pr), —O(n-Pr), —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr);

Q represents —ORc, —OCORc, —NRcRd, or a halogen atom; Rc and Rd, which may be the same or different, each represent a hydrogen atom or a $C_{1-5}$ alkyl group;

$R_1$, $R_2$, $R_3$, $R_4$, Z', W', and Q may have protecting group(s) required for the synthesis, to thereby obtain compound (O) represented by the following formula (16):

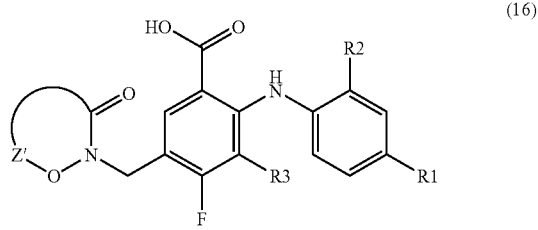

or compound (P) represented by the following formula (17):

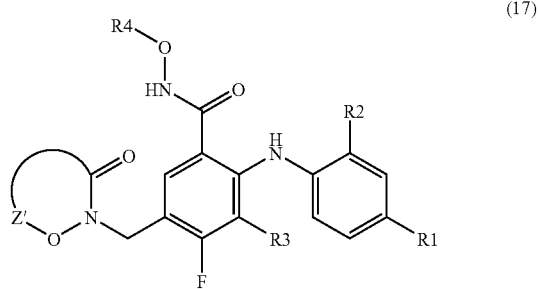

in the formula (16) and (17), $R_1$, $R_2$, $R_3$, $R_4$, and Z' are defined herein above in formulae (12) and (13);

[43] a method for producing compound (S) or compound (T), wherein the method comprises reacting, in the presence of a base or an acid, or at neutral pH, in a solvent that optionally contains a condensing agent, the synthetic intermediate (I) of the compound represented by the formula (1) according to [1], the intermediate being represented by the following formula (10):

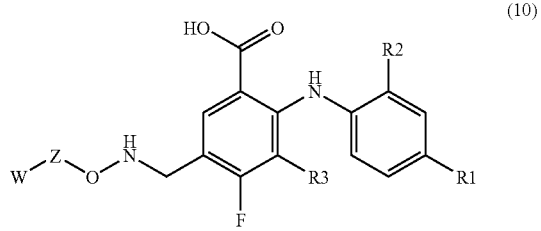

or the synthetic intermediate (J) of the compound represented by the formula (1) according to [1], the intermediate being represented by the following formula (11):

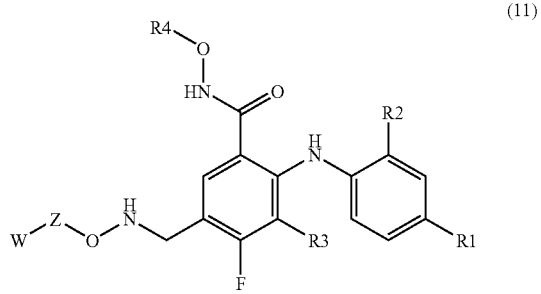

in the formulae (10) and (11), $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom;

$R_4$ represents a hydrogen atom, an alkyl group, an alkenyl group, or an alkynyl group;

the alkyl group, the alkenyl group, and the alkynyl group may have one to three substituents selected from the group consisting of —ORa, —NRaRb, —NRaCORb, a heterocyclic group, and a heteroaryl group; the heterocyclic group and the heteroaryl group may have one to three substituents selected from the group consisting of a $C_{1-5}$ alkyl group, —ORa, and —NRaRb; Ra and Rb, which may be the same or different, each represent a hydrogen atom or a $C_{1-5}$ alkyl group; the alkyl group may be substituted by a hydroxyl group, a $C_{1-5}$ alkoxy group, or an amino group;

Z represents a $C_{1-8}$ alkylene chain that may be substituted by one to three groups represented by W';

W or W', which may be the same or different, each represent a hydrogen atom, a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group;

the heterocyclic group and the heteroaryl group may have a substituent selected from the group consisting of a $C_{1-5}$ alkyl group, —ORa, and —NRaRb; the alkyl group may be substituted by a hydroxyl group, a $C_{1-5}$ alkoxy group, or an amino group;

the above substituents except the oxo group and the halogen may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group that may be substituted with —ORa;

Ra and Rb, which may be the same or different, each represent a hydrogen atom or a $C_{1-5}$ alkyl group; the alkyl group may be substituted by a hydroxyl group, a $C_{1-5}$ alkoxy group, or an amino group;

$R_1$, $R_2$, $R_3$, $R_4$, Z, W, and W' may have protecting group(s) required for the synthesis with a carboxylic acid derivative represented by the following formula:

$R_9$CO-Q wherein $R_9$ represents a hydrogen atom, an alkyl group, or —ORa; the alkyl group may be substituted by a halogen atom, —ORa, or —NRaRb;

Q represents —ORc, —OCORc, —NRcRd, or a halogen atom; Rc and Rd, which may be the same or different, each represent a hydrogen atom or a $C_{1-5}$ alkyl group;

Ra and Rb, which may be the same or different, each represent a hydrogen atom or a $C_{1-5}$ alkyl group; and the alkyl group may be substituted by a hydroxyl group, a $C_{1-5}$ alkoxy group, or an amino group;

$R_9$ and Q may have protecting group(s) required for the synthesis, to thereby obtain compound (S) represented by the following formula (18):

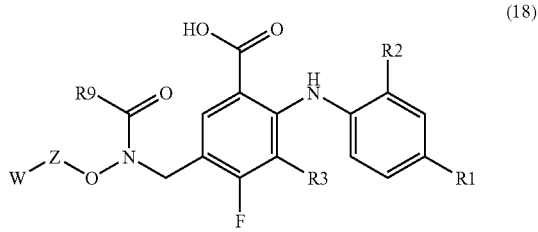

or compound (T) represented by the following formula (19):

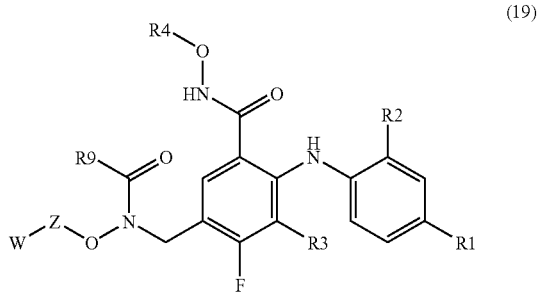

in the formulae (18) and (19), $R_1$, $R_2$, $R_3$, $R_4$, Z, and W are defined herein above in formulae (10) and (11); and $R_9$ is the carboxylic acid derivative defined herein above;

[44] a pharmaceutical composition comprising as an active ingredient the compound according to any one of [1] to [28] or a pharmaceutically acceptable salt thereof;

[45] an MEK inhibitor comprising as an active ingredient the compound according to any one of [1] to [28] or a pharmaceutically acceptable salt thereof;

[46] a preventive or therapeutic agent for a proliferative disease, which comprises as an active ingredient the compound according to any one of [1] to [28] or a pharmaceutically acceptable salt thereof;

[47] the preventive or therapeutic agent for a proliferative disease according to [46], wherein the proliferative disease is a cancer;

[48] the preventive or therapeutic agent for a proliferative disease according to [47], wherein the cancer is a cancer depending on the Ras-MAPK signaling pathway;

[49] the preventive or therapeutic agent for a proliferative disease according to [47] or [48], wherein the cancer is breast, lung, colorectal, prostate, liver, ovarian, uterine, or pancreatic cancer;

[50] a method for preventing or treating a proliferative disease, wherein the method comprises administering a pharmaceutically effective dose of a composition that comprises as an active ingredient the compound according to any one of [1] to [28] or a pharmaceutically acceptable salt thereof to a patient who needs prevention or treatment for the proliferative disease;

[51] the method according to [50], wherein the proliferative disease is a cancer;

[52] the method according to [50], wherein the cancer is a cancer depending on the Ras-MAPK signaling pathway;

[53] the method according to [51] or [52], wherein the cancer is breast, lung, colorectal, prostate, liver, ovarian, uterine, or pancreatic cancer;

[54] the method according to any one of [50] to [53], wherein the method further comprises radiotherapy, another chemotherapy, or administration of an angiogenesis inhibitor;

[55] use of the compound according to any one of [1] to [28] or a pharmaceutically acceptable salt thereof in the production of a preventive or therapeutic agent for a disease to which MEK inhibition is effective;

[56] a preventive or therapeutic agent for a joint disorder with inflammation, wherein the agent comprises as an active ingredient the compound according to any one of [1] to [28] or a pharmaceutically acceptable salt thereof;

[57] the preventive or therapeutic agent for a joint disorder with inflammation according to [56], wherein the joint disorder with inflammation is osteoarthritis or rheumatoid arthritis;

[58] a method for preventing or treating osteoarthritis or rheumatoid arthritis, wherein the method comprises administering a pharmaceutically effective dose of a composition that comprises as an active ingredient the compound according to any one of [1] to [28] or a pharmaceutically acceptable salt thereof to a patient who needs prevention or treatment for osteoarthritis or rheumatoid arthritis.

The present inventors synthesized the above-described N-alkoxy-2-phenylaminobenzamide derivatives for the first time. The inventors found that the compounds have an unexpectedly strong MEK inhibitory effect regardless of the substituent in position 5. In addition, the inventors found that the compounds of the present invention have a superior effect with respect to tumor growth suppression activity, as well as a superior effect towards inflammation-related joint disorders.

Interestingly, the compounds of the present invention were found to have superior effects in addition to the MEK inhibitory activity. Specifically, the compounds of the present invention were found to be highly stable in hepatic microsomes, as compared with other N-alkoxy-2-phenylamino-benzamide derivatives. Furthermore, the compounds were found to be more soluble in water in comparison with conventional compounds.

The Cmax and AUC values, and the half-life for the above-described compounds of the present invention are expected to be higher than those of conventional compounds.

Furthermore, the compounds of the present invention are expected to have good in vivo absorption, and low interpatient variability in the PK parameters. The active forms can exist at high concentrations in blood for a long period of time. Thus compared with the conventional compounds, sufficient levels of the active forms of the compounds of the present invention are exposed to the target molecule (i.e., MEK) as. The increased efficacy and the less frequent administration as resulted are expected to reduce the burden of patient.

Herein, the "alkyl group" refers to a monovalent group derived from an aliphatic hydrocarbon by removal of an arbitrary hydrogen atom, and comprises the subgroup structure of a hydrocarbyl group or a hydrocarbon containing hydrogen and carbon atoms, but has no hetero atoms or unsaturated carbon-carbon bonds in the backbone. The alkyl group includes groups comprising a linear or branched structure. The alkyl group is preferably an alkyl group comprising one to eight carbon atoms (hereinafter "$C_{1-8}$" indicates that the number of carbon atoms in the range of one to eight), and more preferably a $C_{1-5}$ alkyl group.

Specifically, the alkyl group includes a methyl group, an ethyl group, an isopropyl group, a butyl group, an n-butyl group, a sec-butyl group, an isobutyl group, a t-butyl group, a pentyl group, an isopentyl group, a 2,3-dimethylpropyl group, a hexyl group, a 2,3-dimethylhexyl group, a 1,1-dimethylpentyl group, a heptyl group, and an octyl group.

Herein, the "alkenyl group" refers to a monovalent group having at least one double bond (two adjacent $SP_2$ carbon atoms). Depending on the configurations of the double bond and the substituent (if exists), the geometry around the double bond can be of the entgegen (E) or zusammen (Z) (trans or cis) configuration. The alkenyl group may be linear or branched, and preferably includes $C_{2-8}$ alkenyl groups, more preferably $C_{2-5}$ alkenyl groups.

Specifically, such alkenyl groups include, for example, a vinyl group, an ally group, a 1-propenyl group, a 2-propenyl group, a 1-butenyl group, a 2-butenyl group (including cis and trans forms), a 3-butenyl group, a pentenyl group, and a hexenyl group.

Herein, the "alkynyl group" refers to a monovalent group having at least one triple bond (two adjacent SP carbon atoms). The alkynyl group may be linear or branched, and preferably includes $C_{2-8}$ alkynyl groups, more preferably $C_{2-5}$ alkynyl groups.

Specifically, the alkynyl group includes, for example, an ethynyl group, a 1-propynyl group, a propargyl group, a 3-butynyl group, a pentynyl group, a hexynyl group, a 3-phenyl-2-propynyl group, a 3-(2'-fluorophenyl)-2-propynyl group, a 2-hydroxy-2-propynyl group, a 3-(3-fluorophenyl)-2-propynyl group, and a 3-methyl-(5-phenyl)-4-pentynyl group.

The alkenyl group and the alkynyl group may each have one or more double bonds or triple bonds. They may also have double bonds and triple bonds at the same time.

Herein, the "cycloalkyl group" refers to a cyclic aliphatic hydrocarbon group comprising a ring. The cycloalkyl group preferably includes $C_{3-8}$ cycloalkyl groups. Specifically, the cycloalkyl group includes, for example, a cyclopropyl group, a cyclobutyl group, a cyclopentyl group, a cyclohexyl group, a cycloheptyl group, and a cyclooctyl group.

Herein, the "alkylene chain" or "alkylene group" refer to a divalent group represented by —(CH$_2$)n-. The alkylene chain preferably includes $C_{1-8}$ alkylene chains (n=1-8), more preferably $C_{1-5}$ alkylene chains (n=1-5), preferably $C_{1-3}$ alkylene chains (n=1-3), in particular.

Herein, the "aryl group" refers to a monovalent aromatic hydrocarbon ring. The aryl group preferably includes $C_{6-10}$ aryl groups. Specifically, the aryl group includes, for example, a phenyl group, a 1-naphthyl group, and a 2-naphthyl group.

Herein, the "hetero atom" refers to a sulfur atom, an oxygen atom, or a nitrogen atom.

Herein, the "heteroaryl group" refers to an aromatic ring group containing one or more of the hetero atoms that constitute the ring. The heteroaryl group may be partially saturated. The heteroaryl group may be a heteroaryl group in which the ring may be a monocyclic or bicyclic group obtained through condensation with a benzene ring or a monocyclic heteroaryl ring. The number of atoms constituting the ring preferably ranges from 5 to 10 ($C_{5-10}$ heteroaryl groups).

Specifically, the heteroaryl group includes, for example, a furyl group, a thienyl group, a pyrrolyl group, an imidazolyl group, a pyrazolyl group, a thiazolyl group, an isothiazolyl group, an oxazolyl group, an isooxazolyl group, an oxadiazolyl group, a thiadiazolyl group, a triazolyl group, a tetrazolyl group, a pyridyl group, a pyrimidyl group, a pyridazinyl group, a pyrazinyl group, a triazinyl group, a benzofuranyl group, a benzothienyl group, a benzothiadiazolyl group, a benzothiazolyl group, a benzooxazolyl group, a benzooxadiazolyl group, a benzoimidazolyl group, an indolyl group, an isoindolyl group, an indazolyl group, a quinolyl group, an isoquinolyl group, a cinnolinyl group, a quinazolinyl group, a quinoxalinyl group, a benzodioxolyl group, an indolidinyl group, and an imidazopyridyl group.

Herein, the "heterocyclic group" refers to a non-aromatic monovalent ring, in which the number of atoms constituting the ring preferably ranges from 3 to 8 ($C_{3-8}$ heterocyclic group), and wherein the ring contains one to three hetero atoms and may have double bonds.

Specifically, the heterocyclic group includes, for example, a morpholino group, a thiomorpholino group, a piperidin-1-yl group, a 4-substituted piperidin-1-yl group, a piperazin-1-yl group, a 4-substituted piperazin-1-yl group, a pyrrolidin-1-yl group, a pyrrolinyl group, an imidazolidinyl group, an imidazolinyl group, a pyrazolidinyl group, a pyrazolinyl group, a [1,3]dioxolan-2-yl group, and a [1,3]dioxan-2-yl group. Among these, groups that can be used preferably are: a morpholino group, a thiomorpholino group, a piperidin-1-yl group, a 4-substituted piperidin-1-yl group, a piperazin-1-yl group, a 4-substituted piperazin-1-yl group, a [1,3]dioxolan-2-yl group, and a [1,3]dioxan-2-yl group.

Herein, the "halogen atom" refers to a fluorine atom, a chlorine atom, a bromine atom, or an iodine atom.

Herein, the "alkoxy group" refers to an oxy group to which the above-defined "alkyl group" has been linked. The alkoxy group preferably includes $C_{1-8}$ alkoxy groups, and more preferably $C_{1-5}$ alkoxy groups. Specifically, the alkoxy group includes, for example, a methoxy group, an ethoxy group, a 1-propoxy group, a 2-propoxy group, an n-butoxy group, an i-butoxy group, a sec-butoxy group, a t-butoxy group, a 1-pentyloxy group, a 2-pentyloxy group, a 3-pentyloxy group, a 2-methyl-1-butyloxy group, a 3-methyl-1-butyloxy group, a 2-methyl-2-butyloxy group, a 3-methyl-2-butyloxy group, a 2,2-dimethyl-1-propyloxy group, a 1-hexyloxy group, a 2-hexyloxy group, a 3-hexyloxy group, a 2-methyl-1-pentyloxy group, a 3-methyl-1-pentyloxy group, a 4-methyl-1-pentyloxy group, a 2-methyl-2-pentyloxy group, a 3-methyl-2-pentyloxy group, a 4-methyl-2-pentyloxy group, a 2-methyl-3-pentyloxy group, a 3-methyl-3-pentyloxy group, a 2,3-dimethyl-1-butyloxy group, a 3,3-dimethyl-1-butyloxy group, a 2,2-dimethyl-1-butyloxy group, a 2-ethyl-1-butyloxy group, a 3,3-dimethyl-2-butyloxy group, a 2,3-dimethyl-2-butyloxy group, and a 1-methyl cyclopropyl methoxy group.

Herein, the "amino group" refers to a monovalent group that has a nitrogen atom with two hydrogen atoms (represented by —NH$_2$).

Herein, the "cycloalkylalkyl group" refers to a group derived from the above-defined "alkyl group" by substitution of the above-defined "cycloalkyl group" at an arbitrary position of the alkyl group. The cycloalkylalkyl group preferably includes $C_{3-8}$ cycloalkyl $C_{1-4}$ alkyl groups. Specifically, the cycloalkylalkyl group includes, for example, a cyclopropylmethyl group, a cyclopropylethyl group, a cyclopentylmethyl group, a cyclopentylethyl group, a cyclohexylmethyl group, and a cyclohexylethyl group.

Herein, the "cycloalkylalkenyl group" refers to a group derived from the above-defined "alkenyl group" by substitution of the above-defined "cycloalkyl group" at an arbitrary position of the alkenyl group. The cycloalkylalkenyl group preferably includes $C_{3-8}$ cycloalkyl $C_{2-4}$ alkenyl groups.

Herein, the "cycloalkylalkynyl group" refers to a group derived from the above-defined "alkynyl group" by substitution of the above-defined "cycloalkyl group" at an arbitrary position of the alkynyl group. The cycloalkylalkynyl group preferably includes $C_{3-8}$ cycloalkyl $C_{2-4}$ alkynyl groups.

Herein, the "arylalkyl group" refers to a group derived from the above-defined "alkyl group" by substitution of the above-defined "aryl group" at an arbitrary position of the aryl group. The arylalkyl group preferably includes $C_{6-10}$ aryl $C_{1-4}$ alkyl groups.

Specifically, the arylalkyl group includes, for example, a benzyl group, a phenethyl group, and a 3-phenyl-1-propyl group.

Herein, the "arylalkenyl group" refers to a group derived from the above-defined "alkenyl group" by substitution of the above-defined "aryl group" at an arbitrary position of the alkenyl group. The arylalkenyl group preferably includes $C_{6-10}$ aryl $C_{2-4}$ alkenyl groups.

Herein, the "arylalkynyl group" refers to a group derived from the above-defined "alkynyl group" by substitution of the above-defined "aryl group" at an arbitrary position of the alkynyl group. The arylalkynyl group preferably includes $C_{6-10}$ aryl $C_{2-4}$ alkynyl groups.

Herein, the "heteroarylalkyl group" refers to a group derived from the above-defined "alkyl group" by substitution of the above-defined "heteroaryl group" at an arbitrary position of the alkyl group. The heteroarylalkyl group preferably includes $C_{5-10}$ heteroaryl $C_{1-4}$ alkyl groups.

Specifically, the heteroarylalkyl group includes, for example, a pyridyl-4-ylmethyl group, an oxazolyl-2-ylmethyl group, a 2-(pyridyl-4-yl)ethyl group, and a 2-(oxazolyl-2-yl)ethyl group.

Herein, the "heteroarylalkenyl group" refers to a group derived from the above-defined "alkenyl group" by substitution of the above-defined "heteroaryl group" at an arbitrary position of the alkenyl group. The heteroarylalkenyl group preferably includes $C_{5-10}$ heteroaryl $C_{2-4}$ alkenyl groups.

Herein, the "heteroarylalkynyl group" refers to a group derived from the above-defined "alkynyl group" by substitution of the above-defined "heteroaryl group" at an arbitrary position of the alkynyl group. The heteroarylalkynyl group preferably includes $C_{5-10}$ heteroaryl $C_{2-4}$ alkynyl groups.

Herein, the "heterocyclic alkyl group" refers to a group derived from the above-defined "alkyl group" by substitution of the above-defined "heterocyclic group" at an arbitrary position of the alkyl group. The heterocyclic alkyl group preferably includes $C_{3-8}$ heterocyclic C1-C4 alkyl groups. Specifically, the heterocyclic alkyl group includes, for example, a morpholin-4-yl-methyl group, a 2-(morpholin-4-yl)ethyl group, a 4-hydroxy-piperidin-1-yl-methyl group, a 2-(4-hydroxy-piperidin-1-yl)ethyl group, a 4-methyl-piperazin-1-yl-methyl group, and a 2-(4-methyl-piperazin-1-yl) ethyl group.

Herein, the "heterocyclic alkenyl group" refers to a group derived from the above-defined "alkenyl group" by substitution of the above-defined "heterocyclic group" at an arbitrary position of the alkenyl group. The heterocyclic alkenyl group preferably includes $C_{3-8}$ heterocyclic $C_{2-4}$ alkenyl groups.

Herein, the "heterocyclic alkynyl group" refers to a group derived from the above-defined "alkynyl group" by substitution of the above-defined "heterocyclic group" at an arbitrary position of the alkynyl group. The heterocyclic alkynyl group preferably includes $C_{3-8}$ heterocyclic $C_{2-4}$ alkynyl groups.

Herein, the "hydroxyalkyl group" refers to a group derived from the above-defined "alkyl group" by substitution of a hydroxyl group at an arbitrary position of the alkyl group. The hydroxyalkyl group preferably includes hydroxy $C_{1-4}$ alkyl groups.

Herein, the "dihydroxyalkyl group" refers to a group derived from the above-defined "alkyl group" by substitution of hydroxyl groups at two arbitrary positions of the alkyl group. The dihydroxyalkyl group preferably includes dihydroroxy $C_{1-4}$ alkyl groups.

Herein, the "alkyloxyalkyl group" refers to a group derived from the above-defined "hydroxyalkyl group" by substitution of a hydroxyl group in the above-defined "alkyl group". The alkyloxyalkyl group preferably includes $C_{1-8}$ alkyloxy $C_{1-4}$ alkyl groups.

Herein, the "hydroxyalkyloxyalkyl group" refers to a group derived from the above-defined "alkyloxyalkyl group" by substitution of a hydroxyl group at an arbitrary position in the terminal alkyl group. The hydroxyalkyloxyalkyl group preferably includes hydroxy $C_{1-8}$alkyloxy $C_{1-4}$ alkyl groups.

Herein, the "aminoalkyl group" refers to a group derived from the above-defined "alkyl group" by substitution of an amino group ($H_2N$—) at an arbitrary position of the alkyl group. The aminoalkyl group preferably includes amino $C_{1-4}$ alkyl groups.

Herein, the "alkylaminoalkyl group" refers to a group derived from the above-defined "aminoalkyl group" by substitution of the above-defined "alkyl group" at one or two arbitrary positions in the amino group. The alkylaminoalkyl group preferably includes $C_{1-8}$ alkylamino $C_{1-4}$ alkyl groups. When two hydrogen atoms are replaced with alkyl groups, the alkyl groups may be the same or different.

Herein, the "hydroxyalkylaminoalkyl group" refers to a group derived from the above-defined "alkylaminoalkyl group" by substitution of a hydroxyl group at an arbitrary position in the terminal alkyl group. The hydroxyalkylaminoalkyl group preferably includes hydroxy $C_{1-8}$ alkylamino $C_{1-4}$ alkyl groups.

Herein, the "iminoalkyl group" refers to a group derived from the above-defined "alkyl group" obtained by substitution of an imino group (=NH) at an arbitrary position of the alkyl group. The iminoalkyl group preferably includes imino $C_{1-4}$ alkyl groups.

Herein, the "hydroxyiminoalkyl group" refers to a group derived from the above-defined "iminoalkyl group" by substituting the hydrogen atom in the imino group with a hydroxyl group. The hydroxyiminoalkyl group preferably includes hydroxyimino $C_{1-4}$ alkyl groups.

Herein, the "alkoxyiminoalkyl group" refers to a group derived from the above-defined "hydroxyiminoalkyl group" by substituting a hydrogen atom of the hydroxyl group with the above-defined "alkyl group". The alkoxyiminoalkyl group preferably includes $C_{1-8}$ alkyloxyimino $C_{1-4}$ alkyl groups.

The compounds of the present invention include the free forms and the pharmaceutically acceptable salts of the compounds. Such "salts" are not limited to any particular salts, as long as they are pharmaceutically acceptable salts derived from the compound represented by formula (1) of the present invention (herein sometimes also referred to as "compound I"). The salts include, for example, acid salts formed by reacting compound I of the present invention with an acid, and base salts formed by reacting compound I of the present invention with a base.

Preferred acids for use in preparing the pharmaceutically acceptable acid salts of compound I of the present invention are acids that form non-toxic acid salts of compound I of the present invention. The acid salts include, for example, hydrochloride, hydrobromate, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate, and 1,1'-methylene-bis-(2-hydroxy-3-naphtoic acid) salt.

Preferred bases for use in preparing pharmaceutically acceptable base salts of compound I of the present invention are bases that form non-toxic base salts of compound I of the present invention. The base salts include, for example, alkali metal salts such as sodium salt and potassium salt, alkali earth metal salts such as calcium salt and magnesium salt, ammonium salts, water-soluble amine addition salts such as the N-methyl glucamine salt, lower-alkanol ammonium salts, and pharmaceutically acceptable salts derived from other organic amines bases.

Compound I of the present invention may contain absorbed water or forms hydrates when it is allowed to stand in the atmosphere and to absorb moisture. Such salts are also included in the salts of compound I of the present invention.

Furthermore, compound I of the present invention may absorb solvents to form solvates. Such salts are also included in the salts of compound I of the present invention.

Herein, "MEK" (MAPK/ERK/Kinase; MAPK is the abbreviation for mitogen-activated protein kinase, and ERK is the abbreviation for extracellular signal-regulated kinase) refers to the dual-specificity kinase that is associated with the MAP kinase and the ERK kinase. "MEK inhibition" refers to the MEK-mediated competition, inhibition, or cancellation of a cascade or of the activities of proteins produced in the cascade. Accordingly, the inhibition includes the competition, inhibition, or cancellation of the activities of the MAP/ERK kinase or of the activities of the genes encoding the MAP/ERK kinase. Herein, the "Ras-MAPK signaling pathway" is defined as the sequential pathway of Ras->Raf->MEK->ERK, and is one of the pathways that transmit growth signals from various growth factor receptors on the cell membrane to the nucleus through the cytoplasm. The phrase "cancer depending on the Ras-MAPK signaling pathway" refers to a cancer that proliferates mainly depending on the Ras-MAPK signaling pathway. In other words, the phrase means a cancer whose growth or survival is reduced by blocking or inhibiting the Ras-MAPK signaling pathway.

Herein, the "proliferative disease" refers to a disorder caused by deficiencies in the cellular signal transduction system or the signal transduction mechanism of a certain protein. The proliferative disease includes, for example, cancers, psoriasis, restenosis, autoimmune diseases, and atherosclerosis.

Herein, the "inflammation-related joint disorders" specifically refers to diseases such as osteoarthritis, rheumatoid arthritis, reactive arthritis, viral arthritis, purulent arthritis, and tuberculous arthritis. The inflammation-related joint disorders also include arthralgia caused by these diseases (for example, knee joint pain caused by rheumatoid arthritis). Herein, the "preventive or therapeutic agent for an inflammation-related joint disorder" includes not only therapeutic agents for the above-described joint diseases, but also preventive agents for the diseases, agents for use in suppressing the advancement of the diseases (to prevent aggravation or to maintain current conditions), and such.

In the present invention, there is no limitation on the type of "protecting group", as long as it is a group commonly used to protect an ethynyl group, a hydroxyl group, or an amino group.

An ethynyl protecting group includes, for example, silyl groups such as a trimethylsilyl group, a triethylsilyl group, an isopropyldimethylsilyl group, a t-butyldimethylsilyl group, a methyldiisopropylsilyl group, a methyl-t-butylsilyl group, a triisopropylsilyl group, a diphenylmethylsilyl group, a diphenylbutylsilyl group, a diphenylisopropylsilyl group, and a phenyldiisopropylsilyl group. Among them, a trimethylsilyl group or such is preferred.

A hydroxyl protecting group includes, for example, alkylsilyl groups such as a trimethylsilyl group, a triethylsilyl group, an isopropyldimethylsilyl group, a t-butyldimethylsilyl group, a methyldiisopropylsilyl group, a methyldi-t-butylsilyl group, a triisopropylsilyl group, a diphenylmethylsilyl group, a diphenylbutylsilyl group, a diphenylisopropylsilyl group, and a phenyldiisopropylsilyl group; $C_{1-6}$ alkylcarbonyl groups such as an acetyl group and a propionyl group; phenylcarbonyl group; $C_{1-6}$ alkyloxycarbonyl groups such as a methoxycarbonyl group, an ethoxycarbonyl group, and a t-butoxycarbonyl group; a vinyl group; a tetrahydrofuranyl group; alkoxymethyl groups such as a methoxymethyl group and an ethoxymethyl group; alkoxylated alkoxymethyl groups such as a 2-methoxyethoxymethyl group; alkoxyethyl groups such as a 1-ethoxyethyl group; a benzyloxymethyl group; substituted benzyl groups such as a benzyl group, a 4-methylbenzyl group, a 4-methoxybenzyl group, and an o-nitrobenzyl group; and formyl groups. Among these, an alkylsilyl group is preferred, and a t-butyldimethylsilyl group or such is more preferred.

Protecting groups that are used to protect an amino group include, for example, a methoxycarbonyl group; substituted $C_1$-$C_6$ alkyl-oxycarbonyl groups such as a cyclopropyl methoxycarbonyl group, a 2,2,2-trichloroethoxycarbonyl group, a 2-iodoethoxycarbonyl group, a 2-trimethylsilylethoxycarbonyl group, a 2-methylthioethoxycarbonyl group, a 2-methylsulfonylethoxycarbonyl group, an isobutyloxy carbonyl group, a t-butoxycarbonyl group (BOC group); C1-C6 alkenyl-oxycarbonyl groups such as a vinyloxycarbonyl group and an allyloxycarbonyl group; a benzyloxycarbonyl group (CBZ group); substituted benzyl-oxycarbonyl groups such as a p-methoxybenzyloxy carbonyl group, a 2,4-dichlorobenzyloxy carbonyl group, and a p-cyanobenzyloxy carbonyl group; formyl groups; acetyl groups; substituted C1-C6 alkyl-carbonyl groups such as a dichloroacetyl group, a trichloroacetyl group, and a trifluoroacetyl group; phthalimide groups (name provided as the protected functional group); benzyl groups; and substituted benzyl groups such as a 3,4-dimethoxybenzyl group. Among these, an alkyl-oxycarbonyl group is preferred, and the t-butoxycarbonyl (BOC) group and such are more preferred.

Compound I of the present invention represented by the above formula (1) preferably includes compounds comprising the following:

(1) $R_1$ is preferably an iodine atom, a bromine atom, a vinyl group, or an ethynyl group, and more preferably an iodine atom or an ethynyl group.

(2) $R_2$ is preferably a chlorine atom, a fluorine atom, a methyl group, or a hydroxymethyl group, more preferably a fluorine atom or a chlorine atom, and particularly preferably a fluorine atom.

(3) $R_3$ is preferably a hydrogen atom or a fluorine atom, and more preferably a fluorine atom.

(4) $R_4$ is preferably an alkyl group that has one to three substituents selected from the group consisting of —ORa, —NRaRb, —NRaCORb, a heterocyclic group, and a heteroaryl group.

Ra and Rb can each represent a hydrogen atom or an alkyl group. The alkyl group may have preferably a hydroxyl group, an alkoxy group, or an amino group as a substituent.

The heterocyclic group and the heteroaryl group may have one to three substituents selected from the group consisting of an alkyl group, —ORa, and —NRaRb. The alkyl group may have a hydroxyl group, an alkoxy group, or an amino group as a substituent. The substituent is preferably an alkyl group or —ORa, more preferably a methyl group, a hydroxyethyl group, or —OH (hydroxyl group).

More preferably, $R_4$ is an alkyl group that has one to three substituents selected from the group consisting of —ORa, —NRaRb, and —NRaCORb.

Still more preferably, $R_4$ is an alkyl group that has one to three —ORa, and particularly preferably an alkyl group that has one to three —OH (hydroxyl group). The alkyl group is preferably a C1-C8 alkyl group, more preferably a C1-C5 alkyl group, and particularly preferably a C1-C3 alkyl group.

Preferably, Ra and Rb can each represent a hydrogen atom or a C1-C5 alkyl group, and more preferably a hydrogen atom.

The $R_4$ includes, for example, a hydroxyalkyl group, a dihydroxyalkyl group, a hydroxyalkyloxyalkyl group, a hydroxyalkylaminoalkyl group, an acylaminoalkyl group, a heteroarylalkyl group, a heterocyclic alkyl group, and a heterocyclic alkyl group containing hydroxy groups.

More preferably, $R_4$ represents a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-methyl-2-hydroxypropyl group, a 1-methyl-2-hydroxyethyl group, a 2-(2-hydroxyethoxy)ethyl group, a 2-(2-hydroxyethylamino)ethyl group, a 2-(morpholin-4-yl) ethyl group, a 2-(4-methylpiperazin-1-yl)ethyl group, a 2-(4-hydroxypiperidin-1-yl)ethyl group, a pyridylmethyl group, an imidazol-2-ylmethyl group, and a 2-acetylaminoethyl group.

Still more preferably, $R_4$ represents a 2-hydroxyethyl group, a 3-hydroxypropyl group, a 2,3-dihydroxypropyl group, a 2-hydroxy-1-(hydroxymethyl)ethyl group, a 2-hydroxypropyl group, a 2-methyl-2-hydroxypropyl group, a 1-methyl-2-hydroxyethyl group, and a 2-(2-hydroxyethoxy) ethyl group. Among these, the 2-hydroxyethyl group, 3-hydroxypropyl group, 2,3-dihydroxypropyl group, and 2-hydroxy-1-(hydroxymethyl)ethyl group shown below are preferred.

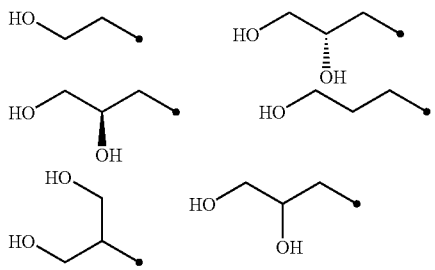

Among these, the particularly preferred $R_4$ includes a 2-hydroxyethyl group and a 2,3-dihydroxypropyl group.

In the embodiments of the present invention, the above-defined $R_1$, $R_2$, $R_3$, and $R_4$ can be combined appropriately. For example, the specific combinations that are preferred are as follows:

$R_1$ represents an iodine atom, a bromine atom, a vinyl group, or an ethynyl group;

$R_2$ represents a chlorine atom, a fluorine atom, a methyl group, or a hydroxymethyl group;

$R_3$ represents a fluorine atom; and $R_4$ represents an alkyl group that is substituted by one to three hydroxyl groups; or alternatively $R_1$ represents an iodine atom or an ethynyl group;

$R_2$ represents a fluorine atom;

$R_3$ represents a fluorine atom; and $R_4$ represents a group selected from the following groups:

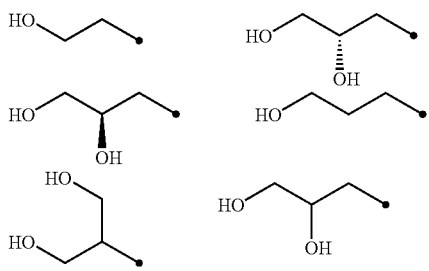

(5) the above-defined X represents the group represented by formula (i) or formula (ii) below:

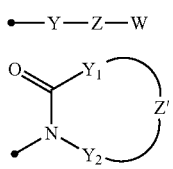

In formula (i), Y represents —O—, —$NR_8O$—, —$ONR_8$—, —$NR_8CO$—, or —$NR_8SO_2$— (unless otherwise indicated, these substituents have Z bonded to their right-hand side);

Z represents a $C_{1-8}$ alkylene chain which may be substituted by one to three groups represented by W';

$R_8$ represents a hydrogen atom, an alkyl group, —ORa, or —$COR_9$; and the alkyl group may have a halogen atom, —ORa, or —NRaRb as a substituent;

$R_9$ represents a hydrogen atom, an alkyl group, or —ORa; and the alkyl group may have a halogen atom, —ORa, or —NRaRb as a substituent;

$R_8$ and $R_9$ may be linked to the alkylene chain of Z, or form a heterocyclic group through a linkage to the substituent represented by Ra or Rb in W.

In formula (ii), $Y_1$ and $Y_2$, which may be the same or different, each represent a single bond, —CO—, —COO—, —O—, —OCO—, —NRa—, or —$SO_2$—;

Z' represents a $C_{1-8}$ alkylene chain which may be substituted by one to three groups represented by W'.

In formulae (i) and (ii) above, W and W', which may be the same or different, each represent a $C_{1-5}$ alkyl group, a halogen atom, an oxo group, —ORa, —COORa, —COOCORa, —CO-[halogen atom], —OCORa, —CONRaRb, —SRa, —SORa, —$SO_2$Ra, —NRaRb, —NRaCORb, —NRa$SO_2$Rb, —$SO_2$NRaRb, a heterocyclic group, or a heteroaryl group. The heterocyclic group and the heteroaryl group may have a substituent selected from the group consisting of a $C_{1-5}$ alkyl group, —ORa, and —NRaRb; and the alkyl group may have a hydroxyl group, a $C_{1-5}$ alkoxy group, or an amino group as a substituent.

The above-mentioned substituents, except the oxo group and the halogen atom, may be linked to each other to form a cycloalkyl group or a heterocyclic group. The cycloalkyl group or heterocyclic group may have a substituent selected from the group consisting of a $C_{1-5}$ alkyl group which may be substituted with —ORa, —ORa, and —NRaRb.

When X is the group represented by the above formula (i) and Y is not —O—, W may be a hydrogen atom.

Ra and Rb, which may be the same or different, each represent a hydrogen atom or a $C_{1-5}$ alkyl group; and the alkyl group may have one to three substituents selected from hydroxyl groups, $C_{1-5}$ alkoxy groups, and amino groups.

Herein, the above-defined Ra and Rb, which may be the same or different, preferably each represent a group selected from the group consisting of: a hydrogen atom, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a hydroxymethyl group, a 1-hydroxyethyl group, a 1-hydroxy-1-methylethyl group, a 2-hydroxy-1-methylethyl group, a 2-hydroxy-1,1-dimethylethyl group, a 2-hydroxyethyl group, a 1-hydroxypropyl group, a 2-hydroxypropyl group, and a 3-hydroxypropyl group.

A preferred embodiment of the group represented by formula (i) above is as follows:

(i-1) In the above-defined X, the $R_8$ in Y preferably represents a hydrogen atom, a hydroxyl group, a $C_{1-5}$ alkyl group, or —$COR_9$, and more preferably, a hydrogen atom, a hydroxyl group, a methyl group, an ethyl group, an n-propyl group, an i-propyl group, an n-butyl group, a sec-butyl group, an i-butyl group, a t-butyl group, a 1,1-dimethylpropyl group, a 2,2-dimethylpropyl group, a 1,2-dimethylpropyl group, a pentyl group, or —$COR_9$.

In this case, $R_9$ preferably represents a hydrogen atom, a hydroxyl group, a $C_{1-5}$ alkyl group, or a $C_{1-5}$ alkoxy group, and more preferably, a hydrogen atom, a methyl group, an ethyl group, an n-propyl group, an i-propyl group, an n-butyl group, a sec-butyl group, a t-butyl group, a 2,2-dimethylpropyl group, a 1,2-dimethylpropyl group, a pentyl group, a methoxy group, an ethoxy group, an n-propoxy group, an i-propoxy group, an n-butoxy group, an i-butoxy group, a sec-butoxy group, an i-butyl group, a t-butoxy group, a 1,1-dimethylpropyl group, a 2,2-dimethylpropoxy group, a 1,2-dimethylpropoxy group, or a pentyloxy group.

The alkyl group and the alkoxy group represented by $R_8$ and $R_9$ may contain substitutions of one to three hydroxyl groups at arbitrary positions of the hydrocarbon moiety.

Ra and Rb, which may be the same or different, each represent a hydrogen atom or a $C_{1-5}$ alkyl group; and the alkyl group may have a hydroxyl group, a $C_{1-5}$ alkoxy group, or an amino group as a substituent.

(i-2) More preferably, the $R_8$ in Y represents a hydrogen atom, a hydroxyl group, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a formyl group, an acetyl group, a 2-methoxyacetyl group, a 2-ethoxyacetyl group, a 2-hydroxyacetyl group, a propionyl group, a 2-methylpropionyl group, a 2-methoxypropionyl group, a 2-ethoxypropionyl group, a 2-hydroxypropionyl group, a 3-methoxypropionyl group, a 3-ethoxypropionyl group, a 3-hydroxypropionyl group, a methoxy group, an ethoxy group, an n-propyloxy group, an i-propyloxy group, a hydroxymethyl group, or a 2-hydroxyethyl group.

(i-3) More preferably, the Y in the above-defined X represents —O—, —NHO—, —N(COCH$_3$)O—, —N(COCH$_2$OH)O—, —N(COCH$_2$CH$_3$)O—, —N(COCH(OH)CH$_3$)O—, —N(COCH$_2$CH$_2$OH)O—, —N(COCH(OH)CH$_2$OH)O—, —N(COCH$_2$CH$_2$CH$_3$)O—, —N(COCH$_2$CH$_2$CH$_2$OH)O—, —N(COCH(OH)CH$_2$CH$_3$)O—, —N(COCH$_2$CH(OH)CH$_3$)O—, —NHCO—, or —NHSO$_2$—.

(i-4) More preferably, the above-defined W and W', which may be the same or different, each represent —OH, —OMe, —OEt, —OCH$_2$OH, —O(CH$_2$)$_2$OH, —O(i-Pr), —O(n-Pr), —COOH, —COOMe, —COOEt, —COOCOMe, —COCl, —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH 2OH, —NH Et, —NMe$_2$, —N(Et)Me, —NHCOMe, —NMeCOMe, —NHCOEt, —NHCO(n-Pr), or —NHCO(i-Pr); and when Y is not —O—, W may be a hydrogen atom.

(i-5) In formula (i) above, the alkylene chain of Z in the above X preferably represents an alkylene chain having one to five carbon atoms.

The alkylene chain may have one to three substituents selected from the group consisting of: a $C_{1-5}$ alkyl group, a halogen atom, —ORa, —NRaRb, and an oxo group, and the above substituents except the oxo group and the halogen atom may be linked to each other to form a cycloalkyl group or a heterocyclic group. The cycloalkyl group and the heterocyclic group may have a substituent selected from the group consisting of a $C_{1-5}$ alkyl group, which may be substituted with —ORa, —ORa, and —NRaRb.

Ra and Rb, which may be the same or different, each represent a hydrogen atom or a $C_{1-5}$ alkyl group; and the alkyl group may have a hydroxyl group, a $C_{1-5}$ alkoxy group, or an amino group as a substituent.

(i-6) In the above-defined W or W', Ra and Rb may be the same or different, preferably each representing a hydrogen atom or a $C_{1-5}$ alkyl group; and the alkyl group may have a hydroxyl group or a $C_{1-5}$ alkoxy group.

(i-7) More preferably, in the X of formula (i) above, the alkylene chain of Z is any one of the groups represented by the following formulae:

—CH$_2$—, —(CH$_2$)$_2$—, —(CH$_2$)$_3$—, —(CH$_2$)$_4$—, —CH$_2$CH(Me)—, —CH$_2$C(Me)$_2$-, —C(Me)$_2$CH$_2$—, —(CH$_2$)$_2$CH(Me)—, —(CH$_2$)$_2$C(Me)$_2$-, —CH(Me)(CH$_2$)$_2$—, —C(Me)$_2$(CH$_2$)$_2$—, —CH$_2$CH(Me)CH$_2$—, —CH$_2$C(Me)$_2$CH$_2$—, —CH$_2$C(CH$_2$CH$_2$)CH$_2$— (where C(CH$_2$CH$_2$) represents a divalent cyclopropane ring), —CO—, —CH$_2$CO—, —COCH$_2$—, —(CH$_2$)$_2$CO—, —CO(CH$_2$)$_2$—, —CHOH—, —CH$_2$CH(OH)—, —CH(OH)CH$_2$—, —CH$_2$CH(OH)CH$_2$—, —CH(OH)CH$_2$CH$_2$—, and —CH$_2$CH$_2$CH(OH)—.

A preferred embodiment of the group represented by the above formula (ii) is as follows:

(ii-1) The above-defined X is preferably any one of the groups represented by the following formulae:

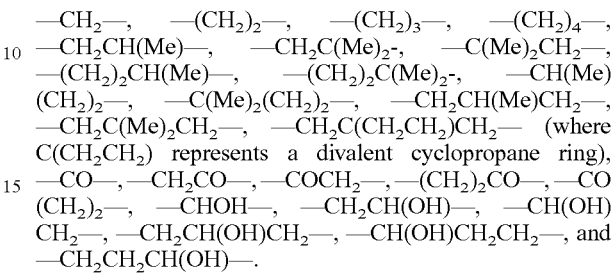

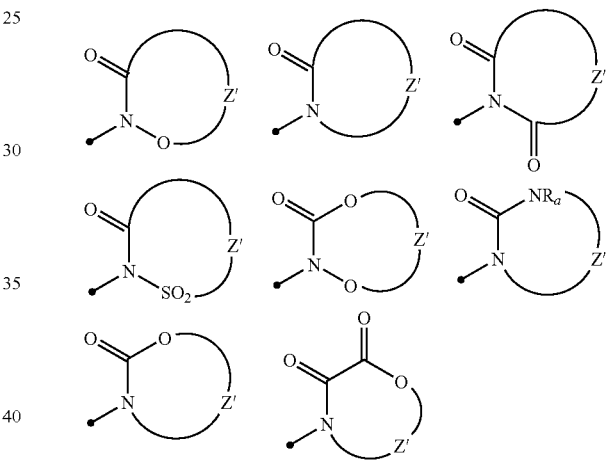

[wherein, Z' preferably represents a $C_{1-5}$ alkylene chain which may be substituted by one to three groups represented by W';

W' represents a $C_{1-5}$ alkyl group, a halogen atom, an oxo group, —ORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group; the heterocyclic group and the heteroaryl group may have a substituent selected from the group consisting of a $C_{1-5}$ alkyl group, —ORa, and —NRaRb; the alkyl group may have a hydroxyl group, a $C_{1-5}$ alkoxy group, or an amino group as a substituent;

the above substituents except the oxo group and the halogen atom may be linked to each other to form a cycloalkyl group or a heterocyclic group; the cycloalkyl group or the heterocyclic group may have a substituent selected from the group consisting of: a $C_{1-5}$ alkyl group which may be substituted with —ORa, —ORa, and —NRaRb;

Ra and Rb, which may be the same or different, each represent a hydrogen atom or a $C_{1-5}$ alkyl group; and the alkyl group may have a hydroxyl group, a $C_{1-5}$ alkoxy group, or an amino group as a substituent].

(ii-2) More preferably, the above-defined Z' represents a C$_{1-3}$ alkylene chain which may be substituted by one to three groups represented by W'.

W' represents a C$_{1-3}$ alkyl group, an oxo group, —ORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group; the heterocyclic group and the heteroaryl group may have a substituent selected from the group consisting of: a C$_{1-5}$ alkyl group, —ORa, and —NRaRb; and the alkyl group may have a hydroxyl group, a C$_{1-5}$ alkoxy group, or an amino group as a substituent.

Ra and Rb, which may be the same or different, each represent a hydrogen atom or a C$_{1-5}$ alkyl group; and the alkyl group may have a hydroxyl group, a C$_{1-5}$ alkoxy group, or an amino group as a substituent.

(ii-3) Furthermore, W' which may substitute for the arbitrary positions in the alkylene chain of the above-defined Z' represents any one of the groups represented by the following formulae:

-Me, -Et, -n-Pr, -i-Pr, —CH$_2$OH, —CH$_2$CH$_2$OH, —CH(OH)CH$_3$, —OH, —OMe, —OEt, —OCH$_2$OH, —O(CH$_2$)$_2$OH, —O(i-Pr), —O(n-Pr), —COOH, —COOMe, —COOEt, —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr).

(ii-4) Furthermore, W' which may substitute for the arbitrary positions in the alkylene chain of the above-defined Z' represents any one of the groups represented by the following formulae:

-Me, -Et, -n-Pr, -i-Pr, —CH$_2$OH, —CH$_2$CH$_2$OH, —CH(OH)CH$_3$, —OH, —OMe, —OEt, —OCH$_2$OH, —O(CH$_2$)$_2$OH, —O(i-Pr), —O(n-Pr), —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr).

(ii-5) In W' of the above-defined Z', Ra and Rb, which may be the same or different, preferably each represent a hydrogen atom or an alkyl group having one to five carbon atoms; and the alkyl group may have a hydroxyl group or an alkoxy group having one to five carbon atoms.

(ii-6) The alkylene chain of Z' in the above-defined X preferably represents any one of the groups represented by the following formulae:

—CH$_2$—, —(CH$_2$)$_2$—, —(CH$_2$)$_3$—, —(CH$_2$)$_4$—, —CH$_2$CH(Me)—, —CH$_2$C(Me)$_2$-, —C(Me)$_2$CH$_2$—, —(CH$_2$)$_2$CH(Me)—, —(CH$_2$)$_2$C(Me)$_2$-, —CH(Me)(CH$_2$)$_2$—, —C(Me)$_2$(CH$_2$)$_2$—, —CH$_2$CH(Me)CH$_2$—, —CH$_2$C(Me)$_2$CH$_2$—, —CHOH—, —CH$_2$CH(OH)—, —CH(OH)CH$_2$—, —CH$_2$CH(OH)CH$_2$—, —CH(OH)CH$_2$CH$_2$—, —CH$_2$CH$_2$CH(OH)—, —CO—, —CH$_2$CO—, —COCH$_2$—, —(CH$_2$)$_2$CO—, —CO(CH$_2$)$_2$—, and —CH$_2$CH(OH)CH$_2$—.

X represented by the above formula (i) or (ii) is more preferably groups represented by formula (iv) or (iii) below:

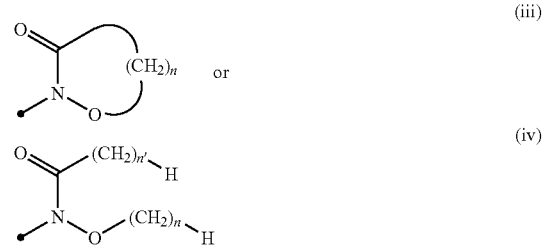

[wherein, n represents an integer of 1 to 5, and n' represents an integer of 0 to 5; the repeating units represented by —(CH$_2$)n- or —(CH$_2$)n'- may be substituted at arbitrary positions by one to three substituents selected from the group consisting of: a C$_{1-5}$ alkyl group, a halogen atom, —ORa, —NRaRb, and an oxo group; Ra and Rb, which may be the same or different, each represent a hydrogen atom or a C$_{1-5}$ alkyl group; and the alkyl group may have a hydroxyl group, a C$_{1-5}$ alkoxy group, or an amino group as a substituent].

In another preferred embodiment, X—CH$_2$—* in the compound of the present invention represented by formula (1) includes compounds comprising the structure shown below as a substructure. In the formula, * represents linkage at position 5 of the parent benzamide ring.

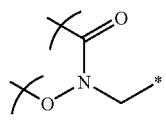

More specifically, X represented by the above formula (i) or (iv) includes the following groups:

a 2-hydroxyethoxy group, a 3-hydroxy-2-dimethylpropoxy group, a 3-hydroxypropoxy group, a 2-carbamoylethoxy group, a 2-methylcarbamoylethoxy group, a 2-methanesulfonyl-ethoxy group, a 2-acetylamino-ethoxy group, a 2-hydroxyethoxy-amino group, a 3-hydroxypropionylamino group, a 2-hydroxyethanesulfonamide group, a 1-hydroxymethyl-cyclopropylmethoxy group, a 2,3-dihydroxy-propoxy group, a 1H-imidazol-2-ylmethoxy group, a 2-methylcarbamoyl-ethoxyamino group, a 2-acetylamino-ethoxyamino group, a 2-methanesulfonyl-ethoxyamino group, a 1H-imidazol-2-ylmethoxyamino group, a 3-hydroxypropoxyamino group, a 2-(2-hydroxy-ethoxy)-ethoxy group, a 2-methylamino-ethoxy group, a 2-(2-hydroxy-ethylamino)-ethoxy group, a 2-morpholin-4-yl-ethoxy group, a 2-(4-hydroxy-piperidin-1-yl)-ethoxy group, a 2-methylamino-ethoxyamino group, a 2,3-dihydroxy-propoxyamino group;

a formyl-methoxyamino group, an acetyl-methoxyamino group, a methoxy-propionylamino group, an isobutyryl-methoxy-amino group, a (2-hydroxy-acetyl)-methoxyamino group, a methoxy-(2-methoxy-acetyl)-amino group, an acetyl-ethoxy-amino group, an ethoxy-propionyl-amino group, an acetyl-isopropoxy-amino group, an acetyl-hydroxy-amino group, an acetoxy-acetyl-amino group, an acetyl-(2-hydroxy-ethoxy)-amino group, an acetyl-(3-hydroxy-propoxy)-amino group, an acetyl-(2-hydroxy-2-methyl-propoxy)-amino group, an acetyl-(2-acetylamino-ethoxy)-amino group, an acetyl-(2-propionyl-amino-ethoxy)-amino group, an acetyl-(2-isobutyrylaminoethoxy)-amino group, an acetyl-(2-methylsulfanyl-ethoxy)-amino group, an acetyl-(3-methylsulfanyl-propoxy)-amino group;

a 2-hydroxy-1,1-dimethyl-ethoxy group;

a methylcarbamoylmethoxyamino group, an ethylcarbamoylmethoxyamino group, a propylcarbamoylmethoxyamino group, an isopropylcarbamoyl-methoxyamino group, a dimethylcarbamoylmethoxyamino group, a 2-ethylcarbamoyl-ethoxyamino group, a 2-propylcarbamoyl-ethoxyamino group, a 2-isopropylcarbamoyl-ethoxyamino group, a 3-methylcarbamoyl-propoxyamino group, a 2-methoxycarbonyl-ethoxyamino group, a methoxyamino group, a methoxy-methyl-amino group, an ethoxyamino group, an isopropoxyamino group, a 2-hydroxy-2-methyl-propoxyamino group, a 2-methylsulfanyl-ethoxyamino group, a 2-methanesulfinyl-ethoxyamino group, a 3-methylsulfanyl-propoxyamino group, a 3-methanesulfinyl-propoxyamino group, a 2-propionylamino-ethoxyamino group, a 2-isobutyrylamino-ethoxyamino group; a 2-hydroxy-acetylamino group, and an acetyl-(2-hydroxy-ethyl)-amino group.

More specifically, X represented by the above formula (ii) or (iii) preferably includes the following groups:

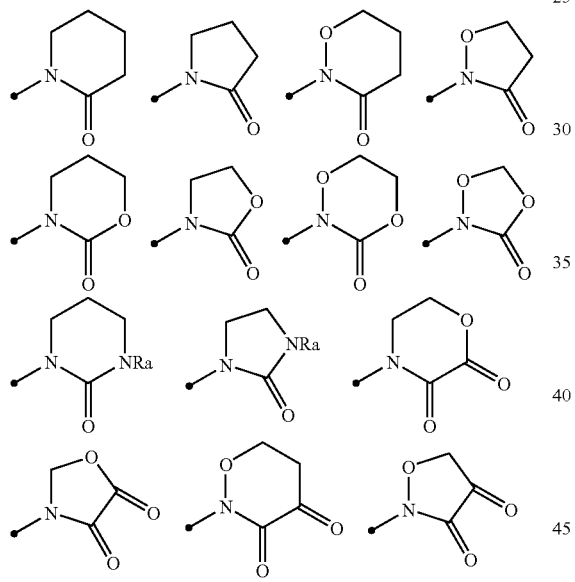

[wherein, the alkylene chain may be substituted at arbitrary positions by one to three substituents selected from the group consisting of: a $C_{1-5}$ alkyl group, a halogen atom, —ORa, —NRaRb, and an oxo group; Ra and Rb, which may be the same or different, each represent a hydrogen atom or a $C_{1-5}$ alkyl group; and the alkyl group may have a hydroxyl group, a $C_{1-5}$ alkoxy group, or an amino group as a substituent; Ra represents a hydrogen atom or a $C_{1-5}$ alkyl group; and the alkyl group may have a hydroxyl group, a $C_{1-5}$ alkoxy group, or an amino group as a substituent.

More specifically, X represented by the above formula (ii) or (iii) includes the following groups:

a 3-oxo-[1,2]oxazinan-2-yl group, a 3-oxo-isoxazolidin-2-yl group, a 4,4-dimethyl-3-oxo-isoxazolidin-2-yl group, a 4-hydroxy-3-oxo-[1,2]oxazinan-2-yl group, a 3-oxo-[1,4,2]dioxazinan-2-yl group, a 2-oxo-pyrrolidin-1-yl group, a 2-oxo-piperidin-1-yl group, a 2-oxo-oxazolidin-3-ylmethyl group, a 2-oxo-tetrahydro-pyrimidin-1-yl group, and a 2,3-dioxo-morpholin-4-yl group.

From the preferred embodiments (1)-(5) described above, the preferred embodiments of $R_1$ to $R_4$, and X can be selected at one's discretion, and combined into compounds of the present invention.

More specifically, compound I of the present invention represented by formula (1) includes, for example, those described below, but is not limited tereto.

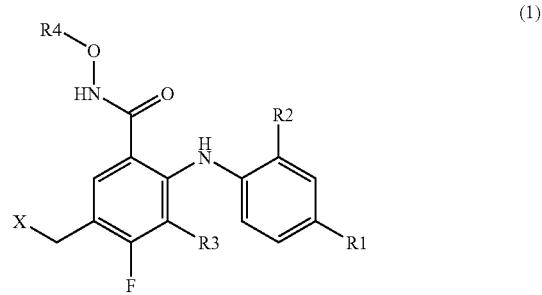

(1)

In the Table, compound names are also shown together with their compound numbers.

TABLE 1

| Compound No. | Structure | Compound name |
|---|---|---|
| B-1 | 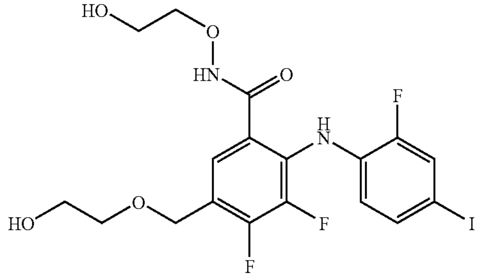 | 3,4-difluoro-2-(2-fluoro-4-iodo-phenylamino)-N-(2-hydroxy-ethoxy)-5-(2-hydroxy-ethoxymethyl)-benzamide |

TABLE 1-continued

| Compound No. | Structure | Compound name |
|---|---|---|
| B-2 | 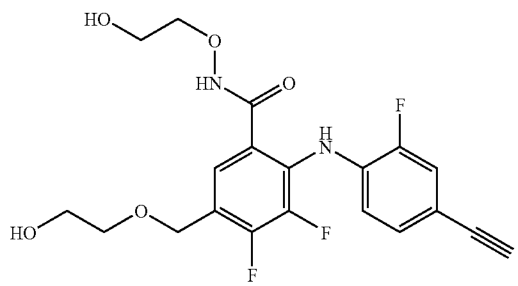 | 2-(4-ethynyl-2-fluoro-phenylamino)-3,4-difluoro-N-(2-hydroxy-ethoxy)-5-(2-hydroxy-ethoxymethyl)-benzamide |
| B-3 | 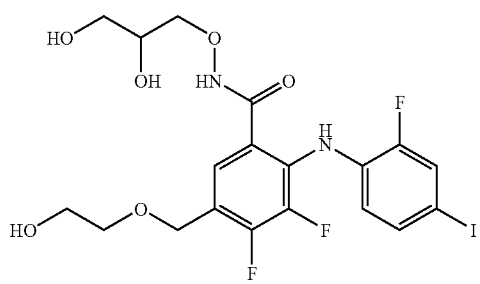 | N-(2,3-dihydroxy-propoxy)-3,4-difluoro-2-(2-fluoro-4-iodo-phenylamino)-5-(2-hydroxy-ethoxymethyl)-benzamide |
| B-4 | 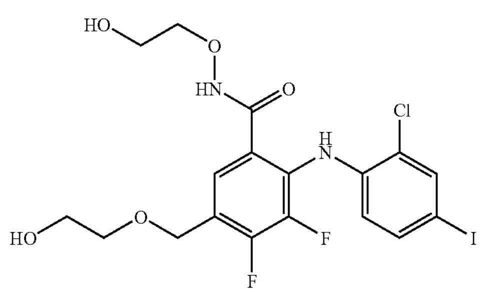 | 2-(2-chloro-4-iodo-phenylamino)-3,4-difluoro-N-(2-hydroxy-ethoxy)-5-(2-hydroxy-ethoxymethyl)-benzamide |
| B-5 | 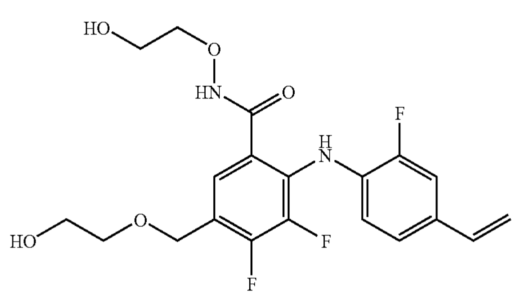 | 3,4-difluoro-2-(2-fluoro-4-vinyl-phenylamino)-N-(2-hydroxy-ethoxy)-5-(2-hydroxy-ethoxymethyl)-benzamide |
| B-6 | 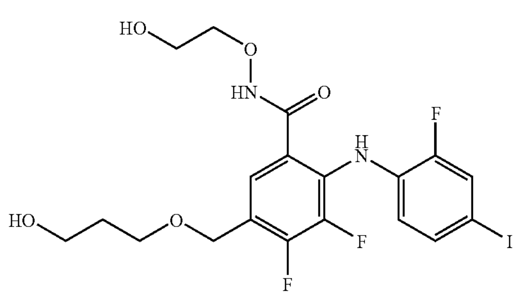 | 3,4-difluoro-2-(2-fluoro-4-iodo-phenylamino)-N-(2-hydroxy-ethoxy)-5-(3-hydroxypropoxymethyl)-benzamide |

TABLE 1-continued

| Compound No. | Structure | Compound name |
| --- | --- | --- |
| B-7 | 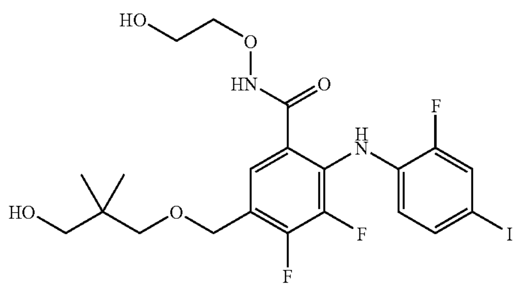 | 3,4-difluoro-2-(2-fluoro-4-iodo-phenylamino)-5-(3-hydroxy-2,2-dimethyl-propoxymethyl)-N-(2-hydroxy-ethoxy)-benzamide |
| B-8 | 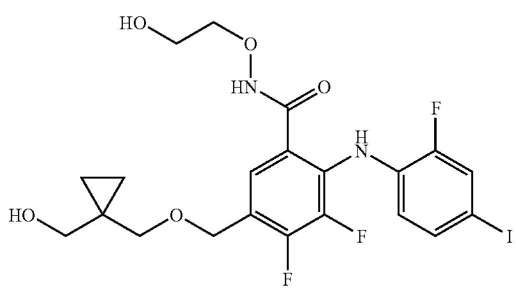 | 3,4-difluoro-2-(2-fluoro-4-iodo-phenylamino)-N-(2-hydroxy-ethoxy)-5-(1-hydroxymethyl-cyclopropylmethoxymethyl)-benzamide |
| B-9 | 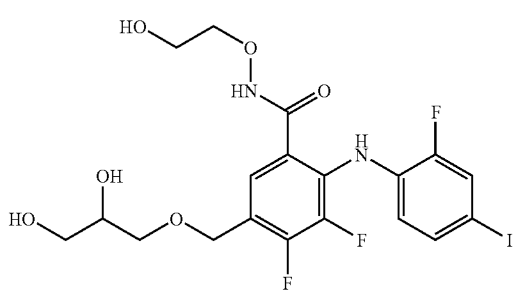 | d,l-5-(2,3-dihydroxy-propoxymethyl)-3,4-difluoro-2-(2-fluoro-4-iodo-phenylamino)-N-(2-hydroxy-ethoxy)-benzamide |
| B-10 | 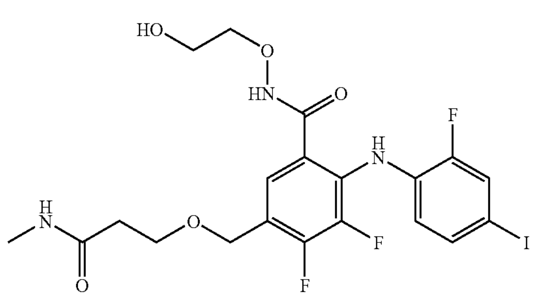 | 3,4-difluoro-2-(2-fluoro-4-iodo-phenylamino)-N-(2-hydroxy-ethoxy)-5-(2-methylcarbamoyl-ethoxymethyl)-benzamide |
| B-11 | 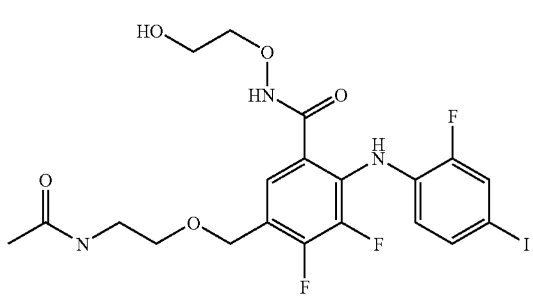 | 5-(2-acetylamino-ethoxymethyl)-3,4-difluoro-2-(2-fluoro-4-iodo-phenylamino)-N-(2-hydroxy-ethoxy)-benzamide |

TABLE 1-continued

| Compound No. | Structure | Compound name |
|---|---|---|
| B-12 | 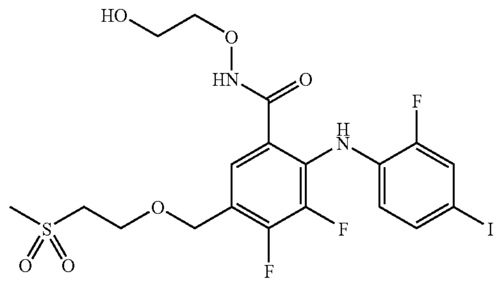 | 3,4-difluoro-2-(2-fluoro-4-iodo-phenylamino)-N-(2-hydroxy-ethoxy)-5-(2-methanesulfonyl-ethoxymethyl)-benzamide |
| B-13 | 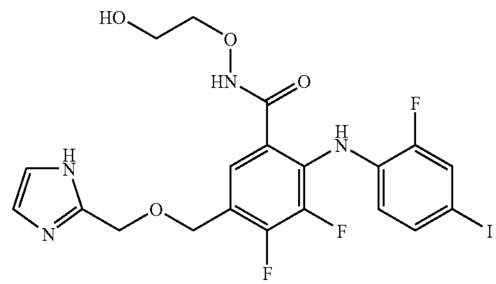 | 3,4-difluoro-2-(2-fluoro-4-iodo-phenylamino)-N-(2-hydroxy-ethoxy)-5-(1H-imidazol-2-yl methoxymethyl)-benzamide |
| B-14 | 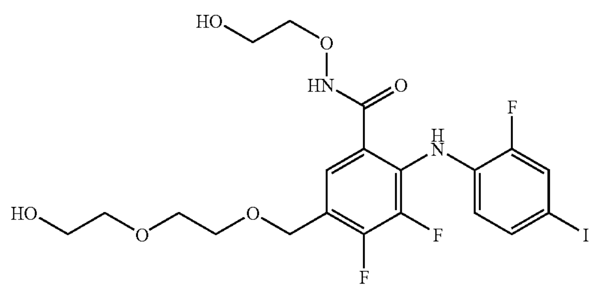 | 3,4-difluoro-2-(2-fluoro-4-iodo-phenylamino)-N-(2-hydroxy-ethoxy)-5-[2-(2-hydroxy-ethoxy)-ethoxymethyl]-benzamide |
| B-15 | 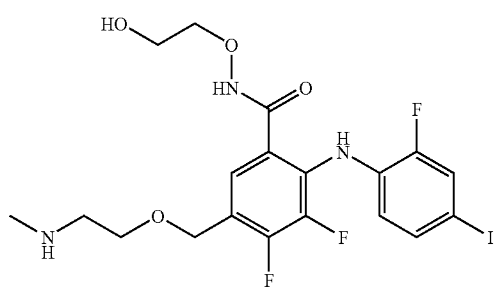 | 3,4-difluoro-2-(2-fluoro-4-iodo-phenylamino)-N-(2-hydroxy-ethoxy)-5-(2-methylamino-ethoxymethyl)-benzamide |
| B-16 | 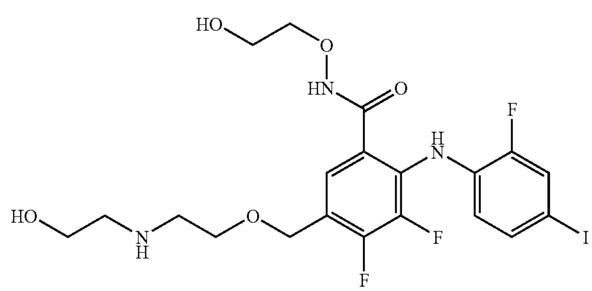 | 3,4-difluoro-2-(2-fluoro-4-iodo-phenylamino)-N-(2-hydroxy-ethoxy)-5-[2-(2-hydroxy-ethylamino)-ethoxymethyl]-benzamide |

TABLE 1-continued

| Compound No. | Structure | Compound name |
|---|---|---|
| B-17 | 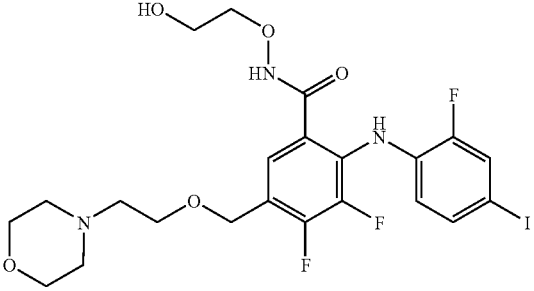 | 3,4-difluoro-2-(2-fluoro-4-iodo-phenylamino)-N-(2-hydroxy-ethoxy)-5-(2-morpholin-4-yl-ethoxymethyl)-benzamide |
| B-18 | 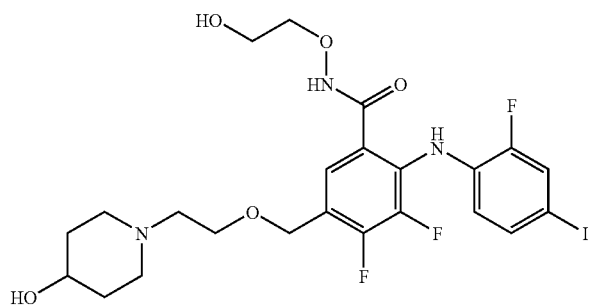 | 3,4-difluoro-2-(2-fluoro-4-iodo-phenylamino)-N-(2-hydroxy-ethoxy)-5-[2-(4-hydroxy-piperidin-1-yl)-ethoxymethyl]-benzamide |
| B-19 | 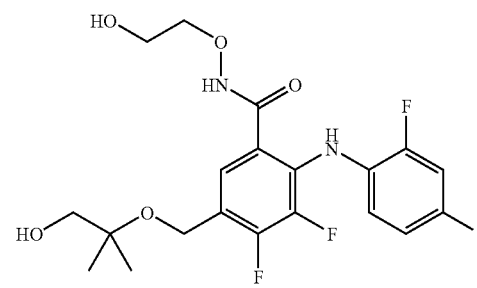 | 3,4-difluoro-2-(2-fluoro-4-iodo-phenylamino)-5-(2-hydroxy-1,1-dimethyl-ethoxymethyl)-N-(2-hydroxy-ethoxy)-benzamide |
| C-1 | 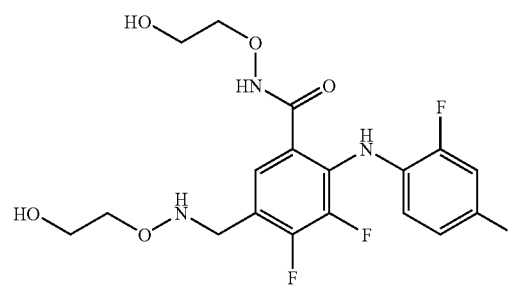 | 3,4-difluoro-2-(2-fluoro-4-iodo-phenylamino)-N-(2-hydroxy-ethoxy)-5-[(2-hydroxy-ethoxyamino)-methyl]-benzamide |
| C-2 | 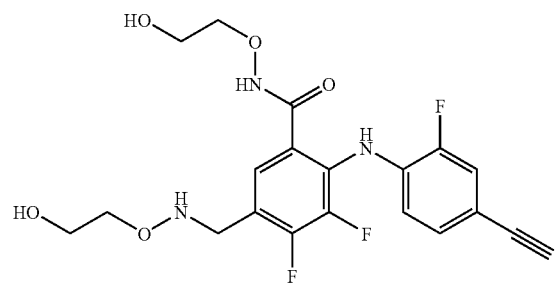 | 2-(4-ethynyl-2-fluoro-phenylamino)-3,4-difluoro-N-(2-hydroxy-ethoxy)-5-[(2-hydroxy-ethoxyamino)-methyl]-benzamide |

TABLE 1-continued

| Compound No. | Structure | Compound name |
| --- | --- | --- |
| C-3 | 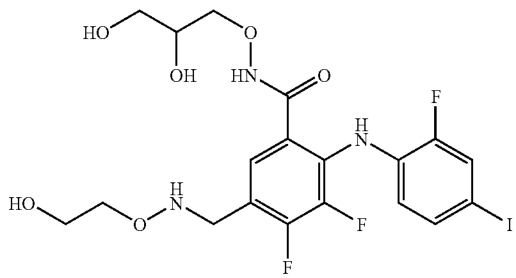 | N-(2,3-dihydroxy-propoxy)-3,4-difluoro-2-(2-fluoro-4-iodo-phenylamino)-5-[(2-hydroxy-ethoxyamino)-methyl]-benzamide |
| C-4 | 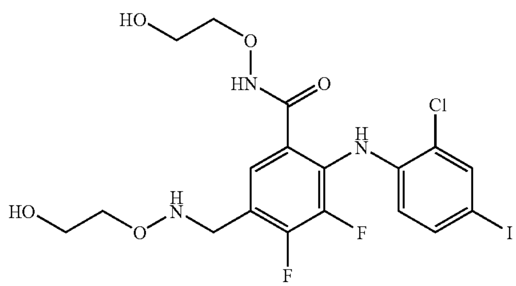 | 2-(2-chloro-4-iodo-phenylamino)-3,4-difluoro-N-(2-hydroxy-ethoxy)-5-[(2-hydroxy-ethoxyamino)-methyl]-benzamide |
| C-5 | 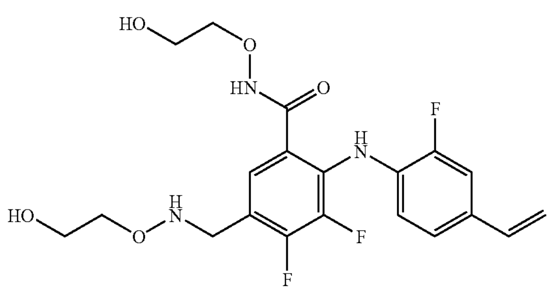 | 3,4-difluoro-2-(2-fluoro-4-vinyl-phenylamino)-N-(2-hydroxy-ethoxy)-5-[(2-hydroxy-ethoxyamino)-methyl]-benzamide |
| C-6 | 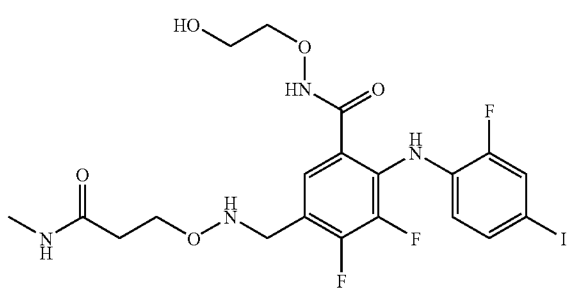 | 3,4-difluoro-2-(2-fluoro-4-iodo-phenylamino)-N-(2-hydroxy-ethoxy)-5-[(2-methylcarbamoyl-ethoxyamino)-methyl]-benzamide |
| C-7 | 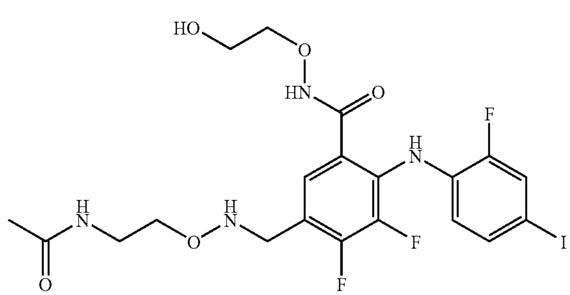 | 5-[(2-acetylamino-ethoxyamino)-methyl]-3,4-difluoro-2-(2-fluoro-4-iodo-phenylamino)-N-(2-hydroxy-ethoxy)-benzamide |

TABLE 1-continued

| Compound No. | Structure | Compound name |
|---|---|---|
| C-8 | 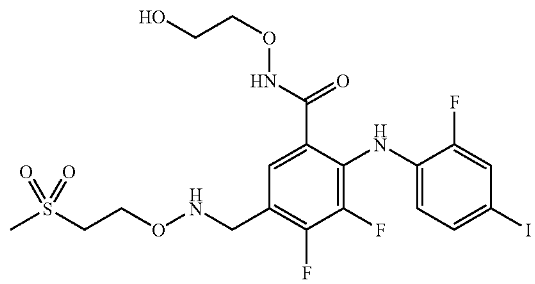 | 3,4-difluoro-2-(2-fluoro-4-iodo-phenylamino)-N-(2-hydroxy-ethoxy)-5-[(2-methanesulfonyl-ethoxyamino)-methyl]-benzamide |
| C-9 | 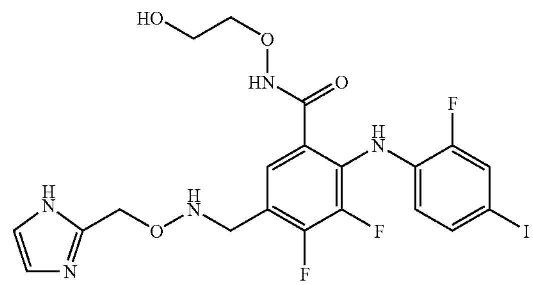 | 3,4-difluoro-2-(2-fluoro-4-iodo-phenylamino)-N-(2-hydroxy-ethoxy)-5-[(1H-imidazol-2-ylmethoxyamino)-methyl]-benzamide |
| C-10 | 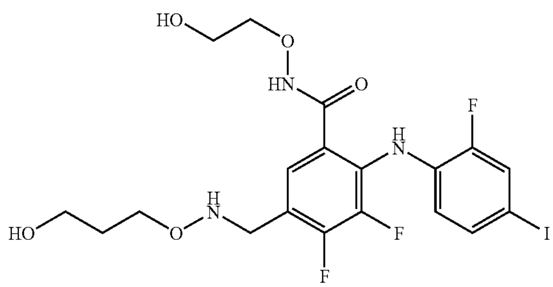 | 3,4-difluoro-2-(2-fluoro-4-iodo-phenylamino)-N-(2-hydroxy-ethoxy)-5-[(3-hydroxy-propoxyamino)-methyl]-benzamide |
| C-11 | 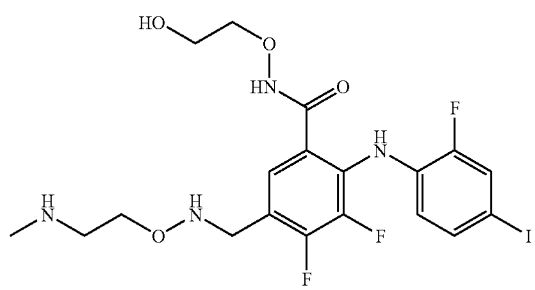 | 3,4-difluoro-2-(2-fluoro-4-iodo-phenylamino)-N-(2-hydroxy-ethoxy)-5-[(2-methylamino-ethoxyamino)-methyl]-benzamide |
| C-12 | 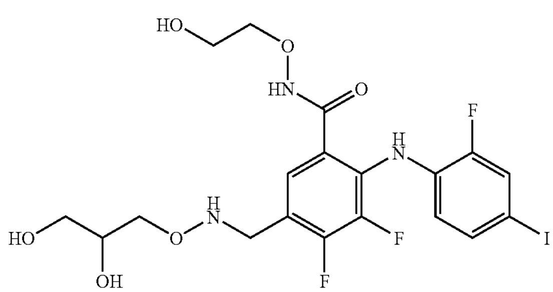 | 5-[(2,3-dihydroxy-propoxyamino)-methyl]-3,4-difluoro-2-(2-fluoro-4-iodo-phenylamino)-N-(2-hydroxy-ethoxy)-benzamide |

TABLE 1-continued

| Compound No. | Structure | Compound name |
| --- | --- | --- |
| C-13 | 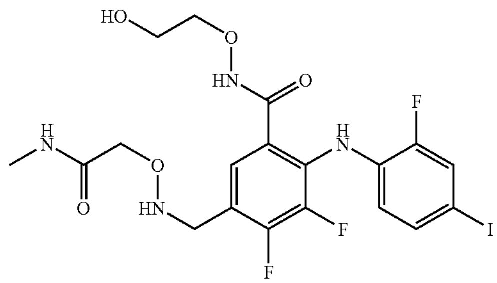 | 3,4-difluoro-2-(2-fluoro-4-iodo-phenylamino)-N-(2-hydroxy-ethoxy)-5-(methylcarbamoylmethoxyamino-methyl)-benzamide |
| C-14 | 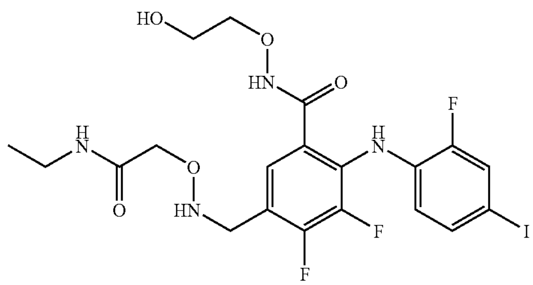 | 5-(ethylcarbamoylmethoxyamino-methyl)-3,4-difluoro-2-(2-fluoro-4-iodo-phenylamino)-N-(2-hydroxy-ethoxy)-benzamide |
| C-15 | 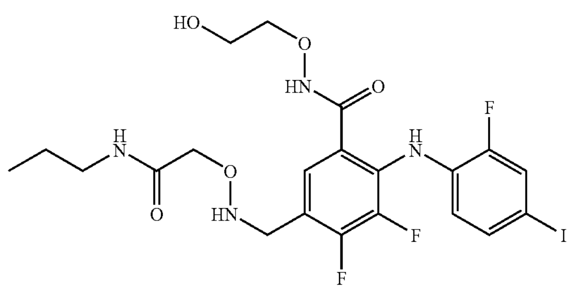 | 3,4-difluoro-2-(2-fluoro-4-iodo-phenylamino)-N-(2-hydroxy-ethoxy)-5-(propylcarbamoylmethoxyamino-methyl)-benzamide |
| C-16 | 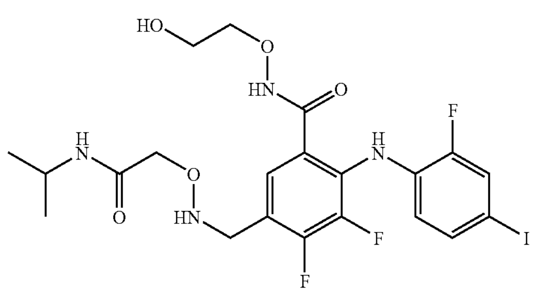 | 3,4-difluoro-2-(2-fluoro-4-iodo-phenylamino)-N-(2-hydroxy-ethoxy)-5-[(isopropylcarbamoyl-methoxyamino)-methyl]-benzamide |
| C-17 | 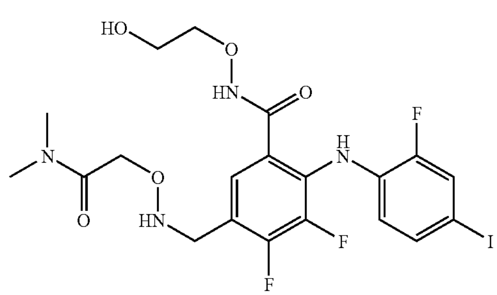 | 5-(dimethylcarbamoylmethoxyamino-methyl)-3,4-difluoro-2-(2-fluoro-4-iodo-phenylamino)-N-(2-hydroxy-ethoxy)-benzamide |

TABLE 1-continued

| Compound No. | Structure | Compound name |
|---|---|---|
| C-18 | 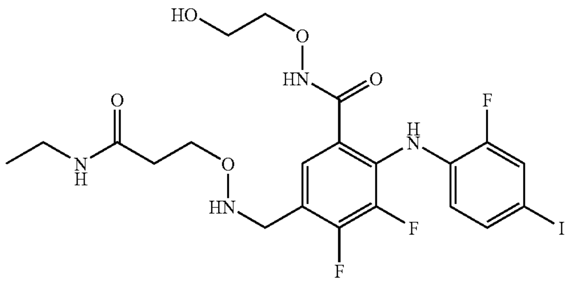 | 5-[(2-ethylcarbamoyl-ethoxyamino)-methyl]-3,4-difluoro-2-(2-fluoro-4-iodo-phenylamino)-N-(2-hydroxy-ethoxy)-benzamide |
| C-19 | 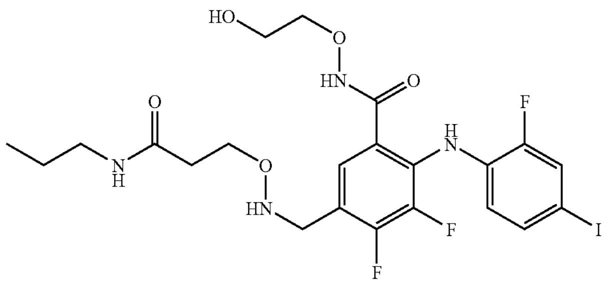 | 5-[(2-propylcarbamoyl-ethoxyamino)-methyl]-3,4-difluoro-2-(2-fluoro-4-iodo-phenylamino)-N-(2-hydroxy-ethoxy)-benzamide |
| C-20 | 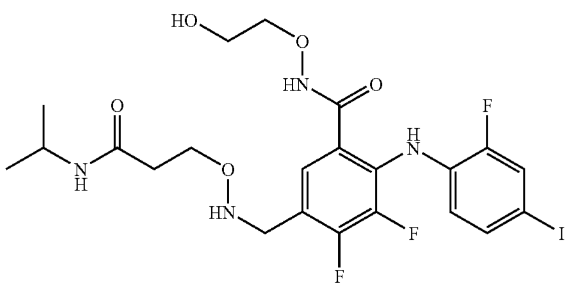 | 5-[(2-isopropylcarbamoyl-ethoxyamino)-methyl]-3,4-difluoro-2-(2-fluoro-4-iodo-phenylamino)-N-(2-hydroxy-ethoxy)-benzamide |
| C-21 | 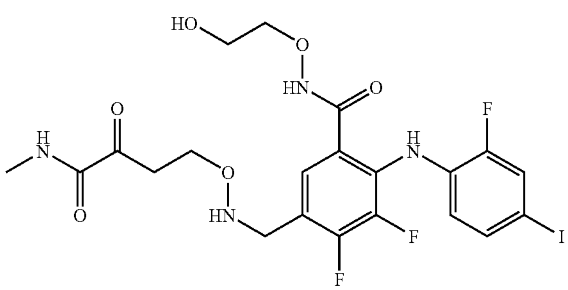 | 3,4-difluoro-2-(2-fluoro-4-iodo-phenylamino)-N-(2-hydroxy-ethoxy)-5-[(3-methylcarbamoyl-propoxyamino)-methyl]benzamide |
| C-22 | 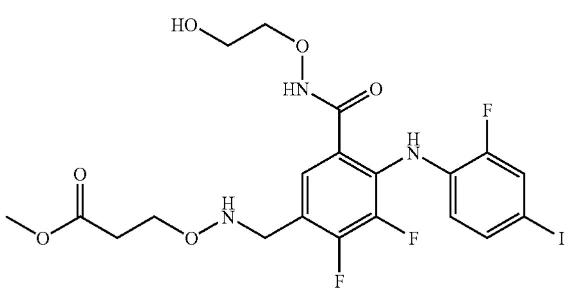 | 3-[N-[2,3-difluoro-4-(2-fluoro-4-iodo-phenylamino)-5-(2-hydroxyethoxycarbamoyl)benzyl]aminooxy]propionic acid methyl ester |

TABLE 1-continued

| Compound No. | Structure | Compound name |
|---|---|---|
| C-23 | 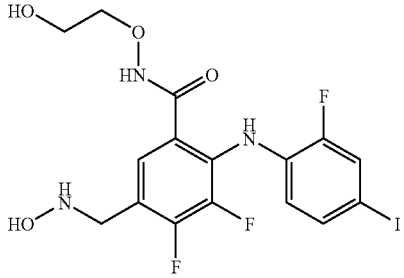 | 3,4-difluoro-2-(2-fluoro-4-iodo-phenylamino)-5-hydroxyaminomethyl-N-(2-hydroxy-ethoxy)-benzamide |
| C-24 | 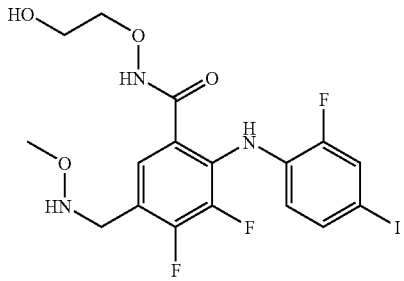 | 3,4-difluoro-2-(2-fluoro-4-iodo-phenylamino)-N-(2-hydroxy-ethoxy)-5-(methoxyamino-methyl)-benzamide |
| C-25 | 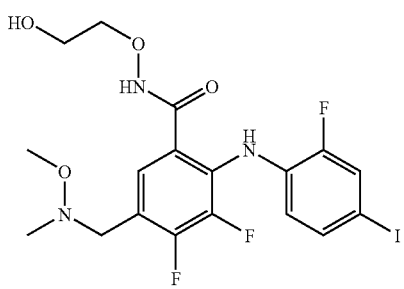 | 3,4-difluoro-2-(2-fluoro-4-iodo-phenylamino)-N-(2-hydroxy-ethoxy)-5-[(methoxy-methyl-amino)-methyl]-benzamide |
| C-26 | 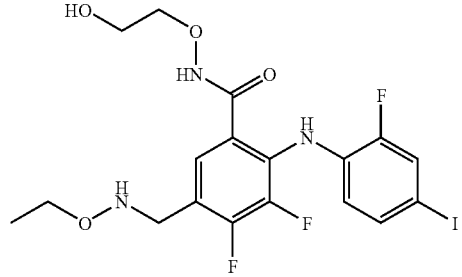 | 5-(ethoxyamino-methyl)-3,4-difluoro-2-(2-fluoro-4-iodo-phenylamino)-N-(2-hydroxy-ethoxy)-benzamide |
| C-27 | 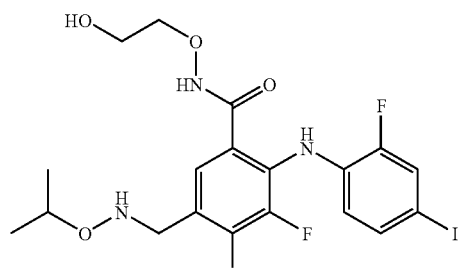 | 3,4-difluoro-2-(2-fluoro-4-iodo-phenylamino)-N-(2-hydroxy-ethoxy)-5-(isopropoxyamino-methyl)-benzamide |

TABLE 1-continued

| Compound No. | Structure | Compound name |
| --- | --- | --- |
| C-28 | 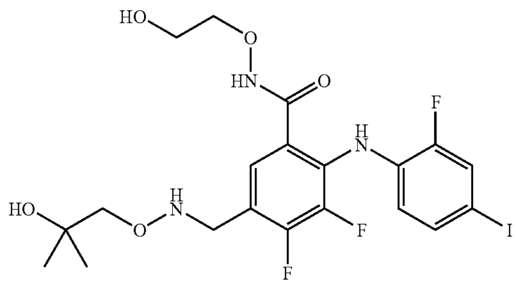 | 3,4-difluoro-2-(2-fluoro-4-iodo-phenylamino)-N-(2-hydroxy-ethoxy)-5-[(2-hydroxy-2-methyl-propoxyamino)-methyl]-benzamide |
| C-29 | 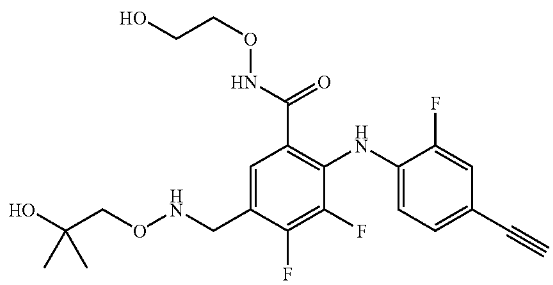 | 2-(4-ethynyl-2-fluoro-phenylamino)-3,4-difluoro-N-(2-hydroxy-ethoxy)5-[(2-hydroxy-2-methyl-propoxyamino)-methyl]-benzamide |
| C-30 | 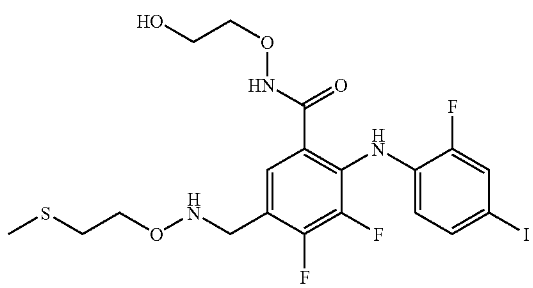 | 3,4-difluoro-2-(2-fluoro-4-iodo-phenylamino)-N-(2-hydroxy-ethoxy)-5-[(2-methylsulfanyl-ethoxyamino)-methyl]-benzamide |
| C-31 | 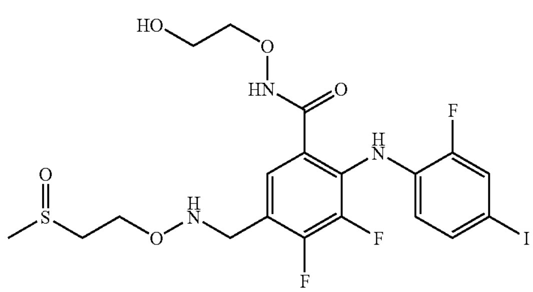 | 3,4-difluoro-2-(2-fluoro-4-iodo-phenylamino)-N-(2-hydroxy-ethoxy)-5-[(2-methanesulfinyl-ethoxyamino)-methyl]-benzamide |
| C-32 | 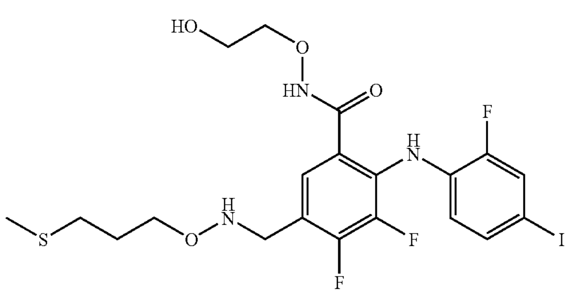 | 3,4-difluoro-2-(2-fluoro-4-iodo-phenylamino)-N-(2-hydroxy-ethoxy)-5-[(3-methylsulfanyl-propoxyamino)-methyl]-benzamide |

TABLE 1-continued

| Compound No. | Structure | Compound name |
|---|---|---|
| C-33 | 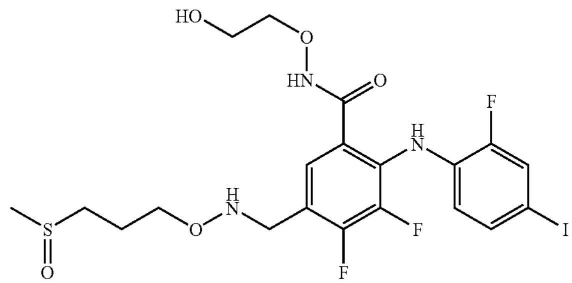 | 3,4-difluoro-2-(2-fluoro-4-iodo-phenylamino)-N-(2-hydroxy-ethoxy)-5-[(3-methanesulfinyl-propoxyamino)-methyl]-benzamide |
| C-34 | 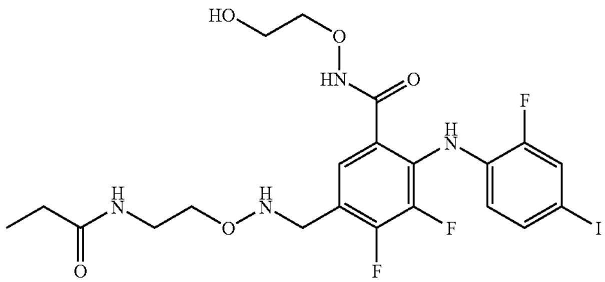 | 3,4-difluoro-2-(2-fluoro-4-iodo-phenylamino)-N-(2-hydroxy-ethoxy)-5-[(2-propoionylamino-ethoxyamino)-methyl]-benzamide |
| C-35 | 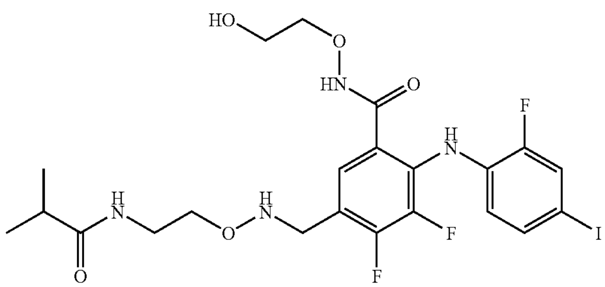 | 3,4-difluoro-2-(2-fluoro-4-iodo-phenylamino)-N-(2-hydroxy-ethoxy)-5-[(2-isobutyrylamino-ethoxyamino)-methyl]-benzamide |
| E-1 | 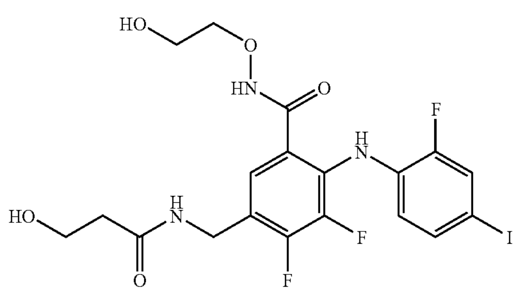 | 3,4-difluoro-2-(2-fluoro-4-iodo-phenylamino)-N-(2-hydroxy-ethoxy)-5-[(3-hydroxy-propionylamino)-methyl]-benzamide |
| E-2 | 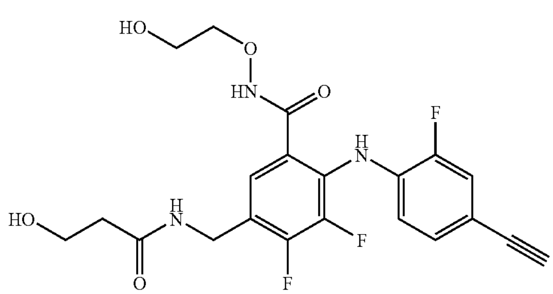 | 2-(4-ethynyl-2-fluoro-phenylamino)-3,4-difluoro-N-(2-hydroxy-ethoxy)-5-[(3-hydroxy-propionylamino)-methyl]-benzamide |

TABLE 1-continued

| Compound No. | Structure | Compound name |
| --- | --- | --- |
| E-3 | 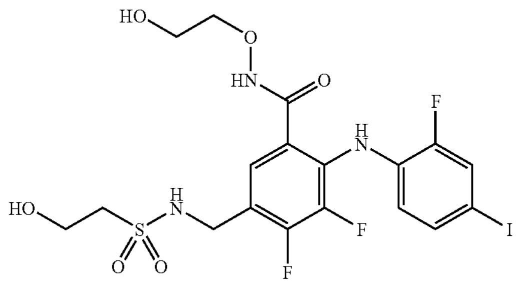 | 3,4-difluoro-2-(2-fluoro-4-iodo-phenylamino)-5-[(2-hydroxy-ethanesulfonylamino)-methyl]-N-(2-hydroxy-ethoxy)-benzamide |
| E-4 | 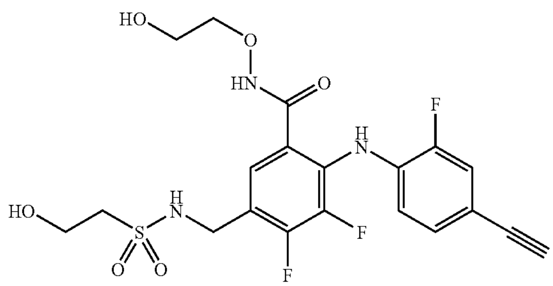 | 2-(4-ethynyl-2-fluoro-phenylamino)-3,4-difluoro-5-[(2-hydroxy-ethanesulfonylamino)-methyl]-N-(2-hydroxy-ethoxy)-benzamide |
| E-5 | 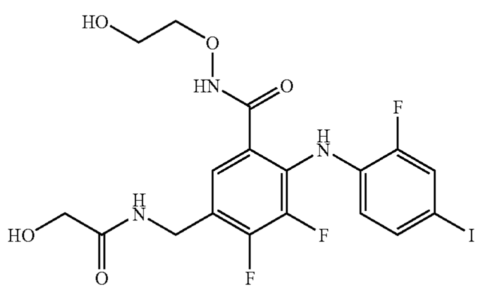 | 3,4-difluoro-2-(2-fluoro-4-iodo-phenylamino)-5-[(2-hydroxy-acetylamino)-methyl]-N-(2-hydroxy-ethoxy)-benzamide |
| E-6 | 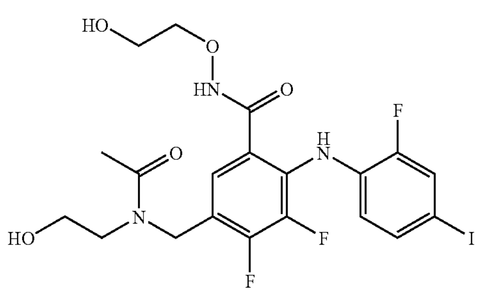 | 5-{[acetyl-(2-hydroxy-ethyl)-amino]-methyl}-3,4-difluoro-2-(2-fluoro-4-iodo-phenylamino)-N-(2-hydroxy-ethoxy)-benzamide |
| F-1 | 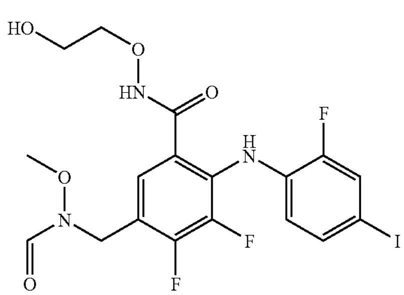 | 3,4-difluoro-2-(2-fluoro-4-iodo-phenylamino)-5-[(formyl-methoxy-amino)-methyl]-N-(2-hydroxy-ethoxy)-benzamide |

TABLE 1-continued

| Compound No. | Structure | Compound name |
|---|---|---|
| F-2 | 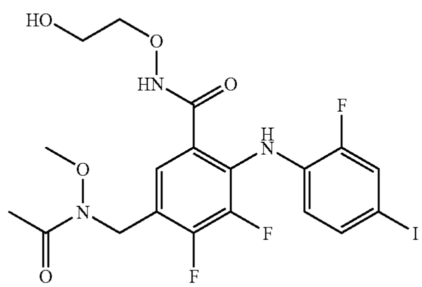 | 5-[acetyl-methoxy-amino-methyl]-3,4-difluoro-2-(2-fluoro-4-iodo-phenylamino)-N-(2-hydroxy-ethoxy)-benzamide |
| F-3 | 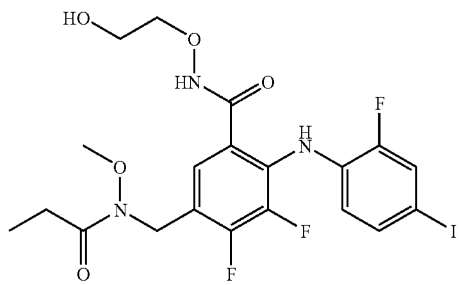 | 3,4-difluoro-2-(2-fluoro-4-iodo-phenylamino)-N-(2-hydroxy-ethoxy)-5-[(methoxy-propionyl-amino)-methyl]-benzamide |
| F-4 | 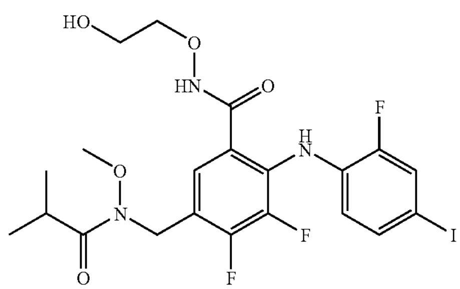 | 3,4-difluoro-2-(2-fluoro-4-iodo-phenylamino)-N-(2-hydroxy-ethoxy)-5-[(isobutyryl-methoxy-amino)-methyl]-benzamide |
| F-5 | 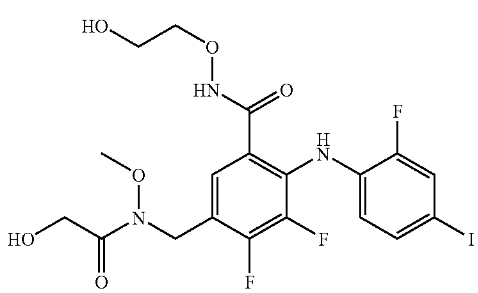 | 3,4-difluoro-2-(2-fluoro-4-iodo-phenylamino)-5-{[(2-hydroxy-acetyl)-methoxy-amino[methyl}-N-(2-hydroxy-ethoxy)-benzamide |
| F-6 | 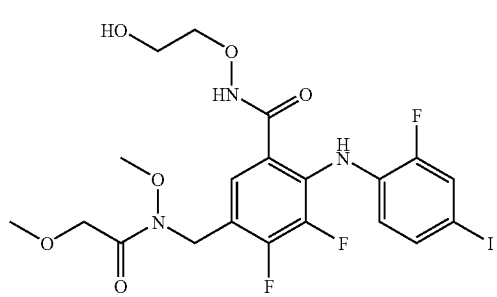 | 3,4-difluoro-2-(2-fluoro-4-iodo-phenylamino)-N-(2-hydroxy-ethoxy)-5-{[methoxy-(2-methoxy-acetyl)-amino]-methyl}-benzamide |

TABLE 1-continued

| Compound No. | Structure | Compound name |
|---|---|---|
| F-7 | 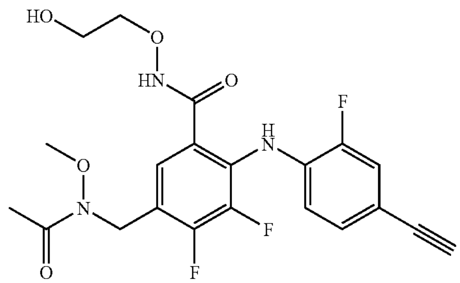 | 5-[(acetyl-methoxy-amino)-methyl]-2-(4-ethynyl-2-fluoro-phenylamino)-3,4-difluoro-N-(2-hydroxy-ethoxy)-benzamide |
| F-8 | 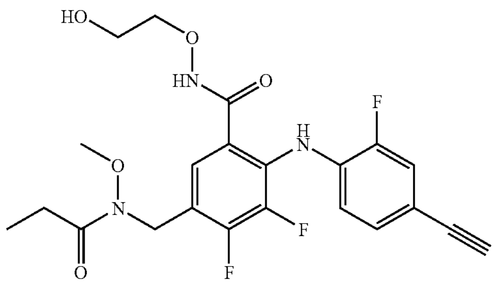 | 2-(4-ethynyl-2-fluoro-phenylamino)-3,4-difluoro-N-(2-hydroxy-ethoxy)-5-[(methoxy-propionyl-amino)-methyl]-benzamide |
| F-9 | 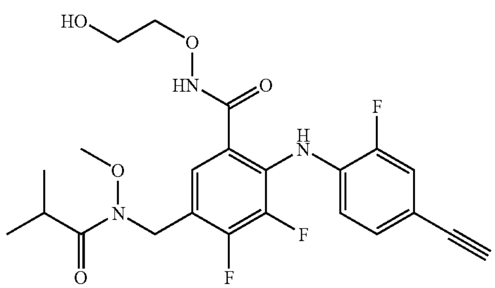 | 2-(4-ethynyl-2-fluoro-phenylamino)-3,4-difluoro-N-(2-hydroxy-ethoxy)-5-[(isobutyryl-methoxy-amino)-methyl]-benzamide |
| F-10 | 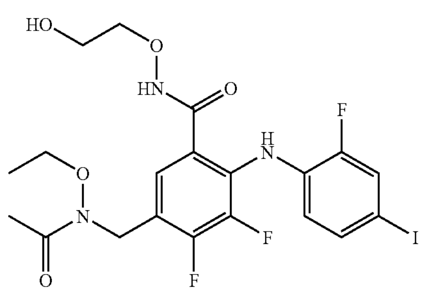 | 5-[(acetyl-ethoxy-amino)-methyl]-methyl]-3,4-difluoro-2-(2-fluoro-4-iodo-phenylamino)-N-(2-hydroxy-ethoxy)-benzamide |
| F-11 | 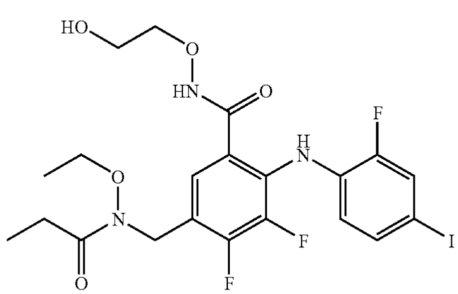 | 5-[(ethoxy-propionyl-amino)-methyl]-3,4-difluoro-2-(2-fluoro-4-iodo-phenylamino)-N-(2-hydroxy-ethoxy)-benzamide |

TABLE 1-continued

| Compound No. | Structure | Compound name |
|---|---|---|
| F-12 | 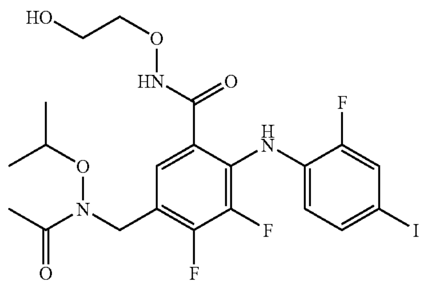 | 5-[(acetyl-isopropoxy-amino)-methyl]-3,4-difluoro-2-(2-fluoro-4-iodo-phenylamino)-N-(2-hydroxy-ethoxy)-benzamide |
| F-13 | 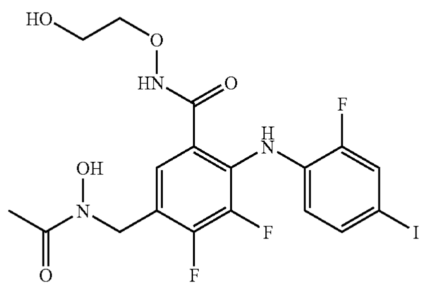 | 5-[(acetyl-hydroxy-amino)-methyl]-3,4-difluoro-2-(2-fluoro-4-iodo-phenylamino)-N-(2-hydroxy-ethoxy)-benzamide |
| F-14 | 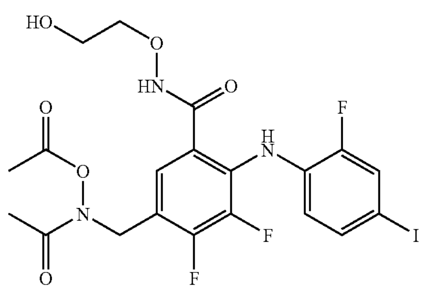 | 5-[(acetoxy-acetyl-amino)-methyl]-3,4-difluoro-2-(2-fluoro-4-iodo-phenylamino)-N-(2-hydroxy-ethoxy)-benzamide |
| F-15 | 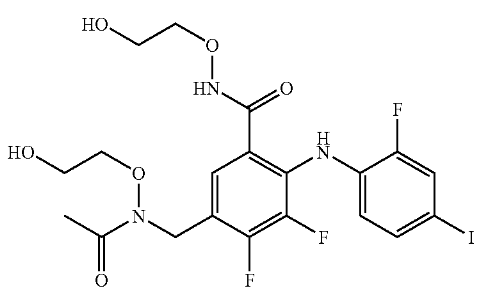 | 5-{[acetyl-(2-hydroxy-ethoxy)-amino]-methyl}-3,4-difluoro-2-(2-fluoro-4-iodo-phenylamino)-N-(2-hydroxy-ethoxy)-benzamide |
| F-16 | 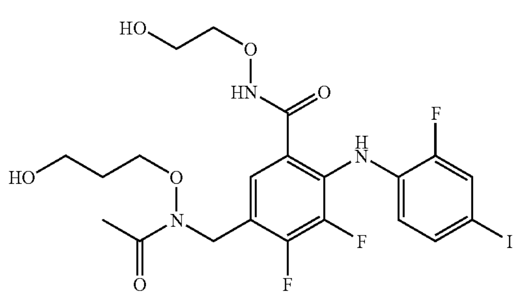 | 5-{[acetyl-(3-hydroxy-propoxy)-amino]-methyl}-3,4-difluoro-2-(2-fluoro-4-iodo-phenylamino)-N-(2-hydroxy-ethoxy)-benzamide |

TABLE 1-continued

| Compound No. | Structure | Compound name |
| --- | --- | --- |
| F-17 | 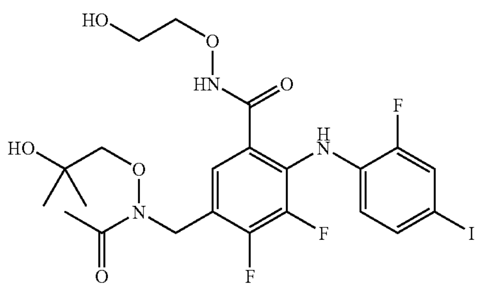 | 5-{[acetyl-(2-hydroxy-2-methyl-propoxy)-amino]-methyl}-3,4-difluoro-2-(2-fluoro-4-iodo-phenylamino)-N-(2-hydroxy-ethoxy)-benzamide |
| F-18 | 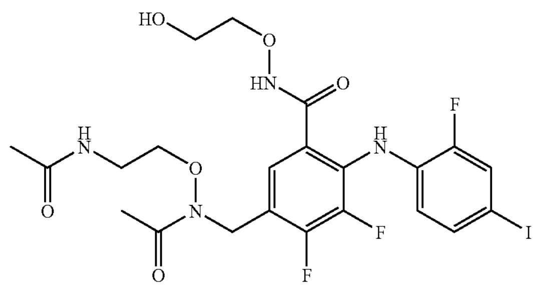 | 5-{[acetyl-(2-acetylamino-ethoxy)-amino]-methyl}-3,4-difluoro-2-(2-fluoro-4-iodo-phenylamino)-N-(2-hydroxy-ethoxy)-benzamide |
| F-19 | 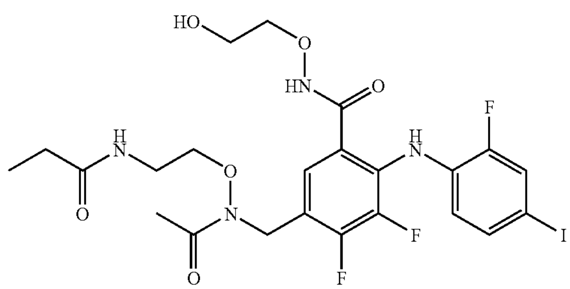 | 5-{[acetyl-(2-propionylamino-ethoxy)-amino]-methyl}-3,4-difluoro-2-(2-fluoro-4-iodo-phenylamino)-N-(2-hydroxy-ethoxy)-benzamide |
| F-20 | 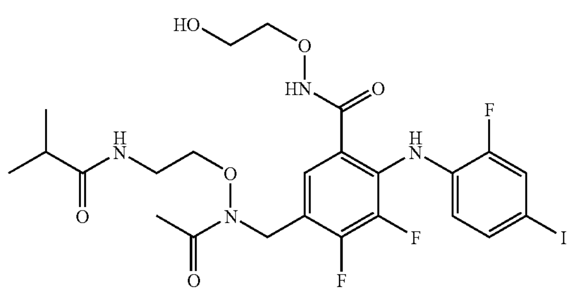 | 5-{[acetyl-(2-isobutyrylamino-ethoxy)-amino]-methyl}-3,4-difluoro-2-(2-fluoro-4-iodo-phenylamino)-N-(2-hydroxy-ethoxy)-benzamide |
| F-21 | 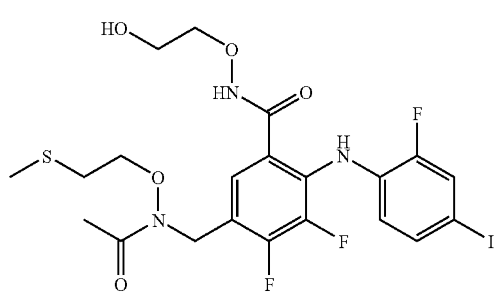 | 5-{[acetyl-(2-methylsulfanyl-ethoxy)-amino]-methyl}-3,4-difluoro-2-(2-fluoro-4-iodo-phenylamino)-N-(2-hydroxy-ethoxy)-benzamide |

TABLE 1-continued

| Compound No. | Structure | Compound name |
|---|---|---|
| F-22 | 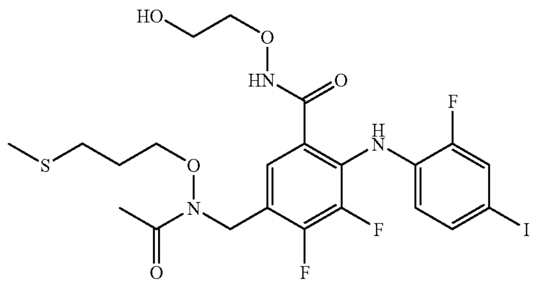 | 5-{[acetyl-(3-methylsulfanyl-propoxy)-amino]-methyl}-3,4-difluoro-2-(2-fluoro-4-iodo-phenylamino)-N-(2-hydroxy-ethoxy)-benzamide |
| F-23 | 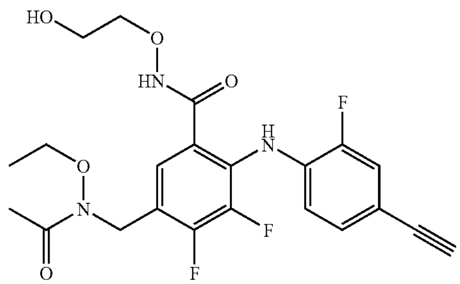 | 5-[(acetyl-ethoxy-amino)-methyl]-2-(4-ethynyl-2-fluoro-phenylamino)-3,4-difluoro-N-(2-hydroxy-ethoxy)-benzamide |
| F-24 | 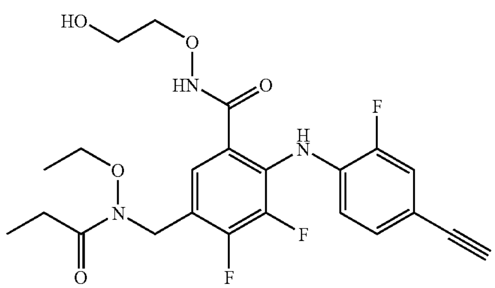 | 5-[(ethoxy-propionyl-amino)-methyl]-2-(4-ethynyl-2-fluoro-phenylamino)-3,4-difluoro-N-(2-hydroxy-ethoxy)-benzamide |
| F-25 | 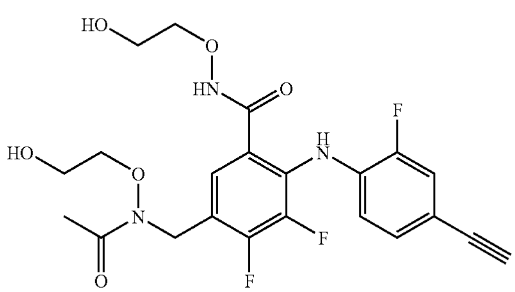 | 5-{[acetyl-(2-hydroxy-ethoxy)-amino]-methyl}-2-(4-ethynyl-2-fluoro-phenylamino)-3,4-difluoro-N-(2-hydroxy-ethoxy)-benzamide |
| F-26 | 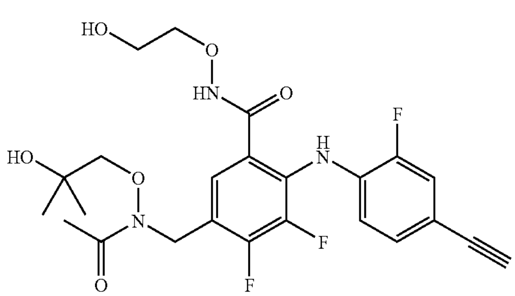 | 5-{[acetyl-(2-hydroxy-2-methyl-propoxy)-amino]-methyl}-2-(4-ethynyl-2-fluoro-phenylamino)-3,4-difluoro-N-(2-hydroxy-ethoxy)-benzamide |

TABLE 1-continued

| Compound No. | Structure | Compound name |
|---|---|---|
| G-1 | 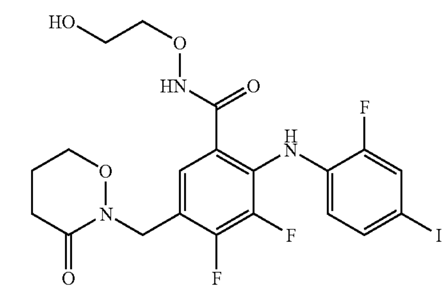 | 3,4-difluoro-2-(2-fluoro-4-iodo-phenylamino)-N-(2-hydroxy-ethoxy)-5-(3-oxo-[1,2]oxazinan-2-ylmethyl)-benzamide |
| G-2 | 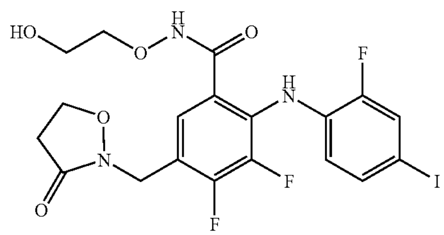 | 3,4-difluoro-2-(2-fluoro-4-iodo-phenylamino)-N-(2-hydroxy-ethoxy)-5-(3-oxo-isoxazolidin-2-ylmethyl)-benzamide |
| G-3 | 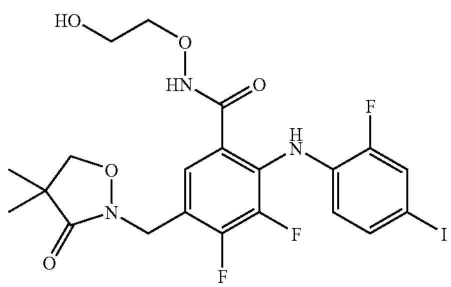 | 5-(4,4-dimethyl-3-oxo-isoxazolidin-2-ylmethyl)-3,4-difluoro-2-(2-fluoro-4-iodo-phenylamino)-N-(2-hydroxy-ethoxy)-benzamide |
| G-4 | 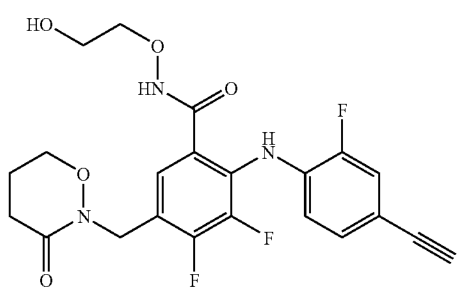 | 2-(4-ethynyl-2-fluoro-phenylamino)-3,4-difluoro-N-(2-hydroxy-ethoxy)-5-(3-oxo-[1,2]oxazinan-2-ylmethyl)-benzamide |
| G-5 | 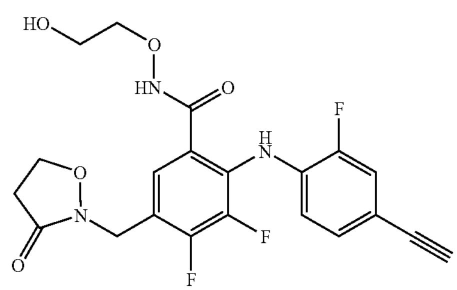 | 2-(4-ethynyl-2-fluoro-phenylamino)-3,4-difluoro-N-(2-hydroxy-ethoxy)-5-(3-oxo-isoxazolidin-2-ylmethyl)-benzamide |

TABLE 1-continued

| Compound No. | Structure | Compound name |
|---|---|---|
| G-6 | 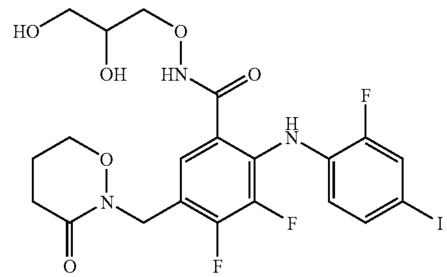 | N-(2,3-dihydroxy-propoxy)-3,4-difluoro-2-(2-fluoro-4-iodo-phenylamino)-5-(3-oxo-[1,2]oxazinan-2-ylmethyl)-benzamide |
| G-7 | 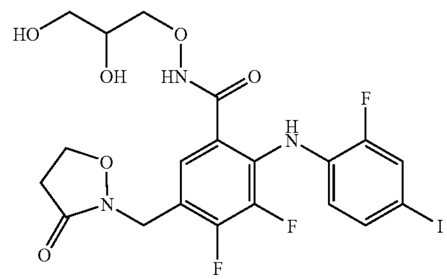 | N-(2,3-dihydroxy-propoxy)-3,4-difluoro-2-(2-fluoro-4-iodo-phenylamino)-5-(3-oxo-isoxazolidin-2-ylmethyl)-benzamide |
| G-8 | 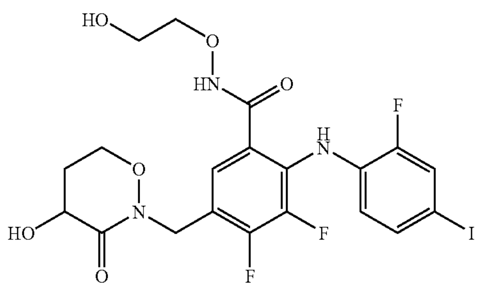 | 3,4-difluoro-2-(2-fluoro-4-iodo-phenylamino)-N-(2-hydroxy-ethoxy)-5-(4-hydroxy-3-oxo-[1,2]oxazinan-2-ylmethyl)-benzamide |
| H-1 | 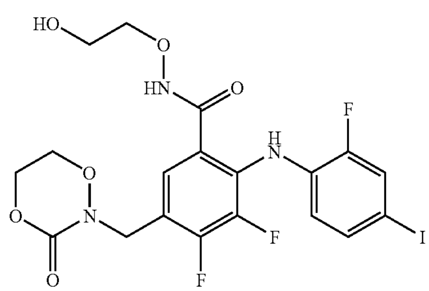 | 3,4-difluoro-2-(2-fluoro-4-iodo-phenylamino)-N-(2-hydroxy-ethoxy)-5-(3-oxo-[1,4,2]dioxazinan-2-ylmethyl)-benzamide |
| H-2 | 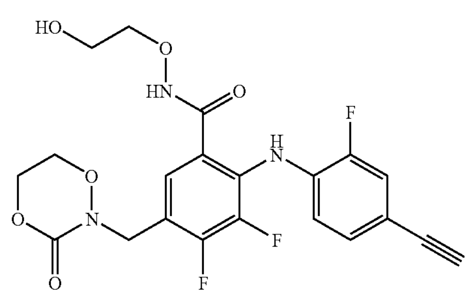 | 2-(4-ethynyl-2-fluoro-phenylamino)-3,4-difluoro-N-(2-hydroxy-ethoxy)-5-(3-oxo-[1,4,2]dioxazinan-2-ylmethyl)-benzamide |

TABLE 1-continued

| Compound No. | Structure | Compound name |
| --- | --- | --- |
| H-3 | 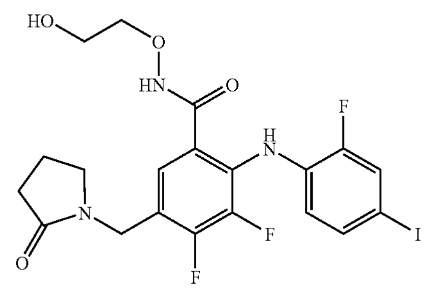 | 3,4-difluoro-2-(2-fluoro-4-iodo-phenylamino)-N-(2-hydroxy-ethoxy)-5-(2-oxo-pyrrolidin-1-ylmethyl)-benzamide |
| H-4 | 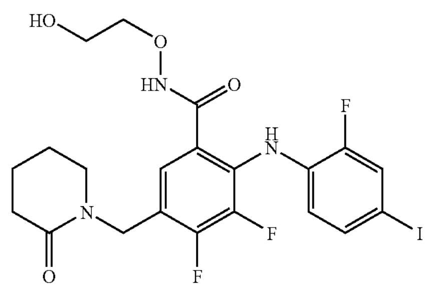 | 3,4-difluoro-2-(2-fluoro-4-iodo-phenylamino)-N-(2-hydroxy-ethoxy)-5-(2-oxo-piperidin-1-ylmethyl)-benzamide |
| H-5 | 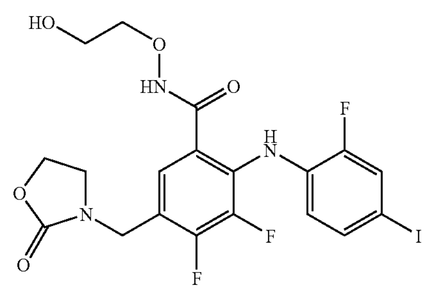 | 3,4-difluoro-2-(2-fluoro-4-iodo-phenylamino)-N-(2-hydroxy-ethoxy)-5-(2-oxo-oxazolidin-3-ylmethyl)-benzamide |
| H-6 | 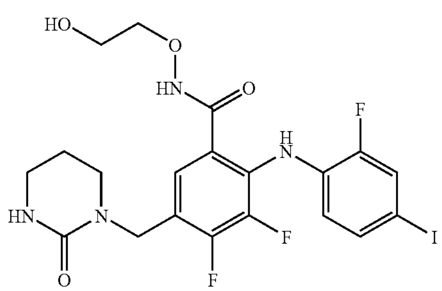 | 3,4-difluoro-2-(2-fluoro-4-iodo-phenylamino)-N-(2-hydroxy-ethoxy)-5-(2-oxo-tetrahydro-pyrimidin-1-ylmethyl)-benzamide |
| H-7 | 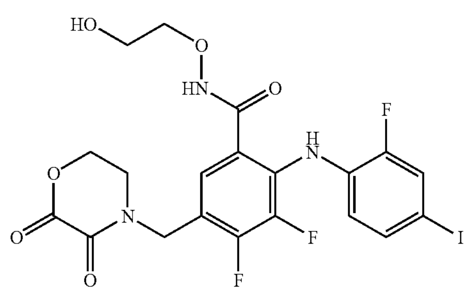 | 5-(2,3-dioxo-morpholin-4-ylmethyl)-3,4-difluoro-2-(2-fluoro-4-iodo-phenylamino)-N-(2-hydroxy-ethoxy)-benzamide |

Compound I of the present invention preferably includes, Exemplary Compound NOs. B-1, B-2, B-6, B-9, B-12, C-1, C-2, C-6, C-7, C-8, C-10, C-13, C-24, C-28, C-29, C-31, C-34, C-35, F-1, F-2, F-3, F-4, F-5, F-6, F-7, F-8, F-9, G-1, G-2, G-3, G-4, and G-5, more preferably Exemplary Compound NOs. B-1, B-2, B-9, B-12, C-1, C-6, C-7, C-8, C-10, C-13, C-24, C-28, C-31, C-35, F-1, F-2, F-3, F-4, F-5, F-6, F-7, F-8, F-9, G-1, G-2, G-3, G-4, and G-5, particularly preferably Exemplary Compound NOs. B-1, C-1, C-10, C-13, F-1, F-2, F-5, G-1, G-2, G-3, G-4, and G-5.

Synthetic intermediates are used to produce compound I. For example, synthetic intermediates A, B, C, D, E, F, G, H, I, J, K, and L represented by the following formulae (2) to (13) can be preferably used, but they are not limited thereto.

Synthetic Intermediate (A)

Synthetic intermediate (A) represented by formula (2):

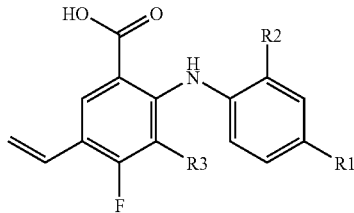

(2)

wherein, $R_1$, $R_2$, and $R_3$ are the same as $R_1$, $R_2$, and $R_3$ in the above formula (1). Preferred embodiments thereof are the same. These may comprise protecting group(s) required for the synthesis.

For example, as preferred embodiments, $R_1$ is an iodine atom, a bromine atom, an ethynyl group, a vinyl group, or a carbamoyl group, $R_2$ is a chlorine atom or a fluorine atom, and $R_3$ is a fluorine atom.

The compounds represented by the formula (2) include, for example, 3,4-difluoro-2-(2-fluoro-4-iodo-phenylamino)-5-vinyl-benzoic acid ($R_1$=I, $R_2$=F, $R_3$=F).

Synthetic Intermediate (B)

Synthetic intermediate (B) represented by formula (3):

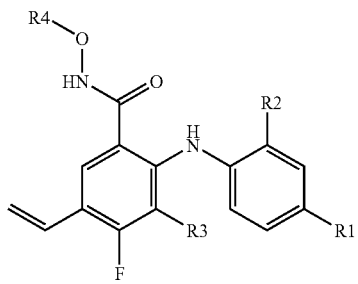

(3)

wherein, $R_1$, $R_2$, $R_3$, and $R_4$ are the same as $R_1$, $R_2$, $R_3$, and $R_4$ in the above formula (1). Preferred embodiments thereof are the same. These may comprise protecting group(s) required for the synthesis.

For example, as preferred embodiments of intermediate (B), $R_1$ is an iodine atom, a bromine atom, an ethynyl group, or a vinyl group, $R_2$ is a chlorine atom or a fluorine atom, $R_3$ is a fluorine atom, and $R_4$ is a hydroxyalkyl group.

The compounds represented by the formula (3) include, for example, N-[2-tert-butyl-dimethyl-silanyloxy)-ethoxy]-3,4-difluoro-2-(2-fluoro-4-iodo-phenylamino)-5-vinyl-benzamide ($R_1$=I, $R_2$=F, $R_3$=F, $R_4$=2-t-butyl-dimethyl-silanyloxy-ethyl).

Synthetic Intermediate (C)

Synthetic intermediate (C) represented by formula (4):

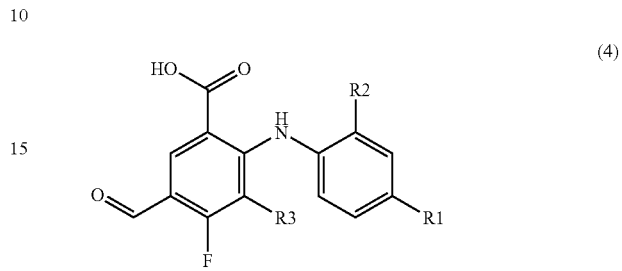

(4)

wherein, $R_1$, $R_2$, and $R_3$ are the same as $R_1$, $R_2$, and $R_3$ in the above formula (1). Preferred embodiments thereof are the same. These may comprise protecting group(s) required for the synthesis.

For example, as preferred embodiments, $R_1$ is an iodine atom, a bromine atom, an ethynyl group, or a vinyl group, $R_2$ is a chlorine atom or a fluorine atom, and $R_3$ is a fluorine atom.

The compounds represented by the formula (4) include, for example, 3,4-difluoro-2-(2-fluoro-4-iodo-phenylamino)-5-formyl-benzoic acid ($R_1$=I, $R_2$=F, $R_3$=F).

Synthetic Intermediate (D)

Synthetic intermediate (D) represented by formula (5):

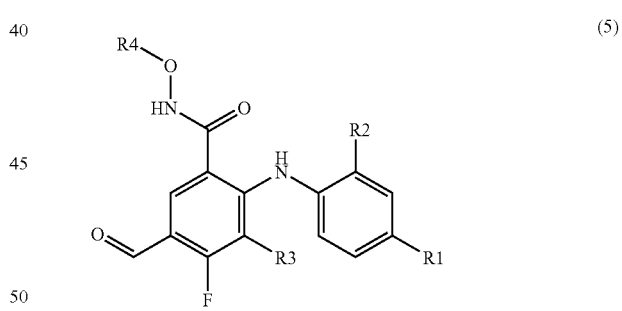

(5)

wherein, $R_1$, $R_2$, $R_3$, and $R_4$ are the same as $R_1$, $R_2$, $R_3$, and $R_4$ in the above formula (1). Preferred embodiments thereof are the same. These may comprise protecting group(s) required for the synthesis.

For example, as preferred embodiments, $R_1$ is an iodine atom, a bromine atom, an ethynyl group, or a vinyl group, $R_2$ is a chlorine atom or a fluorine atom, $R_3$ is a fluorine atom, and $R_4$ is a hydroxyalkyl group.

The compounds represented by the formula (5) include, for example, 3,4-difluoro-2-(2-fluoro-4-iodo-phenylamino)-5-formyl-N-(2-hydroxy-ethoxy)-benzamide ($R_1$=I, $R_2$=F, $R_3$=F, $R_4$=2-hydroxyethyl).

Synthetic Intermediate (E)

Synthetic intermediate (E) represented by formula (6):

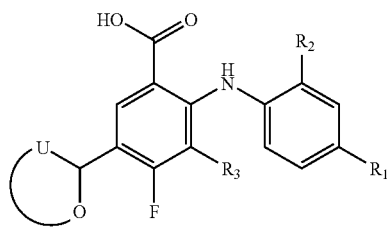

(6)

wherein, $R_1$, $R_2$, and $R_3$ are the same as $R_1$, $R_2$, and $R_3$ in the above formula (1). Preferred embodiments thereof are the same. $R_1$, $R_2$, $R_3$, and U may comprise protecting group(s) required for the synthesis.

For example, $R_1$ is preferably an iodine atom, a bromine atom, an ethynyl group, or a vinyl group; $R_2$ is preferably a chlorine atom or a fluorine atom; and $R_3$ is preferably a fluorine atom.

In the above formula (6), a group represented by formula (a):

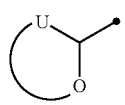

(a)

indicates a 3 to 10-membered heterocyclic group which may have one to three substituents selected from the group consisting of a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, and a heteroaryl group.

The heterocyclic group and the heteroaryl group in the (a) may have a substituent selected from the group consisting of a $C_{1-5}$ alkyl group, —ORa, and —NRaRb The alkyl group may be substituted by a hydroxyl group, a $C_{1-5}$ alkoxy group, or an amino group. The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

The group represented by the above (a) more preferably indicates a 3 to 10-membered heterocyclic group which may have one to three substituents selected from the group consisting of a $C_{1-5}$ alkyl group, a halogen atom, —ORa, —NRaRb, and an oxo group, and still more preferably indicates a 3 to 10-membered heterocyclic group which may be substituted by one to three hydroxyl groups or $C_{1-5}$ alkyl groups. The above substituents except the above oxo group and halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa. Ra and Rb, which may be the same or different, each represent a hydrogen atom or a $C_{1-5}$ alkyl group; the alkyl group may be substituted by a hydroxyl group, a $C_{1-5}$ alkoxy group, or an amino group.

U represents —O—, —CONRd-, —S—, —SO—, —SO$_2$—, —NRd-, —NRdCO—, —NRdSO$_2$—, —SO$_2$NRd-, a bivalent heterocyclic group, or a bivalent heteroaryl group. Rd represents a hydrogen atom or a $C_{1-5}$ alkyl group; the alkyl group may be substituted by a hydroxyl group, a $C_{1-5}$ alkoxy group, or an amino group.

The above U is preferably —O—, —CONRd-, —SO$_2$—, —NRdCO—, a heterocyclic group, or a heteroaryl group, and more preferably —O—, —CONRd-, —SO$_2$—, —NRdCO—, or a heteroaryl group. Rb is preferably a hydrogen atom, a methyl group or an ethyl group.

The above U is more preferably —O—, —CONH—, —SO$_2$—, —NHCO—, a bivalent imidazolyl group, and particularly preferably —O—.

Alternatively, the (a) is preferably a 5- or 6-membered heterocyclic group which may be substituted by one to three hydroxyl groups or $C_{1-5}$ alkyl groups, and more preferably a [1,3]dioxolan-2-yl group or a [1,3]dioxan-2-yl group which may be substituted by one to three hydroxyl groups or $C_{1-5}$ alkyl groups.

More specifically, preferred embodiments include the case where the $R_1$ is an iodine atom, a bromine atom, an ethynyl group, or a vinyl group; the $R_2$ is a chlorine atom or a fluorine atom; the $R_3$ is a fluorine atom; and the U is —O—.

The compounds represented by the formula (6) include, for example, 5-[1,3]dioxolan-2-yl-3,4-difluoro-2-(2-fluoro-4-iodo-phenylamino)-benzoic acid ($R_1$=I, $R_2$=F, $R_3$=F, U=—O— ((a) is a [1,3]dioxolan-2-yl group)).

Synthetic Intermediate (F)

Synthetic intermediate (F) represented by formula (7):

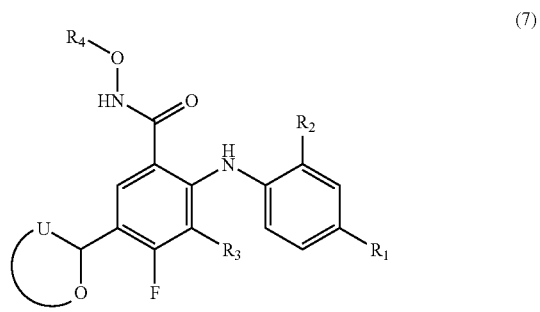

(7)

wherein, $R_1$, $R_2$, $R_3$, and $R_4$ are the same as $R_1$, $R_2$, $R_3$, and $R_4$ in the above formula (1). Preferred embodiments thereof are the same. These may comprise protecting group(s) required for the synthesis.

For example, as preferred embodiments, $R_1$ is preferably an iodine atom, a bromine atom, an ethynyl group, or a vinyl group, $R_2$ is preferably a chlorine atom or a fluorine atom, $R_3$ is preferably a fluorine atom, and $R_4$ is preferably a hydroxyalkyl group.

In the above formula (7), a group represented by formula (a):

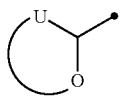

(a)

indicates a 3 to 10-membered heterocyclic group which may have one to three substituents selected from the group consisting of a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, and a heteroaryl group.

The heterocyclic group and the heteroaryl group in the (a) may have a substituent selected from the group consisting of a $C_{1-5}$ alkyl group, —ORa, and —NRaRb. The alkyl group may be substituted by a hydroxyl group, a $C_{1-5}$ alkoxy group, or an amino group. The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

The group represented by the above (a) more preferably indicates a 3 to 10-membered heterocyclic group which may have one to three substituents selected from the group consisting of a $C_{1-5}$ alkyl group, a halogen atom, —ORa, —NRaRb, and an oxo group, and still more preferably indicates a 3 to 10-membered heterocyclic group which may be substituted by one to three hydroxyl groups or $C_{1-5}$ alkyl groups. The above substituents except the above oxo group and halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa. Ra and Rb, which may be the same or different, each represent a hydrogen atom or a $C_{1-5}$ alkyl group; the alkyl group may be substituted by a hydroxyl group, a $C_{1-5}$ alkoxy group, or an amino group.

U represents —O—, —CONRd-, —S—, —SO—, —SO$_2$—, —NRd-, —NRdCO—, —NRdSO$_2$—, —SO$_2$NRd-, a bivalent heterocyclic group or a bivalent heteroaryl group. Rd and Re which may be the same or different, each represent a hydrogen atom or a $C_{1-5}$ alkyl group; the alkyl group may be substituted a hydroxyl group, a $C_{1-5}$ alkoxy group, or an amino group. U may comprise protecting group(s) required for the synthesis.

The above U is preferably —O—, —CONRd-, —SO$_2$—, —NRdCO—, the heterocyclic group or the heteroaryl group, and more preferably —O—, —CONRd-, —SO$_2$—, —NRdCO—, or the heteroaryl group. Rd is preferably a hydrogen atom, a methyl group or an ethyl group.

The above U is still more preferably —O—, —CONH—, —SO$_2$—, —NHCO—, a bivalent imidazolyl group, and particularly preferably —O—.

Alternatively, the (a) is preferably a 5- or 6-membered heterocyclic group which may be substituted by one to three hydroxyl groups or $C_{1-5}$ alkyl groups.

The (a) is more preferably a 5- or 6-membered ring which may be substituted by one to three hydroxyl groups or $C_{1-5}$ alkyl groups, and U is —O—. Still more preferably, the (a) is a [1,3]dioxolan-2-yl group or a [1,3]dioxan-2-yl group which may be substituted by one to three hydroxyl groups or $C_{1-5}$ alkyl groups.

More specifically, preferred embodiments include the case where the $R_1$ is an iodine atom, a bromine atom, an ethynyl group, or a vinyl group; the $R_2$ is a chlorine atom or a fluorine atom; the $R_3$ is a fluorine atom; $R_4$ is a hydroxyalkyl group; and the U is —O—.

The compounds represented by the formula (7) include, for example, 5-[1,3]dioxolane-2-yl-3,4-difluoro-2-(2-fluoro-4-iodo-phenylamino)-N-(2-hydroxy-ethoxy)-benzamide ($R_1$=I, $R_2$=F, $R_3$=F, $F_4$=2-hydroxyethyl, U=—O— ((a) is a [1,3]dioxolan-2-yl group)).

Synthetic Intermediate (G)

Synthetic intermediate (G) represented by formula (8):

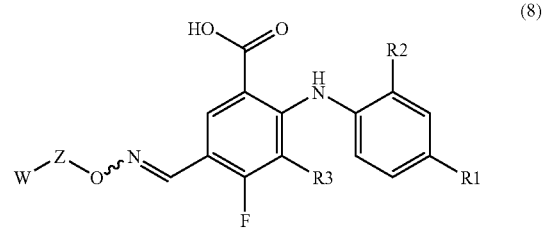

(8)

wherein $R_1$ represents a halogen atom, an alkenyl group, or an alkynyl group;

$R_2$ represents a halogen atom or an alkyl group; the alkyl group may be substituted by a hydroxyl group; and $R_3$ represents a hydrogen atom or a halogen atom.

Z represents an alkylene chain having one to eight carbon atoms, which may be substituted by one to three groups represented by W'];

W and W', which may be the same or different, each represent a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group. The heterocyclic group and the heteroaryl group may have a substituent selected from the group consisting of a $C_{1-5}$ alkyl group, —ORa, and —NRaRb. The alkyl group may be substituted by a hydroxyl group, a $C_{1-5}$ alkoxy group or an amino group.

The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa;

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

Furthermore, the preferred embodiments of W or W' are the same as the above.

The above $R_1$, $R_2$, $R_3$, Z, W, and W' may comprise protecting group(s) required for the synthesis.

The $R_1$ is preferably an iodine atom, a bromine atom, an ethynyl group, or a vinyl group, the $R_2$ is preferably a chlorine atom or a fluorine atom, and the $R_3$ is preferably a fluorine atom.

Synthetic Intermediate (H)

Synthetic intermediate (H) represented by formula (9):

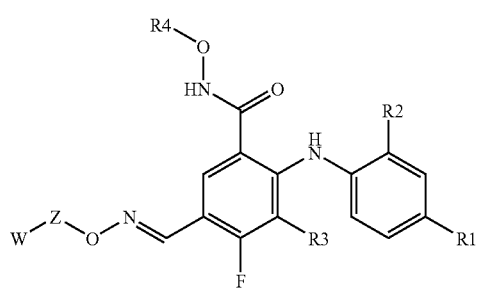

(9)

wherein $R_1$ represents a halogen atom, an alkenyl group, or an alkynyl group;

$R_2$ represents a halogen atom or an alkyl group; the alkyl group may be substituted by a hydroxyl group;

$R_3$ represents a hydrogen atom or a halogen atom; and $R_4$ represents a hydrogen atom, an alkyl group, an alkenyl group, or an alkynyl group. The alkyl group, the alkenyl group, and the alkynyl group may have one to three substituents selected from the group consisting of —ORa, —NRaRb, —NRaCORb, a heterocyclic group, and a heteroaryl group. The heterocyclic group and the heteroaryl group may have one to three substituents selected from the group consisting $C_{1-5}$ alkyl groups, —ORa, and —NRaRb.

Ra and Rb, which may be the same or different, each represent a hydrogen atoms or a $C_{1-5}$ alkyl group; the alkyl group may be substituted by a hydroxyl group, a $C_{1-5}$ alkoxy group, or an amino group.

Z represents an alkylene chain having one to eight carbon atoms, which may be substituted by one to three groups represented by W'.

W and W', which may be the same or different, each represent a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group. The heterocyclic group and the heteroaryl group may have substituents selected from the group consisting of a $C_{1-5}$ alkyl group, —ORa, and —NRaRb. The alkyl group may be substituted by a hydroxyl group, a $C_{1-5}$ alkoxy group, or an amino group.

The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

Furthermore, the preferred embodiments of W or W' are the same as the above.

The above $R_1$, $R_2$, $R_3$, Z, W, and W' may comprise protecting group(s) required for the synthesis.

The $R_1$ is preferably an iodine atom, a bromine atom, an ethynyl group, or a vinyl group, the $R_2$ is preferably a chlorine atom or a fluorine atom, the $R_3$ is preferably a fluorine atom, and the $R_4$ is preferably a hydroxyalkyl group. The hydroxyalkyl group may be protected.

Synthetic Intermediate (I)

Synthetic intermediate (I) represented by formula (10):

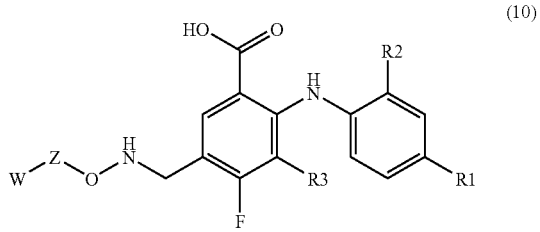

(10)

wherein $R_1$ represents a halogen atom, an alkenyl group, or an alkynyl group;

$R_2$ represents a halogen atom or an alkyl group; the alkyl group may have a hydroxyl group as a substituent; and $R_3$ represents a hydrogen atom or a halogen atom.

Z represents an alkylene chain having one to eight carbon atoms, which may be substituted by one to three groups represented by W'.

W and W', which may be the same or different, each represent a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group. The heterocyclic group and the heteroaryl group may have substituents selected from the group consisting of a $C_{1-5}$ alkyl group, —ORa, and —NRaRb. The alkyl group may be substituted by a hydroxyl group, a $C_{1-5}$ alkoxy group, or an amino group.

The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

Furthermore, the preferred embodiments of W or W' are the same as the above.

The above $R_1$, $R_2$, $R_3$, Z, W, and W' may comprise protecting group(s) required for the synthesis.

The $R_1$ is preferably an iodine atom, a bromine atom, an ethynyl group, or a vinyl group, the $R_2$ is preferably a chlorine atom or a fluorine atom, and the $R_3$ is preferably a fluorine atom.

Synthetic Intermediate (J)

Synthetic intermediate (J) represented by formula (11).

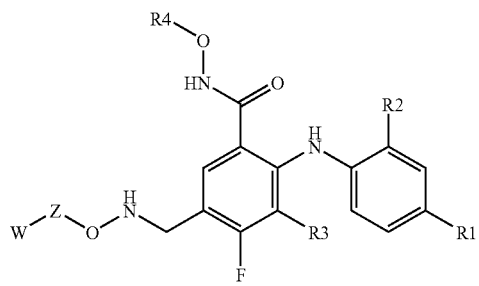
(11)

wherein $R_1$ represents a halogen atom, an alkenyl group, or an alkynyl group;

$R_2$ represents a halogen atom or an alkyl group; the alkyl group may have a hydroxyl group as a substituent;

$R_3$ represents a hydrogen atom or a halogen atom; and $R_4$ represents a hydrogen atom, an alkyl group, an alkenyl group, or an alkynyl group. The alkyl group, the alkenyl group, and the alkynyl group may have one to three substituents selected from the group consisting of —ORa, —NRaRb, —NRaCORb, a heterocyclic group, and a heteroaryl group. The heterocyclic group and the heteroaryl group may have one to three substituents selected from the group consisting of a $C_{1-5}$ alkyl group, —ORa, and —NRaRb. Ra and Rb, which may be the same or different, each represent a hydrogen atom or a $C_{1-5}$ alkyl group; the alkyl group may be substituted by a hydroxyl group, a $C_{1-5}$ alkoxy group, or an amino group.

Z represents an alkylene chain having one to eight carbon atoms, which may be substituted by one to three groups represented by W.

W and W', which may be the same or different, each represent a $C_{1-5}$ alkyl group, a halogen atom, an oxo group, —ORa, —COORa, —COOCORa, —CO-[halogen atom], —OCORa, —CONRaRb, —SRa, —SORa, —SO₂Ra, —NRaRb, —NRaCORb, —NRaSO₂Rb, —SO₂NRaRb, a heterocyclic group, or a heteroaryl group. The heterocyclic group and the heteroaryl group may have substituents selected from the group consisting of a $C_{1-5}$ alkyl group, —ORa, and —NRaRb. The alkyl group may be substituted by a hydroxyl group, a $C_{1-5}$ alkoxy group, or an amino group as substituents.

The above substituents except the oxo group and the halogen atom may be linked to each other to form a cycloalkyl group or a heterocyclic group. The cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

Furthermore, the preferred embodiments of W or W' are the same as the above.

The above $R_1$, $R_2$, $R_3$, $R_4$, Z, W, and W' may comprise protecting group(s) required for the synthesis.

The $R_1$ is preferably an iodine atom, a bromine atom, an ethynyl group, or a vinyl group, the $R_2$ is preferably a chlorine atom or a fluorine atom, the $R_3$ is preferably a fluorine atom, and the $R_4$ is preferably a hydroxyalkyl group. The hydroxyalkyl group may be protected.

Synthetic Intermediate (K)

Synthetic intermediate (K) represented by formula (12):

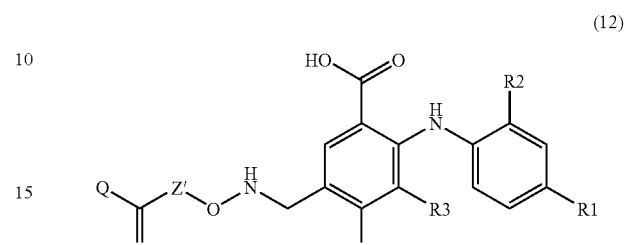
(12)

wherein $R_1$ represents a halogen atom, an alkenyl group, or an alkynyl group;

$R_2$ represents a halogen atom or an alkyl group; the alkyl group may have a hydroxyl group as a substituent;

$R_3$ represents a hydrogen atom or a halogen atom; and

Q is —ORc, —OCORc, —NRcRd, or a halogen atom, Rc and Rd are the same or different, and each represent a hydrogen atom or an alkyl group.

Z' represents an alkylene chain having one to five carbon atoms, which may be substituted by one to three groups represented by W'.

W' preferably represents a $C_{1-5}$ alkyl group, a halogen atom, an oxo group, —ORa, —COORa, —COOCORa, —CO-[halogen atom], —OCORa, —CONRaRb, —SRa, —SORa, —SO₂Ra, —NRaRb, —NRaCORb, —NRaSO₂Rb, —SO₂NRaRb, a heterocyclic group, or a heteroaryl group. The heterocyclic group and the heteroaryl group may have substituents selected from the group consisting of a $C_{1-5}$ alkyl group, —ORa, and —NRaRb. The alkyl group may have a hydroxyl group, a $C_{1-5}$ alkoxy group, or an amino group as substituents. The above substituents except the oxo group and the halogen atom may be linked to each other to form a cycloalkyl group or a heterocyclic group. The cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

W' is more preferably a group represented by the following formulae, —OH, —OMe, —OEt, —OCH₂OH, —O(CH₂)₂OH, —O(i-Pr), —O(n-Pr), —CONH₂, —CONHMe, —CONHEt, —CONH(n-Pr), —CONH(i-Pr), —CONMe₂, —CON(Et)Me, —SO₂Me, —SOMe, —SMe, —NH₂, —NHMe, —NHCH₂OH, —NH(CH₂)₂OH, —N(Me)CH₂CH₂OH, —NH Et, —NMe₂, —N(Et)Me, —NHCOMe, —NMeCOMe, —NHCOEt, —NHCO(n-Pr), or —NHCO(i-Pr).

Furthermore, the preferred embodiments of W' are the same as the above.

The above $R_1$, $R_2$, $R_3$, Z', Q, and W' may comprise protecting group(s) required for the synthesis.

The $R_1$ is preferably an iodine atom, a bromine atom, an ethynyl group, or a vinyl group, the $R_2$ is preferably a chlorine atom or a fluorine atom, and the $R_3$ is preferably a fluorine atom.

Synthetic Intermediate (L)

Synthetic intermediate (L) represented by formula (13):

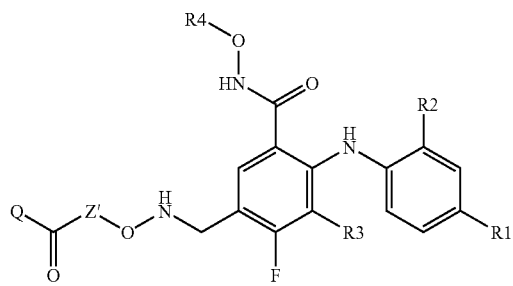

(13)

wherein $R_1$ represents a halogen atom, an alkenyl group, or an alkynyl group;

$R_2$ represents a halogen atom or an alkyl group; the alkyl group may have a hydroxyl group as a substituent;

$R_3$ represents a hydrogen atom or a halogen atom; and $R_4$ represents a hydrogen atom, an alkyl group, an alkenyl group, or an alkynyl group. The alkyl group, the alkenyl group; and the alkynyl group may have one to three substituents selected from the group consisting of —ORa, —NRaRb, —NRaCORb, a heterocyclic group, and a heteroaryl group. The heterocyclic group and the heteroaryl group may have one to three substituents selected from the group consisting of a $C_{1-5}$ alkyl group, —ORa, and —NRaRb. Ra and Rb, which may be the same or different, each represent a hydrogen atom or a $C_{1-5}$ alkyl group; the alkyl group may be substituted by a hydroxyl group, a $C_{1-5}$ alkoxy group, and an amino group.

Z' represents an alkylene chain having one to five carbon atoms, which may be substituted by one to three groups represented by W'.

W' preferably represents a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group. The heterocyclic group and the heteroaryl group may have substituents selected from the group consisting of a $C_{1-5}$ alkyl group, —ORa, and —NRaRb. The alkyl group may be substituted by a hydroxyl group, a $C_{1-5}$ alkoxy group, or an amino group. The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

W' is more preferably a group represented by the following formulae, —OH, —OMe, —OEt, —OCH$_2$OH, —O(CH$_2$)$_2$OH, —O(i-Pr), —O(n-Pr), —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NH Et, —NMe$_2$, —N(Et)Me, —NHCOMe, —NMeCOMe, —NHCOEt, —NHCO(n-Pr), or —NHCO(i-Pr).

Furthermore, the preferred embodiments of W' are the same as the above.

Q is —ORc, —OCORc, —NRcRd, or a halogen atom, Rc and Rd are the same or different, and represent a hydrogen atom or a $C_{1-5}$ alkyl group.

The above $R_1$, $R_2$, $R_3$, $R_4$, Z', W', and Q may comprise protecting group(s) required for the synthesis.

The $R_1$ is preferably an iodine atom, a bromine atom, an ethynyl group, or a vinyl group, the $R_2$ is preferably a chlorine atom or a fluorine atom, the $R_3$ is preferably a fluorine atom, the $R_4$ is preferably a hydroxyalkyl group, and the hydroxyalkyl group may be protected.

Methods for producing compound (1) according to the present invention using these synthetic intermediates of compound (1) include the following methods (1) to (4).

(1) Production Method when Z is —Y—Z—W

This method comprises reacting synthetic intermediate (E) represented by the above formula (6) with a reducing agent in a solvent at a neutral pH or in the presence of an acid, to thereby obtain compound (M) or (M') represented by formula (14) or (14') respectively.

Alternatively, this method comprises reacting the synthetic intermediate (F) represented by the above formula (7) with a reducing agent in a solvent at a neutral pH or in the presence of an acid, to thereby obtain compound (N) or (N') represented by formula (15) or (15') respectively.

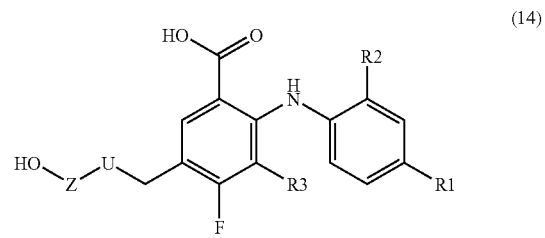

(14)

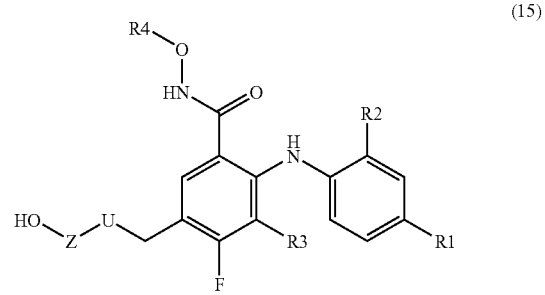

(15)

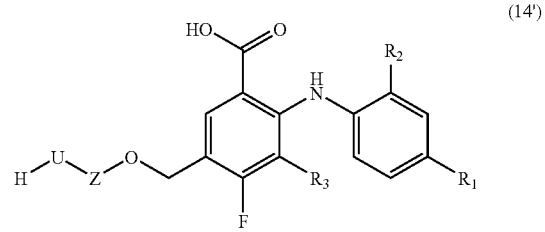

(14')

-continued

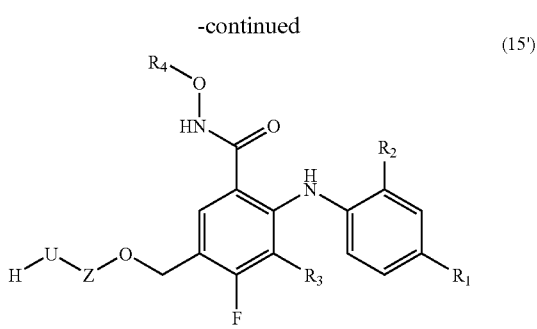

(15')

In the formulae (14), (14'), (15), and (15'), $R_1$, $R_2$, $R_3$, $R_4$, and U each are the same as those in the formulae (6) and (7). In the formulae (14), (14'), (15), and (15'), Z corresponds to the cyclized alkylene chain in the above (a), and the Z represents an alkylene chain having one to eight carbon atoms, which may be substituted by one to three groups represented by W'.

W' preferably includes a group selected from the group consisting of a $C_{1-5}$ alkyl group, a halogen atom, an oxo group, —ORa, —COORa, —COOCORa, —CO-[halogen atom], —OCORa, —CONRaRb, —SRa, —SORa, —SO$_2$Ra, —NRaRb, —NRaCORb, —NRaSO$_2$Rb, —SO$_2$NRaRb, a heterocyclic group, and a heteroaryl group.

The heterocyclic group and the heteroaryl group in the (a) may have substituents selected from the group consisting of a $C_{1-5}$ alkyl group, —ORa, and —NRaRb. The alkyl group may have a hydroxyl group, a $C_{1-5}$ alkoxy group, or an amino group as a substituent. The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

The above W' includes more preferably a group selected from the group consisting of a $C_{1-5}$ alkyl group, a halogen atom, —ORa, —NRaRb, and an oxo group, and still more preferably a hydroxyl group or a $C_{1-5}$ alkyl group. The above substituents except the oxo group and the halogen atom may be linked to each other to form a cycloalkyl group or a heterocyclic group; the cycloalkyl group or the heterocyclic group may have a substituent selected from the group consisting of —ORa, —NRaRb, and a $C_{1-5}$ alkyl group which may be substituted with —ORa.

Ra and Rb, which may be the same or different, each represent a hydrogen atom or a $C_{1-5}$ alkyl group; the alkyl group may be substituted by one to three groups selected from a hydroxyl group, a $C_{1-5}$ alkoxy group, and an amino group.

The above solvent includes methanol, ethanol, diethyl ether, tetrahydrofuran, toluene, methylene chloride, and acetonitrile.

The above reducing agent includes sodium boron hydride, sodium borocyanohydride, triethylsilane, trimethylsilane, lithium aluminum hydride, diisopropyl aluminum hydride, borane-pyridine complex, decaborane, diborane, borane-dimethylsulfide complex, borane-THF complex, hydrogen, zinc boron hydride, samarium (II) iodide, and tributyltin hydride. Preferable examples include, diisopropyl aluminum hydride, sodium boron hydride, and triethylsilane.

The above acid includes acetic acid, hydrochloric acid, trifluoroacetic acid, trifluoroboron-diethyl ether complex, trimethylsilyl triflate, BiCl$_3$, AlCl$_3$, titanium tetrachloride, and trimethylsilyl chloride.

The above reaction can be performed typically at about −78° C. to about 120° C. for about one hour to about 2 days.

(2) Production Method when Z is —Y—Z—W (2)

Compound (I) represented by the above formula (10) can be obtained by reacting synthetic intermediate (G) represented by the above formula (8) with a reducing agent in a solvent at a neutral pH or in the presence of an acid. Alternatively, compound (J) represented by the above formula (11) can be obtained by reacting synthetic intermediate (H) represented by the above formula (9) with a reducing agent in a solvent at a neutral pH or in the presence of an acid.

The above solvent include methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, zinc boron hydride, and tributyltin hydride. Preferably, sodium boron cyanohydride, sodium boron hydride, triethylsilane, and borane-pyridine complex can be included.

The above acid includes acetic acid, hydrochloric acid, trifluoroacetic acid, dichloroacetic acid, trifluoroboron-diethyl ether complex, trimethylsilyl triflate, AlCl$_3$, titanium tetrachloride, and trimethylsilyl chloride. Preferable examples include dichloroacetic acid, hydrochloric acid, and trifluoroacetic acid.

The above reaction can be performed typically at about −78° C. to about 120° C. for about one hour to about 2 days.

(3) Production Method when Z is a Heterocyclic Group

Compound (O) represented by the following formula (16) can be obtained by intramolecularly cyclizing synthetic intermediate (K) represented by the above formula (12) in a solvent at a neutral pH, in the presence of an acid or in the presence of a base, and further in the presence of a peptide condensing agent if necessary, for example, in the case of Q=OH. Alternatively, compound (P) represented by the following formula (17) can be obtained by intramolecularly cyclizing synthetic intermediate (L) represented by the above formula (13) in a solvent at a neutral pH, in the presence of an acid or in the presence of a base, and further in the presence of a peptide condensing agent if necessary, for example, in the case of Q=OH.

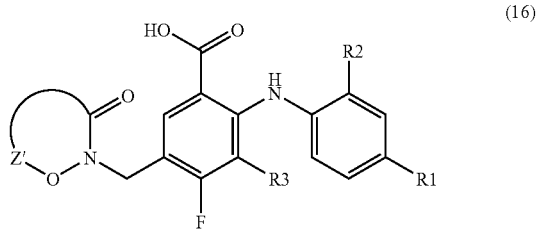

(16)

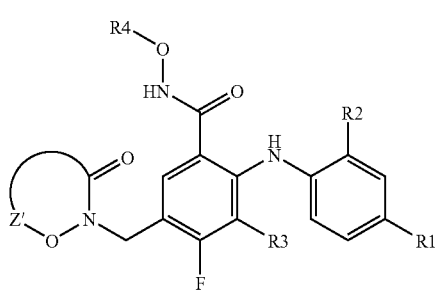

(17)

In the above formulae (16) and (17), $R_1$, $R_2$, $R_3$, $R_4$, and $Z'$ each are the same as those in the above formulae (12) and (13).

Preparation of Compound (XXV)

The above solvent includes methanol, ethanol, diethyl ether, tetrahydrofuran, toluene, methylene chloride, and acetonitrile.

The above acid includes $AlMe_3$, acetic acid, hydrochloric acid, trifluoroacetic acid, dichloroacetic acid, trifluoroboron-diethyl ether complex, trimethylsilyl triflate, $AlCl_3$, titanium tetrachloride, and trimethylsilyl chloride.

The above base includes triethylamine, Hunig's base, DBU, sodium methylate, and potassium carbonate.

The above reaction can be performed typically at room temperature to about 80° C. for about one hour to about one day.

In the case of Q=OH, compound (16) or (17) can be obtained by treating compound (12) or (13) with a condensing agent for peptide synthesis and a base in an appropriate solvent. In this case, the above solvent may be dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt).

The above reaction can be performed typically at about 10° C. to about 30° C., preferably about 22° C. (room temperature) for about one hour to about 2 days, preferably about 10 hours.

(4) Production Method when Z is a Chain Substituent Having a Partial Structure —N(OR)CO—R'

This method comprises reacting synthetic intermediate (I) represented by the above formula (10) with a carboxylate derivative (including carboxylic acid) represented by $R_9CO-Q$ in a solvent in the presence of a base or an acid or at a neutral pH, in the presence of a condensing agent if necessary to thereby obtain compound (S) represented by the following formula (18). Alternatively, this method comprises reacting synthetic intermediate (J) represented by the above formula (11) with a carboxylate derivative (including carboxylic acid) represented by $R_9CO-Q$ in a solvent in the presence of a base or an acid or at a neutral pH, in the presence of a condensing agent if necessary, to thereby obtain compound (T) represented by the following formula (19).

$R_9$ represents a hydrogen atom, an alkyl group, or —ORa; the alkyl group may be substituted by a halogen atom, —ORa, or —NRaRb.

Q is —ORc, —OCORc, —NRcRd, or a halogen atom, and Rc and Rd are the same or different and represent a hydrogen atom or a $C_{1-5}$ alkyl group.

Ra and Rb are the same or different, and represent a hydrogen atom or a $C_{1-5}$ alkyl group; the alkyl group may have a hydroxyl group, a $C_{1-5}$ alkoxy group, or an amino group as substituents.

$R_9$ and Q may comprise protecting group(s) required for the synthesis.

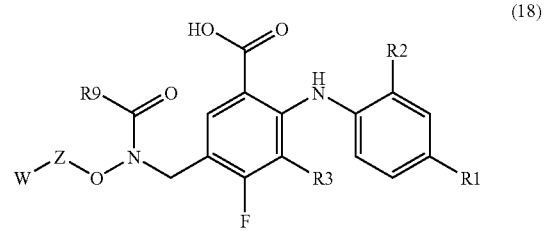

(18)

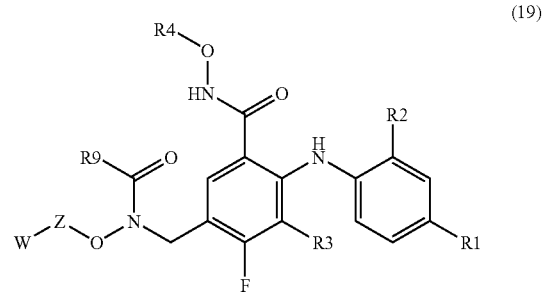

(19)

In the formulae (18) and (19), $R_1$, $R_2$, $R_3$, $R_4$, Z, and W each are the same as those in the formulae (10) and (11), and $R_9$ is the same as that defined for the above carboxylate derivative.

The above solvent includes dichloromethane, THF, and dimethylformamide. The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl) carbodiimide (EDC), (benzotriazolyloxy) tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 0° C. to about 30° C., preferably about 22° C. (room temperature) for about one hour to about 2 days, preferably about 10 hours.

Compound I represented by the formula (1) according to the present invention can be produced, for example in accordance with the following methods. In the following reaction processes 1 to 4 and descriptions thereof, $R_1$ to $R_4$, $R_8$, $R_9$, X, Y, Z, Z', W, Ra, Rb, and compound I are the same as those described in the above formula (1).

Reaction process 1
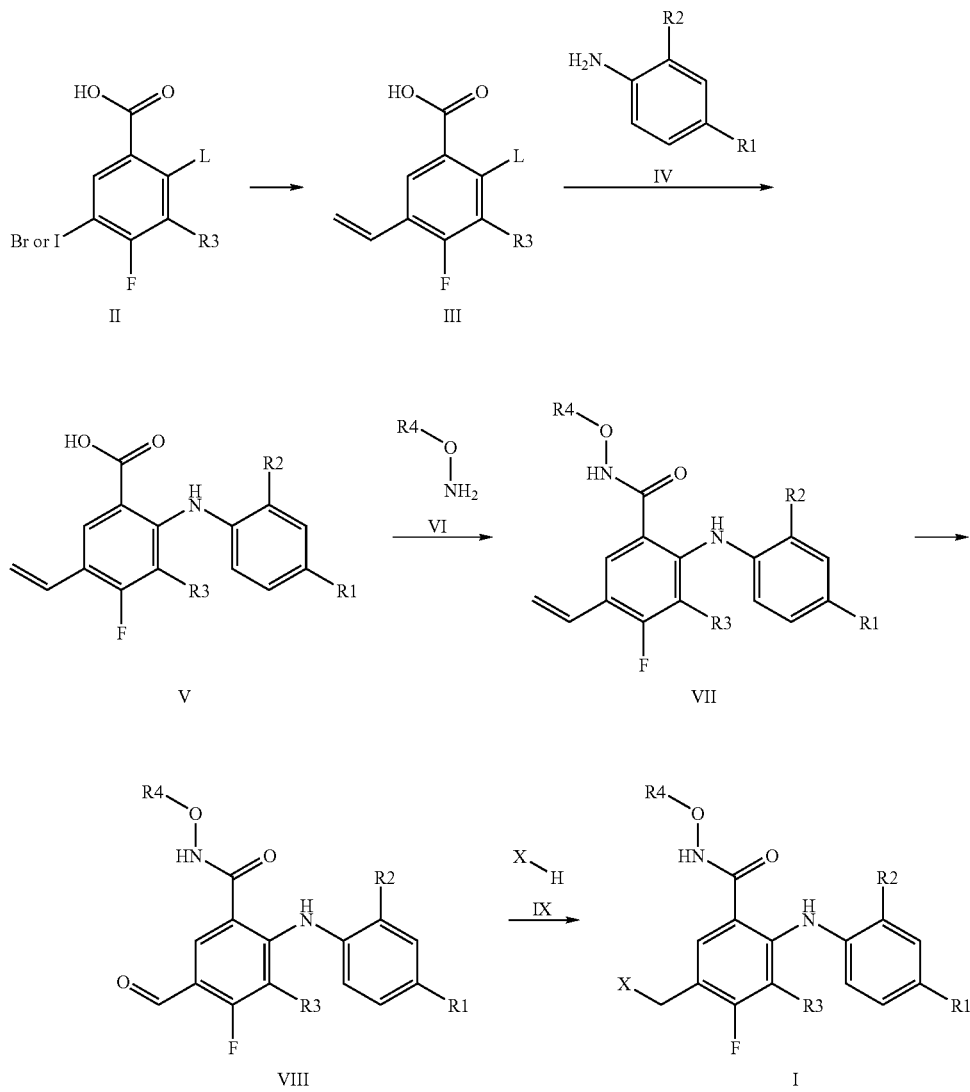
Reaction process 2
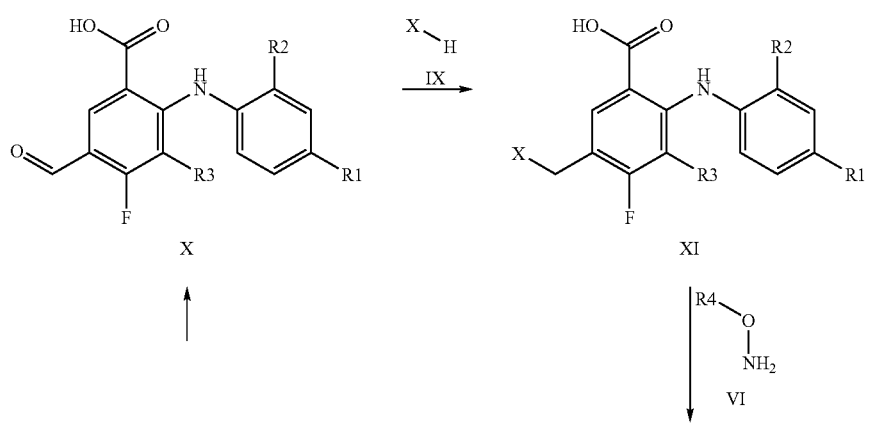

-continued
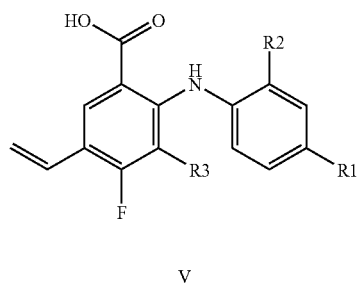
V
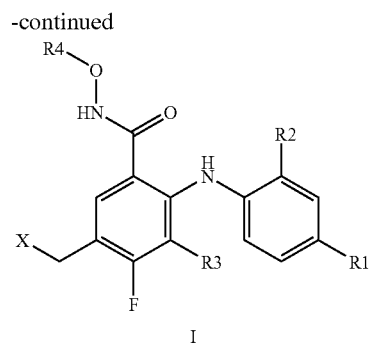
I
Reaction process 3
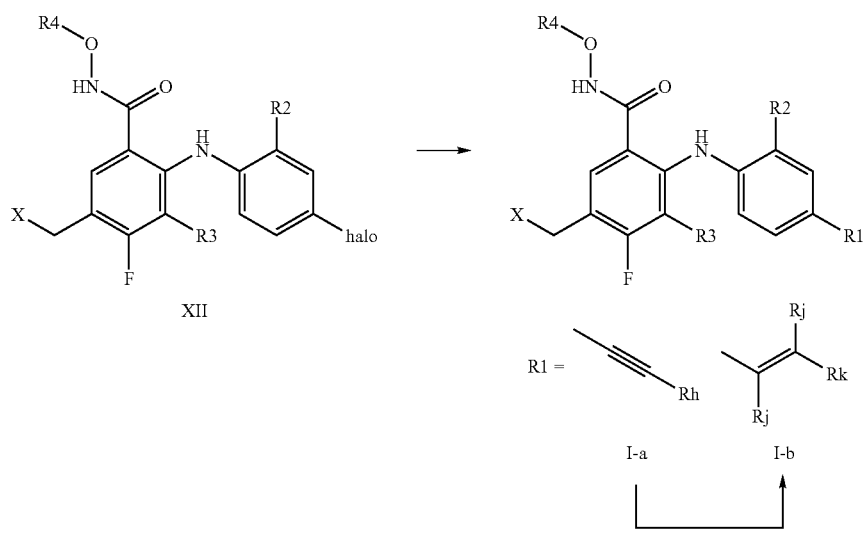
Reaction process 4
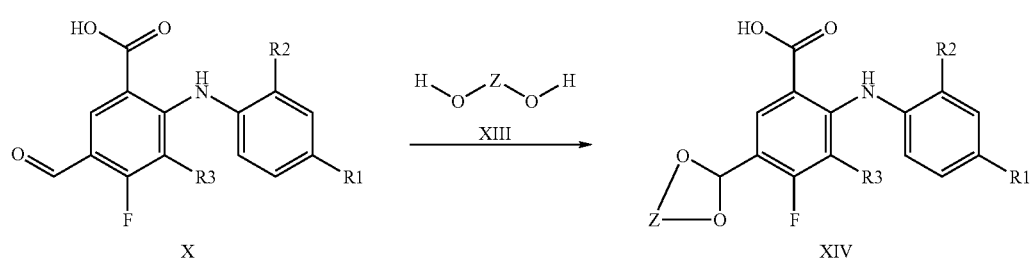
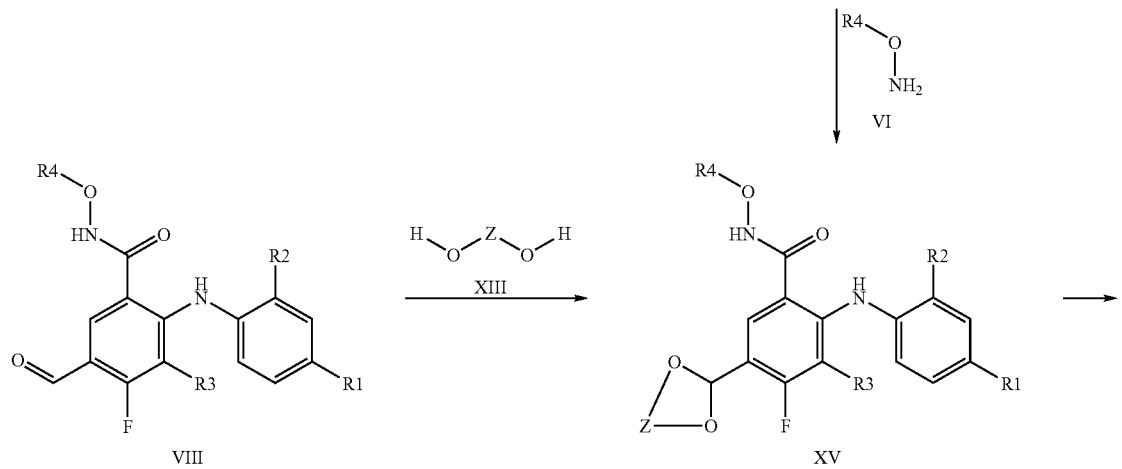

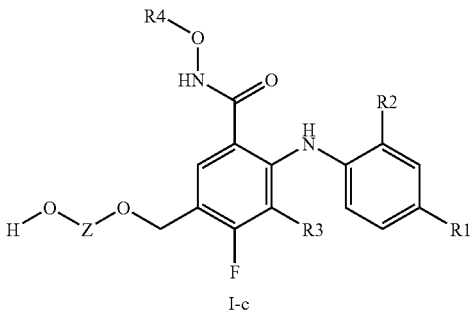
-continued
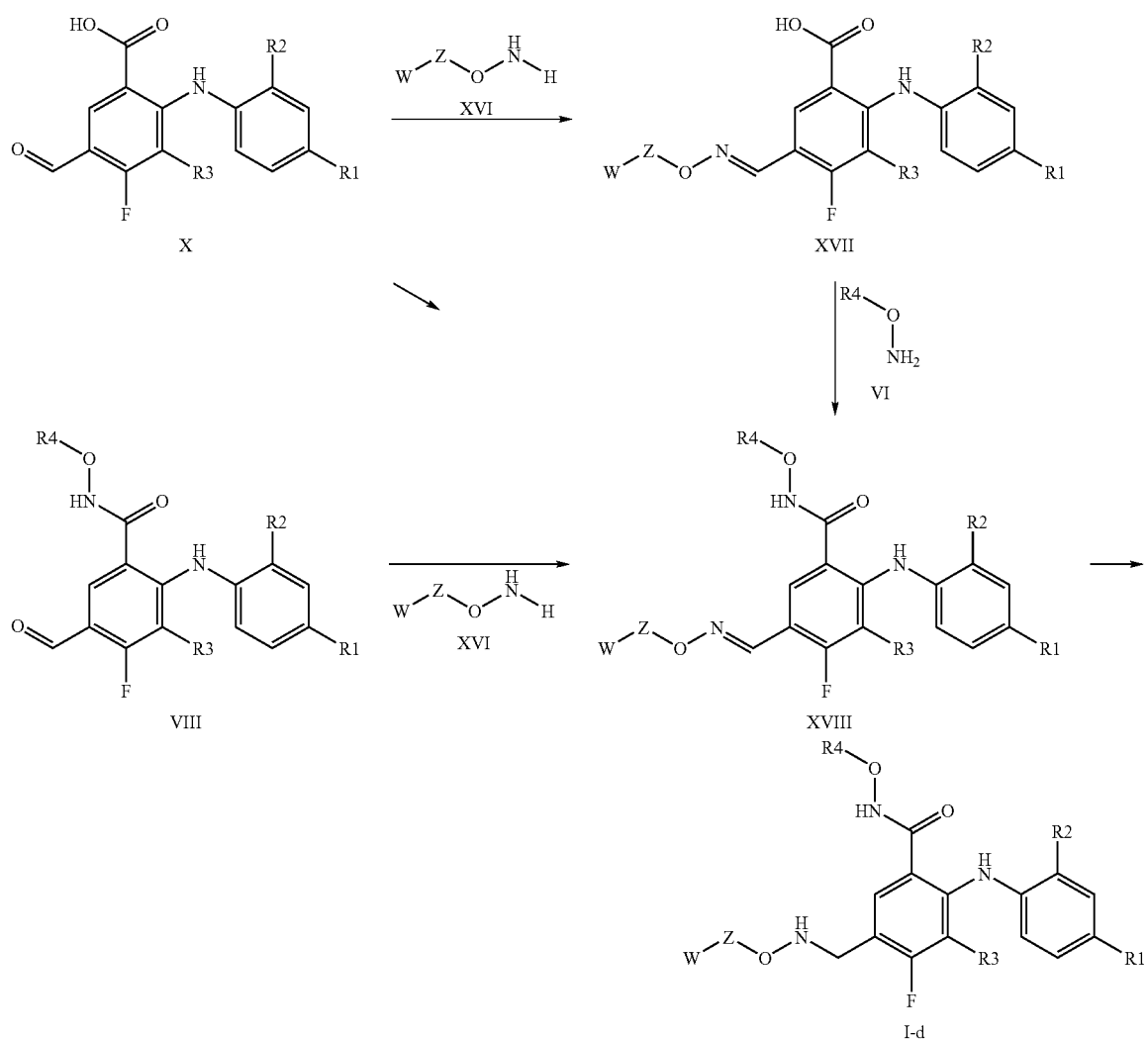
Reaction Process 5
Reaction process 6
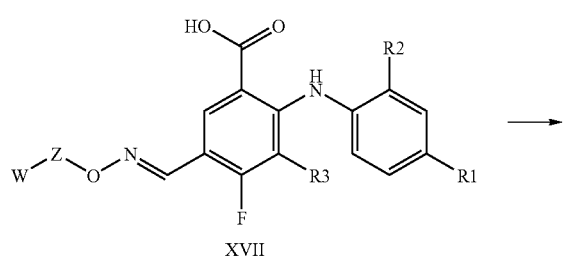

-continued
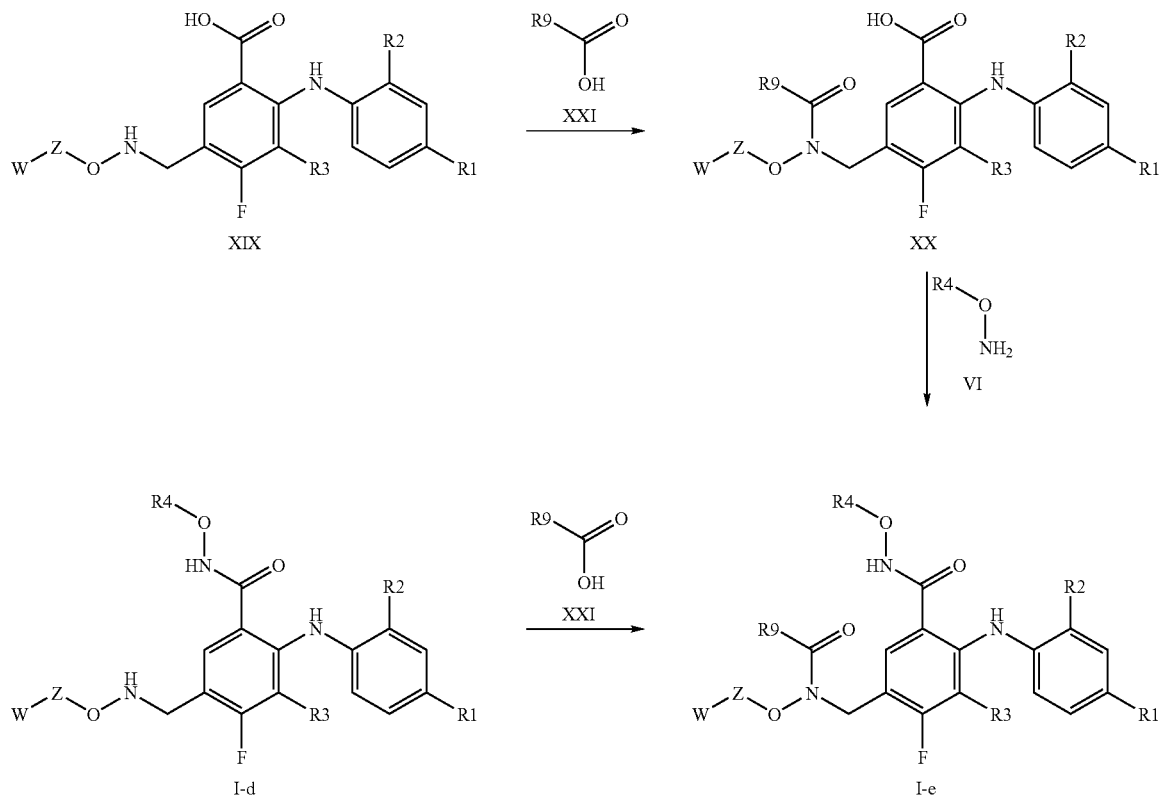
Reaction process 7
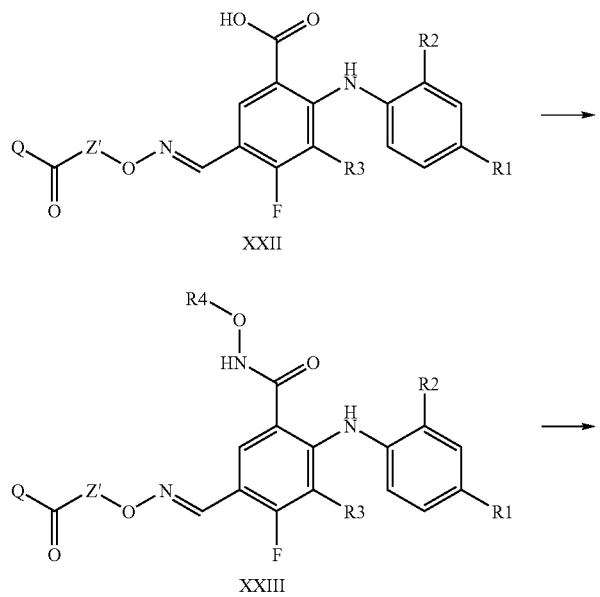

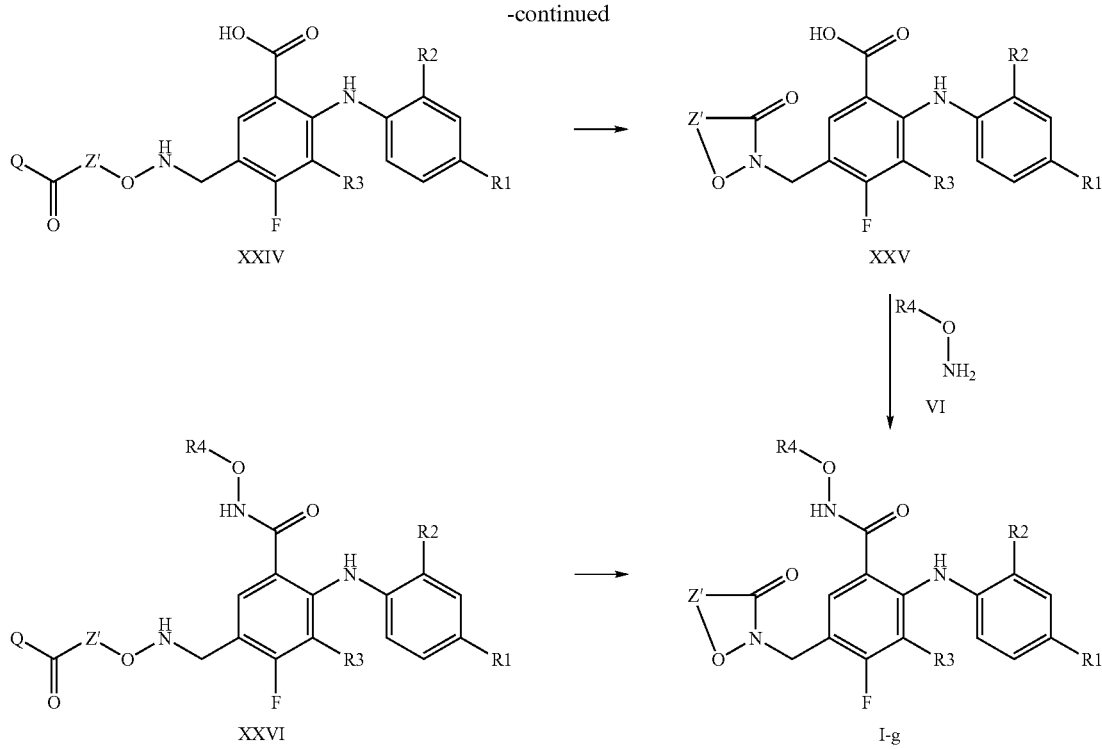

Reaction Process 1

Reaction process 1 indicates a method for producing compound I represented by the formula (1). In this process, L means a leaving group, for example, fluorine, chlorine, bromine, or iodine, or an activated hydroxyl group, for example, phosphate ester and sulfonate ester.

The compound (5-iodinated or 5-brominated benzoic acid derivative) represented by the formula (II) can be easily obtained by, for example, using methods described in publicly known literature (F. Mongin, E. Marzi, and M. Schlosser, European Journal of Organic Chemistry, 2771-2777 (2001) or A. Groweiss, Organic Process Research & Development, 4, 30-33 (2000)) or similar methods thereto.

Preparation of 5-Vinylbenzoic Acid Derivative (III)

5-Vinylbenzoic acid derivative (III) can be obtained by, for example, reacting 5-iodinated or 5-brominated benzoic acid derivative (II) with a vinylated organic metal reagent in an appropriate solvent in the presence of a transition metal catalyst.

The above solvent includes, for example, dimethylformamide, THF (tetrahydrofuran), DMSO (dimethyl sulfoxide), isopropanol, methanol, and ethanol, and preferably, THF or isopropanol is used.

As the above transition metal catalyst, for example, palladium complex can be preferably used. As the palladium complex, for example, Pd(PPh$_3$)$_4$, (PhCN)$_2$PdCl$_2$, (MeCN)$_2$PdCl$_2$, and (PPh$_3$)$_2$PdCl$_2$ can be used.

The above vinylated organic metal reagent includes, for example, vinylated organic magnesium, vinylated organic aluminum, vinylated organic silicon, vinylated organic boron, vinylated organic zinc, and vinylated organic tin. Among them, vinyl organic tin (Stille's method) or vinyl borate (Suzuki's method) can be preferably used. If necessary, it is possible to add an appropriate base such as t-butylamine, triethylamine, or Hunig's base in the reaction system.

The reaction can be performed typically at about 15° C. to about 130° C., preferably about 60° C. for about four hours to about four days, preferably about 10 hours.

The reaction can be easily performed with reference to the following literature.

a) J. K. Stille, Angew. Chem., Int. Ed. Engl. 1986, 25, 508-524.
b) N. Miyaura, A. Suzuki, Chem. Rev. 1995, 95, 2457-2483
c) A. Suzuki, J. Organomet. Chem., 1999, 576, 147-168.
d) Suzuki, A, In Metal-Catalyzed Cross Coupling Reactions; Diederich, F., Stang, P. J., Eds.; VCH: Weinheim, 1998; pp 49-97.

Preparation of 2-(Phenylamino)-5-Vinylbenzoic Acid Derivative (V)

2-(Phenylamino)-5-vinylbenzoic acid derivative (V) can be synthesized by reacting aniline derivative (IV) with 5-vinylbenzoic acid derivative (III). This reaction can be performed using, for example, methods described in a patent document (WO 00/64856) and literature (M. H. Chen, V. G. Beylin, E. Iakovleva, S. J. Kesten, J. Magano, D. Drieze, Synthetic Communications, 32(3), 411-417 (2002)) or similar methods thereto.

Specifically, the reaction can be performed by reacting 5-vinylbenzoic acid derivative (III) with an equal or excessive amount of aniline derivative (IV) in a solvent in the presence of a base.

The above solvent includes, for example, THF and toluene, and preferably THF.

The above base includes, for example, lithium diisopropylamide, lithium hexamethyldisilazide, lithium n-butyl, sodium hydride, and sodium amide, and preferably lithium isopropylamide or lithium hexamethyldisilazide.

The above reaction can be performed typically at about −78° C. to about 25° C. for about four hours to about four days, preferably about one day.

Preparation of Hydroxamic Acid Derivative (VII)

A 2-phenylamino-5-vinylbenzoic acid derivative (V) can be converted into a hydroxamic acid derivative (VII) by reacting (V) with a hydroxylamine derivative (VI) represented by $NH_2OR_4$ in an appropriate solvent in the presence of a condensing agent for peptide synthesis and in the presence or the absence of a base.

The above solvent includes dichloromethane, THF, and dimethylformamide, and preferably dichloromethane.

The above base includes triethylamine, Hunig's base, or DBU (1,8-diazabicyclo[5.4.0]-undecene), or DMAP (4-dimethylaminopyridine), and preferably Hunig's base.

The above peptide condensing agent include 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

Preparation of Aldehyde (VIII)

A hydroxamic acid derivative (VII) can be converted into an aldehyde (VIII) by reacting (VIII) with an appropriate oxidizing agent in an appropriate solvent.

The above solvent includes THF, diethyl ether, dichloromethane, dimethylformamide, DMSO, chloroform, carbon tetrachloride, or acetonitrile, and preferably THF and dichloromethane.

The above oxidizing agent includes ozone, osmium tetroxide-sodium metaperiodate, and ruthenium chloride-sodium metaperiodate.

The above reaction can be performed typically at about 10° C. to about 30° C., preferably about 22° C. (room temperature) for about two hours to about two days, preferably about 10 hours.

Preparation of Compound (I)

An aldehyde (VIII) can be converted into compound (I) by reacting (VIII) with compound (IX) in an appropriate solvent in the presence of an appropriate reducing agent and if necessary an appropriate acid.

The above solvent includes methanol, ethanol, diethyl ether, tetrahydrofuran, toluene, and methylene chloride.

The above reducing agent includes sodium boron hydride, sodium boron cyanohydride, triethylsilane, lithium aluminum hydride, diisopropyl aluminum hydride, borane-pyridine complex, and decaborane.

The above acid includes acetic acid, hydrochloric acid, trifluoroacetic acid, trifluoroboron-diethyl ether complex, trimethylsilyl triflate, $BiCl_3$, trifluoromethanesulfonic acid, p-toluenesulfonic acid, and pyridinium-p-toluenesulfonic acid.

The above reaction can be performed typically at about −78° C. to about 120° C. for about one hour to about two days.

The reaction can be easily performed by, for example, using methods described in the following literature or similar methods thereto.

a) Daniel Dube and Adrew A. Scholte, Tetrahedron Letters, 1999, 40, 2295-2298
b) Koich Fukase, Yoshiyuki Fukase, Masato Oikawa, Wen-Chi Liu, Yasuo, Suda, and Shoichi Kusumoto, Tetrahedron, 1998, 54, 4033-4050
c) Seung Hwan Lee, Yong Lune Park, and Cheol Min Yoon, Tetrahedron Letters, 1999, 40, 6049-6050
d) Makoto Wada, Sonoe Nagayama, Kaori Mizurtani, Ryoichi Hiroi, and Norikazu Miyoshi, Chemistry Letters, 2002, 248-249
e) Kikkugawa, Y, Ogawa, Y, Chem. Pharm. Bull., 1979, 27, 2405-2410

Reaction Process 2

Reaction process 2 is an example process for preparing compound I from 2-(phenylamino)-5-vinylbenzoic acid derivative (V) shown in reaction process 1 by a process other than reaction process 1.

Preparation of Carbonyl (XI)

2-(Phenylamino)-5-vinylbenzoic acid derivative (V) can be converted into a carbonyl (X) in accordance with the method for converting a hydroxamic acid derivative (VII) into a carbonyl (VIII) described above.

More specifically, the conversion can be accomplished by reacting a 2-(4-iodophenylamino)-5-vinylbenzoic acid derivative (V) with an appropriate oxidizing agent in an appropriate solvent.

The appropriate solvent includes THF, diethyl ether, dichloromethane, dimethylformamide, DMSO, chloroform, carbon tetrachloride, or acetonitrile, and preferably THF and dichloromethane. The above oxidizing agent includes ozone, osmium tetroxide-sodium metaperiodate, and ruthenium chloride-sodium metaperiodate. The above reaction can be performed typically at about 10° C. to about 30° C., preferably about 22° C. (room temperature) for about two hours to about two days, preferably about 10 hours.

Preparation of Compound (XI)

A carbonyl (X) can be converted into compound (XI) in accordance with the method for converting an aldehyde (VIII) into compound I described above.

More specifically, the conversion can be accomplished by reacting a carbonyl (X) with compound (IX) in an appropriate solvent in the presence of an appropriate reducing agent and if necessary an appropriate acid.

The above solvent includes methanol, ethanol, diethyl ether, tetrahydrofuran, toluene, and methylene chloride.

The above reducing agent includes sodium boron hydride, sodium boron cyanohydride, triethylsilane, lithium aluminum hydride, diisopropyl aluminum hydride, borane-pyridine complex, and decaborane.

The above acid includes acetic acid, hydrochloric acid, trifluoroacetic acid, trifluoroboron-diethyl ether complex, trimethylsilyl triflate, $BiCl_3$, trifluoromethanesulfonic acid, p-toluenesulfonic acid, and pyridinium-p-toluenesulfonic acid.

The above reaction can be performed typically at about −78° C. to about 120° C. for about one hour to about two days.

The reaction can be easily performed by, for example, using methods described in the following literature or similar methods thereto.

a) Daniel Dube and Adrew A. Scholte, Tetrahedron Letters, 1999, 40, 2295-2298
b) Koich Fukase, Yoshiyuki Fukase, Masato Oikawa, Wen-Chi Liu, Yasuo, Suda, and Shoichi Kusumoto, Tetrahedron, 1998, 54, 4033-4050 c) Seung Hwan Lee, Yong Lune Park, and Cheol Min Yoon, Tetrahedron Letters, 1999, 40, 6049-6050 d) Makoto Wada, Sonoe Nagayama, Kaori Mizurtani, Ryoichi Hiroi, and Norikazu Miyoshi, Chemistry Letters, 2002, 248-249 e) Kikkugawa, Y., Ogawa, Y., Chem. Pharm. Bull., 1979, 27, 2405-2410

Preparation of Compound I (1)

Compound (XI) can be converted into compound I in accordance with the method for converting a 2-(phenylamino)-5-vinylbenzoic acid derivative (V) into a hydroxamic acid derivative (VII) described above.

More specifically, compound I can be obtained by reacting compound (XI) with a hydroxylamine derivative (VI) represented by $NH_2OR_4$ in an appropriate solvent in the presence of a peptide condensing agent and in the presence or the absence of a base.

The above solvent include dichloromethane, THF, and dimethylformamide, and preferably dichloromethane.

The above base include triethylamine, Hunig's base, or DBU, and preferably Hunig's base.

The above peptide condensing agent include 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

Reaction Process 3

Reaction process 3 is an example process for preparing, from compound (XII), compounds (I-a) and (I-b), in particular among compounds I represented by the formula (1).

Compound (XII) is one of compound I where $R_1$ is a halogen atom such as iodine atom, bromine atom, or chlorine atom, and preferably iodine atom.

In compounds (I-a) and (I-b), $R_1$ is an alkynyl group or an alkenyl group; an unsaturated bond is present between a carbon directly bound to a benzene ring containing $R_2$ and an adjacent carbon thereto. $R_h$ to $R_k$ represent substituents on the carbon atoms that are connected by an unsaturated bond. Rh, Ri, Rj, Rk independently represent a hydrogen atom or a $C_{1-6}$ alkyl group.

Preparation of Compound (I-a)

Compound (XII) can be converted into compound (I-a) using, for example, Sonogashira method described in literature (K. Sonogashira, Y Tohda and N. Hagihara, Tetrahedron Lett. 16, 4467-4470 (1975)). Specifically, compound (1-a) can be obtained by reacting compound (XII) with alkyne in an appropriate solvent, e.g., THF, in the presence of a catalytic amount of palladium complex, e.g., $(PPh_3)_2PdCl_2$, as well as a catalytic amount of a copper reagent, e.g., copper iodide, and an appropriate base, e.g., triethylamine or Hunig's base.

The above reaction can be performed typically at about 10° C. to about 100° C., preferably about 40° C. to 60° C. for about two hours to about two days.

Preparation of Compound (I-b) (1)

Compound (XII) can be converted into compound (I-b) in accordance with the method for converting a 5-iodinated, 5-brominated benzoic acid derivative (II) into a 5-vinylbenzoic acid derivative (III) shown in reaction process 1.

More specifically, compound (I-b) can be obtained by reacting compound (XII) with a vinylated organic metal reagent in an appropriate solvent in the presence of a transition metal catalyst. The above solvent includes dimethylformamide, THF, DMSO, isopropanol, methanol, and ethanol, and preferably THF or isopropanol. The above transition metal catalyst includes, for example palladium complex, and specifically $Pd(PPh_3)_4$, $(PhCN)_2PdCl_2$, $(MeCN)_2PdCl_2$, or $(PPh_3)_2PdCl_2$. The above vinylated organic metal reagent includes, for example, vinylated organic magnesium, vinylated organic aluminum, vinylated organic silicon, vinylated organic boron, vinylated organic zinc, and vinylated organic tin. Preferable examples include vinyl organic tin (Stille's method) or vinyl borate (Suzuki's method). If necessary, it is possible to add an appropriate base such as triethylamine, t-butylamine, or Hunig's base in the reaction system.

The above reaction can be performed typically at about 15° C. to about 130° C., preferably about 60° C. for about four hours to about four days, preferably about 10 hours.

The reaction can be easily performed with reference to the following literature:

a) J. K. Stille, Angew. Chem., Int. Ed. Engl. 1986, 25, 508-524.

b) N. Miyaura, A. Suzuki, Chem. Rev. 1995, 95, 2457-2483 c) A. Suzuki, J. Organomet. Chem., 1999, 576, 147-168.

d) Suzuki, A, In Metal-Catalyzed Cross Coupling Reactions; Diederich, F., Stang, P. J., Eds.; VCH: Weinheim, 1998; pp 49-97.

Preparation of Compound (I-b) (2)

Compound (I-b) can also be obtained by reducing compound (I-a). A reducing method includes, for example, a method of hydrogenating in a solvent in the presence of Lindler catalyst. The above solvent includes ethanol, methanol, and hexane. The reaction can be performed typically at about 10° C. to about 30° C., preferably about 22° C. (room temperature) for about 10 minutes to about two days.

Reaction Process 4

Reaction process 4 is an example process for preparing compound I represented by the formula (1), particularly compound (I-c) having Y=O (oxygen atom) and W=OH, from compound (X) or (VIII).

Preparation of Compound (XIV)

An acetal compound (XIV) can be prepared by reacting carbonyl compound (X) with a diol (XIII) in an appropriate solvent in the presence of an acid in a catalytic amount.

The above solvent includes THF, DMF, and dichloromethane.

The above acid includes p-toluene sulfonic acid, camphor sulfonic acid, hydrochloric acid, and pyridinium-p-toluenesulfonic acid.

The reaction can be performed typically at about 10° C. to about 30° C., preferably about 22° C. (room temperature) for about one hour to about two days.

Preparation of Compound (XV)

Carboxylic acid (XIV) can be converted into hydroxamate ester (XV) in accordance with the method for converting a 2-(phenylamino)-5-vinylbenzoic acid derivative (V) into a hydroxamic acid derivative (VII) described above.

More specifically, compound (XV) can be obtained by reacting compound (XIV) with a hydroxylamine derivative (VI) represented by $NH_2OR_4$ in an appropriate solvent in the presence of a peptide condensing agent and in the presence or the absence of a base.

The above solvent includes dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferably, the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt) can be included.

The above reaction can be performed typically at about 10° C. to about 30° C., preferably about 22° C. (room temperature) for about one hour to about two days, preferably about 10 hours.

An aldehyde (VIII) can be converted into a cyclic acetal (XV) by the same method as the above method for conversion of an aldehyde (X) into a cyclic acetal (XIV). More specifically, the conversion can be accomplished by reacting a carbonyl compound (VIII) with a diol (XIII) in an appropriate solvent in the presence of an acid in a catalytic amount.

The above solvent includes THF, DMF, and dichloromethane.

The above acid includes p-toluenesulfonic acid, camphor sulfonic acid, hydrochloric acid, and pyridinium-p-toluenesulfonic acid.

The reaction can be performed typically at about 10° C. to about 30° C., preferably about 22° C. (room temperature) for about one hour to about two days.

Preparation of Compound (I-c)

A cyclic acetal (XV) can be converted into compound (I-c) by reacting a cyclic acetal (XV) with an appropriate reducing agent in an appropriate solvent and if necessary in the presence of an appropriate acid.

The above solvent includes methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, hydrogen, zinc boron hydride, samarium (II) iodide, and tributyltin hydride. Preferable examples include, diisopropyl aluminum hydride, sodium boron hydride, and triethylsilane.

The above acid includes acetic acid, hydrochloric acid, trifluoroacetic acid, trifluoroboron-diethyl ether complex, trimethylsilyl triflate, $BiCl_3$, $AlCl_3$, titanium tetrachloride, trimethylsilyl chloride, trifluoromethanesulfonic acid, p-toluenesulfonic acid, and pyridinium-p-toluenesulfonic acid.

The above reaction can be performed typically at about −78° C. to about 120° C. for about one hour to about two days.

The above reaction can be performed by using methods described in the following literature or similar methods thereto.

a) E. L. Eliel, V. G. Badding, and M. N. Rerick, J. Am. Chem. Soc., 1962, 84, 2371.

b) A. R. Abdum-Nur, and C. H. Issidorides, J. Org. Chem., 1962, 27, 67.

c) L. I. Zakharkin and I. M. Khorlina, Izvest. Akad. Nauk S. S. S. R., Otd. Khim. Nauk. 1959, 2255; Chem. Abs. 1960, 54, 10837 h.

d) W. L. Howard, and J. H. Jr. Brown, J. Org. Chem., 1961, 26, 1026.

e) B. Fleming, and H. I. Bolker, Can. J. Chem. 1974, 52, 888.

f) L. I. Zakharkin, V. I. Stanko, Y A. Chapovskii, Izvest. Akad. Nauk S. S. S. R., Otd. Khim. Nauk. 1962, 1118; Chem. Abs. 1962, 981b.

g) D. A. Hove, and A. Jordan, Tetrahedron Lett., 1978, 19, 1357.

h) T. Tsunoda, M. Suzuki, and R. Noyori, Tetrahedron Lett., 1979, 20, 4679.

i) D. N. Kursanov, Z. N. Parnes, N. M. Loim, Synthesis, 1974, 633.

j) H. Kotsuki, Y. Ushio, N. Yoshimura, and M. Ochi, J. Org. Chem., 1987, 52, 2594-2596.

k) B. Bartels, and R. Hunter, J. Org. Chem., 1993, 58, 6756-6765.

l) G Adam, and D. Seebach, Synthesis, 1988, 5, 373-375.

m) B-Z. Zheng, M. Yamauchi, H. Dei, S-I. Kusaka, K. Matusui, and O. Yonemitsu, Tetrahedron Lett., 2000, 41, 6441-6446.

n) T. Ohta, T. Michibata, K. Yamada, R. Omori, I. Furukawa, Chem. Commun., 2003, 10, 1192-1193.

o) Org. Prep. Proc. Int. 1985, 17, 11.

Reaction Process 5

Reaction process 5 is an example process for preparing compound I represented by the formula (1), particularly compound (I-d) having Y=—NHO—, from compound (X) or compound (VIII).

Preparation of Compound (XVII)

An aldehyde (X) can be converted into oxime ether (XVII) by stirring an aldehyde (X) with an o-alkyl-hydroxylamine derivative (XVI) in an appropriate solvent.

The above solvent includes dichloromethane, ethanol, chloroform, THF, dimethylformamide, and diethyl ether, and preferably dichloromethane or ethanol.

Preparation of Compound (XVIII)

Compound (XVII) can be converted into hydroxamate ester (XVIII) in accordance with the method for converting a 2-(phenylamino)-5-vinylbenzoic acid derivative (V) into a hydroxamic acid derivative (VII) described above.

More specifically, hydroxamate ester (XVIII) can be obtained by reacting compound (XVII) with a hydroxylamine derivative (VI) represented by $NH_2OR_4$ in an appropriate solvent in the presence of a peptide condensing agent and in the presence or the absence of a base.

The above solvent includes dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

Compound (XVIII) can also be prepared from the aldehyde (VIII). Specifically, compound (XVIII) can be obtained by stirring an aldehyde (VIII) with an o-alkyl-hydroxylamine derivative (XVI) in an appropriate solvent.

The above solvent includes dichloromethane, ethanol, chloroform, THF, dimethylformamide, and diethyl ether, and preferably dichloromethane or ethanol.

Preparation of Compound (I-d)

Oxime ether (XVIII) can be converted into compound (I-d) by reacting oxime ether (XVIII) with an appropriate reducing agent in an appropriate solvent and if necessary in the presence of an appropriate acid.

The above solvent includes methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, zinc boron hydride, and tributyltin hydride. Preferable examples include sodium boron cyanohydride, sodium boron hydride, triethylsilane, and borane-pyridine complex.

The above acid includes acetic acid, hydrochloric acid, trifluoroacetic acid, dichloroacetic acid, trifluoroboron-diethyl ether complex, trimethylsilyl triflate, $AlCl_3$, titanium tetrachloride, and trimethylsilyl chloride. Preferable examples include dichloroacetic acid, hydrochloric acid, trifluoroacetic acid, trifluoromethanesulfonic acid, p-toluenesulfonic acid, and pyridinium-p-toluenesulfonic acid.

The above reaction can be performed typically at about −78° C. to about 120° C. for about one hour to about two days.

The reaction can be performed by using methods described in the following literature or similar methods thereto.

a) M. Kawase, and Y. Kikugawa, J. Chem. Soc. Perkin Trans. 1, 1979, 643-645.
b) B. Hegedues, and A. F. Krasso, Helv. Chim. Acta, 1970, 53, 959-963.
c) R. F. Borch, et al, J. Am. Chem. Soc., 1971, 93, 2897-2904.
d) D D. Sternbach, W. C. L. Jamison, Tetrahedron Lett., 1981, 22, 3331-3334.
e) M. Ueda, H. Miyabe, M. Namba, T. Nakabayashi, and T. Naito, Tetrahedron Lett., 2002, 43, 4369-4372.
f) M. Gustafsson, R. Olsson, C-M. Andersson, Tetrahedron Lett., 2001, 42, 133-136.
g) M. Fujita, H. Oishi, T. Hiyama, Chem. Lett., 1986, 837-838.
h) R. Camehn, K. Rehse, Arch. Pharma. (Weinheim Ger.), 2000, 333, 130-134.

Reaction Process 6

Reaction process 6 is an example process for preparing compound I represented by the formula (1), particularly compound (I-e) having $Y=-NR_8O-$ and $R=C(=O)R_9$, from compound (I-d) or compound (XVII).

Preparation of Compound (I-E) from Compound (I-D)

Compound (I-e) can be prepared from compound (I-d) by making carboxylic acid (XXI) represented by $R_9-COOH$ into an active ester with an appropriate peptide condensing agent in an appropriate solvent, and reacting the ester with compound (I-d) in the presence or the absence of an appropriate base.

The above solvent includes dichloromethane, THF, and dimethylformamide.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 0° C. to about 30° C., preferably about 22° C. (room temperature) for about one hour to about two days, preferably about 10 hours.

Compound (I-e) can be prepared from compound (XVII).

Preparation of Compound (XIX)

Oxime ether (XVII) can be converted into a reduced compound (XIX) thereof in accordance with the method for converting a oxime (XVIII) into compound (I-d) described above.

Specifically, the conversion can be accomplished by reacting oxime ether (XVII) with an appropriate reducing agent in an appropriate solvent and if necessary in the presence of an appropriate acid.

The above solvent includes methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, zinc boron hydride, and tributyltin hydride. Preferable examples include sodium boron cyanohydride, sodium boron hydride, triethylsilane, and borane-pyridine complex.

The above acid includes acetic acid, hydrochloric acid, trifluoroacetic acid, dichloroacetic acid, trifluoroboron-diethyl ether complex, trimethylsilyl triflate, $AlCl_3$, titanium tetrachloride, and trimethylsilyl chloride. Preferable examples include dichloroacetic acid, hydrochloric acid, trifluoroacetic acid, trifluoromethanesulfonic acid, p-toluenesulfonic acid, and pyridinium-p-toluenesulfonic acid.

The above reaction can be performed typically at about −78° C. to about 120° C. for about one hour to about five days.

Preparation of Compound (XX)

An alkoxyamine (XIX) can be converted into an amide (XX) in accordance with the method for converting compound (I-d) into compound (I-e) described above.

More specifically, the preparation can be performed by making carboxylic acid (XXI) represented by $R_9-COOH$ into an active ester with an appropriate peptide condensing agent in an appropriate solvent, and reacting the ester with the amine (XIX) in the presence or the absence of an appropriate base.

The above solvent includes dichloromethane, THF, and dimethylformamide.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 0° C. to about 30° C., preferably about 22° C. (room temperature) for about one hour to about two days, preferably about 10 hours.

Preparation of Compound (I-e)

A carboxylic acid (XX) can be converted into a desired compound (I-e) in accordance with the method for converting a 2-(phenylamino)-5-vinylbenzoic acid derivative (V) into a hydroxamic acid derivative (VII) described above.

More specifically, compound (I-e) can be obtained by reacting compound (XX) with a hydroxylamine derivative (VI) represented by $NH_2OR_4$ in an appropriate solvent in the presence of a peptide condensing agent and in the presence or the absence of a base.

The above solvent includes dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

Reaction Process 7

Reaction process 7 shows a method of synthesizing compound I represented by the formula (1), particularly compound (I-g) where X is particularly represented by the following formula.

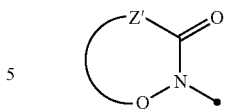

The preparation can be performed by using compounds (XXII) and (XXIII) where W is represented by C(=O)Q in an oxime ether represented by (XVII) or (XVIII) in reaction process 5. Here, Q represents —ORc, —OCORc, —NRcRd, or a halogen atom; Rc and Rd, which may be the same or different, each represent a hydrogen atom or a $C_{1-5}$ alkyl group.

Preparation of Compound (XXIV)

A carboxylic acid-oxime (XXII) can be converted into carboxylic acid-alkoxyamine (XXIV) in accordance with the method for converting an oxime (XVIII) into compound (I-d) described above.

More specifically, the conversion can be accomplished by reacting oxime ether (XVII) with an appropriate reducing agent in an appropriate solvent and if necessary in the presence of an appropriate acid.

The above solvent includes methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, zinc boron hydride, and tributyltin hydride. Preferable examples include sodium boron cyanohydride, sodium boron hydride, triethylsilane, and borane-pyridine complex.

The above acid includes acetic acid, hydrochloric acid, trifluoroacetic acid, dichloroacetic acid, trifluoroboron-diethyl ether complex, trimethylsilyl triflate, $AlCl_3$, titanium tetrachloride, trimethylsilyl chloride, trifluoromethanesulfonic acid, p-toluenesulfonic acid, and pyridinium-p-toluenesulfonic acid. Preferable examples include dichloroacetic acid, hydrochloric acid, and trifluoroacetic acid.

The above reaction can be performed typically at about −78° C. to about 120° C. for about one hour to about five days.

Preparation of Compound (XXV)

Alkoxyamine (XXIV) can be converted into a cyclized compound (XXV) by stirring in an appropriate solvent at a neutral pH or in the presence of an appropriate acid or an appropriate base at an appropriate temperature.

In some cases, during the preparation of alkoxyamine (XXIV), cyclization can be accomplished only by heating the reaction system.

The above solvent includes methanol, ethanol, diethyl ether, tetrahydrofuran, toluene, methylene chloride, and acetonitrile.

The above acid includes $AlMe_3$, acetic acid, hydrochloric acid, trifluoroacetic acid, dichloroacetic acid, trifluoroboron-diethyl ether complex, trimethylsilyl triflate, $AlCl_3$, titanium tetrachloride, trimethylsilyl chloride, trifluoromethanesulfonic acid, p-toluenesulfonic acid, and pyridinium-p-toluenesulfonic acid.

The above base includes triethylamine, Hunig's base, DBU, sodium methylate, and potassium carbonate.

The above reaction can be performed typically at room temperature to about 80° C. for about one hour to about one day.

Preparation of Compound (I-g)

Compound (XXV) can be converted into compound (I-g) in accordance with the method for converting a 2-(phenylamino)-5-vinylbenzoic acid derivative (V) into a hydroxamic acid derivative (VII) described above.

More specifically, compound (I-g) can be obtained by reacting compound (XXV) with a hydroxylamine derivative (VI) represented by $NH_2OR_4$ in an appropriate solvent in the presence of a peptide condensing agent and in the presence or the absence of a base.

The above solvent includes dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

Compound (I-g) can also be obtained, by the same conversion method, from oxime (XXIII) to which hydroxamic acid ester has been already introduced.

Preparation of Compound (XXVI)

Reduction of oxime (XXIII) can be performed in accordance with the method for converting oxime (XVIII) into compound (I-d) described above.

More specifically, the conversion can be accomplished by reacting oxime ether (XVII) with an appropriate reducing agent in an appropriate solvent and if necessary an appropriate acid.

The above solvent includes methanol, ethanol, diethyl ether, tetrahydrofuran, toluene, methylene chloride, and acetonitrile.

The above reducing agent includes sodium boron hydride, sodium boron cyanohydride, triethylsilane, trimethylsilane, lithium aluminum hydride, diisopropyl aluminum hydride, borane-pyridine complex, decaborane, diborane, borane-dimethylsulfide complex, borane-THF complex, hydrogenated zinc boron, and tributyltin hydride. Preferable examples include sodium boron cyanohydride, sodium boron hydride, triethylsilane, and borane-pyridine complex.

The above acid includes acetic acid, hydrochloric acid, trifluoroacetic acid, dichloroacetic acid, trifluoroboron-diethyl ether complex, trimethylsilyl triflate, $AlCl_3$, titanium tetrachloride, trimethylsilyl chloride, trifluoromethanesulfonic acid, p-toluenesulfonic acid, and pyridinium-p-toluenesulfonic acid. Preferable examples include dichloroacetic acid, hydrochloric acid, and trifluoroacetic acid.

The above reaction can be performed typically at about −78° C. to about 120° C. for about one hour to about five days.

Preparation of Compound (I-g)

A cyclized compound (XXVI) can be converted into compound (I-g) in accordance with the method for converting alkoxyamine (XXIV) into a cyclized compound (XXV) described above.

More specifically, the conversion can be accomplished by stirring in an appropriate solvent at a neutral pH or in the presence of an appropriate acid or an appropriate base at an appropriate temperature.

In some cases, during the preparation of alkoxyamine (XXIV), cyclization can be accomplished only by heating the reaction system. The cyclization can also be accomplished in the presence of an acid catalyst without the addition of a condensing agent when Q is OH in the above alkoxyamine (XXVI).

The above solvent includes methanol, ethanol, diethyl ether, tetrahydrofuran, toluene, methylene chloride, and acetonitrile.

The above acid includes $AlMe_3$, acetic acid, hydrochloric acid, trifluoroacetic acid, dichloroacetic acid, trifluoroboron-diethyl ether complex, trimethylsilyl triflate, $AlCl_3$, titanium tetrachloride, trimethylsilyl chloride, trifluoromethanesulfonic acid, p-toluenesulfonic acid, and pyridinium-p-toluenesulfonic acid.

The above base includes triethylamine, Hunig's base, DBU, sodium methylate, and potassium carbonate.

The above reaction can be performed typically at room temperature to about 80° C. for about one hour to about one day.

In particular, when Q is OH, compound (I-g) can be obtained by treating compound (XXVI) with a peptide condensing agent in the presence or the absence of a base and in an appropriate solvent.

The above solvent includes dichloromethane, THF, and dimethylformamide, and preferably dichloromethane.

The above base includes triethylamine, Hunig's base, or DBU, and preferably Hunig's base.

The above peptide condensing agent includes 1,3-dicyclohexylcarbodiimide (DCC), 2-ethoxy-1-ethoxycarbonyl-1,2-dihydroquinoline (EEDQ), bromo-tris(pyrrolidino)-phosphonium hexafluorophosphate (PyBrOP), 1-ethyl-3-(3'-dimethylaminopropyl)carbodiimide (EDC), (benzotriazolyloxy)tripyrrolidino-phosphonium hexafluorophosphate (PyBOP), 3-hydroxy-4-oxo-3,4-dihydro-1,2,3-benzotriazine (HODhBt), and hydroxybenzotriazole (HOBt). Preferable examples include the combination of 1-ethyl-3-(3'-dimethylaminopropyl)carbodiimide (EDC) with N-hydroxybenzotriazole (HOBt), and the combination of 1-ethyl-3-(3'-dimethylaminopropyl)carbodiimide (EDC) with 3-hydroxy-4-oxo-3,4-dihydro-1,2,3-benzotriazine (HODhBt).

The above reaction can be performed typically at about 10° C. to about 30° C., preferably about 22° C. (room temperature) for about one hour to about two days, preferably about 10 hours.

As in the above, examples of methods for producing compound I according to the present invention have been described. Isolation and purification of desired compounds shown in reaction processes 1 to 7 above can be performed by applying standard chemical manipulations such as extraction, concentration, evaporation, crystallization, filtration, recrystallization, and various chromatographic operations.

The compounds of the present invention and pharmaceutically acceptable salts thereof include all stereoisomers of compound I represented by the formula (1) (e.g., enantiomers, diastereomers (including cis and trans geometric isomers)), racemic bodies of the above isomers and mixtures thereof. Particularly, in the present invention, compound I includes stereoisomers.

The compounds of the present invention and pharmaceutically acceptable salts thereof can be in some tautomer forms, e.g., enol and imine forms, keto and enamine forms, and mixture thereof. The tautomers are present as a mixture of a tautomer set in a solution. In a solid form, typically one tautomer is dominant. One tautomer is sometimes described, but all tautomers of the compounds of the present invention are included in the present invention.

Furthermore, the present invention includes atropisomers. The atropisomer means compound I represented by the formula (1), which can be divided into isomers whose rotation is limited.

These isomers can be isolated by standard methods utilizing physicochemical difference between the isomers. For example, a racemic compound can be made into a sterically purified isomer by a general optical resolution, e.g., the optical resolution method by leading to a diastereomer salt with an optically active acid such as tartaric acid. A mixture of diastereomers can be separated using fractional crystallization or various chromatographic operations (e.g., thin layer chromatography, column chromatography, gas chromatography and such).

When compound I according to the present invention is obtained as a free compound, it is possible to convert it into a salt which the above compound I may form, or a hydrate or a solvate thereof in accordance with standard methods.

When compound I according to the present invention is obtained as a salt, a hydrate or a solvate of compound I, it is possible to convert it into compound I in a free form in accordance with standard methods.

Compound I of the present invention or pharmaceutically acceptable salts thereof have a strong MEK inhibitory effect, are excellent in stability in vivo and solubility in water, and are useful as preventing agents or therapeutic agents for proliferative diseases.

Compound I of the present invention or pharmaceutically acceptable salts thereof are particularly useful as preventing agents or therapeutic agents for cancers and joint disorders with inflammation.

The cancers include, for example, breast cancer, lung cancer, colorectal cancer, prostate cancer, liver cancer, ovarian cancer, uterine cancer, and pancreatic cancer. The joint disorders with inflammation include, for example, osteoarthritis, rheumatoid arthritis, reactive arthritis, viral arthritis, purulent arthritis, and tuberculous arthritis.

Furthermore, they are useful as preventing agents or therapeutic agents (especially, therapeutic agents) for other various cancers such as brain cancer acute leukemia, stomach cancer and non-small cell lung cancer, and diseases such as psoriasis, restenosis, autoimmune diseases, and atherosclerosis, as well as sequelae of heart failure, heterograft rejection, osteoarthritis, chronic rheumatoid arthritis, asthma, cystic fibrosis, hepatomegalia, cardiac hypertrophy, Alzheimer disease, diabetes, septic shock, and HIV infection.

They are particularly useful as preventing agents or therapeutic agents (especially, therapeutic agents) for cancers depending on the Ras-MAPK signaling pathway.

Furthermore, the present invention relates to methods for preventing or treating proliferative diseases, e.g., cancers or joint diseases with inflammation. Another embodiment of the present invention includes methods for preventing or treating solid or hematopoietic MEK-related (including Ras-related) cancers or joint diseases with inflammation. Examples of the cancers are the same as the above. Examples of the other cancer and disease are the same as the above.

These methods include a step of administering a pharmaceutically effective dose of a pharmaceutical composition comprising compound I disclosed herein or a pharmaceutically acceptable salt thereof to a patient in need of such a treatment or with such a disease or condition.

When the pharmaceutical compositions of the present invention are used as an MEK inhibitor, therapeutic agents or preventing agents for the proliferative diseases, administration methods thereof include oral, rectal, parenteral (intravenous, intramuscular, subcutaneous), intracisternal, intravaginal, intraperitoneal, intrabladder, topical (infusion, powder medicine, ointment, gel or cream) administrations and inhalation (oral or nasal spray). Dosage forms thereof include, for example, tablets, capsules, granules, powder, pills, aqueous and non-aqueous oral solutions and suspensions, and parenteral solutions filled in containers which adapt for dispensing an individual dosage. The dosage form can also be adapted to various administration methods which comprise controlled release formulations such as subcutaneous implant.

The above formulations are produced by well-known methods using additives such as an excipient, a lubricant (coating agent), a binder, a disintegrating agent, a stabilizer, a taste masking/flavoring agent, and a diluting agent.

For example, the excipient includes lactose, crystalline cellulose, calcium hydrogenphosphate, and starches such as starch, potato starch, and corn starch.

The coating agent includes, for example, ethylcellulose, hydroxypropylcellulose, hydroxypropylmethylcellulose, shellac, talc, carnauba wax, and paraffin.

The binder includes, for example, polyvinyl pyrrolidone, macrogol, and the same compounds as in the above excipients.

The disintegrating agent includes, for example, the same compounds as in the above excipients, and chemically modified starches and celluloses such as cross carmellose sodium, sodium carboxymethylstarch, and crosslinked polyvinyl pyrrolidone.

The stabilizer includes, for example, paraoxybenzoic acid esters such as methylparaben and propylparaben; alcohols such as chlorobutanol, benzyl alcohol and phenylethyl alcohol; benzalkonium chloride; phenols such as phenol and cresol; thimerosal; dehydroacetic acid; and sorbic acid.

The taste masking/flavoring agent includes, for example, sweeteners, acidifiers and flavors usually used.

As solvents for producing liquid formulations, it is possible to use ethanol, phenol, chlorocresol, purified water, distilled water and such.

A surfactant or an emulsifier includes, for example, polysorbate 80, polyoxyl stearate 40, and lauromacrogol.

When the pharmaceutical compositions of the present invention are used as a MEK inhibitor, or therapeutic agents or preventing agents for proliferative diseases, amounts of the compounds of the present invention and pharmaceutically acceptable salts thereof to be used vary depending on condition, age, body weight, relative health state, presence of other medicaments, administration method and such. For example, for a patient (warm-blooded animal, especially human), in the case of an oral agent, an effective amount is preferably 0.1 to 1000 mg, more preferably 1 to 300 mg per kg of body weight per day, and an amount to be used per day is preferably in the range of 10 to 800 mg for an adult patient with usual body weight as an active ingredient (compound I). In the case of a parenteral agent, an effective amount is preferably 0.1 to 1000 mg, and more preferably 10 to 800 mg per kg of body weight per day. It is desirable to administer this once a day or by dividing into several times a day depending on the condition.

The above pharmaceutical compositions of the present invention can be used in combination with the other radiation therapy, chemotherapy and administration of an angiogenesis inhibitor.

The compounds according to the present invention and the pharmaceutically acceptable salts thereof have a MEK inhibitory effect, a cell growth inhibitory effect, are excellent in stability in vivo and solubility in water, and are useful as preventing agents or therapeutic agents for proliferative diseases, e.g., cancers and joint diseases with inflammation.

Any patents, published patent applications, and publications cited herein are incorporated by reference.

DETAILED DESCRIPTION

Figure 1:
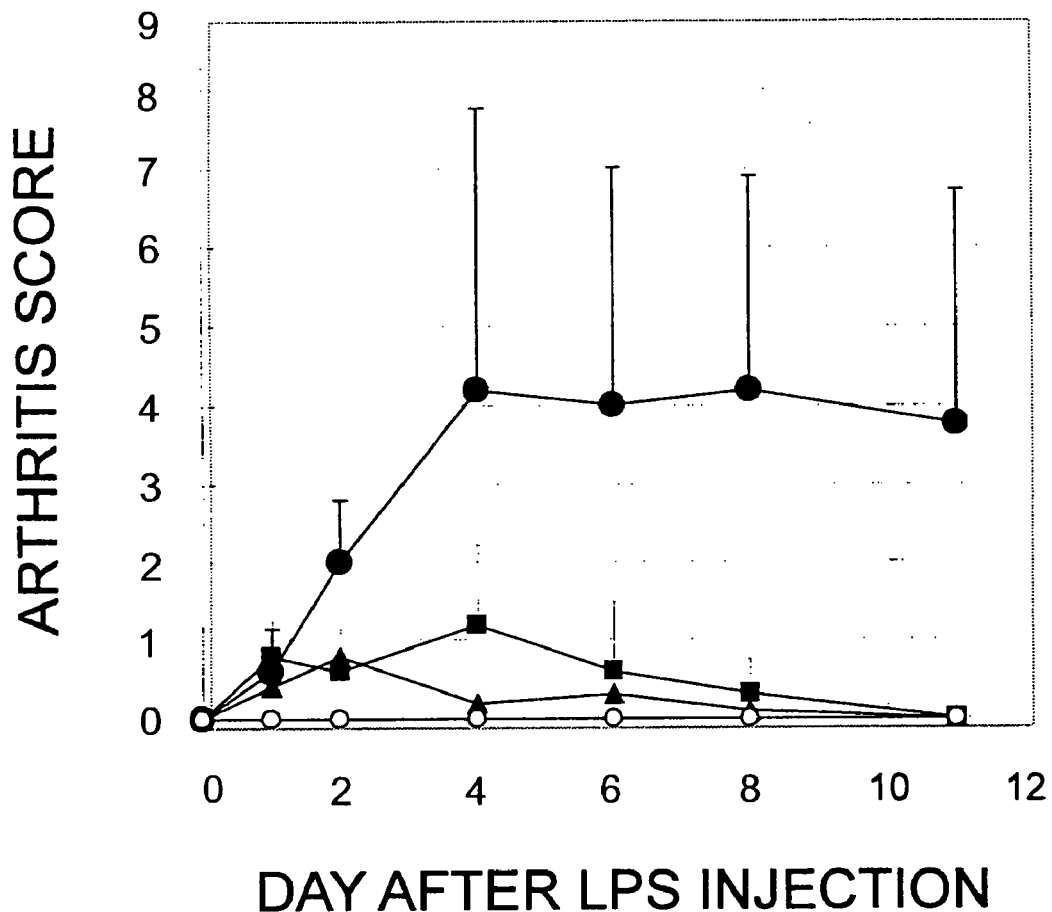
FIG. 1 is a graph showing the inhibitory effect on the development of arthritis in terms of the relation between arthritis score (Y axis) and days after LPS administration (X axis). (Test Example 6).

The present invention is illustrated in more detail below with reference to Examples. However, the present invention is not to be construed as being limited thereto.

NMR analyses were performed on JNM-EX270 (270 MHz, JEOL) or JNM-GSX400 (400 MHz, JEOL), and the NMR data are expressed as ppm (parts per million, δ) referencing the deuterium lock signal from the sample solvent.

Mass spectral data were obtained using JMS-DX303 (JEOL) or JMS-SX/SX102A (JEOL), or a micromass spectrometer (Navigator, Finnigan) equipped with a gradient high performance liquid chromatography (Agilent 1100, Agilent Technologies).

Specific rotation was measured using sodium D line (589 nm) at room temperature.

Commercially available reagents were used without further purification. Room temperature represents a range from about 20 to about 25° C. All the non-aqueous reactions were carried out under a nitrogen atmosphere. Concentration or evaporation of the solvent under reduced pressure was done using a rotary evaporator.

In the preparation of a compound, functional groups were protected with protecting groups as needed, and after having prepared the target molecule, the protecting groups were removed. The selection of the protecting groups and the procedures for protection and deprotection were done according to the methods described in, for example, Greene and Wuts, "Protective Groups in Organic Synthesis" (2nd Ed., John Wiley & Sons, 1991).

Example 1

3,4-Difluoro-2-(2-fluoro-4-iodo-phenylamino)-N-(2-hydroxy-ethoxy)-5-(2-hydroxy-ethoxymethyl)-benzamide (Compound B-1)

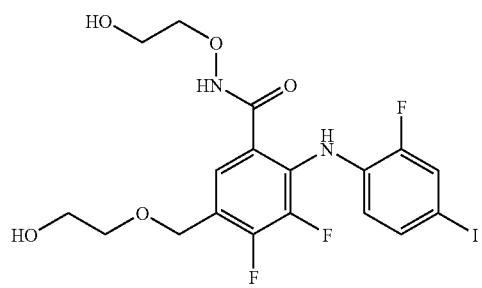

Step A

Preparation of 2,3,4-trifluoro-5-iodo-benzoic acid

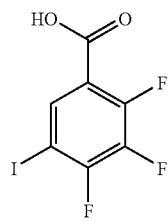

2,3,4-Trifluoro-5-iodo-benzoic acid was prepared according to the method described in literature (F. Mongin, E. Marzi, and M. Schlosser, European Journal of Organic Chemistry, 2771-2777 (2001)).

Step B

Preparation of 2,3,4-trifluoro-5-vinyl-benzoic acid

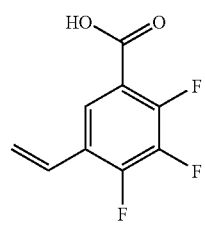

To a solution of 2,3,4-trifluoro-5-iodo-benzoic acid (447 mg, 1.48 mmol) prepared in Step A in tetrahydrofuran (10 mL) were added tris(dibenzylideneacetone)dipalladium (45 mg, 0.05 mmol, product No. 32877-4, Aldrich), tri-2-furylphosphine (23 mg, 0.01 mmol), and vinyltributyltin (865 μL, 3.0 mmol) under an argon atmosphere, and the mixture was stirred at 40° C. for 3 hours.

After completion of the reaction, insoluble matter was removed through a celite column. One mol/L sodium hydroxide solution (30 mL), and then methylene chloride were added to the reaction solution, and the layers were separated. Another 1 mol/L sodium hydroxide solution (30 mL) was added to the organic layer, and the layers were separated. One mol/L hydrochloric acid solution (60 mL) was added to acidify the resultant aqueous layer, and the aqueous layer was extracted twice with methylene chloride (50 mL). The resultant organic layer was dried over anhydrous sodium sulfate and filtered. The solvent was evaporated under reduced pressure, and the residue was washed with hexane, filtered, and dried to give 2,3,4-trifluoro-5-vinyl-benzoic acid (248.9 mg, 83% yield) as a pale yellow solid.

$^1$H-NMR (CDCl$_3$, 270 MHz) δ(PPM): 5.54 (1H, d, J=11.2 Hz), 5.92 (1H, d, J=17.8 Hz), 6.78 (1H, dd, J=17.8, 11.2 Hz), 7.95 (1H, td, J=7.6, 2.6 Hz)

EIMS m/z 202 (M+H)

Step C

Preparation of 3,4-difluoro-2-(2-fluoro-4-iodo-phenylamino)-5-vinyl-benzoic acid

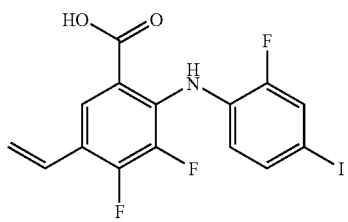

To a solution of 2-fluoro-4-iodoaniline (5.056 g, 21.336 mmol) in tetrahydrofuran (anhydrous, 30 mL) was added dropwise 2.0 M lithium diisopropylamide (a solution in heptane/tetrahydrofuran/ethylbenzene, 13 mL, 26 mmol) with stirring at −78° C. under an argon atmosphere.

After 5 minutes, a solution of 2,3,4-trifluoro-5-vinyl-benzoic acid (1.724 g, 8.534 mmol) prepared in Step B in tetrahydrofuran (anhydrous, 20 mL) was added dropwise to the reaction mixture. The reaction mixture was warmed gradually to room temperature, and stirred for 3 days.

One mol/L hydrochloric acid solution was added to the reaction mixture to bring pH to 3. Then, the solution was extracted with ethyl acetate. The extract was washed sequentially with water and saturated brine, and the organic layer was dried over anhydrous sodium sulfate and filtered. The solvent was evaporated under reduced pressure, and the resultant dark brown solid was triturated with methylene chloride to give 3,4-difluoro-2-(2-fluoro-4-iodo-phenylamino)-5-vinyl-benzoic acid (2.352 g, 66% yield) as a pale yellow solid.

$^1$H-NMR (CD$_3$OD, 270 MHz) δ(PPM): 5.41 (1H, d, J=11.5 Hz), 5.86 (1H, d, J=17.2 Hz), 6.76 (1H, td, J=8.6, 5.6 Hz), 6.79 (1H, dd, J=17.2, 11.5 Hz), 7.41 (1H, m), 7.48 (1H, dd, J=10.6, 2.0 Hz), 8.05 (1H, dd, 7.9, 2.0 Hz)

ESI (LC/MS positive mode) m/z 420 (M+H)

Step D

Preparation of N-[2-(tert-butyldimethylsilanyloxy)-ethoxy]-3,4-difluoro-2-(2-fluoro-4-iodophenylamino)-5-vinyl-benzamide

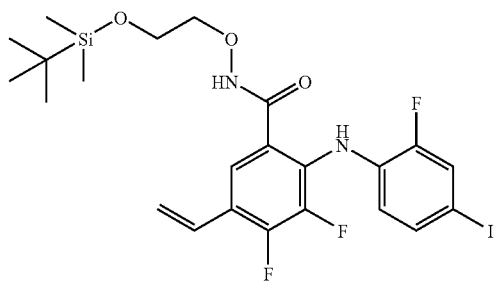

To a solution of 3,4-difluoro-2-(2-fluoro-4-iodo-phenylamino)-5-vinyl-benzoic acid (6.2 g, 14.8 mmol) prepared in Step C in methylene chloride (100 ml) were added O-[2-(tert-butyldimethylsilanyloxy)-ethyl]-hydroxylamine (3.40 g, 17.8 mmol), 1-ethyl-3-(3-dimethylaminopropyl)-carbodiimide hydrochloride (3.40 g, 17.8 mmol), 1-hydroxybenzotriazole monohydrate (3.0 g, 22.1 mmol), and N,N-diisopropylethylamine (5.1 ml, 29.6 mmol), and the mixture was stirred at room temperature for 20 hours.

The reaction mixture was concentrated under reduced pressure, and water (300 ml) was added thereto. The mixture was extracted with ethyl acetate (500 ml), and the organic layer was washed with saturated brine (200 ml), dried over anhydrous sodium sulfate, and concentrated under reduced pressure. The residue was purified by silica gel column chromatography (500 g, n-hexane/ethyl acetate (20:1)) to give N-[2-(tert-butyldimethylsilanyloxy)ethoxy]-3,4-difluoro-2-(2-fluoro-4-iodophenylamino)-5-vinylbenzamide (6.36 g, 73%) as a pale yellow solid.

$^1$H-NMR (CD$_3$OD, 270 MHz) δ(PPM) 0.07 (6H, s), 0.86 (9H, s), 3.91 (2H, dd, J=5.0, 4.0 Hz), 4.07 (2H, dd, J=5.0, 4.0 Hz), 5.44 (1H, d, J=11.2 Hz), 5.81 (1H, d, J=17.5 Hz), 6.57 (1H, td, J=8.9, 5.0 Hz), 6.74 (1H, dd, J=17.8, 10.9 Hz), 7.32 (1H, br. d, J=7.9 Hz), 7.37-7.42 (2H, m), 8.20 (1H, br. s), 9.38 (1H, br. s)

ESI (LC/MS positive mode) m/z 593 (M+H)

Step E

Preparation of N-[2-(tert-butyldimethylsilanyloxy)-ethoxy]-3,4-difluoro-2-(2-fluoro-4-iodophenylamino)-5-formyl-benzamide

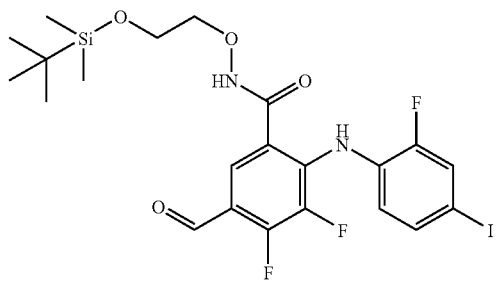

N-[2-(Tert-butyldimethylsilanyloxy)-ethoxy]-3,4-difluoro-2-(2-fluoro-4-iodophenylamino)-5-vinyl-benzamide (27.4 g, 46.27 mmol) prepared in Step D was dissolved in a mixed solvent of tetrahydrofuran (300 ml) and water (90 ml). To this solution, an aqueous solution of osmium tetroxide (0.1 mM, 9.25 ml, 0.95 mmol) and sodium metaperiodate (38.6 g, 0.180 mol) were added at 0° C., and the mixture was stirred at room temperature for 3 hours.

Insoluble matter was removed by celite filtration, and washed with ethyl acetate. The combined filtrate and washing were washed with an aqueous solution of 0.2 M sodium thiosulfate and saturated brine, dried over magnesium sulfate, and evaporated under reduced pressure to give a mixture (37.1 g) of N-[2-(tert-butyldimethylsilanyloxy)-ethoxy]-3,4-difluoro-2-(2-fluoro-4-iodophenylamino)-5-formyl-benzamide and a desilylated product, 3,4-difluoro-2-(2-fluoro-4-iodophenylamino)-5-formyl-N-(2-hydroxy-ethoxy)-benzamide (the same compound as the product in the next step). (Pure N-[2-(tert-butyldimethylsilanyloxy)-ethoxy]-3,4-difluoro-2-(2-fluoro-4-iodophenylamino)-5-formyl-benzamide can be obtained by purification with silica gel chromatography (300 g, n-hexane/ethyl acetate (5:1)).

$^1$H-NMR (CD$_3$OD, 270 MHz) δ(PPM) 0.11 (6H, s), 0.78 (9H, s), 3.97 (2H, dd, J=5.1, 4.3 Hz), 4.13 (2H, dd, J=4.6, 4.3 Hz), 6.82 (1H, td, J=8.6, 4.1 Hz), 7.30-7.38 (2H, m), 7.78 (1H, dd, J=6.8, 2.2 Hz), 9.64 (2H, br s), 10.15 (1H, s)

ESI (LC/MS positive mode) m/z 595 (M+H)

Step F

Preparation of 3,4-difluoro-2-(2-fluoro-4-iodo-phenylamino)-5-formyl-N-(2-hydroxy-ethoxy)-benzamide

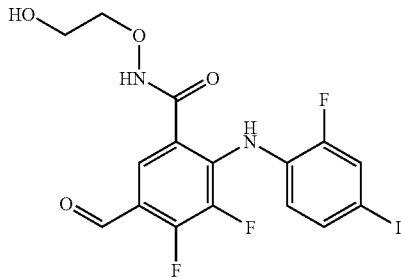

N-[2-(Tert-butyldimethylsilanyloxy)-ethoxy]-3,4-difluoro-2-(2-fluoro-4-iodophenylamino)-5-formyl-benzamide (37.1 g as a crude product containing the desilylated product) prepared in Step E was dissolved in a mixed solvent of tetrahydrofuran (200 ml) and water (16 ml). To this solution, p-toluenesulfonic acid monohydrate (1.76 g, 9.25 mmol) was added, and the mixture was stirred at room temperature for 12 hours. The reaction mixture was extracted with ethyl acetate, and the organic layer was washed with saturated brine, dried over magnesium sulfate, and evaporated under reduced pressure. The resultant residue was triturated with ethyl acetate to give 3,4-difluoro-2-(2-fluoro-4-iodo-phenylamino)-5-formyl-N-(2-hydroxy-ethoxy)-benzamide (16.0 g, 72% yield in two steps) as a yellow solid.

$^1$H-NMR (DMSO-d$_6$ 270 MHz) δ(PPM) 3.17 (1H, d, J=4.6 Hz), 3.59 (2H, t, J=4.6 Hz), 3.85 (2H, t, J=4.6 Hz), 6.99 (1H, td, J=8.9, 3.0), 7.48 (1H, d=8.3 Hz), 7.67 (1H, d, J=10.9 Hz), 7.86 (1H, d, J=6.9 Hz), 9.64 (1H, br.s), 10.02 (1H, s)

ESI (LC/MS positive mode) m/z 481 (M+H)

Step G

Preparation of 5-[1,3]dioxolan-2-yl-3,4-difluoro-2-(2-fluoro-4-iodo-phenylamino)-N-(2-hydroxy-ethoxy)-benzamide

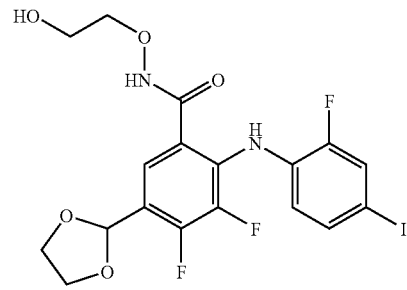

To a solution of 3,4-difluoro-2-(2-fluoro-4-iodo-phenylamino)-5-formyl-N-(2-hydroxy-ethoxy)-benzamide (15.99 g, 33.3 mmol) prepared in Step F in anhydrous THF (150 ml) were added ethylene glycol (70 ml) and p-toluenesulfonic acid monohydrate (316.6 mg, 1.66 mmol) at room temperature, and the mixture was stirred for 14 hours. Then ethylene glycol (100 ml) was added, and the reaction mixture was stirred for additional 8 hours. The reaction mixture was poured into saturated aqueous sodium bicarbonate, and extracted with ethyl acetate. The organic layer was washed with saturated aqueous sodium bicarbonate and saturated brine, dried over magnesium sulfate, and concentrated under reduced pressure to give 5-[1,3]dioxolan-2-yl-3,4-difluoro-2-(2-fluoro-4-iodo-phenylamino)-N-(2-hydroxy-ethoxy)-benzamide (21.69 g) as a crude product.

$^1$H-NMR (CDCl$_3$, 270 MHz) δ(PPM) 3.76 (1H, br. s, OH), 4.04~4.23 (8H, m), 6.00 (1H, s), 6.60 (1H, td, J=8.6, 4.3 Hz), 7.33 (1H, dt, J=6.9, 1.3 Hz), 7.42 (1H, dd, J=9.9, 1.7 Hz), 7.52 (1H, br. d, J=6.9 Hz), 8.32 (1H, br. s), 9.09 (1H, br. s)

ESI (LC/MS positive mode) m/z 525 (M+H)

Step H

Preparation of 3,4-difluoro-2-(2-fluoro-4-iodo-phenylamino)-N-(2-hydroxy-ethoxymethyl)-benzamide

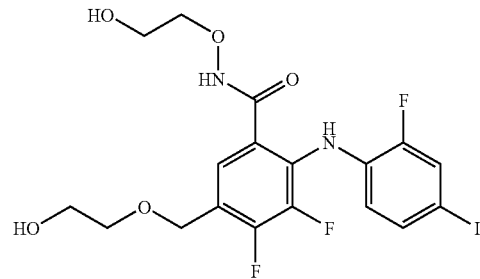

To a solution of 5-[1,3]dioxolan-2-yl-3,4-difluoro-2-(2-fluoro-4-iodo-phenylamino)-N-(2-hydroxy-ethoxy)-benzamide (21.69 g) obtained in Step G in anhydrous THF (100 ml) were added sodium borohydride (4.21 g, 111.4 mmol) and trifluoroacetic acid (5.08 ml, 66.8 mmol) with ice-cooling, and the mixture was stirred at room temperature overnight. The reaction mixture was poured into saturated aqueous sodium bicarbonate, and extracted with ethyl acetate. The organic layer was washed with saturated aqueous sodium bicarbonate and saturated brine, dried over magnesium sulfate, and concentrated under reduced pressure. The residue was purified by silica gel column chromatography ($SiO_2$ 600 g, 100% AcOEt to AcOEt/MeOH (50:1 to 20:1)) to give 3,4-difluoro-2-(2-fluoro-4-iodo-phenylamino)-N-(2-hydroxy-ethoxy)-5-(2-hydroxy-ethoxymethyl)-benzamide (13.9 g, 80%) as a white powder.

$^1$H-NMR ($CD_3OD$, 270 MHz) δ(PPM) 3.51 (2H, dd, J=3.9, 3.3 Hz), 3.60~3.63 (4H, m), 3.86 (2H, dd, J=4.9, 4.3 Hz), 4.52 (2H, s), 6.50 (1H, td, J=8.6, 4.6 Hz), 7.23 (1H, ddd, J=8.6, 2.0, 1.0 Hz), 7.33 (1H, dd, J=10.9, 2.0 Hz), 7.43 (1H, dd, J=6.9, 2.0 Hz)

ESI (LC/MS positive mode) m/z 527 (M+H)

Example 2

2-(4-Ethynyl-2-fluoro-phenylamino)-3,4-difluoro-N-(2-hydroxy-ethoxy)-5-(2-hydroxy-ethoxymethyl)-benzamide (Compound B-2)

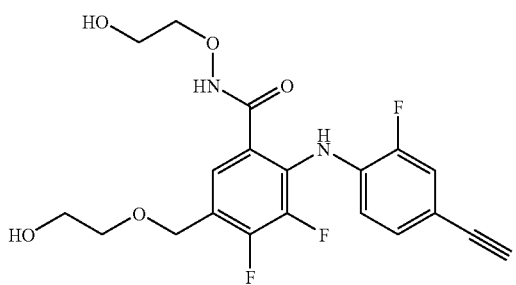

To a solution of 3,4-difluoro-2-(2-fluoro-4-iodo-phenylamino)-N-(2-hydroxy-ethoxy)-5-(2-hydroxy-ethoxymethyl)-benzamide (46.1 mg, 87.6 μmol) obtained in Step H of Example 1 in tetrahydrofuran (anhydrous, 2.0 ml) were added trimethylsilylacetylene (48.5 μL, 0.350 mmol), copper iodide (3.3 mg, 17.5 μmol), $(PPh_3)_2PdCl_2$ (3.7 mg, 5.3 μmol), and Hunig's base (diisopropylethylamine, 149 μL, 0.876 mmol), and the mixture was stirred at 50° C. for 2 hours.

The reaction mixture was concentrated under reduced pressure. 0.1 N Hydrochloric acid was added to the resultant residue, and the mixture was extracted with ethyl acetate. The organic layer was washed with 0.1 N hydrochloric acid and brine, dried over anhydrous magnesium sulfate, and concentrated under reduced pressure. The resultant residue was purified by silica gel column chromatography (Presep Silica Gel Type S (Wako Pure Chemical Industries), 10 g, $CH_2Cl_2$/MeOH (10:1)) to give 3,4-difluoro-2-(2-fluoro-4-trimethylsilanylethynyl-phenylamino)-N-(2-hydroxy-ethoxy)-5-(2-hydroxy-ethoxymethyl)-benzamide (37.6 mg, 86%).

To a solution of the resultant 3,4-difluoro-2-(2-fluoro-4-trimethylsilanylethynyl-phenylamino)-N-(2-hydroxy-ethoxy)-5-(2-hydroxy-ethoxymethyl)-benzamide (37.6 mg) in tetrahydrofuran (anhydrous, 1.0 ml) was added tetra-n-butylammonium fluoride (1 M solution in THF, 113 μL, 113 μmol) at room temperature, and the mixture was stirred for 3 hours. The reaction mixture was concentrated under reduced pressure. 0.1 N Hydrochloric acid was added to the resultant residue, and the mixture was extracted with ethyl acetate. The combined organic layers were washed with 0.1 N hydrochloric acid and saturated brine, dried over anhydrous magnesium sulfate, and concentrated under reduced pressure. The resultant residue was purified by silica gel column chromatography (Presep Silica Gel Type S (Wako Pure Chemical Industries), 10 g, $CH_2Cl_2$/MeOH (10:1 to 5:1)) to give 2-(4-ethynyl-2-fluoro-phenylamino)-3,4-difluoro-N-(2-hydroxy-ethoxy)-5-(2-hydroxy-ethoxymethyl)-benzamide (21.9 mg, 68%) as a yellow powder.

$^1$H-NMR ($CD_3OD$, 270 MHz) δ(PPM) 3.03 (1H, s), 3.66 (2H, dd, J=4.6, 3.6 Hz), 3.75 (2H, t, J=4.3 Hz), 3.83 (2H, t, J=4.3 Hz), 4.04 (2H, dd, J=4.6, 3.6 Hz), 4.58 (2H, s), 6.68 (1H, td, J=8.3, 5.6 Hz), 7.14 (d, J=8.6 Hz), 7.18 (dd, J=11.2, 1.6 Hz), 7.54 (d, J=5.3 Hz), 8.50 (1H, br. s)

ESI (LC/MS positive mode) m/z 425 (M+H)

The compounds of Examples 3 and 4 below were synthesized by preparing cyclic acetal compounds using an aldehyde, 3,4-difluoro-2-(2-fluoro-4-iodo-phenylamino)-5-formyl-N-(2-hydroxy-ethoxy)-benzamide obtained in Step F of Example 1 as a starting material, and 1,3-propanediol or 2,2-dimethyl-1,3-propanediol, respectively, instead of ethylene glycol used as a reagent in Step G of Example 1, and subjecting the acetal compounds to reducing conditions similar to those in Step H of Example 1.

Example 3

3,4-Difluoro-2-(2-fluoro-4-iodophenylamino)-N-(2-hydroxy-ethoxy)-5-(3-hydroxy-propoxymethyl)-benzamide (Compound B-6)

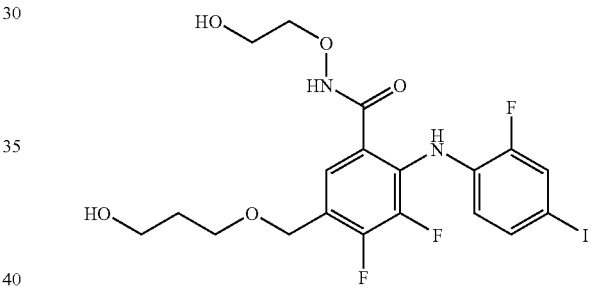

$^1$H-NMR ($CD_3OD$, 270 MHz) δ(PPM) 1.83 (2H, quin., J=6.3 Hz), 3.64 (4H, m), 3.68 (2H, m), 3.95 (2H, m), 4.57 (2H, br.s), 6.59 (1H, td, J=8.9, 4.6 Hz), 7.34 (1H, dd, J=8.6, 1.3 Hz), 7.43 (1H, dd, J=10.9, 2.0 Hz), 7.50 (1H, m)

ESI (LC/MS positive mode) m/z 541 (M+H)

Example 4

3,4-Difluoro-2-(2-fluoro-4-iodo-phenylamino)-5-(3-hydroxy-2,2-dimethyl-propoxymethyl)-N-(2-hydroxy-ethoxy)-benzamide (Compound B-7)

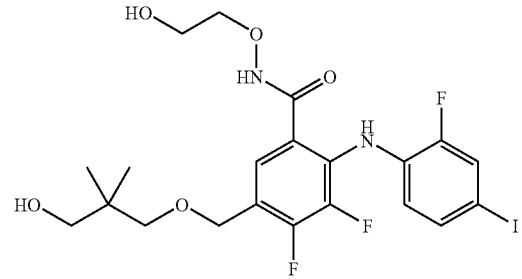

¹H-NMR (CD₃OD, 270 MHz) δ(PPM) 0.90 (6H, s), 3.37 (2H, s), 3.70 (2H, dd, J=4.9, 4.3 Hz), 3.93 (2H, dd, J=4.9, 4.3 Hz), 4.57 (2H, s), 6.60 (1H, td, J=8.9, 4.6 Hz), 7.34 (1H, d, J=8.6 Hz), 7.44 (1H, dd, J=10.6, 2.0 Hz), 7.47 (1H, m)

ESI (LC/MS positive mode) m/z 569 (M+H)

Example 5

5-(2,3-Dihydroxy-propoxymethyl)-3,4-difluoro-2-(2-fluoro-4-iodo-phenylamino)-N-(2-hydroxy-ethoxy)benzamide

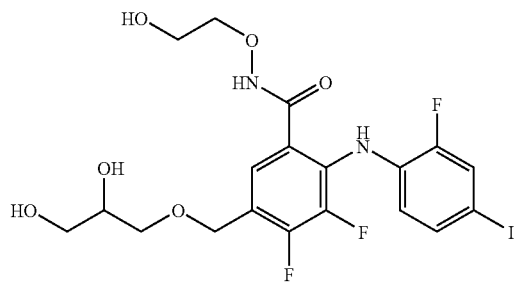

Step A

Preparation of 3,4-difluoro-2-(2-fluoro-4-iodo-phenylamino)-5-formyl-benzoic acid

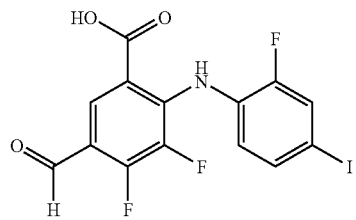

3,4-Difluoro-2-(2-fluoro-4-iodo-phenylamino)-5-vinyl-benzoic acid (200 mg, 0.477 mmol) prepared in Step C of Example 1 was dissolved in tetrahydrofuran (20 ml) and water (1 mL). To this reaction mixture, an aqueous solution of 0.1 M osmium tetroxide (1.0 mL) and sodium metaperiodate (510 mg, 2.39 mmol) were added at room temperature, and the mixture was stirred for 2 hours. Insoluble matter was removed through a celite column, and ethyl acetate extraction was performed.

The extract was washed sequentially with water and saturated brine, and the organic layer was dried over anhydrous sodium sulfate, and filtered. The solvent was evaporated under reduced pressure, and the resultant dark brown solid was triturated with methanol to give 3,4-difluoro-2-(2-fluoro-4-iodophenylamino)-5-formyl-benzoic acid (133.6 mg, 66% yield) as a pale yellow solid.

¹H-NMR (DMSO-d₆, 270 MHz) δ(PPM) 7.11 (1H, td, J=8.6, 3.6), 7.53 (1H, m), 7.71 (1H, dd, J=10.2, 1.7 Hz), 8.27 (1H, dd, J=7.3, 1.3 Hz), 10.00 (1H, s), 10.08 (1H, br.s)

ESI (LC/MS positive mode) m/z 422 (M+H)

Step B

Preparation of 5-allyloxymethyl-3,4-difluoro-2-(2-fluoro-4-iodo-phenylamino)-benzoic acid

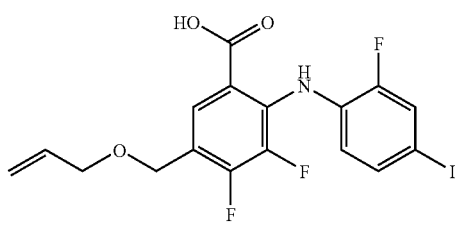

To bismuth (III) chloride (37 mg, 0.188 mmol) that was dried by heating under reduced pressure, methylene chloride (anhydrous, 3 ml suspension) was added under argon flow, and the mixture was stirred thoroughly. To this suspension, allyl alcohol (40 μL, 0.57 mmol), triethylsilane (107 μL, 0.671 mmol), and 3,4-difluoro-2-(2-fluoro-4-iodophenylamino)-5-formyl-benzoic acid (200 mg, 0.475 mmol) prepared in Step A were added at room temperature, and the mixture was stirred for a whole day and night. After completion of the reaction, the reaction mixture was extracted with ethyl acetate.

The extract was washed sequentially with water and saturated brine, and the organic layer was dried over anhydrous sodium sulfate, and filtered. The solvent was evaporated under reduced pressure, and the resultant dark brown solid was purified with Presep (Wako Pure Chemical Industries, 10 g). 5-Allyloxymethyl-3,4-difluoro-2-(2-fluoro-4-iodophenylamino)benzoic acid (140.7 mg, 64% yield) was obtained as a light brown solid from fractions eluted with 100% ethyl acetate.

¹H-NMR (CD₃OD, 270 MHz) δ(PPM) 4.08 (2H, m), 4.56 (2H, s), 5.25 (1H, d, J=10.2 Hz), 5.32 (1H, d, J=17.1 Hz), 5.92 (1H, m), 6.80 (1H, m), 7.41 (1H, d, J=10.2 Hz), 7.48 (1H, d, J=10.6 Hz), 7.96 (1H, m)

ESI (LC/MS positive mode) m/z 464 (M+H)

Step C

Preparation of 5-allyloxymethyl-N-[2-(tert-butyldimethylsilanyloxy)ethoxy]-3,4-difluoro-2-(2-fluoro-4-iodophenylamino)-benzamide

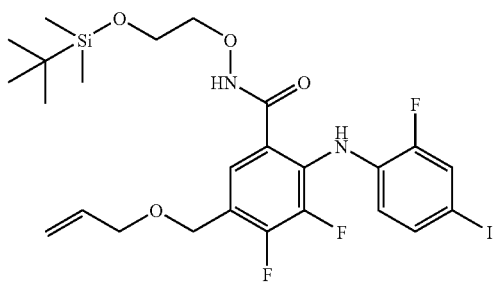

To a solution of 5-allyloxymethyl-3,4-difluoro-2-(2-fluoro-4-iodophenylamino)benzoic acid (140 mg, 0.302 mmol) prepared in Step B in N,N-dimethylformamide (anhydrous, 4 mL) were added N-hydroxysuccinimide (41 mg, 0.363 mmol) and 1-ethyl-3-(3-dimethylaminopropyl)carbodiimide hydrochloride (70 mg, 0.363 mmol) at room temperature under argon flow, and the mixture was stirred thoroughly. Subsequently, O-[2-(t-butyldimethylsilanyloxy)ethyl]-hydroxyamine (86 mg, 0.453 mmol) was added thereto, and the mixture was stirred for 2 hours. After completion of the reaction, the reaction mixture was extracted with ethyl acetate.

The extract was washed sequentially with water and saturated brine, and the organic layer was dried over anhydrous sodium sulfate, and filtered. The solvent was evaporated under reduced pressure, and the resultant brown oil was purified with Mega Bond Elut silica gel (Varian, 5 g). 5-Allyloxymethyl-N-[2-(tert-butyldimethylsilanyloxy)ethoxy]-3,4-difluoro-2-(2-fluoro-4-iodophenylamino)benzamide (35.5 mg, 18% yield) was obtained as a pale yellow oil from fractions eluted with 10% ethyl acetate/hexane.

$^1$H-NMR (CDCl$_3$, 270 MHz) δ(ppm) 0.04 (6H, s), 0.79 (9H, s), 3.83 (2H, m), 4.03 (2H, m), 4.44 (2H, s), 5.18 (1H, d, J=11.5 Hz), 5.26 (1H, m), 5.87 (1H, m), 6.48 (1H, td, J=8.6, 4.9 Hz), 7.23 (1H, d, J=8.9 Hz), 7.31 (1H, m), 7.32 (1H, m), 8.30 (1H, br.s), 9.25 (1H, br.s)

ESI (LC/MS positive mode) m/z 637 (M+H)

Step D

Preparation of 5-allyloxymethyl-3,4-difluoro-2-(2-fluoro-4-iodo-phenylamino)-N-(2-hydroxy-ethoxy)-benzamide

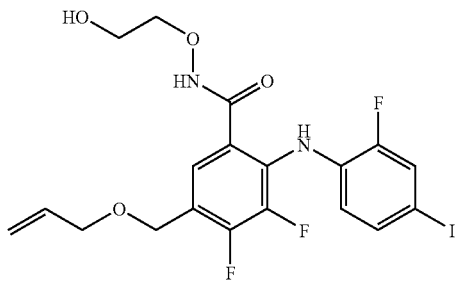

To a solution of 5-allyloxymethyl-N-[2-(tert-butyl-dimethyl-silanyloxy)-ethoxy]-3,4-difluoro-2-(2-fluoro-4-iodophenylamino)-benzamide (35.5 mg, 0.056 mmol) prepared in Step C in tetrahydrofuran (anhydrous, 4 mL) was added dropwise tetra-n-butylammonium fluoride (1 mol/L solution in tetrahydrofuran, 0.5 mL, 0.5 mmol) at room temperature, and the mixture was stirred for 4 hours.

After completion of the reaction, the solvent was evaporated under reduced pressure, and the yellow oil was extracted with ethyl acetate. The extract was washed sequentially with water and saturated brine, and the organic layer was dried over anhydrous sodium sulfate, and filtered. The solvent was evaporated under reduced pressure, and the resultant brown oil was purified by preparative TLC (60% ethyl acetate/hexane as a developing solvent) to give 5-allyloxymethyl-3,4-difluoro-2-(2-fluoro-4-iodo-phenylamino)-N-(2-hydroxyethoxy)-benzamide (11 mg, 38% yield) as a white solid.

$^1$H-NMR (CD$_3$OD, 270 MHz) δ(PPM) 3.70 (2H, dd, J=4.9, 4.3 Hz), 3.93 (2H, dd, J=4.9, 4.3 Hz), 4.09 (2H, dt, J=5.6, 1.3 Hz), 4.57 (2H, s), 5.21 (1H, ddd, J=10.2, 3.0, 1.3 Hz), 5.33 (1H, ddd, J=17.1, 4.9, 1.6 Hz), 5.96 (1H, m), 6.61 (1H, td, J=8.6, 4.3 Hz), 7.34 (1H, dt, J=8.6, 1.0 Hz), 7.45 (1H, dd, J=8.6, 2.0 Hz), 7.46 (1H, dd, J=6.9, 2.0 Hz)

ESI (LC/MS positive mode) m/z 523 (M+H)

Step E

Preparation of d,l-5-(2,3-dihydroxy-propoxymethyl)-3,4-difluoro-2-(2-fluoro-4-iodo-phenylamino)-N-(2-hydroxyethoxy)-benzamide

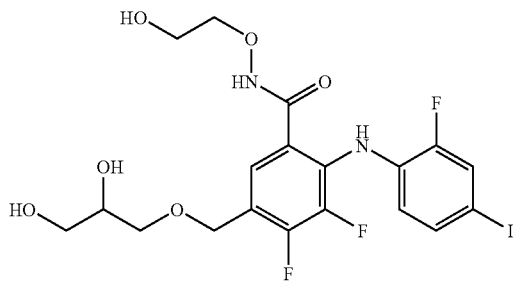

To a solution of 5-allyloxymethyl-3,4-difluoro-2-(2-fluoro-4-iodo-phenylamino)-N-(2-hydroxy-ethoxy)-benzamide (11 mg, 0.021 mmol) prepared in Step D in tetrahydrofuran (anhydrous, 4 mL) and water (1 mL) were added 4% osmium tetroxide solution (100 μL) and 30% hydrogen peroxide solution (0.5 mL) at room temperature, and the mixture was stirred for 3 hours. After completion of the reaction, the reaction mixture was extracted with ethyl acetate.

The extract was washed sequentially with water and saturated brine, and the organic layer was dried over anhydrous sodium sulfate, and filtered. The solvent was evaporated under reduced pressure, and the resultant brown oil was purified with Mega Bond Elut silica gel (Varian, 5 g). d,l-5-(2,3-Dihydroxy-propoxymethyl)-3,4-difluoro-2-(2-fluoro-4-iodo-phenylamino)-N-(2-hydroxy-ethoxy)-benzamide (6.8 mg, 58%) was obtained as a white solid from fractions eluted with 10% methanol/methylene chloride.

$^1$H-NMR (CD$_3$OD, 270 MHz) δ(PPM) 3.51-3.64 (4H, m), 3.70 (2H, dd, J=5.3, 4.6 Hz), 3.81 (1H, quin. J=5.3 Hz), 3.94 (2H, t, J=4.9), 4.63 (2H, s), 6.61 (1H, td, J=8.6, 4.6 Hz), 7.35 (1H, m), 7.50 (1H, br. d, J=5.9 Hz)

ESI (LC/MS positive mode) m/z 557 (M+H)

Example 6

3,4-Difluoro-2-(2-fluoro-4-iodo-phenylamino)-N-(2-hydroxy-ethoxy)-5-[(2-hydroxy-ethoxyamino)-methyl]-benzamide (Compound C-1)

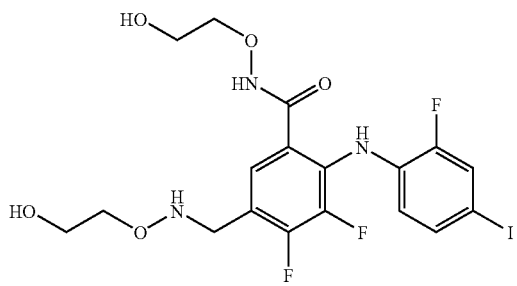

Step A

Preparation of (E)-N-[2-(t-butyl-dimethyl-silanyloxy)-ethoxy]-5-{[2-(t-butyl-dimethyl-silanyloxy)-ethoxyimino]-methyl}-3,4-difluoro-2-(2-fluoro-4-iodo-phenylamino)-benzamide

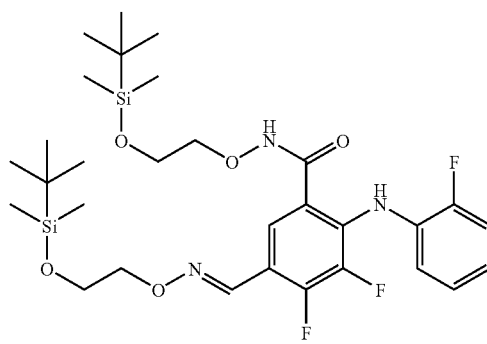

To a solution of 3,4-difluoro-2-(2-fluoro-4-iodophenylamino)-5-formyl-benzoic acid (130 mg, 0.309 mmol) prepared in Step A of Example 5 in methylene chloride (anhydrous, 5 mL) were added 1-hydroxybenzotriazole (42 mg, 0.309 mmol), 1-ethyl-3-(3-dimethylaminopropyl)carbodiimide hydrochloride (177 mg, 0.926 mmol), and N,N-diisopropylethylamine (161 µL, 0.926 mmol) at room temperature under argon flow, and the mixture was stirred thoroughly. Subsequently, O-[2-(t-butyl-dimethyl-silanyloxy)-ethyl]-hydroxyamine (177 mg, 0.926 mmol) was added thereto, and the mixture was stirred for 17 hours. After completion of the reaction, the reaction mixture was extracted with ethyl acetate.

The extract was washed sequentially with water and saturated brine, and the organic layer was dried over anhydrous sodium sulfate, and filtered. The solvent was evaporated under reduced pressure, and the resultant brown oil was purified with Mega Bond Elut silica gel (Varian, 10 g). (E)-N-[2-(t-Butyl-dimethyl-silanyloxy)-ethoxy]-5-{[2-(t-butyl-dimethyl-silanyloxy)-ethoxyimino]-methyl}-3,4-difluoro-2-(2-fluoro-4-iodo-phenylamino)-benzamide (137.1 mg, 58% yield) was obtained as a pale yellow solid from fractions eluted with 10% ethyl acetate/hexane.

$^1$H-NMR (CDCl$_3$, 270 MHz) δ(PPM): 0.08 (6H, s), 0.09 (6H, s), 0.87 (9H, s), 0.91 (9H, s), 3.92 (4H, m), 4.12 (2H, m), 4.26 (2H, m), 6.64 (1H, td, J=8.6, 5.3 Hz), 7.35 (1H, m), 7.41 (1H, dd, J=10.3, 1.7 Hz), 7.73 (1H, br.s), 8.22 (1H, s), 8.78 (1H, br.s), 9.43 (1H, br.s)

EIMS m/z 767 (M+H)

Step B

Preparation of (E)-3,4-difluoro-2-(2-fluoro-4-iodo-phenylamino)-N-(2-hydroxy-ethoxy)-5-[(2-hydroxy-ethoxyimino)-methyl]-benzamide

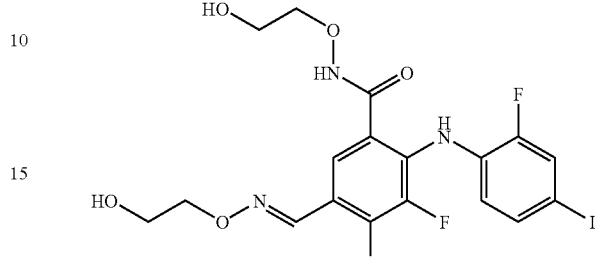

To a solution of (E)-N-[2-(t-butyl-dimethyl-silanyloxy)-ethoxy]-5-{[2-(t-butyl-dimethyl-silanyloxy)-ethoxyimino]-methyl}-3,4-difluoro-2-(2-fluoro-4-iodo-phenylamino)-benzamide (410 mg, 0.534 mmol) prepared in Step A in tetrahydrofuran (anhydrous, 20 mL) was added dropwise tetra-n-butylammonium fluoride (1 mol/L solution in tetrahydrofuran, 1.4 mL, 1.4 mmol) at room temperature, and the mixture was stirred for 4 hours.

After completion of the reaction, the solvent was evaporated under reduced pressure, and the yellow oil was extracted with ethyl acetate. The extract was washed sequentially with water and saturated brine, and the organic layer was dried over anhydrous sodium sulfate, and filtered. The solvent was evaporated under reduced pressure, and the resultant brown oil was purified with Mega Bond Elut silica gel (Varian, 5 g). The pale yellow solid obtained from fractions eluted with 100% ethyl acetate was triturated with ethyl acetate to give (E)-3,4-difluoro-2-(2-fluoro-4-iodo-phenylamino)-N-(2-hydroxy-ethoxy)-5-[(2-hydroxy-ethoxyimino)-methyl]-benzamide (134 mg, 47% yield) as a white solid.

$^1$H-NMR (CD$_3$OD, 270 MHz) δ(PPM): 3.72 (2H, t, J=4.9 Hz), 3.82 (2H, t, J=4.9 Hz), 3.95 (2H, dd, J=4.9, 4.3 Hz), 4.26 (2H, dd, J=4.9, 4.6), 6.72 (1H, td, J=8.6, 4.3 Hz), 7.39 (1H, m), 7.47 (1H, dd, J=10.6, 1.6 Hz), 7.81 (1H, dd, J=4.9, 1.6 Hz), 8.29 (1H, s)

ESI (LC/MS positive mode) m/z 540 (M+H)

Step C

Preparation of 3,4-difluoro-2-(2-fluoro-4-iodo-phenylamino)-N-(2-hydroxy-ethoxy)-5-[(2-hydroxy-ethoxyamino)-methyl]-benzamide

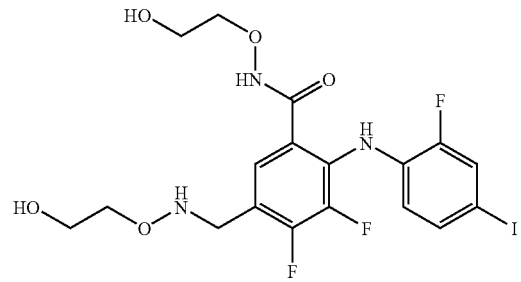

To a solution of (E)-3,4-difluoro-2-(2-fluoro-4-iodo-phenylamino)-N-(2-hydroxy-ethoxy)-5-[(2-hydroxy-ethoxyimino)-methyl]-benzamide (3.62 g, 6.70 mmol) obtained in Step B in methanol (100 ml) were added portionwise trifluoroacetic acid (6.5 ml) and sodium cyanoborohydride (3.78 g, 60.2 mmol) over 2 days while monitoring the progression of the reaction by TLC. The reaction mixture was poured into water, and extracted with ethyl acetate. The organic layer was washed with saturated aqueous sodium bicarbonate, dried over magnesium sulfate, and concentrated under reduced pressure. The residue was purified by silica gel column chromatography ($CH_2Cl_2$/MeOH (15:1)), and the resultant crude compound was crystallized from methylene chloride to give 3,4-difluoro-2-(2-fluoro-4-iodo-phenylamino)-N-(2-hydroxy-ethoxy)-5-[(2-hydroxy-ethoxyamino)-methyl]-benzamide (1.66 g, 46%, as a total of first and second crystals).

$^1$H-NMR ($CD_3OD$, 270 MHz) δ(PPM): 3.63-3.70 (6H, m), 3.94 (2H, dd, J=4.9, 4.3 Hz), 4.08 (2H, s), 6.59 (1H, td, J=8.6, 4.3 Hz), 7.34 (1H, d, J=8.2 Hz), 7.44 (1H, dd, J=10.9, 2.0 Hz), 7.50 (1H, dd, J=6.9, 2.0 Hz).

ESI (LC/MS positive mode) m/z 542 (M+H)

Step B'

The oxime compound, (E)-3,4-difluoro-2-(2-fluoro-4-iodo-phenylamino)-N-(2-hydroxy-ethoxy)-5-[(2-hydroxy-ethoxyimino)-methyl]-benzamide obtained in Step B of Example 6 may be easily prepared from 3,4-difluoro-2-(2-fluoro-4-iodo-phenylamino)-5-formyl-N-(2-hydroxy-ethoxy)-benzamide obtained in Step F of Example 1 by a reaction with 2-aminooxyethanol in THF at room temperature.

Namely, 3,4-difluoro-2-(2-fluoro-4-iodo-phenylamino)-5-formyl-N-(2-hydroxy-ethoxy)-benzamide (1.37 g) and aminooxy ethanol (262 mg) were mixed in THF at room temperature for 12 hours, and then the solvent was evaporated to give 3,4-difluoro-2-(2-fluoro-4-iodo-phenylamino)-N-(2-hydroxy-ethoxy)-5-[(2-hydroxy-ethoxyimino)-methyl]-benzamide.

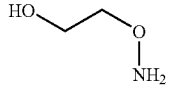

Step C'

3,4-Difluoro-2-(2-fluoro-4-iodo-phenylamino)-N-(2-hydroxy-ethoxy)-5-[(2-hydroxy-ethoxyamino)-methyl]-benzamide obtained in Step C of Example 6 may be prepared in another condition. Namely, 3,4-difluoro-2-(2-fluoro-4-iodo-phenylamino)-N-(2-hydroxy-ethoxy)-5-[(2-hydroxy-ethoxyimino)-methyl]-benzamide (1.76 g, 3.27 mmol) obtained in Step B (or Step B') of Example 6 was suspended in methylene chloride, and borane-pyridine complex (1.21 g, 13.1 mmol) and dichloroacetic acid (1.69 g, 13.1 mmol) were added thereto at room temperature. The mixture was stirred for 3 hours. The solvent was evaporated, and the residue was purified by silica gel chromatography using $CH_2Cl_2$/MeOH as a developing solvent to give 3,4-difluoro-2-(2-fluoro-4-iodo-phenylamino)-N-(2-hydroxy-ethoxy)-5-[(2-hydroxy-ethoxyamino)-methyl]-benzamide (1.40 g).

Example 7

3,4-Difluoro-2-(2-fluoro-4-iodo-phenylamino)-N-(2-hydroxy-ethoxy)-5-[(3-hydroxy-propoxyamino)-methyl]-benzamide (Compound C-10)

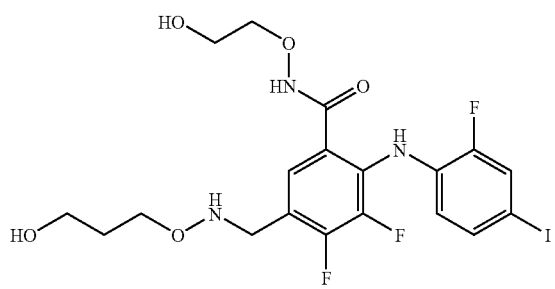

Step A

Synthesis of (E)-3,4-difluoro-2-(2-fluoro-4-iodo-phenylamino)-N-(2-hydroxy-ethoxy)-5-[(3-hydroxy-propoxyimino)-methyl]-benzamide

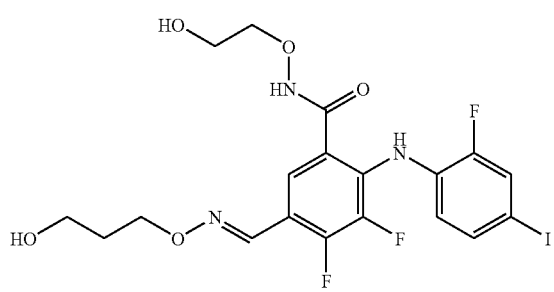

The title compound was obtained by a procedure similar to that in Step B' of Example 6 using 3,4-difluoro-2-(2-fluoro-4-iodo-phenylamino)-5-formyl-N-(2-hydroxy-ethoxy)-benzamide obtained in Step F of Example 1 as a starting material and 3-aminooxy n-propanol as a reagent.

$^1$H-NMR (DMSO-$d_6$, 400 MHz) δ(PPM) 1.58 (2H, m), 3.37 (2H, t, J=6.4 Hz), 3.55 (4H, m), 3.81 (2H, t, J=4.6 Hz), 3.93 (2H, d, J=5.9 Hz), 4.38 (1H, br), 4.71 (1H, br), 6.59 (1H, m), 6.77 (1H, t, J=5.9 Hz), 7.34 (1H, d, J=8.8 Hz), 7.48 (1H, d, J=6.9 Hz), 7.55 (1H, dd, J=10.7 Hz, 2.0 Hz), 8.63 (1H, br), 11.72 (1H, br)

ESI (LC/MS positive mode) m/z 556 (M+H)

Step B 3,4-Difluoro-2-(2-fluoro-4-iodo-phenylamino)-N-(2-hydroxy-ethoxy)-5-[(3-hydroxy-propoxyamino)-methyl]-benzamide (Compound C-10)

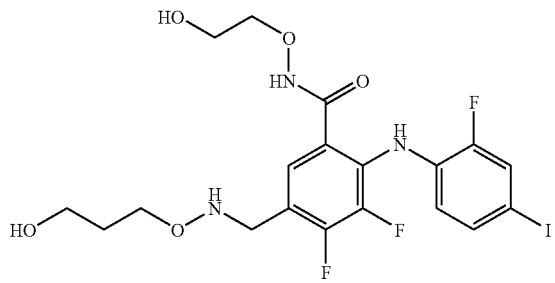

The title compound was obtained by a procedure similar to that in Step C' of Example 6 from (E)-3,4-difluoro-2-(2-fluoro-4-iodo-phenylamino)-N-(2-hydroxy-ethoxy)-5-[(3-hydroxy-propoxy imino)-methyl]-benzamide obtained in Step A.

$^1$H-NMR (DMSO-d$_6$, 400 MHz) δ(PPM) 1.58 (2H, m), 3.37 (2H, t, J=6.4 Hz), 3.55 (4H, m), 3.81 (2H, t, J=4.6 Hz), 3.93 (2H, d, J=5.9 Hz), 4.38 (1H, br), 4.71 (1H, br), 6.59 (1H, m), 6.77 (1H, t, J=5.9 Hz), 7.34 (1H, d, J=8.8 Hz), 7.48 (1H, d, J=6.9 Hz), 7.55 (1H, dd, J=10.7 Hz, 2.0 Hz), 8.63 (1H, br), 11.72 (1H, br)

ESI (LC/MS positive mode) m/z 556 (M+H)

Example 8

3,4-Difluoro-2-(2-fluoro-4-iodo-phenylamino)-N-(2-hydroxy-ethoxy)-5-[(2-hydroxy-2-methyl-propoxyamino)-methyl]-benzamide (Compound C-28)

Step A

Preparation of 1-aminooxy-2-methyl-propan-2-ol hydrochloride

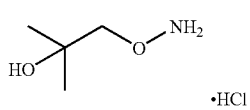

Preparation of 1-aminooxy-2-methyl-propan-2-ol hydrochloride was performed as described in the following literature:

Monatsh Chem Verw Teile Andere Wiss (1961) 92 p 725-739.

Step B (E)-3,4-Difluoro-2-(2-fluoro-4-iodophenylamino)-N-(2-hydroxy-ethoxy)-5-[(2-hydroxy-2-methyl-propoxyimino)-methyl]-benzamide

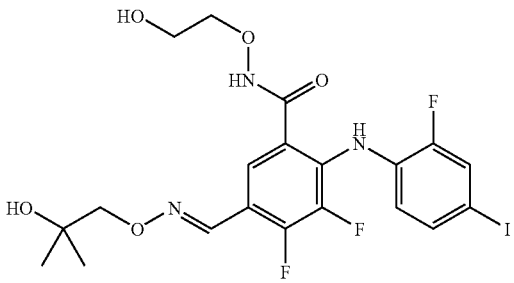

The title compound was obtained by a procedure similar to that in Step B' of Example 6 using 3,4-difluoro-2-(2-fluoro-4-iodo-phenylamino)-5-formyl-N-(2-hydroxy-ethoxy)-benzamide obtained in Step F of Example 1 as a starting material and 1-aminooxy-2-methyl-propan-2-ol hydrochloride obtained in Step A.

$^1$H-NMR (CD$_3$OD, 270 MHz) δ(PPM) 3.30 (6H, s), 3.72 (2H, m), 3.94 (2H, m), 4.08 (2H, s), 6.72 (1H, m), 7.38 (1H, d=8.6 Hz), 7.47 (1H, d, J=10.9 Hz), 7.80 (1H, br. d, J=5.3 Hz), 8.30 (1H, s)

ESI (LC/MS positive mode) m/z 568 (M+H)

Step C 3,4-Difluoro-2-(2-fluoro-4-iodo-phenylamino)-N-(2-hydroxy-ethoxy)-5-[(2-hydroxy-2-methyl-propoxyamino)-methyl]-benzamide (Compound C-28)

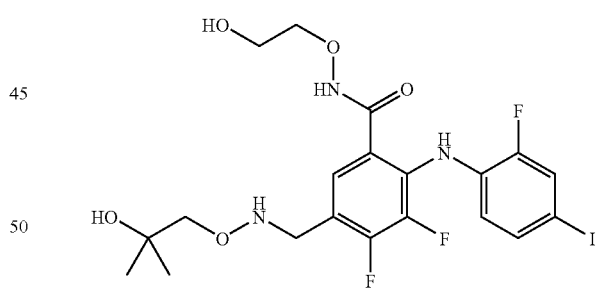

The title compound was obtained by a procedure similar to that in Step C' of Example 6 from (E)-3,4-difluoro-2-(2-fluoro-4-iodophenylamino)-N-(2-hydroxy-ethoxy)-5-[(2-hydroxy-2-methyl-propoxyimino)-methyl]-benzamide obtained in Step A.

$^1$H-NMR (DMSO-d$_6$, 400 MHz) δ(PPM) 1.01 (6H, s), 3.55 (2H, t, J=4.4 Hz), 3.82 (2H, t, J=4.4 Hz), 3.95 (2H, d, J=4.9 Hz), 4.40 (1H, br), 4.70 (1H, br), 6.58 (1H, m), 6.96 (1H, t, J=4.9 Hz), 7.34 (1H, d, J=8.3 Hz), 7.49 (1H, d, J=6.8 Hz), 7.55 (1H, d, J=10.8 Hz), 8.56 (1H, br), 11.72 (1H, br). The peak of a methylene group is overlapping with that of H$_2$O peak.

ESI (LC/MS positive mode) m/z 570 (M+H)

Example 9

3,4-Difluoro-2-(2-fluoro-4-iodo-phenylamino)-N-(2-hydroxy-ethoxy)-5-[(2-methylsulfanyl-ethoxyamino)-methyl]-benzamide (Compound C-30)

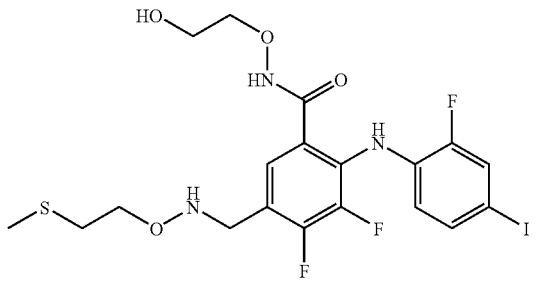

Step A

Synthesis of O-(2-methylsulfanyl-ethyl)-hydroxylamine

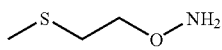

O-(2-Methylsulfanyl-ethyl)-hydroxylamine (CAS No. 101512-32-7) was prepared according to the method described in the following literature:
Bull. Acad. Sci. USSR Div. Chem. Sci. (Engl. Transl.); 1967; 1743-1745.

Step B

Synthesis of (E)-3,4-difluoro-2-(2-fluoro-4-iodo-phenylamino)-N-(2-hydroxy-ethoxy)-5-[(2-methyl-sulfanyl-ethyoxyimino)-methyl]-benzamide

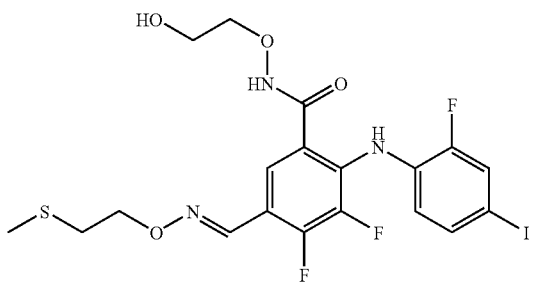

The title compound was obtained by a procedure similar to that in Step B' of Example 6 using 3,4-difluoro-2-(2-fluoro-4-iodo-phenylamino)-5-formyl-N-(2-hydroxy-ethoxy)-benzamide obtained in Step F of Example 1 as a starting material and O-(2-methylsulfanyl-ethyl)-hydroxylamine obtained in Step A as a reagent. Namely, 3,4-difluoro-2-(2-fluoro-4-iodo-phenylamino)-5-formyl-N-(2-hydroxy-ethoxy)-benzamide (2.6 g, 5.415 mmol) was dissolved in a mixed solvent of methylene chloride (50 mL), THF (20 mL), and methanol (10 mL).

O-(2-Methylsulfanyl-ethyl)-hydroxylamine (924 mg, 8.621 mmol) was added thereto, and the mixture was stirred at room temperature for 3 hours.

After completion of the reaction, the solvent was evaporated under reduced pressure to give a pale yellow crude product. The residue was triturated with a proper amount of ethyl acetate:hexane (7:3) to give (E)-3,4-difluoro-2-(2-fluoro-4-iodo-phenylamino)-N-(2-hydroxy-ethoxy)-5-[(2-methylsulfanyl-ethoxyimino)-methyl]-benzamide (1.1 g) as a white solid.

$^1$H-NMR (CD$_3$OD, 270 MHz) δ(PPM) 2.15 (3H, s), 2.82 (2H, dd, J=6.9, 6.6 Hz), 3.72 (2H, dd, J=4.9, 4.3 Hz), 3.95 (2H, dd, J=4.9, 4.3 Hz), 4.34 (2H, dd, J=6.9, 6.6 Hz), 6.72 (1H, td, J=8.6, 4.3 Hz), 7.39 (1H, m), 7.47 (1H, dd, J=10.6, 2.0 Hz), 7.81 (1H, dd, J=7.3, 2.0 Hz), 8.25 (1H, s)

ESI (LC/MS positive mode) m/z 570 (M+H)

Step C 3,4-Difluoro-2-(2-fluoro-4-iodo-phenylamino)-N-(2-hydroxy-ethoxy)-5-[(2-methylsulfanyl-ethoxyamino)-methyl]-benzamide (Compound C-30)

The title compound was obtained by a procedure similar to that in Step C' of Example 6 using (E)-3,4-difluoro-2-(2-fluoro-4-iodo-phenylamino)-N-(2-hydroxy-ethoxy)-5-[(2-methylsulfanyl-ethyoxyimino)-methyl]-benzamide obtained in Step B as a starting material.

Namely, (E)-3,4-difluoro-2-(2-fluoro-4-iodo-phenylamino)-N-(2-hydroxy-ethoxy)-5-[(2-methylsulfanyl-ethyoxyimino)-methyl]-benzamide (104.8 mg, 0.184 mmol) was dissolved in methylene chloride (anhydrous, 10 mL). Borane-pyridine complex (140 μL, 1.38 mmol) and then dichloroacetic acid (115 μL, 1.38 mmol) were added thereto with cooling the reaction vessel in an ice-bath under a nitrogen atmosphere. The ice-bath was removed, and the mixture was stirred at room temperature for 17 hours. After completion of the reaction, the reaction mixture was extracted with ethyl acetate, and the organic layer was washed sequentially with water and saturated brine, dried over anhydrous Na$_2$SO$_4$, and concentrated under reduced pressure. The resultant yellow residue was purified by silica gel column chromatography (Mega Bond Elut, Varian, 5% methanol/methylene chloride as an eluent). The resultant fraction was concentrated under reduced pressure and the oily residue was triturated with 5% ethyl acetate/hexane to give 3,4-difluoro-2-(2-fluoro-4-iodo-phenylamino)-N-(2-hydroxy-ethoxy)-5-[(2-methylsulfanyl-ethoxyamino)-methyl]-benzamide (110 mg) as a white solid.

$^1$H-NMR (CD$_3$OD, 270 MHz) δ(PPM) 2.06 (3H, s), 2.62 (2H, t, J=6.6 Hz), 3.70 (2H, m), 3.77 (2H, t, J=6.6 Hz), 3.94 (2H, m), 4.07 (2H, s), 6.56 (1H, td, J=8.7, 4.8 Hz), 7.32 (1H, m), 7.43 (1H, dd, J=10.7, 2.0 Hz), 7.53 (1H, dd, J=7.3, 2.0 Hz)

ESI (LC/MS positive mode) m/z 572 (M+H)

Example 10

3,4-Difluoro-2-(2-fluoro-4-iodo-phenylamino)-N-(2-hydroxy-ethoxy)-5-[(2-methanesulfinyl-ethoxyamino)-methyl]-benzamide (Compound C-31)

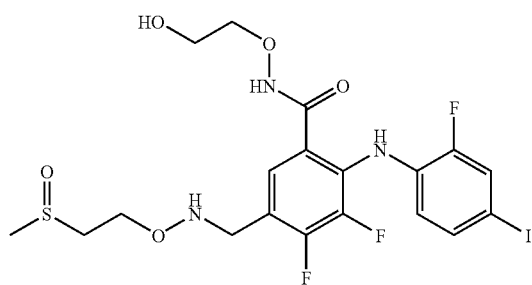

To a solution of 3,4-difluoro-2-(2-fluoro-4-iodo-phenylamino)-N-(2-hydroxy-ethoxy)-5-[(2-methylsulfanyl-ethoxyamino)-methyl]-benzamide (10 mg, 0.017 mmol) obtained in Step C of Example 9 in a mixed solvent of acetone (1.8 mL) and water (0.2 mL) was added 30% aqueous hydrogen peroxide (3 μL, 0.026 mmol), and the mixture was stirred for 17 hours.

After completion of the reaction, the reaction mixture was extracted with ethyl acetate, and the organic layer was washed sequentially with water and saturated brine, dried over anhydrous sodium sulfate, and concentrated under reduced pressure. The resultant residue was purified by preparative TLC (No. 5744, Merck, 5% methanol/methylene chloride as a developing solvent) to give 3,4-difluoro-2-(2-fluoro-4-iodo-phenylamino)-N-(2-hydroxy-ethoxy)-5-[(2-methanesulfinyl-ethoxyamino)-methyl]-benzamide (4.0 mg, 39%) as an off-white solid.

$^1$H-NMR (CD$_3$OD, 270 MHz) δ(PPM) 2.62 (3H, s), 2.88 (1H, m), 2.92 (1H, m), 3.70 (2H, m), 3.93 (2H, m), 4.00 (2H, m), 4.08 (2H, s), 6.60 (1H, td, J=8.7, 4.6 Hz), 7.34 (1H, m), 7.44 (1H, dd, J=10.6, 2.0 Hz), 7.48 (1H, m)

ESI (LC/MS positive mode) m/z 588 (M+H)

Example 11

3,4-Difluoro-2-(2-fluoro-4-iodo-phenylamino)-N-(2-hydroxy-ethoxy)-5-[(2-methanesulfonyl-ethoxyamino)-methyl]-benzamide (Compound C-8)

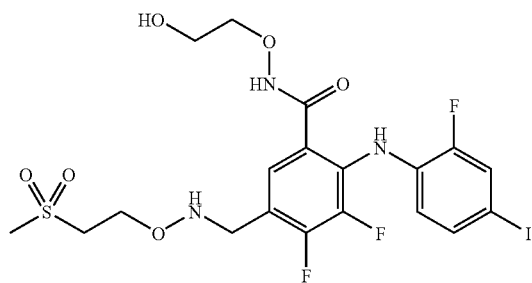

To a solution of 3,4-difluoro-2-(2-fluoro-4-iodo-phenylamino)-N-(2-hydroxy-ethoxy)-5-[(2-methanesulfinyl-ethoxyamino)-methyl]-benzamide (10 mg, 0.017 mmol) obtained in Example 10 in a mixed solvent of methanol (1.8 mL) and water (0.2 mL) was added sodium metaperiodate (6 mg, 0.026 mmol) at room temperature, and the mixture was stirred for 17 hours. After completion of the reaction, the reaction mixture was extracted with ethyl acetate, and the organic layer was washed sequentially with water and saturated brine, dried over anhydrous sodium sulfate, and concentrated under reduced pressure. The resultant residue was purified by preparative TLC (No. 5744, Merck, 5% methanol/methylene chloride as a developing solvent) to give 3,4-difluoro-2-(2-fluoro-4-iodo-phenylamino)-N-(2-hydroxy-ethoxy)-5-[(2-methanesulfonyl-ethoxyamino)-methyl]-benzamide (1.3 mg, 13%) as an off-white solid.

$^1$H-NMR (CD$_3$OD, 270 MHz) δ(PPM) 2.94 (3H, s), 3.26 (2H, partial hidden), 3.71 (2H, dd, J=4.9, 4.3 Hz), 3.93 (2H, dd, J=4.9, 4.3 Hz), 4.04 (2H, dd, J=5.7, 5.4 Hz), 4.10 (2H, s), 6.61 (1H, td, J=8.7, 4.6 Hz), 7.33 (1H, m), 7.43 (1H, dd, J=10.7, 1.8 Hz), 7.50 (1H, m)

ESI (LC/MS positive mode) m/z 604 (M+H)

Example 12

3,4-Difluoro-2-(2-fluoro-4-iodo-phenylamino)-N-(2-hydroxy-ethoxy)-5-[(3-methylsulfanyl-propoxyamino)-methyl]-benzamide (Compound C-32)

Step A

Preparation of 2-(3-methylsulfanyl-propoxy)-isoindole-1,3-dione

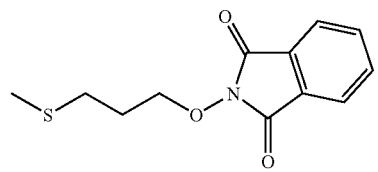

3-Methylsulfanyl-propan-1-ol (4.133 g, 38.92 mmol) was dissolved in THF (anhydrous, 100 mL). To this solution, triphenylphosphine (10.2 g, 38.92 mmol) and N-hydroxyphthalimide (6.4 mg, 38.92 mmol) were added and dissolved with stirring. Diisopropyl azodicarboxylate (8.5 mL, 42.812 mmol) was added dropwise thereto with cooling the reaction vessel in an ice-bath under nitrogen atmosphere. The reaction mixture was warmed to room temperature, and stirred for 5 hours. After completion of the reaction, the reaction mixture was concentrated under reduced pressure, and triturated with diethyl ether:hexane (1:1, about 100 ml) to precipitate triphenylphosphine oxide as a white solid, which was filtered off. The filtrate was concentrated under reduced pressure to give a yellow oily residue. The resultant yellow oil was purified by silica gel flash chromatography (BW300, Fuji Silysia Chemical, 20% ethyl acetate/hexane as an eluent) to give 2-(3-methylsulfanyl-propoxy)-isoindole-1,3-dione (6.4 g, 65%).

$^1$H-NMR (CDCl$_3$, 270 MHz) δ(PPM) 2.04 (2H, m), 2.15 (3H, s), 2.78 (2H, m), 4.33 (2H, dd, J=6.3, 6.1 Hz), 7.72-7.88 (4H, m)

ESI (LC/MS positive mode) m/z 252 (M+H)

Step B

Synthesis of O-(3-methylsulfanyl-propyl)-hydroxylamine

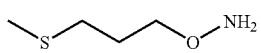

2-(3-Methylsulfanyl-propoxy)-isoindole-1,3-dione (6.4 g, 25.5 mmol) obtained in Step A was dissolved in methylene chloride (anhydrous, 50 mL). To this solution, methylhydrazine (1.5 mL, 28 mmol) was added dropwise, and the mixture was stirred for 1 hour. The precipitated white solid was filtered off, and the filtrate was concentrated under reduced pressure. The yellow oily residue was extracted with ethyl acetate, and the organic layer was washed sequentially with water and saturated brine, dried over anhydrous sodium sulfate, and concentrated under reduced pressure. The resultant yellow oily residue was purified by vacuum distillation (1 mmHg, 57° C.) to give O-(3-methylsulfanyl-propyl)-hydroxylamine (3.15 g, 68%) as a colorless oil.

$^1$H-NMR (CDCl$_3$, 270 MHz) δ(PPM) 1.88 (2H, m), 2.11 (3H, s), 2.55 (2H, dd, J=7.6, 7.1 Hz), 3.75 (2H, dd, J=6.3, 6.1 Hz), 5.37 (2H, br.s)

ESI (LC/MS positive mode) m/z 122 (M+H)

Step C

Synthesis of (E)-3,4-difluoro-2-(2-fluoro-4-iodo-phenylamino)-N-(2-hydroxy-ethoxy)-5-[(3-methylsulfanyl-propoxyimino)-methyl]-benzamide

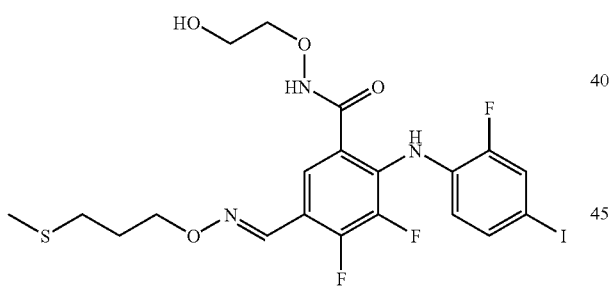

The title compound was obtained by a procedure similar to that in Step B of Example 9 using 3,4-difluoro-2-(2-fluoro-4-iodo-phenylamino)-5-formyl-N-(2-hydroxy-ethoxy)-benzamide obtained in Step F of Example 1 as a starting material and O-(3-methylsulfanyl-propyl)-hydroxylamine obtained in Step B as a reagent. Namely, 3,4-difluoro-2-(2-fluoro-4-iodo-phenylamino)-5-formyl-N-(2-hydroxy-ethoxy)-benzamide (76 mg, 0.158 mmol) was dissolved in a mixed solvent of methylene chloride (5 mL) and methanol (1 mL). O-(3-Methylsulfanyl-propyl)-hydroxylamine (100 µL) was added thereto, and the mixture was stirred at room temperature for 3 hours. After completion of the reaction, the solvent was evaporated under reduced pressure to give a pale yellow crude product. The residue was triturated with a proper amount of ethyl acetate:hexane (1:9) to give (E)-3,4-difluoro-2-(2-fluoro-4-iodo-phenylamino)-N-(2-hydroxy-ethoxy)-5-[(3-methylsulfanyl-propoxyimino)-methyl]-benzamide (88.8 mg, 96%) as a white solid.

$^1$H-NMR (CDCl$_3$, 270 MHz) δ(PPM) 2.03 (2H, m), 2.13 (3H, s), 2.63 (2H, dd, J=7.3, 7.1 Hz), 3.79 (2H, m), 4.30 (2H, t, J=6.3 Hz), 6.66 (1H, td, J=8.6, 4.5 Hz), 7.35 (1H, m), 7.42 (1H, dd, J=10.2, 1.8 Hz), 7.77 (1H, dd, J=6.8, 2.0 Hz), 8.21 (1H, s), 8.60 (1H, br.s), 9.15 (1H, br.s)

ESI (LC/MS positive mode) m/z 584 (M+H)

Step D

Synthesis of 3,4-difluoro-2-(2-fluoro-4-iodo-phenylamino)-N-(2-hydroxy-ethoxy)-5-[(3-methylsulfanyl-prop oxyamino)-methyl]-benzamide (Compound C-32)

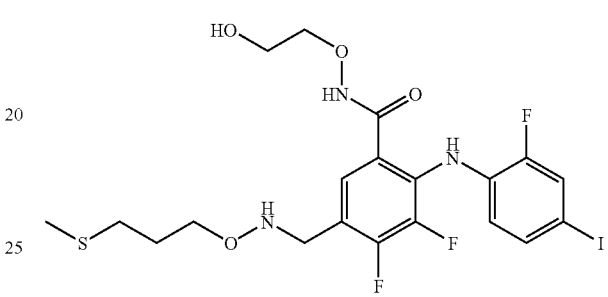

The title compound was obtained by a procedure similar to that in Step C of Example 9. Namely, (E)-3,4-difluoro-2-(2-fluoro-4-iodo-phenylamino)-N-(2-hydroxy-ethoxy)-5-[(3-methylsulfanyl-propoxyimino)-methyl]-benzamide was reduced with borane-pyridine complex in the presence of dichloroacetic acid to give 3,4-difluoro-2-(2-fluoro-4-iodo-phenylamino)-N-(2-hydroxy-ethoxy)-5-[(3-methylsulfanyl-prop oxyamino)-methyl]-benzamide (26.54 mg, 79%).

$^1$H-NMR (CD$_3$OD, 270 MHz) δ(PPM) 1.78 (2H, m), 2.03 (3H, s), 2.47 (2H, dd, J=7.4, 7.1 Hz), 3.70 (2H, t, J=6.1 Hz), 3.71 (2H, m), 3.92 (2H, m), 4.06 (2H, s), 6.59 (1H, td, J=8.7, 4.3 Hz), 7.34 (1H, dd, J=8.4, 1.1 Hz), 7.44 (1H, dd, J=10.7, 1.8 Hz), 7.49 (1H, m)

ESI (LC/MS positive mode) m/z 586 (M+H)

Example 13

3,4-Difluoro-2-(2-fluoro-4-iodo-phenylamino)-N-(2-hydroxy-ethoxy)-5-[(3-methanesulfinyl-propoxyamino)-methyl]-benzamide (Compound C-33)

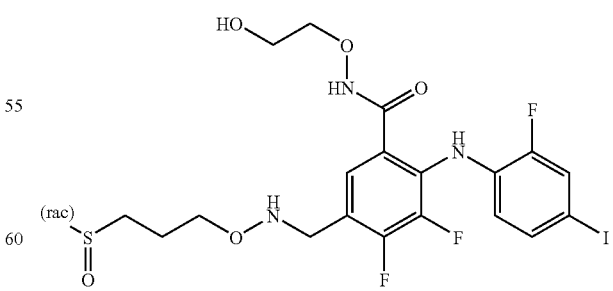

The title compound was obtained by a procedure similar to that in Example 10 using 3,4-difluoro-2-(2-fluoro-4-iodo-phenylamino)-N-(2-hydroxy-ethoxy)-5-[(3-methylsulfanyl-prop oxyamino)-methyl]-benzamide obtained in Example 12 as a starting material. Namely, 3,4-difluoro-2-(2-fluoro-4-iodo-phenylamino)-N-(2-hydroxy-ethoxy)-5-[(3-methylsulfanyl-prop oxyamino)-methyl]-benzamide was treated with 30% aqueous hydrogen peroxide in aqueous acetone to synthesize 3,4-difluoro-2-(2-fluoro-4-iodo-phenylamino)-N-(2-hydroxy-ethoxy)-5-[(3-methanesulfinyl-prop oxyamino)-methyl]-benzamide (6.34 mg, 62%).

$^1$H-NMR (CD$_3$OD, 270 MHz) δ(PPM) 1.96 (2H, m), 2.64 (3H, s), 2.83 (2H, m), 3.71 (2H, m), 3.75 (2H, dd, J=6.1, 5.9 Hz), 3.92 (2H, dd, J=4.9, 4.3 Hz), 6.59 (1H, td J=8.7, 4.3 Hz), 7.34 (1H, br, d, J=8.6 Hz), 7.44 (1H, dd, J=10.7, 2.0 Hz), 7.49 (1H, dd, J=7.3, 1.8 Hz)

ESI (LC/MS positive mode) m/z 602 (M+H)

Example 14

3,4-Difluoro-2-(2-fluoro-4-iodo-phenylamino)-5-hydroxyaminomethyl-N-(2-hydroxy-ethoxy)-benzamide (Compound C-23)

Step A

Synthesis of (E)-3,4-difluoro-2-(2-fluoro-4-iodo-phenylamino)-N-(2-hydroxy-ethoxy)-5-(hydroxy-imino-methyl)-benzamide

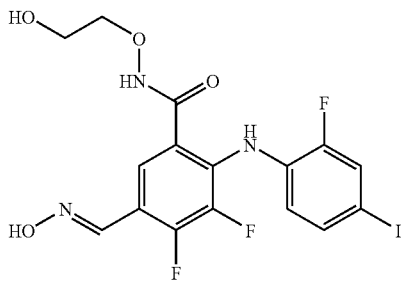

The title compound was obtained by a procedure similar to that in Step B of Example 9 using 3,4-difluoro-2-(2-fluoro-4-iodo-phenylamino)-5-formyl-N-(2-hydroxy-ethoxy)-benzamide obtained in Step F of Example 1 as a starting material and N-hydroxyamine hydrochloride (commercially available) as a reagent. 111.7 mg (100%).

$^1$H-NMR (CD$_3$OD, 270 MHz) δ(PPM) 3.71 (2H, dd, J=4.9, 4.3 Hz), 3.93 (2H, dd, J=4.6, 4.3 Hz), 6.70 (1H, td, J=8.6, 4.3 Hz), 7.38 (1H, dt, J=8.3, 1.3 Hz), 7.46 (1H, dd, J=10.9, 2.0 Hz), 7.80 (1H, br. d, J=5.9 Hz), 8.21 (1H, s)

ESI (LC/MS positive mode) m/z 496 (M+H)

Step B

Synthesis of 3,4-difluoro-2-(2-fluoro-4-iodo-phenylamino)-5-hydroxyaminomethyl-N-(2-hydroxy-ethoxy)-benzamide (Compound C-23)

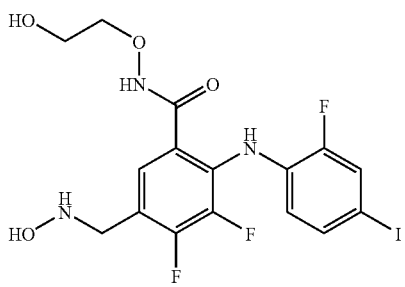

The title compound was obtained by a procedure similar to that in Step C of Example 9. Namely, (E)-3,4-difluoro-2-(2-fluoro-4-iodo-phenylamino)-N-(2-hydroxy-ethoxy)-5-(hydroxyimino-methyl)-benzamide was reduced with borane-pyridine complex in the presence of dichloroacetic acid to give 3,4-difluoro-2-(2-fluoro-4-iodo-phenylamino)-5-hydroxyaminomethyl-N-(2-hydroxy-ethoxy)-benzamide (28.14 mg, 81%).

$^1$H-NMR (CD$_3$OD, 270 MHz) δ(PPM) 3.71 (2H, dd, J=4.8, 4.4 Hz), 3.94 (2H, dd, J=4.8, 4.1 Hz), 4.08 (2H, s), 6.60 (1H, td, J=8.7, 4.5 Hz), 7.35 (1H, br. d, J=8.6 Hz), 7.44 (1H, dd, J=10.6, 1.8 Hz), 7.52 (1H, br. d, J=7.4 Hz)

ESI (LC/MS positive mode) m/z 498 (M+H)

Example 15

3,4-Difluoro-2-(2-fluoro-4-iodo-phenylamino)-N-(2-hydroxy-ethoxy)-5-(methoxyamino-methyl)-benzamide (Compound C-24)

Step A

Synthesis of (E)-3,4-difluoro-2-(2-fluoro-4-iodo-phenylamino)-N-(2-hydroxy-ethoxy)-5-(methoxy-imino-methyl)-benzamide

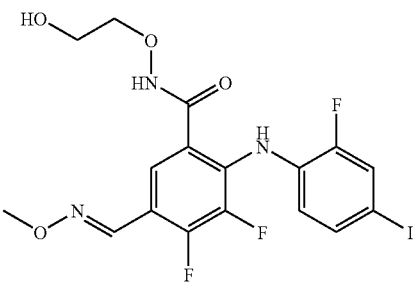

The title compound was obtained by a procedure similar to that in Step B of Example 9 using 3,4-difluoro-2-(2-fluoro-4-iodo-phenylamino)-5-formyl-N-(2-hydroxy-ethoxy)-benzamide obtained in Step F of Example 1 as a starting material and N-methoxyamine hydrochloride (commercially available) as a reagent. 128 mg (99%).

$^1$H-NMR (CD$_3$OD, 270 MHz) δ(PPM) 3.72 (2H, dd, J=4.8, 4.6 Hz), 3.95 (2H, dd, J=4.8, 4.6 Hz), 3.98 (3H, s), 6.71 (1H, td, J=8.7, 4.5 Hz), 7.41 (1H, m), 7.47 (1H, dd, J=10.6, 2.0 Hz), 7.81 (1H, dd, J=7.4, 2.1 Hz), 8.22 (1H, s)

ESI (LC/MS positive mode) m/z 510 (M+H)

Step B

Synthesis of 3,4-difluoro-2-(2-fluoro-4-iodo-phenylamino)-N-(2-hydroxy-ethoxy)-5-(methoxyamino-methyl)-benzamide (Compound C-24)

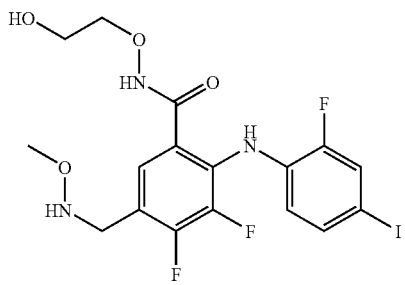

The title compound was obtained by a procedure similar to that in Step C of Example 9. Namely, (E)-3,4-difluoro-2-(2-fluoro-4-iodo-phenylamino)-N-(2-hydroxy-ethoxy)-5-(methoxyimino-methyl)-benzamide was reduced with borane-pyridine complex in the presence of dichloroacetic acid to give 3,4-difluoro-2-(2-fluoro-4-iodo-phenylamino)-N-(2-hydroxy-ethoxy)-5-(methoxyamino-methyl)-benzamide (28.14 mg, 81%).

$^1$H-NMR (CD$_3$OD, 270 MHz) δ(PPM) 3.50 (3H, s), 3.70 (2H, m), 3.93 (2H, m), 4.08 (2H, s), 6.59 (1H, td, J=8.9, 4.2 Hz), 7.34 (1H, m), 7.44 (1H, dd, J=10.6, 1.8 Hz), 7.48 (1H, br.s)

ESI (LC/MS positive mode) m/z 512 (M+H)

Example 16

3,4-Difluoro-2-(2-fluoro-4-iodo-phenylamino)-N-(2-hydroxy-ethoxy)-5-[(methoxy-methyl-amino)-methyl]-benzamide (Compound C-25)

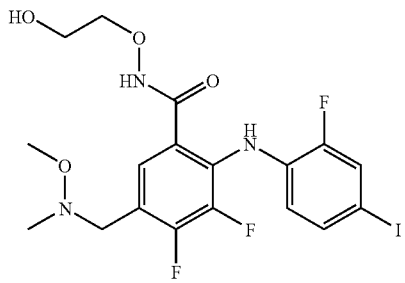

To a solution of 3,4-difluoro-2-(2-fluoro-4-iodo-phenylamino)-5-formyl-N-(2-hydroxy-ethoxy)-benzamide (56.2 mg, 0.117 mmol) in tetrahydrofuran (anhydrous) were added O,N-dimethyl-hydroxylamine hydrochloride (commercially available, 34 mg, 0.351 mmol) and sodium cyanoborohydride (34 mg, 0.541 mmol) under nitrogen atmosphere, and the mixture was stirred at room temperature for 3 hours. After completion of the reaction, the reaction mixture was extracted with ethyl acetate, and the organic layer was washed sequentially with water and saturated brine, dried over anhydrous sodium sulfate, and concentrated under reduced pressure. The resultant residue was purified by silica gel flash chromatography (Mega Bond Elut, Varian, 5% methanol/methylene chloride as an eluent) to give 3,4-difluoro-2-(2-fluoro-4-iodo-phenylamino)-N-(2-hydroxy-ethoxy)-5-[(methoxy-methyl-amino)-methyl]-benzamide (9.72 mg, 17%) as a white solid.

$^1$H-NMR (CD$_3$OD, 270 MHz) δ(PPM) 2.63 (3H, s), 3.37 (3H, s), 3.71 (2H, dd, J=4.9, 4.3 Hz), 3.85 (2H, s), 3.94 (2H, dd, J=4.8, 4.5 Hz), 6.59 (1H, td, J=8.9, 4.6 Hz), 7.34 (1H, m), 7.44 (1H, dd, J=10.6, 1.8 Hz), 7.47 (1H, dd, J=8.7, 2.0 Hz)

ESI (LC/MS positive mode) m/z 526 (M+H)

Example 17

5-(Ethoxyamino-methyl)-3,4-difluoro-2-(2-fluoro-4-iodo-phenylamino)-N-(2-hydroxy-ethoxy)-benzamide (Compound C-26)

Step A

Synthesis of (E)-5-(ethoxyimino-methyl)-3,4-difluoro-2-(2-fluoro-4-iodo-phenylamino)-N-(2-hydroxy-ethoxy)-benzamide

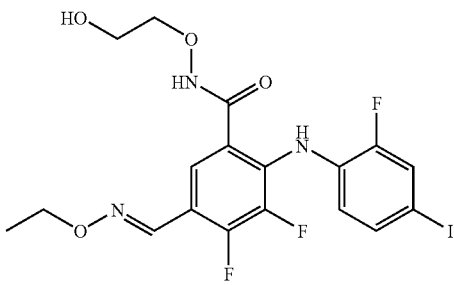

The title compound was obtained by a procedure similar to that in Step B of Example 9 using 3,4-difluoro-2-(2-fluoro-4-iodo-phenylamino)-5-formyl-N-(2-hydroxy-ethoxy)-benzamide obtained in Step F of Example 1 as a starting material and N-ethoxyamine hydrochloride (commercially available) as a reagent.

$^1$H-NMR (CD$_3$OD, 270 MHz) δ(PPM) 1.31 (3H, t, J=7.0 Hz), 3.72 (2H, m), 3.94 (2H, m), 4.23 (2H, q, J=7.0 Hz), 6.70 (1H, m), 7.39 (1H, br. d, J=8.4 Hz), 7.47 (1H, dd, J=10.7, 2.0 Hz), 7.80 (1H, m), 8.22 (1H, s)

ESI (LC/MS positive mode) m/z 524 (M+H)

Step B

Synthesis of 5-(ethoxyamino-methyl)-3,4-difluoro-2-(2-fluoro-4-iodo-phenylamino)-N-(2-hydroxy-ethoxy)-benzamide (Compound C-26)

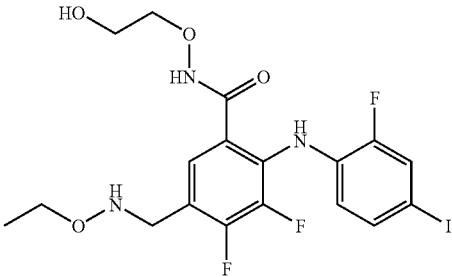

The title compound was obtained by a procedure similar to that in Step C of Example 9. Namely, (E)-5-(ethoxyimino-methyl)-3,4-difluoro-2-(2-fluoro-4-iodo-phenylamino)-N-(2-hydroxy-ethoxy)-benzamide was reduced with borane-pyridine complex in the presence of dichloroacetic acid to give 5-(ethoxyamino-methyl)-3,4-difluoro-2-(2-fluoro-4-iodo-phenylamino)-N-(2-hydroxy-ethoxy)-benzamide (97.7 mg, 80% in 2 steps).

$^1$H-NMR (DMSO-d$_6$, 270 MHz) δ(PPM) 1.03 (3H, t, J=6.9 Hz), 3.55 (2H, m), 3.57 (2H, q, J=6.9 Hz), 3.83 (2H, m), 3.99 (2H, m), 4.71 (1H, br.s), 6.60 (1H, m), 7.39 (1H, d, J=8.7 Hz), 7.47 (1H, d, J=6.6 Hz), 7.57 (1H, dd, J=10.9, 1.8 Hz), 8.50 (1H, br.s), 11.80 (1H, br.s)

ESI (LC/MS positive mode) m/z 526 (M+H)

Example 18

3,4-Difluoro-2-(2-fluoro-4-iodo-phenylamino)-N-(2-hydroxy-ethoxy)-5-(isopropoxyamino-methyl)-benzamide (Compound C-27)

Step A

Synthesis of (E)-3,4-difluoro-2-(2-fluoro-4-iodo-phenylamino)-N-(2-hydroxy-ethoxy)-5-(isopropoxy-imino-methyl)-benzamide

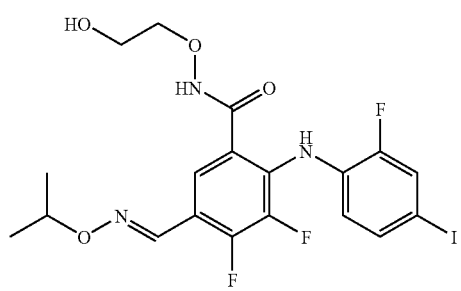

The title compound was obtained by a procedure similar to that in Step B of Example 9 using 3,4-difluoro-2-(2-fluoro-4-iodo-phenylamino)-5-formyl-N-(2-hydroxy-ethoxy)-benzamide obtained in Step F of Example 1 as a starting material and O-isopropylhydroxylamine hydrochloride (commercially available) as a reagent.

$^1$H-NMR (DMSO-d$_6$, 270 MHz) δ(PPM) 1.27 (6H, d, J=6.3 Hz), 3.57 (2H, br. q, J=4.3 Hz), 3.84 (2H, t, J=4.6 Hz), 4.44 (1H, qui, J=6.3 Hz) 4.73 (1H, br. t, J=5.6 Hz), 6.80 (1H, td, J=9.2, 4.3 Hz), 7.40 (1H, br. d, J=7.9 Hz), 7.61 (1H, dd, J=10.9, 2.0 Hz), 7.69 (1H, br. d, J=6.9 Hz), 8.22 (1H, s), 8.84 (1H, br. s, NH), 11.98 (1H, br. s, NH).

ESI (LC/MS positive mode) m/z 538 (M+H)

Step B

Synthesis of 3,4-difluoro-2-(2-fluoro-4-iodo-phenylamino)-N-(2-hydroxy-ethoxy)-5-(isopropoxyamino-methyl)-benzamide (Compound C-27)

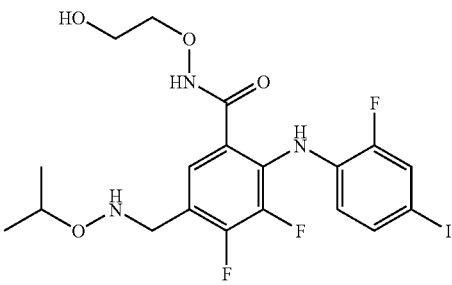

The title compound was obtained by a procedure similar to that in Step C of Example 9. Namely, (E)-3,4-difluoro-2-(2-fluoro-4-iodo-phenylamino)-N-(2-hydroxy-ethoxy)-5-(isopropoxyimino-m ethyl)-benzamide was reduced with borane-pyridine complex in the presence of dichloroacetic acid to give 3,4-difluoro-2-(2-fluoro-4-iodo-phenylamino)-N-(2-hydroxy-ethoxy)-5-(isopropoxyamino-methyl)-benzamide (65.0 mg, 89% in 2 steps).

$^1$H-NMR (DMSO-d$_6$, 270 MHz) δ(PPM) 1.02 (6H, d, J=6.2 Hz), 3.56 (2H, br. t, J=4.9 Hz), 3.67 (1H, qui, J=6.2 Hz), 3.83 (2H, br. t, J=4.9 Hz), 3.92 (2H, br. d, J=ca 5 Hz), 4.72 (1H, br. s), 6.59 (1H, td, J=8.9, 4.1 Hz), 7.36 (1H, br. d, J=8.1 Hz), 7.48 (1H, br. d, J=7.0 Hz), 7.57 (1H, dd, J=10.8, 1.9 Hz), 8.57 (1H, br. s).

ESI (LC/MS positive mode) m/z 540 (M+H)

Example 19

3,4-Difluoro-2-(2-fluoro-4-iodo-phenylamino)-N-(2-hydroxy-ethoxy)-5-(methylcarbamoyl-methoxyamino-methyl)-benzamide (Compound C-13)

Step A

Synthesis of (1,3-dioxo-1,3-dihydro-isoindol-2-yloxy)-acetic acid methyl ester

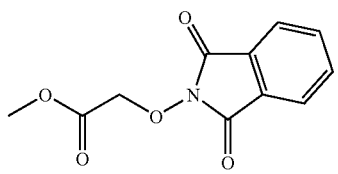

The title compound was prepared according to the method described in the following literature:

Sheppard, andrew et al.; J. Chem. Soc. Perkin Trans 1; 1990; 2519-2525.

Step B

Synthesis of 2-aminooxy-N-methyl-acetamide

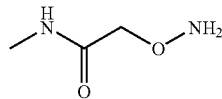

To a solution of (1,3-dioxo-1,3-dihydro-isoindol-2-yloxy)-acetic acid methyl ester (120.9 g, 0.51 mol) obtained in Step A in methanol (300 ml) was added methylamine (40% solution in methanol, 1.0 L) at room temperature, and stirred at 60° C. over night. The reaction mixture was concentrated under reduced pressure, and methylene chloride was added to the resultant residue to precipitate a solid, which was filtered and washed with methylene chloride. The combined filtrate and washing were concentrated under reduced pressure. The residue was purified by silica gel column chromatography (1.4 kg, $CH_2Cl_2$/MeOH (30:1 to 10:1)) to give 2-aminooxy-N-methyl-acetamide (50.3 g, 94%) as a colorless syrup.

$^1$H-NMR ($CDCl_3$, 270 MHz) δ(PPM) 2.88 (3H, d, J=5.0 Hz), 4.17 (2H, s), 5.69 (2H, br. s).

Step C

Synthesis of (E)-3,4-difluoro-2-(2-fluoro-4-iodo-phenylamino)-N-(2-hydroxy-ethoxy)-5-[methylcarbamoylmethoxyimino-methyl]-benzamide

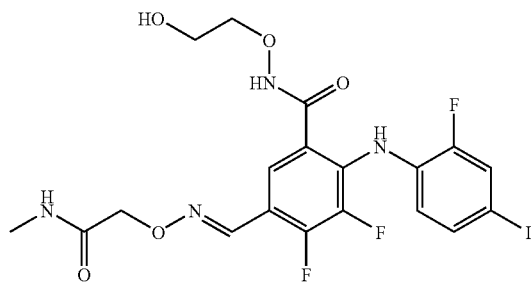

To a solution of 2-aminooxy-N-methyl-acetamide (1.71 g, 16.4 mmol) obtained in Step B in a mixed solvent of methylene chloride (50 ml) and THF (25 ml) was added 3,4-difluoro-2-(2-fluoro-4-iodo-phenylamino)-5-formyl-N-(2-hydroxy-ethoxy)-benzamide (3.94 g, 8.20 mmol) obtained in Step F of Example 1 at room temperature, and the mixture was stirred for 15 hours. The reaction mixture was concentrated under reduced pressure, and methylene chloride (40 ml) was added to the resultant residue to precipitate a solid, which was filtered and washed with methylene chloride. The resultant solid was dried under reduced pressure to give (E)-3,4-difluoro-2-(2-fluoro-4-iodo-phenylamino)-N-(2-hydroxy-ethoxy)-5-[methylcarbamoylmethoxyimino-methyl]-benzamide (3.57 g, 77%) as a white solid.

$^1$H-NMR (DMSO-$d_6$, 270 MHz) δ(PPM) 2.63 (3H, d, J=4.6 Hz), 3.56 (2H, t, J=4.6 Hz), 3.83 (2H, t, J=4.3 Hz), 4.57 (2H, s), 4.73 (1H, br. s), 6.82 (1H, td, J=8.9, 4.0 Hz), 7.41 (1H, br. d, J=8.6 Hz), 7.61 (1H, dd, J=10.9, 2.0 Hz), 7.69 (1H, br. d, J=6.3 Hz), 7.87 (1H, br q, J=4.6 Hz), 8.40 (1H, s), 8.92 (1H, br. s), 12.01 (1H, br. s).

ESI (LC/MS positive mode) m/z 567 (M+H)

Step D

3,4-Difluoro-2-(2-fluoro-4-iodo-phenylamino)-N-(2-hydroxy-ethoxy)-5-(methylcarbamoyl-methoxyamino-methyl)-benzamide (Compound C-13)

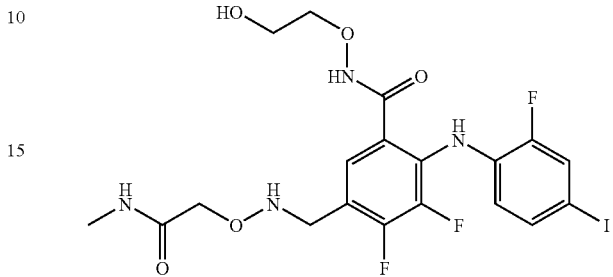

To a solution of (E)-3,4-difluoro-2-(2-fluoro-4-iodo-phenylamino)-N-(2-hydroxy-ethoxy)-5-[methylcarbamoylmethoxyimino-methyl]-benzamide (69.8 mg, 0.12 mmol) obtained in Step C in methylene chloride (15 ml) were added borane-pyridine complex (199 µl, 1.92 mmol) and dichloroacetic acid (162 µl, 1.92 mmol) at room temperature, and the mixture was stirred for 3.5 days. Additional borane-pyridine complex (199 µl, 1.92 mmol) and dichloroacetic acid (162 µl, 1.92 mmol) were added, and the mixture was stirred for 1 day. The reaction mixture was diluted with methylene chloride (20 ml), and washed with saturated brine (2×20 ml). The organic layer was dried over anhydrous magnesium sulfate, and concentrated under reduced pressure. The resultant residue was purified by preparative TLC (EtOAc/MeOH (9:1)) to give 3,4-difluoro-2-(2-fluoro-4-iodo-phenylamino)-N-(2-hydroxy-ethoxy)-5-(methylcarbamoylmethoxyamino-methyl)-benzamide (36.9 mg, 53%) as a colorless oil.

$^1$H-NMR ($CD_3OD$, 270 MHz) δ(PPM) 2.77 (3H, s), 3.68-3.76 (2H, m), 3.92-3.98 (2H, m), 4.09 (2H, s), 4.13 (2H, s), 6.61 (1H, dt, J=4.3, 8.6 Hz), 7.34 (1H, ddd, J=1.2, 1.9, 8.6 Hz), 7.45 (1H, dd, J=1.9, 10.8 Hz), 7.50 (1H, dd, J=1.9, 7.3 Hz).

ESI (LC/MS positive mode) m/z 569 (M+H)

Example 20

5-(Ethylcarbamoylmethoxyamino-methyl)-3,4-difluoro-2-(2-fluoro-4-iodo-phenylamino)-N-(2-hydroxy-ethoxy)-benzamide (Compound C-14)

Step A

Synthesis of 2-aminooxy-N-ethyl-acetamide

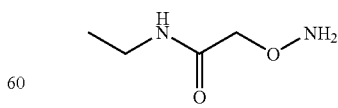

To a suspension of (1,3-dioxo-1,3-dihydro-isoindol-2-yloxy)-acetic acid methyl ester (996 mg, 4.23 mmol) obtained in Step A of Example 19 in THF (5 mL) was added ethylamine (2.0 M solution in THF, 25 ml) at room temperature, and the mixture was stirred at 60° C. for 18 hours. The reaction mixture was concentrated under reduced pressure, and methylene chloride was added to the resultant residue to precipitate a solid, which was filtered and washed with methylene chloride. The combined filtrate and washing were concentrated under reduced pressure. The residue was purified by silica gel column chromatography (40 g, $CH_2Cl_2$/MeOH (30:1 to 20:1)) to give 2-aminooxy-N-ethyl-acetamide (160 mg, 32%) as a colorless syrup.

$^1$H-NMR ($CD_3OD$, 270 MHz) δ(PPM) 1.14 (3H, t, J=7.3 Hz), 3.27 (2H, q, J=7.3 Hz), 4.07 (2H, s).

Step B

Synthesis of (E)-5-(ethylcarbamoylmethoxyimino-methyl)-3,4-difluoro-2-(2-fluoro-4-iodo-phenylamino)-N-(2-hydroxy-ethoxy)-benzamide

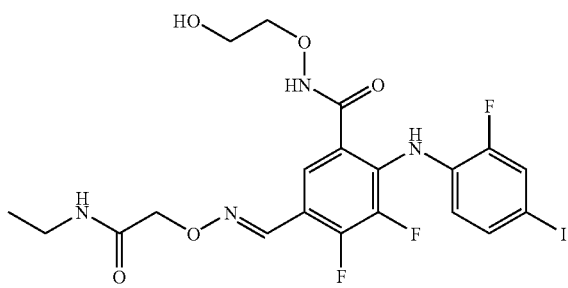

Using 2-aminooxy-N-ethyl-acetamide obtained in Step A, synthesis was performed according to the procedure described in Step C of Example 19 to give (E)-5-(ethylcarbamoylmethoxyimino-methyl)-3,4-difluoro-2-(2-fluoro-4-iodo-phenylamino)-N-(2-hydroxy-ethoxy)-benzamide.

$^1$H-NMR (DMSO-$d_6$, 270 MHz) δ(PPM) 1.03 (3H, t, J=7.3 Hz), 3.14 (2H, quint., J=7.3 Hz), 3.56 (2H, br), 3.83 (2H, br), 4.55 (2H, s), 4.72 (1H, br), 6.82 (1H, dt, J=3.8, 8.9 Hz), 7.40 (1H, br. d, J=8.9 Hz), 7.61 (1H, dd, J=1.6, 10.8 Hz), 7.67 (1H, br. d, J=5.1 Hz), 7.92 (1H, t, J=5.7 Hz), 8.40 (1H, s), 8.92 (1H, br), 11.98 (1H, br).

ESI (LC/MS positive mode) m/z 581 (M+H)

Step C

Synthesis of 5-(ethylcarbamoylmethoxyamino-methyl)-3,4-difluoro-2-(2-fluoro-4-iodo-phenylamino)-N-(2-hydroxy-ethoxy)-benzamide (Compound C-14)

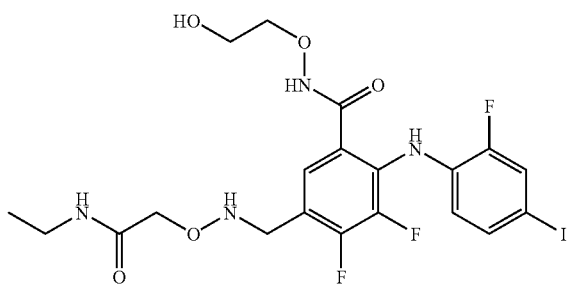

Using (E)-5-(ethylcarbamoylmethoxyimino-methyl)-3,4-difluoro-2-(2-fluoro-4-iodo-phenylamino)-N-(2-hydroxy-ethoxy)-benzamide obtained in Step B, synthesis was performed according to the procedure described in Step D of Example 19 to give 5-(ethylcarbamoylmethoxyamino-methyl)-3,4-difluoro-2-(2-fluoro-4-iodo-phenylamino)-N-(2-hydroxy-ethoxy)-benzamide.

$^1$H-NMR ($CD_3OD$, 270 MHz) δ(PPM) 1.14 (3H, t, J=7.3 Hz), 3.26 (2H, q, J=7.3 Hz), 3.68-3.76 (2H, m), 3.91-3.99 (2H, m), 4.09 (2H, s), 4.13 (2H, s), 6.61 (1H, dt, J=4.6, 8.6 Hz), 7.35 (1H, ddd, J=1.1, 1.9, 8.6 Hz), 7.45 (1H, dd, J=1.9, 10.8 Hz), 7.50 (1H, dd, J=1.9, 7.2 Hz).

ESI (LC/MS positive mode) m/z 583 (M+H)

Example 21

3,4-Difluoro-2-(2-fluoro-4-iodo-phenylamino)-N-(2-hydroxy-ethoxy)-5-(propylcarbamoyl-methoxyamino-methyl)-benzamide (Compound C-15)

Step A

Synthesis of 2-aminooxy-N-propyl-acetamide

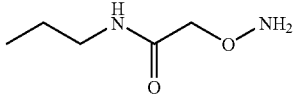

Using (1,3-dioxo-1,3-dihydro-isoindol-2-yloxy)-acetic acid methyl ester obtained in Step A of Example 19 and n-propylamine as an amine, synthesis was performed according to the procedure described in Step A of Example 20 to give 2-aminooxy-N-propyl-acetamide.

$^1$H-NMR ($CD_3OD$, 270 MHz) δ(PPM) 0.93 (3H, t, J=7.3 Hz), 1.54 (2H, hextet, J=7.3 Hz), 3.21 (2H, t, J=7.3 Hz), 4.07 (2H, s).

Step B

Synthesis of (E)-3,4-difluoro-2-(2-fluoro-4-iodo-phenylamino)-N-(2-hydroxy-ethoxy)-5-(propylcarbamoylmethoxyimino-methyl)-benzamide

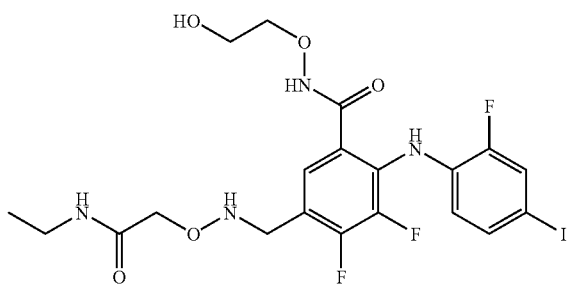

Using 2-aminooxy-N-propyl-acetamide obtained in Step A, synthesis was performed according to the procedure described in Step C of Example 19 to give (E)-3,4-difluoro-2-(2-fluoro-4-iodo-phenylamino)-N-(2-hydroxy-ethoxy)-5-(propylcarbamoylmethoxyimino-methyl)-benzamide.

$^1$H-NMR (DMSO-$d_6$, 270 MHz) δ(PPM) 0.82 (3H, t, J=7.3 Hz), 1.43 (2H, hextet, J=7.3 Hz), 3.07 (2H, q, J=7.3 Hz), 3.51-3.62 (2H, m), 3.76-3.90 (2H, m), 4.56 (2H, s), 4.72 (1H, br), 6.82 (1H, dt, J=4.1, 8.6 Hz), 7.40 (1H, dd, J=0.8, 8.6 Hz), 7.61 (1H, dd, J=1.6, 10.8 Hz), 7.62-7.71 (1H, m), 7.90 (1H, br. t, J=5.7 Hz), 8.40 (1H, s), 8.92 (1H, br), 11.98 (1H, br).

ESI (LC/MS positive mode) m/z 595 (M+H)

Step C

Synthesis of 3,4-difluoro-2-(2-fluoro-4-iodo-phenylamino)-N-(2-hydroxy-ethoxy)-5-(propycarbamoyl-methoxyamino-methyl)-benzamide (Compound C-15)

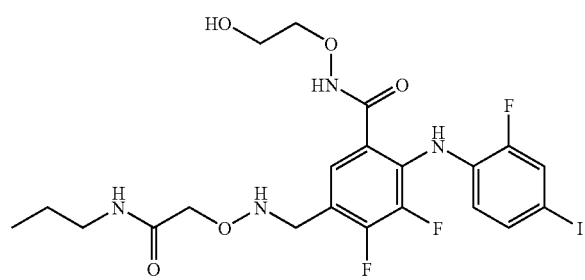

Using (E)-3,4-difluoro-2-(2-fluoro-4-iodo-phenylamino)-N-(2-hydroxy-ethoxy)-5-(propylcarbamoylmethoxyimino-methyl)-benzamide obtained in Step B, synthesis was performed according to the procedure described in Step D of Example 19 to give 3,4-difluoro-2-(2-fluoro-4-iodo-phenylamino)-N-(2-hydroxy-ethoxy)-5-(propylcarbamoyl-methoxyamino-methyl)-benzamide.

$^1$H-NMR (CD$_3$OD, 270 MHz) δ(PPM) 0.93 (3H, t, J=7.3 Hz), 1.54 (2H, hextet, J=7.3 Hz), 3.19 (2H, q, J=7.3 Hz), 3.68-3.76 (2H, m), 3.91-3.99 (2H, m), 4.09 (2H, s), 4.14 (2H, s), 6.61 (1H, dt, J=4.3, 8.6 Hz), 7.35 (1H, ddd, J=1.1, 1.9, 8.6 Hz), 7.46 (1H, dd, J=1.9, 10.8 Hz), 7.50 (1H, dd, J=1.9, 7.2 Hz).

ESI (LC/MS positive mode) m/z 597 (M+H)

Example 22

3,4-Difluoro-2-(2-fluoro-4-iodo-phenylamino)-N-(2-hydroxy-ethoxy)-5-[(isopropylcarbamoyl-methoxyamino)-methyl]-benzamide (Compound C-16)

Step A

Synthesis of 2-aminooxy-N-isopropyl-acetamide

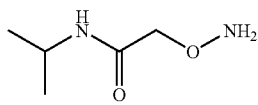

Using (1,3-dioxo-1,3-dihydro-isoindol-2-yloxy)-acetic acid methyl ester obtained in Step A of Example 19 and isopropylamine as an amine, synthesis was performed according to the procedure described in Step A of Example 20 to give 2-aminooxy-N-isopropyl-acetamide.

$^1$H-NMR (CD$_3$OD, 270 MHz) δ(PPM) 1.17 (6H, d, J=6.5 Hz), 3.98-4.12 (1H, m), 4.05 (2H, s).

Step B

Synthesis of (E)-3,4-difluoro-2-(2-fluoro-4-iodo-phenylamino)-N-(2-hydroxy-ethoxy)-5-[(isopropyl-carbamoyl-methoxyimino)-methyl]-benzamide

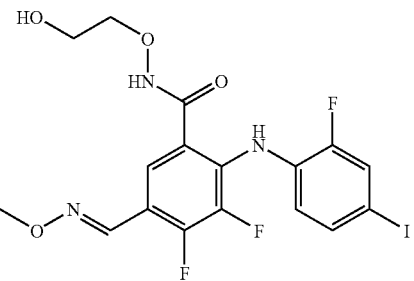

Using 2-aminooxy-N-isopropyl-acetamide obtained in Step A, synthesis was performed according to the procedure described in Step C of Example 19 to give (E)-3,4-difluoro-2-(2-fluoro-4-iodo-phenylamino)-N-(2-hydroxy-ethoxy)-5-[(isopropylcarbamoyl-methoxyimino)-methyl]-benzamide.

$^1$H-NMR (DMSO-d$_6$, 270 MHz) δ(PPM) 1.08 (3H×2, d, J=6.8 Hz), 3.57 (2H, br), 3.83 (2H, br), 3.85-4.02 (1H, m), 4.54 (2H, s), 4.72 (1H, br), 6.82 (1H, dt, J=4.1, 8.6 Hz), 7.41 (1H, br. d, J=8.6 Hz), 7.61 (1H, dd, J=1.6, 10.8 Hz), 7.62-7.76 (1H, m), 7.90 (1H, br. t, J=5.7 Hz), 8.40 (1H, s), 8.88 (1H, br), 11.98 (1H, br).

ESI (LC/MS positive mode) m/z 595 (M+H)

Step C

Synthesis of 3,4-difluoro-2-(2-fluoro-4-iodo-phenylamino)-N-(2-hydroxy-ethoxy)-5-[(isopropylcarbamoyl-methoxyamino)-methyl]-benzamide (Compound C-16)

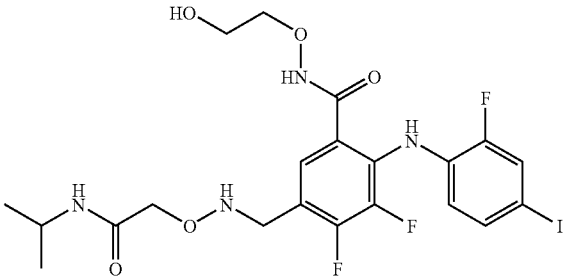

Using (E)-3,4-difluoro-2-(2-fluoro-4-iodo-phenylamino)-N-(2-hydroxy-ethoxy)-5-[(isopropylcarbamoyl-methoxyimino)-methyl]-benzamide obtained in Step B, synthesis was performed according to the procedure described in Step D of Example 19 to give 3,4-difluoro-2-(2-fluoro-4-iodo-phenylamino)-N-(2-hydroxy-ethoxy)-5-[(isopropylcarbamoyl-methoxyamino)-methyl]-benzamide.

$^1$H-NMR (CD$_3$OD, 270 MHz) δ(PPM) 1.16 (3H×2, d, J=6.8 Hz), 3.72 (2H, t, J=4.6 Hz), 3.95 (2H, t, J=4.6 Hz), 3.96-4.12 (1H, m), 4.07 (2H, s), 4.13 (2H, s), 6.61 (1H, dt, J=4.6, 8.6 Hz), 7.32-7.38 (1H, m), 7.46 (1H, dd, J=1.9, 10.8 Hz), 7.51 (1H, dd, J=1.9, 7.0 Hz).

ESI (LC/MS positive mode) m/z 597 (M+H)

Example 23

5-(Dimethylcarbamoylmethoxyamino-methyl)-3,4-difluoro-2-(2-fluoro-4-iodo-phenylamino)-N-(2-hydroxy-ethoxy)-benzamide (Compound C-17)

Step A

Synthesis of 2-aminooxy-N,N-dimethyl-acetamide

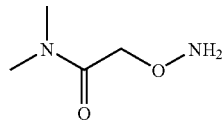

To a solution of (1,3-dioxo-1,3-dihydro-isoindol-2-yloxy)-acetic acid methyl ester (992 mg, 4.22 mmol) obtained in Step A of Example 19 in methanol (4 ml) was added dimethylamine (2.0 M solution in methanol, 10 ml), and the mixture was stirred at 60° C. for 16 hours. After cooling down to room temperature, the reaction mixture was concentrated under reduced pressure. The resultant residue was dissolved in methanol (7 ml), and methylhydrazine (0.27 ml, 6.74 mmol) was added thereto. The mixture was stirred at 60° C. for 15 hours. After cooling down to room temperature, the reaction mixture was concentrated under reduced pressure. The residue was purified by silica gel column chromatography (40 g, $CH_2Cl_2$/MeOH (40:1 to 30:1)) to give 2-aminooxy-N,N-dimethyl-acetamide (125 mg, 25%) as a colorless syrup.

$^1$H-NMR ($CD_3OD$, 270 MHz) δ(PPM) 2.94 (3H, s), 2.97 (3H, s), 4.37 (2H, s).

Step B (E)-5-(Dimethylcarbamoylmethoxyimino-methyl)-3,4-difluoro-2-(2-fluoro-4-iodo-phenylamino)-N-(2-hydroxy-ethoxy)-benzamide

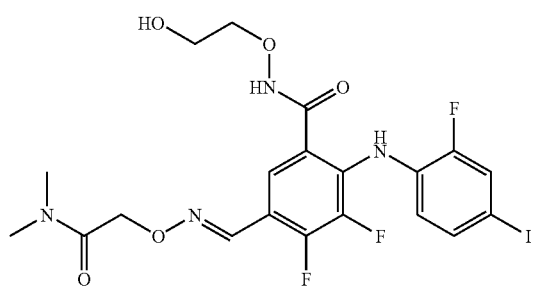

Using 2-aminooxy-N,N-dimethyl-acetamide obtained in Step A, synthesis was performed according to the procedure described in Step C of Example 19 to give (E)-5-(dimethylcarbamoylmethoxyimino-methyl)-3,4-difluoro-2-(2-fluoro-4-iodo-phenylamino)-N-(2-hydroxy-ethoxy)-benzamide.

$^1$H-NMR (DMSO-$d_6$, 270 MHz) δ(PPM) 1.08 (6H, d, J=6.8 Hz), 3.57 (2H, br), 3.83 (2H, br), 3.85-4.02 (1H, m), 4.54 (2H, s), 4.72 (1H, br), 6.81 (1H, dt, J=4.1, 8.6 Hz), 7.40 (1H, dd, J=1.1, 8.6 Hz), 7.61 (1H, dd, J=1.9, 10.8 Hz), 7.63-7.76 (1H, m), 8.36 (1H, s), 8.88 (1H, br), 11.96 (1H, br).

ESI (LC/MS positive mode) m/z 581 (M+H)

Step C

Synthesis of 5-(dimethylcarbamoylmethoxyamino-methyl)-3,4-difluoro-2-(2-fluoro-4-iodo-phenylamino)-N-(2-hydroxy-ethoxy)-benzamide (Compound C-17)

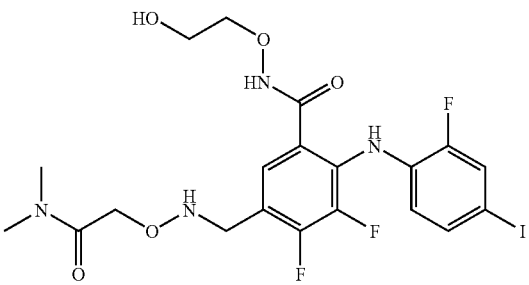

Using (E)-5-(dimethylcarbamoylmethoxyimino-methyl)-3,4-difluoro-2-(2-fluoro-4-iodo-phenylamino)-N-(2-hydroxy-ethoxy)-benzamide obtained in Step B, synthesis was performed according to the procedure described in Step D of Example 19 to give 5-(dimethylcarbamoylmethoxyamino-methyl)-3,4-difluoro-2-(2-fluoro-4-iodo-phenylamino)-N-(2-hydroxy-ethoxy)-benzamide.

$^1$H-NMR ($CD_3OD$, 270 MHz) δ(PPM) 2.93 (3H, s), 2.96 (3H, s), 3.73 (2H, t, J=4.6 Hz), 3.97 (2H, t, J=4.6 Hz), 4.13 (2H, s), 4.38 (2H, s), 6.61 (1H, dt, J=4.6, 8.6 Hz), 7.31-7.38 (1H, m), 7.44 (1H, dd, J=1.9, 10.5 Hz), 7.54 (1H, dd, J=1.9, 7.3 Hz).

ESI (LC/MS positive mode) m/z 583 (M+H)

Example 24

5-[(2-ethylcarbamoyl-ethoxyamino)-methyl]-3,4-difluoro-2-(2-fluoro-4-iodo-phenylamino)-N-(2-hydroxy-ethoxy)-benzamide (Compound C-18)

Step A

Synthesis of N-(2-ethylcarbamoyl-ethoxy)-acetimidic acid ethyl ester

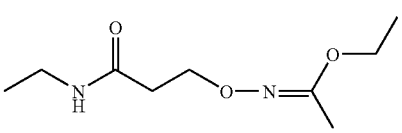

To a known compound, 3-(1-ethoxyethylideneaminooxy)-propanoic acid methyl ester (CAS No. 97164-30-2, 300 mg, 1.585 mmol) was added a 2 M solution of methylamine in methanol (7 ml), and the mixture was stirred at 60° C. for 13 hours. The reaction mixture was concentrated under reduced pressure, and the residue was purified by silica gel column chromatography to give N-(2-ethylcarbamoyl-ethoxy)-acetimidic acid ethyl ester (182 mg, 57% yield).

$^1$H-NMR ($CDCl_3$, 400 MHz) δ(PPM) 1.13 (3H, t, J=7.1 Hz), 1.27 (3H, t, J=7.3 Hz), 1.92 (3H, s), 2.53 (2H, t, J=5.9 Hz), 3.26-3.33 (2H, m), 4.00 (2H, q, J=7.3 Hz), 4.15 (2H, t, J=5.9 Hz), 5.93 (1H, br.s)

Step B

Synthesis of (E)-5-[(2-ethylcarbamoyl-ethoxy-imino)-methyl]-3,4-difluoro-2-(2-fluoro-4-iodo-phenylamino)-N-(2-hydroxy-ethoxy)-benzamide

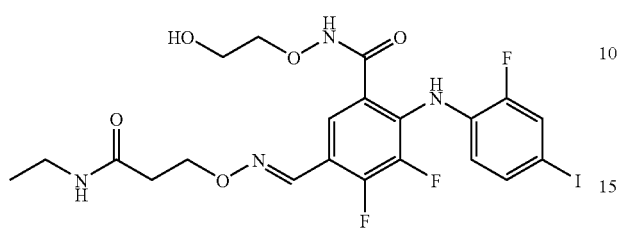

To N-(2-ethylcarbamoyl-ethoxy)-acetimidic acid ethyl ester (180 mg, 0.890 mmol) obtained in Step A was added 2 M hydrochloric acid (2 ml), and the mixture was stirred at room temperature for 30 minutes. The reaction mixture was concentrated to give a crude product of 3-aminooxy-N-ethyl-propionamide hydrochloride as a residue. To this residue, a mixed solvent of tetrahydrofuran/methanol (3:1, 20 ml) and 3,4-difluoro-2-(2-fluoro-4-iodophenylamino-5-formyl-N-(2-hydroxy-ethoxy)-benzamide (500 mg, 1.078 mmol) obtained in Step F of Example 1 were added, and the mixture was stirred for 1 hour. The reaction mixture was poured into purified water, and the resultant mixture was extracted with ethyl acetate. The combined organic layers were dried over anhydrous sodium sulfate, and concentrated under reduced pressure. The residue was purified by silica gel column chromatography to give (E)-5-[(2-ethylcarbamoyl-ethoxyimino)-methyl]-3,4-difluoro-2-(2-fluoro-4-iodo-phenylamino)-N-(2-hydroxy-ethoxy)-benzamide (200 mg, 31% yield).

ESI (LC/MS positive mode) m/z 595 (M+H)

Step C

Synthesis of 5-[(2-ethylcarbamoyl-ethoxyamino)-methyl]-3,4-difluoro-2-(2-fluoro-4-iodo-phenylamino)-N-(2-hydroxy-ethoxy)-benzamide

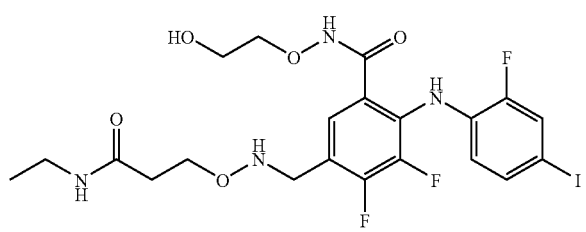

To (E)-5-[(2-ethylcarbamoyl-ethoxyimino)-methyl]-3,4-difluoro-2-(2-fluoro-4-iodo-phenylamino)-N-(2-hydroxy-ethoxy)-benzamide (40 mg, 0.067 mmol) obtained in Step B was added dichloromethane (2 ml). The mixture was stirred at room temperature, and borane-pyridine complex (40 µl) and dichloroacetic acid (40 µl) were added thereto. After stirring for 1 hour, the reaction mixture was poured into purified water, and the resultant mixture was extracted with dichloromethane. The combined organic layers were dried over anhydrous sodium sulfate, and concentrated under reduced pressure. The residue was purified by silica gel column chromatography to give 5-[(2-ethylcarbamoyl-ethoxyamino)-methyl]-3,4-difluoro-2-(2-fluoro-4-iodo-phenylamino)-N-(2-hydroxy-ethoxy)-benzamide (C-18, 29 mg, 75% yield).

$^1$H-NMR (CD$_3$OD, 400 MHz) δ(PPM) 1.07 (3H, t, J=7.2 Hz), 2.37 (2H, t, J=6.2 Hz), 3.16 (2H, q, J=7.2 Hz), 3.71 (2H, t, J=4.4 Hz), 3.86 (2H, t, J=6.2 Hz), 3.95 (2H, t, J=4.4 Hz), 4.04 (2H, s), 6.60 (1H, ddd, J=8.8, 8.8, 4.4 Hz), 7.33 (1H, br. d, J=8.3 Hz), 7.42-7.45 (2H, m)

ESI (LC/MS positive mode) m/z 597 (M+H)

Example 25

5-[(2-Propylcarbamoyl-ethoxyamino)-methyl]-3,4-difluoro-2-(2-fluoro-4-iodo-phenylamino)-N-(2-hydroxy-ethoxy)-benzamide (Compound C-19)

Step A

Synthesis of N-(2-propylcarbamoyl-ethoxy)-acetimidic acid ethyl ester

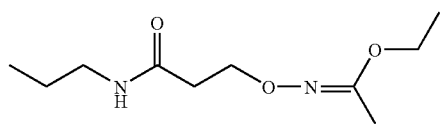

To a known compound, 3-(1-ethoxy-ethylideneaminooxy)-propanoic acid methyl ester (CAS No. 97164-30-2, 300 mg, 1.585 mmol) were added methanol (3 ml) and n-propylamine (1.3 ml), and the mixture was stirred at 55° C. for 15 hours. The reaction mixture was concentrated under reduced pressure, and the residue was purified by silica gel column chromatography to give N-(2-propylcarbamoyl-ethoxy)-acetimidic acid ethyl ester (296 mg, 86% yield).

$^1$H-NMR (CDCl$_3$, 400 MHz) δ(PPM) 0.92 (3H, t, J=7.4 Hz), 1.26 (3H, t, J=6.8 Hz), 1.47-1.56 (2H, m), 1.93 (3H, s), 2.55 (2H, t, J=6.0 Hz), 3.22 (2H, dt, J=6.8, 6.8 Hz), 4.01 (2H, q, J=6.8 Hz), 4.16 (2H, t, J=6.0 Hz), 5.83 (1H, br.s)

ESI (LC/MS positive mode) m/z 217 (M+H)

Step B

Synthesis of (E)-5-[(2-propylcarbamoyl-ethoxy-imino)-methyl]-3,4-difluoro-2-(2-fluoro-4-iodo-phenylamino)-N-(2-hydroxy-ethoxy)-benzamide

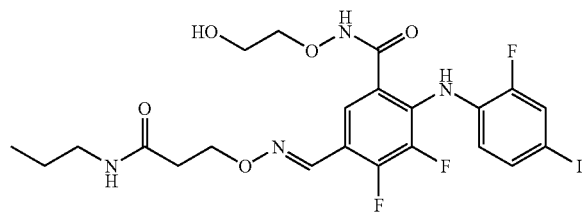

Using N-(2-propylcarbamoyl-ethoxy)-acetimidic acid ethyl ester obtained in Step A, synthesis was performed according to the procedure described in Step B of Example 24 to give (E)-5-[(2-propylcarbamoyl-ethoxyimino)-methyl]-3,4-difluoro-2-(2-fluoro-4-iodo-phenylamino)-N-(2-hydroxy-ethoxy)-benzamide.

¹H-NMR (CD₃OD, 400 MHz) δ(PPM) 0.89 (3H, t, J=7.3 Hz), 1.46-1.52 (2H, m), 2.59 (2H, t, J=6.4 Hz), 3.13 (2H, t, J=7.1 Hz), 3.72 (2H, t, J=4.6 Hz), 3.95 (2H, t, J=4.6 Hz), 4.43 (2H, t, J=6.4 Hz), 6.71 (1H, ddd, J=8.8, 8.8, 4.4 Hz), 7.37-7.39 (1H, m), 7.46 (1H, dd, J=10.7, 2.0 Hz), 7.81 (1H, br. d, J=5.9 Hz), 8.22 (1H, s)

ESI (LC/MS positive mode) m/z 609 (M+H)

Step C

Synthesis of 5-[(2-propylcarbamoyl-ethoxyamino)-methyl]-3,4-difluoro-2-(2-fluoro-4-iodo-phenylamino)-N-(2-hydroxy-ethoxy)-benzamide (Compound C-19)

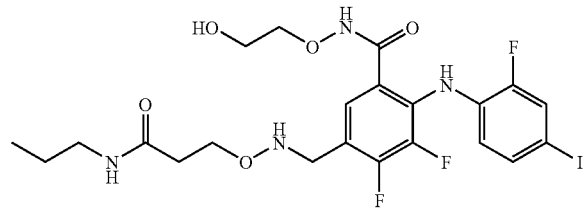

Using (E)-5-[(2-propylcarbamoyl-ethoxyimino)-methyl]-3,4-difluoro-2-(2-fluoro-4-iodo-phenylamino)-N-(2-hydroxy-ethoxy)-benzamide obtained in Step B, synthesis was performed according to the procedure described in Step C of Example 24 to give 5-[(2-propylcarbamoyl-ethoxyamino)-methyl]-3,4-difluoro-2-(2-fluoro-4-iodo-phenylamino)-N-(2-hydroxy-ethoxy)-benzamide (Compound C-19).

¹H-NMR (CD₃OD, 400 MHz) δ(PPM) 0.87 (3H, t, J=7.6 Hz), 1.39-1.50 (2H, m), 2.38 (2H, t, J=6.1 Hz), 3.09 (2H, t, J=7.0 Hz), 3.71 (2H, t, J=4.6 Hz), 3.86 (2H, t, J=6.1 Hz), 3.95 (2H, t, J=4.6 Hz), 4.04 (2H, s), 6.59 (1H, ddd, J=8.8, 8.8, 4.4 Hz), 7.32-7.35 (1H, m), 7.42-7.45 (2H, m)

ESI (LC/MS positive mode) m/z 611 (M+H)

Example 26

5-[(2-Isopropylcarbamoyl-ethoxyamino)-methyl]-3,4-difluoro-2-(2-fluoro-4-iodo-phenylamino)-N-(2-hydroxy-ethoxy)-benzamide (Compound C-20)

Step A

Synthesis of N-(2-isopropylcarbamoyl-ethoxy)-acetimidic acid ethyl ester

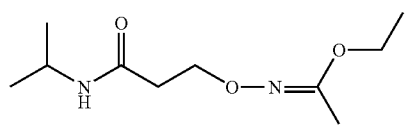

To a known compound, 3-(1-ethoxy-ethylideneaminooxy)-propanoic acid methyl ester (CAS No. 97164-30-2, 300 mg, 1.585 mmol) were added methanol (3 ml) and isopropylamine (1.4 ml), and the mixture was stirred at 55° C. for 14 hours. Additional isopropylamine (1.0 ml) was added, and the mixture was stirred for 3 hours using a focused microwave synthesis system (Discover™, CEM) at 100 W. The reaction mixture was concentrated under reduced pressure, and the residue was purified by silica gel column chromatography to give N-(2-isopropylcarbamoyl-ethoxy)-acetimidic acid ethyl ester (46 mg, 13% yield).

¹H-NMR (CDCl₃, 400 MHz) δ(PPM) 1.12 (6H, d, J=7.3 Hz), 1.28 (3H, t, J=7.1 Hz), 1.91 (3H, s), 2.50 (2H, t, J=5.9), 4.00 (2H, q, J=7.1 Hz), 4.06-4.11 (1H, m), 4.15 (2H, t, J=5.9 Hz), 5.72 (1H, br.s)

Step B

Synthesis of (E)-5-[(2-isopropylcarbamoyl-ethoxyimino)-methyl]-3,4-difluoro-2-(2-fluoro-4-iodo-phenylamino)-N-(2-hydroxy-ethoxy)-benzamide

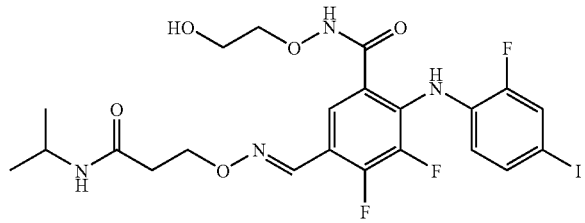

Using N-(2-isopropylcarbamoyl-ethoxy)-acetimidic acid ethyl ester obtained in Step A, synthesis was performed according to the procedure described in Step B of Example 24 to give (E)-5-[(2-isopropylcarbamoyl-ethoxyimino)-methyl]-3,4-difluoro-2-(2-fluoro-4-iodo-phenylamino)-N-(2-hydroxy-ethoxy)-benzamide.

¹H-NMR (CD₃OD, 400 MHz) δ(PPM) 1.02 (6H, d, J=6.4 Hz), 2.47 (2H, t, J=6.4 Hz), 3.63 (2H, t, J=4.6 Hz), 3.84-3.89 (3H, m), 4.34 (2H, t, J=6.4 Hz), 6.62 (1H, ddd, J=8.8, 8.8, 4.4 Hz), 7.29 (1H, br. d, J=8.8 Hz), 7.37 (1H, dd, J=10.3, 2.0 Hz), 7.72 (1H, br. d, J=6.8 Hz), 8.13 (1H, s)

ESI (LC/MS positive mode) m/z 609 (M+H)

Step C

Synthesis of 5-[(2-isopropylcarbamoyl-ethoxyamino)-methyl]-3,4-difluoro-2-(2-fluoro-4-iodo-phenylamino)-N-(2-hydroxy-ethoxy)-benzamide (Compound C-20)

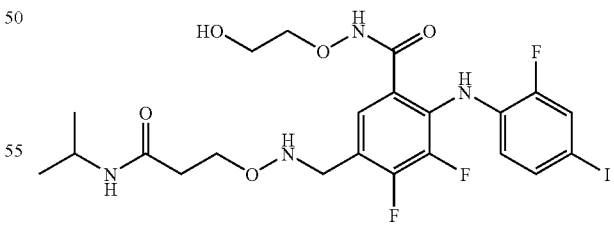

Using (E)-5-[(2-isopropylcarbamoyl-ethoxyimino)-methyl]-3,4-difluoro-2-(2-fluoro-4-iodo-phenylamino)-N-(2-hydroxy-ethoxy)-benzamide obtained in Step B, synthesis was performed according to the procedure described in Step C of Example 24 to give 5-[(2-isopropylcarbamoyl-ethoxyamino)-methyl]-3,4-difluoro-2-(2-fluoro-4-iodo-phenylamino)-N-(2-hydroxy-ethoxy)-benzamide (Compound C-20).

¹H-NMR (CD₃OD, 400 MHz) δ(PPM) 0.99 (6H, d, J=6.4 Hz), 2.27 (2H, t, J=6.1 Hz), 3.62 (2H, t, J=4.6 Hz), 3.76 (2H, t, J=6.1 Hz), 3.80-3.87 (3H, m), 3.95 (2H, s), 6.50 (1H, ddd, J=8.8, 8.8, 4.4 Hz), 7.24 (1H, br. d, J=8.8 Hz), 7.33-7.36 (2H, m)

ESI (LC/MS positive mode) m/z 611 (M+H)

Example 27

3,4-Difluoro-2-(2-fluoro-4-iodo-phenylamino)-N-(2-hydroxy-ethoxy)-5-[(2-methylcarbamoyl-ethoxyamino)-methyl]-benzamide (Compound C-6)

Step A

Synthesis of N-(2-methylcarbamoyl-ethoxy)-acetimidic acid ethyl ester

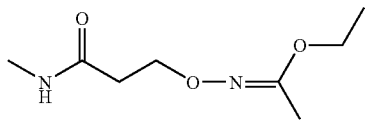

To a solution of a known compound, 3-(1-ethoxyethylideneaminooxy)-propanoic acid methyl ester (CAS No. 97164-30-2, 41.3 g, 0.218 mol) in methanol (150 ml) was added methylamine (40% solution in methanol, 200 ml) at room temperature, and the mixture was stirred at 60° C. for 12 hours. The reaction mixture was concentrated under reduced pressure to give N-(2-methylcarbamoyl-ethoxy)-acetimidic acid ethyl ester (41.0 g, 100%).

¹H-NMR (CDCl₃, 400 MHz) δ(PPM) 1.28 (3H, t, J=7.1 Hz), 1.92 (3H, s), 2.56 (2H, t, J=5.9 Hz), 2.81 (3H, d, J=4.9 Hz), 4.00 (2H, q, J=7.1 Hz), 4.15 (2H, t, J=5.9 Hz), 6.00 (1H, br.s)

Step B

Synthesis of 3-aminooxy-N-methyl-propionamide

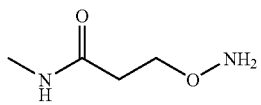

N-(2-Methylcarbamoyl-ethoxy)-acetimidic acid ethyl ester (41.0 g, 0.218 mol) obtained in Step A was dissolved in methanol (210 mL), and the solution was cooled to 0° C. To this solution, conc. hydrochloric acid (28 mL) was added dropwise over 30 minutes, and the mixture was stirred at room temperature for 30 minutes. The reaction mixture was cooled again, to which 28% aqueous ammonia (42 mL) was added portionwise, and then concentrated under reduced pressure. To the resultant residue, acetonitrile was added, and insoluble matter was filtered off. The filtrate was concentrated under reduced pressure to give 3-aminooxy-N-methyl-propionamide (25.8 g, 99%).

¹H-NMR (CDCl₃, 400 MHz) δ(PPM) 2.43 (2H, t, J=6.4 Hz), 2.70 (3H, s), 3.85 (2H, t, J=6.4 Hz)

Step C

Synthesis of (E)-3,4-difluoro-2-(2-fluoro-4-iodo-phenylamino)-N-(2-hydroxy-ethoxy)-5-[(2-methyl-carbamoyl-ethoxyimino)-methyl]-benzamide

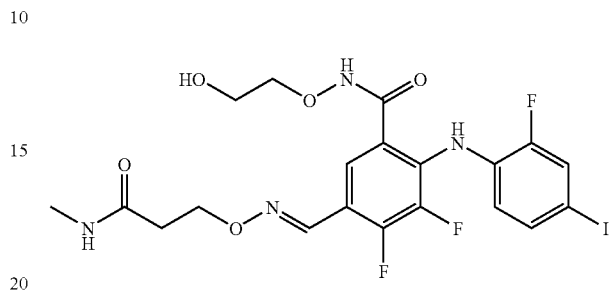

Using 3-aminooxy-N-methyl-propionamide obtained in Step B, synthesis was performed according to the procedure described in Step C of Example 19 to give 3,4-difluoro-2-(2-fluoro-4-iodo-phenylamino)-N-(2-hydroxy-ethoxy)-5-[(2-methylcarbamoyl-ethoxyimino)-methyl]-benzamide as a white solid.

¹H-NMR (CD₃OD, 270 MHz) δ(PPM) 2.59 (2H, t, J=5.9 Hz), 2.72 (3H, s), 3.72 (2H, m), 3.95 (2H, m), 4.43 (2H, t, J=5.9 Hz), 6.72 (1H, dt, J=8.9, 4.3 Hz), 7.39 (1H, m), 7.47 (1H, dd, J=10.9, 2.0 Hz), 7.80 (1H, dd, J=6.9, 2.0 Hz), 8.23 (1H, s)

ESI (LC/MS positive mode) m/z 581 (M+H)

Step D

Synthesis of 3,4-difluoro-2-(2-fluoro-4-iodo-phenylamino)-N-(2-hydroxy-ethoxy)-5-[(2-methylcarbamoyl-ethoxyamino)-methyl]-benzamide (Compound C-6)

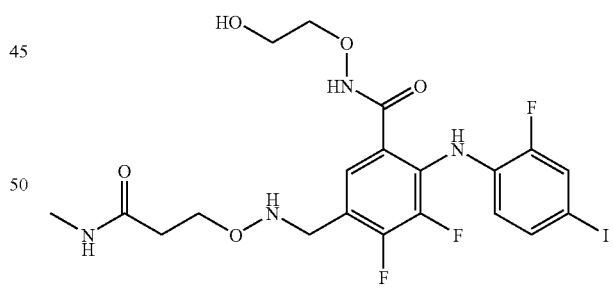

Using 3,4-difluoro-2-(2-fluoro-4-iodo-phenylamino)-N-(2-hydroxy-ethoxy)-5-[(2-methylcarbamoyl-ethoxyimino)-methyl]-benzamide obtained in Step C, synthesis was performed according to the procedure described in Step C of Example 24 to give 3,4-difluoro-2-(2-fluoro-4-iodo-phenylamino)-N-(2-hydroxy-ethoxy)-5-[(2-methylcarbamoyl-ethoxyamino)-methyl]-benzamide (Compound C-6).

¹H-NMR (CD₃OD, 270 MHz) δ(PPM) 2.32-2.41 (2H, m), 2.69 (3H, s), 3.71 (2H, t, J=4.6 Hz), 3.85 (2H, t, J=5.9 Hz), 3.89-3.96 (2H, m), 4.04 (2H, s), 6.54-6.64 (1H, m), 7.34 (1H, br. d, J=9.9 Hz), 7.43 (2H, dd, J=10.6, 1.9 Hz)

ESI (LC/MS positive mode) m/z 583 (M+H)

Example 28

3,4-Difluoro-2-(2-fluoro-4-iodo-phenylamino)-N-(2-hydroxy-ethoxy)-5-[(3-methylcarbamoyl-propoxyamino)-methyl]-benzamide (Compound C-21)

Step A

Synthesis of 4-(1,3-dioxo-1,3-dihydro-isoindol-2-yloxy)-butyric acid ethyl ester

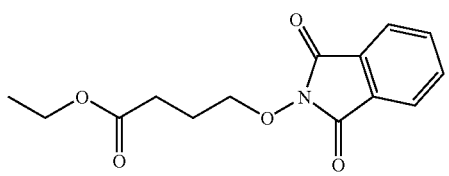

To a solution of 4-bromo-n-butyric acid ethyl ester (1.2 g, 6.13 mmol) in dimethylformamide (9 ml) were added N-hydroxyphthalimide (1.5 g, 9.19 mmol) and Hunig base (N,N-diisopropylethylamine, 2.13 mL) at room temperature, and the mixture was stirred at 80° C. over night. The reaction mixture was poured into saturated aqueous ammonium chloride, and the resultant mixture was extracted with ethyl acetate (3×40 ml). The combined organic layers were washed with saturated brine (2×30 ml), dried over $Na_2SO_4$, and concentrated under reduced pressure. The resultant residue was purified by silica gel column chromatography (100 g, n-hexane/ethyl acetate (2:1)) to give 4-(1,3-dioxo-1,3-dihydro-isoindol-2-yloxy)-butyric acid ethyl ester (1.47 g, 100%).

$^1$H-NMR ($CDCl_3$, 270 MHz) δ(PPM) 1.28 (3H, t, J=6.9 Hz), 2.11 (2H, q, J=6.9 Hz), 2.64 (2H, t, J=7.3 Hz), 4.17 (2H, q, J=7.3 Hz), 4.27 (2H, t, J=6.3 Hz), 7.72-7.79 (2H, m), 7.81-7.89 (2H, m).

Step B

Synthesis of 4-aminooxy-N-methyl-butylamide

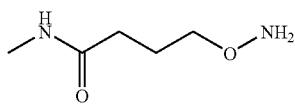

To a solution of 4-(1,3-dioxo-1,3-dihydro-isoindol-2-yloxy)-butyric acid ethyl ester (997.5 mg, 4.59 mmol) obtained in Step A in methanol (4 mL) was added methylamine (40% solution in methanol, 10 ml, 98.0 mmol), and the mixture was stirred at 60° C. overnight. The reaction mixture was concentrated under reduced pressure, and methylene chloride was added to the resultant residue to precipitate a solid, which was filtered and washed with methylene chloride. The combined filtrate and washing were concentrated under reduced pressure. The residue was purified by silica gel column chromatography (30 g, $CH_2Cl_2$/MeOH (8:1)) to give 4-aminooxy-N-methyl-butylamide (467.3 mg, 77%) as a colorless syrup.

$^1$H-NMR ($CDCl_3$, 270 MHz) δ(PPM) 1.94 (2H, q, J=6.3 Hz), 2.25 (2H, t, J=6.9 Hz), 2.81 (3H, d, J=4.6 Hz), 3.70 (t, J=5.9 Hz).

Step C

Synthesis of (E)-3,4-difluoro-2-(2-fluoro-4-iodo-phenylamino)-N-(2-hydroxy-ethoxy)-5-[(3-methylcarbamoyl-propoxyimino)-methyl]-benzamide

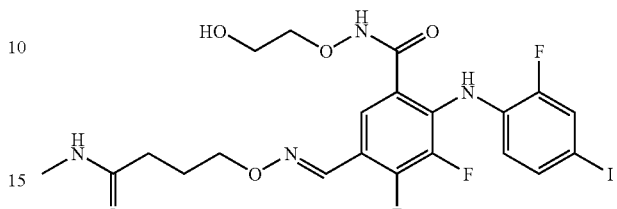

To 4-aminooxy-N-methyl-butylamide (1.79 g, 13.54 mmol) obtained in Step B were added a mixed solvent of tetrahydrofuran/methanol (3:1, 100 ml) and 3,4-difluoro-2-(2-fluoro-4-iodophenylamino-5-formyl-N-(2-hydroxy-ethoxy)-benzamide (5.00 g, 10.41 mmol) obtained in Step F of Example 1, and the mixture was stirred for 13 hours. The reaction mixture was concentrated under reduced pressure to an extent where a little solvent remained, and acetonitrile was added thereto to precipitate the product. This precipitate was filtered, washed with acetonitrile, and dried under reduced pressure to give (E)-3,4-difluoro-2-(2-fluoro-4-iodo-phenylamino)-N-(2-hydroxy-ethoxy)-5-[(3-methylcarbamoyl-propoxyimino)-methyl]-benzamide (4.93 g, 79% yield).

$^1$H-NMR (DMSO-$d_6$, 270 MHz) δ(PPM) 1.88 (2H, qui, J=7.6 Hz), 2.17 (2H, t, J=6.9 Hz), 2.56 (3H, d, J=4.6 Hz), 3.57 (2H, br. q, J=4.6 Hz), 3.83 (2H, t, J=4.6 Hz), 4.14 (2H, t, J=6.3 Hz), 4.73 (1H, t, J=5.6 Hz, OH), 6.80 (1H, td, J 8.9, 4.0 Hz), 7.40 (1H, br. d, J=8.6 Hz), 7.61 (1H, dd, J=10.9, 2.0 Hz), 7.68 (1H, br. d, J=5.6 Hz), 7.77 (1H, br q, J=4.6 Hz, NH), 8.26 (1H, s), 8.87 (1H, br. s, NH), 11.99 (1H, br. s, NH).

ESI (LC/MS positive mode) m/z 595 (M+H)

Step D

Synthesis of 3,4-difluoro-2-(2-fluoro-4-iodo-phenylamino)-N-(2-hydroxy-ethoxy)-5-[(3-methylcarbamoyl-propoxyamino)-methyl]-benzamide (Compound C-21)

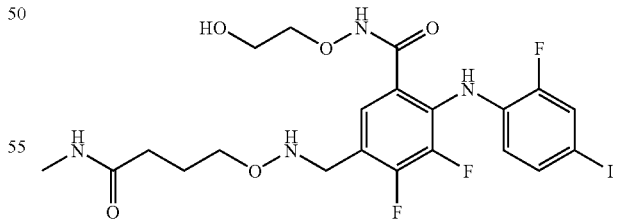

To (E)-3,4-difluoro-2-(2-fluoro-4-iodo-phenylamino)-N-(2-hydroxy-ethoxy)-5-[(3-methylcarbamoyl-propoxyimino)-methyl]-benzamide (50 mg, 0.084 mmol) obtained in Step C was added dichloromethane (6 ml). The mixture was stirred at room temperature, and borane-pyridine complex (67 μl, 0.673 mmol) and dichloroacetic acid (55 μl, 0.673 mmol) were added thereto. After stirring for 14 hours, the reaction mixture was diluted with ethyl acetate, and washed with purified water and saturated aqueous sodium chloride. The organic layer was dried over anhydrous sodium sulfate, and concentrated under reduced pressure. The residue was purified by silica gel column chromatography to give 3,4-difluoro-2-(2-fluoro-4-iodo-phenylamino)-N-(2-hydroxy-ethoxy)-5-[(3-methylcarbamoyl-propoxyamino)-methyl]-benzamide (Compound C-21, 32 mg, 65% yield).

$^1$H-NMR (CD$_3$OD, 400 MHz) δ(PPM) 1.72-1.84 (2H, m), 2.18 (2H, t, J=7.3 Hz), 2.67 (3H, s), 3.63 (2H, t, J=6.4 Hz), 3.70 (2H, t, J=4.4 Hz), 3.94 (2H, t, J=4.4 Hz), 4.05 (2H, s), 6.58 (1H, ddd, J=8.8, 8.8, 4.4 Hz), 7.32-7.35 (1H, m), 7.43 (1H, dd, J=10.5, 1.7 Hz), 6.84 (1H, br. d, J=6.8 Hz)

ESI (LC/MS positive mode) m/z 597 (M+H)

Example 29

5-[(2-Acetylamino-ethoxyamino)-methyl]-3,4-difluoro-2-(2-fluoro-4-iodo-phenylamino)-N-(2-hydroxy-ethoxy)-benzamide (Compound C-7)

Step A

Synthesis of 2-aminooxy-ethyl-carbamic acid t-butyl ester

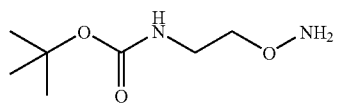

The title compound was synthesized according to the methods described in J. Med. Chem., 1999, 42, 2007 and WO02/06213.

Step B (E)-{2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester

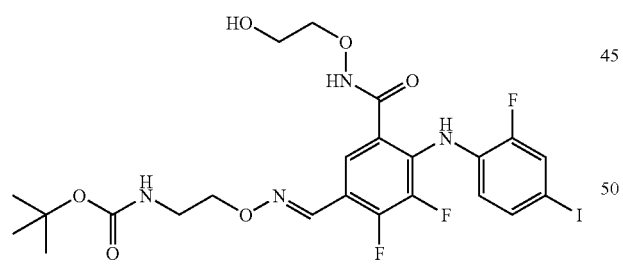

Using 2-aminooxy-ethyl-carbamic acid t-butyl ester obtained in Step A, synthesis was performed according to the procedure described in Step C of Example 19 to give (E)-{2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester.

$^1$H-NMR (DMSO-d$_6$, 270 MHz) δ(PPM) 1.38 (9H, s), 3.26 (2H, t, J=5.9 Hz), 3.56 (2H, t, J=4.3 Hz), 3.83 (2H, t, J=4.3 Hz), 4.36 (2H, t, J=5.9 Hz), 4.72 (1H, s), 6.79 (1H, m), 6.95 (1H, m), 7.38 (1H, d, J=8.9 Hz), 7.60 (1H, d, J=10.6 Hz), 7.69 (1H, d, J=6.3 Hz), 8.27 (1H, s), 8.86 (0.5H, br.s), 11.98 (0.5H, br.s)

ESI (LC/MS positive mode) m/z 639 (M+H)

Step C

Synthesis of (E)-5-[(2-amino-ethoxyimino)-methyl]-3,4-difluoro-2-(2-fluoro-4-iodo-phenylamino)-N-(2-hydroxy-ethoxy)-benzamide

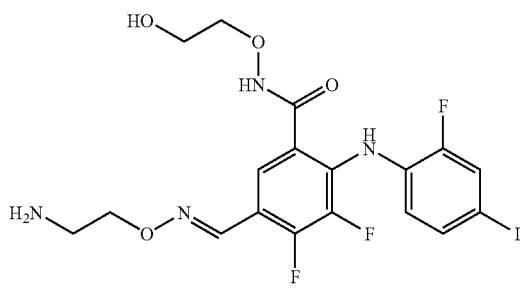

To a solution of {2-[2,3-difluoro-4-(2-fluoro-4-iodo-phenylamino)-5-(2-hydroxy-ethoxycarbamoyl)-benzylideneaminooxy]-ethyl}-carbamic acid tert-butyl ester (55 mg, 0.31 mmol) prepared in Step B in ethyl acetate (5 ml) was added 1 N HCl solution in ethyl acetate (1 ml), and the mixture was stirred at room temperature for 1.5 hours. After completion of the reaction, the reaction mixture was neutralized with saturated solution of sodium bicarbonate (50 ml), and extracted with ethyl acetate (3×100 ml). The extract was washed with saturated brine, and the organic layer was dried over anhydrous sodium sulfate, and filtered. The solvent was evaporated under reduced pressure, and after washing with diethyl ether (10 ml), the residue was recrystallized from methanol to give (E)-5-[(2-amino-ethoxyimino)-methyl]-3,4-difluoro-2-(2-fluoro-4-iodo-phenylamino)-N-(2-hydroxy-ethoxy)-benzamide (17.31 mg, 37% yield) as a pale yellow solid.

$^1$H-NMR (DMSO-d$_6$, 270 MHz) δ(PPM) 3.05 (2H, t, J=5.6), 3.56 (2H, t, J=4.6), 3.80 (2H, t, J=4.6), 4.28 (2H, t, J=5.3 Hz), 6.79 (1H, m), 7.38 (1H, d, J=9.0 Hz), 7.61 (1H, d, J=10.9 Hz), 8.08 (1H, d, J=7.3 Hz), 8.26 (1H, s)

ESI (LC/MS positive mode) m/z 539 (M+H)

Step D

Preparation of (E)-5-[(2-acetylamino-ethoxyimino)-methyl]-3,4-difluoro-2-(2-fluoro-4-iodo-phenylamino)-N-(2-hydroxy-ethoxy)-benzamide

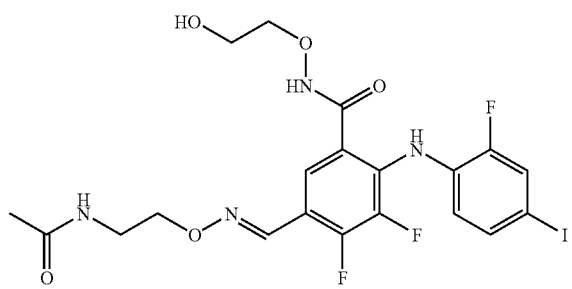

To a solution of (E)-5-[(2-amino-ethoxyimino)-methyl]-3,4-difluoro-2-(2-fluoro-4-iodo-phenylamino)-N-(2-hydroxy-ethoxy)-benzamide (8.14 mg, 0.02 mmol) described in Step C in a mixed solvent of dimethylformamide (1 ml) and methanol (5 ml) was added N-methoxydiacetamide (100 mg, 0.76 mmol), and the mixture was stirred at room temperature for 14 hours. After completion of the reaction, the solvent was evaporated under reduced pressure, and the resultant residue was purified with Mega Bond Elut silica gel (Varian, 5 g). (E)-5-[(2-Acetylamino-ethoxyimino)-methyl]-3,4-difluoro-2-(2-fluoro-4-iodo-phenylamino)-N-(2-hydroxy-ethoxy)-benzamide (8.10 mg, 92% yield) was obtained as a pale yellow solid from fractions eluted with 6% methanol/methylene chloride.

$^1$H-NMR (DMSO-d$_6$, 400 MHz) δ(PPM) 1.82 (3H, s), 3.36 (2H, t, J=5.6), 3.57 (2H, br.s), 3.84 (2H, br.s), 4.15 (2H, t, J=5.6 Hz), 4.73 (1H, s), 6.81 (1H, m), 7.40 (1H, d, J=7.6 Hz), 7.61 (1H, d, J=10.8 Hz), 7.71 (1H, br.s), 8.00 (1H, s), 8.28 (1H, s), 8.90 (0.5H, br.s), 11.98 (0.5H, br.s)

ESI (LC/MS positive mode) m/z 581 (M+H)

Step E

Synthesis of 5-[(2-acetylamino-ethoxyamino)-methyl]-3,4-difluoro-2-(2-fluoro-4-iodo-phenylamino)-N-(2-hydroxy-ethoxy)-benzamide (Compound C-7)

To (E)-5-[(2-acetylamino-ethoxyimino)-methyl]-3,4-difluoro-2-(2-fluoro-4-iodo-phenylamino)-N-(2-hydroxy-ethoxy)-benzamide (57.6 mg, 99.3 μmol) obtained in Step D was added dichloromethane (2.5 ml). The mixture was stirred at room temperature, and borane-pyridine complex (80 μl, 0.79 mmol) and dichloroacetic acid (67 μl, 0.80 mmol) were added thereto. After stirring for 3 hours, water (10 ml) and saturated aqueous sodium bicarbonate (2 ml) were added to the reaction mixture, which was then extracted with methylene chloride (15 ml and 2×8 ml). The combined organic layers were washed with aqueous sodium bicarbonate (8 ml) and saturated aqueous sodium chloride (8 ml), dried over anhydrous sodium sulfate, and concentrated under reduced pressure. The residue was purified by silica gel column chromatography (methylene chloride/methanol (10:1)) to give 5-[(2-acetylamino-ethoxyamino)-methyl]-3,4-difluoro-2-(2-fluoro-4-iodo-phenylamino)-N-(2-hydroxy-ethoxy)-benzamide (Compound C-7, 44.0 mg, 76%).

$^1$H-NMR (CD$_3$OD, 270 MHz) δ(PPM) 1.92 (3H, s), 3.36 (2H, t, J=5.6), 3.67 (2H, t, J=5.4 Hz), 3.70 (2H, t, J=4.8 Hz), 3.93 (2H, t, J=4.3 Hz), 4.07 (2H, s), 6.59 (1H, td, J=8.7, 4.5 Hz), 7.34 (1H, br. d, J=8.4 Hz), 7.44 (1H, dd, J=10.7, 2.0 Hz), 1H is overlapped with the dd peak at 7.44 ppm. 2H is overlapped with the peak of H$_2$O around 3.3 ppm.

ESI (LC/MS positive mode) m/z 583 (M+H)

Example 30

3,4-Difluoro-2-(2-fluoro-4-iodo-phenylamino)-N-(2-hydroxy-ethoxy)-5-[(2-propionylamino-ethoxyamino)-methyl]-benzamide (Compound C-34)

Step A

Synthesis of (E)-3,4-difluoro-2-(2-fluoro-4-iodo-phenylamino)-N-(2-hydroxy-ethoxy)-5-[(2-propionylamino-ethoxyimino)-methyl]-benzamide

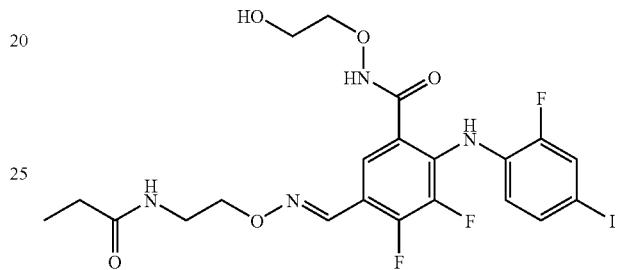

To a solution of propionic acid (84 μl, 1.13 mmol) in methylene chloride (2 ml) were added 1-ethyl-3-(3'-dimethylaminopropyl)carbodiimide hydrochloride (212.0 mg, 1.10 mmol) and N-hydroxybenzotriazole (156.5 mg, 1.17 mmol) at room temperature, and the mixture was stirred at room temperature for 30 minutes to give a solution of an active ester of propionic acid in methylene chloride (0.55 M). To a solution of 5-[(2-amino-ethoxyimino)-methyl]-3,4-difluoro-2-(2-fluoro-4-iodo-phenylamino)-N-(2-hydroxy-ethoxy)-benzamide (101.9 mg, 0.189 mmol) obtained in Step C of Example 29 in DMF (2.5 ml) were added dimethylaminopyridine (54.0 mg, 0.442 mmol) and the solution of the active ester in methylene chloride (0.55 M, 0.35 ml, 0.193 mmol) obtained above, and the mixture was stirred at room temperature. With monitoring the reaction, 0.18 ml (0.10 mmol) and 0.20 ml (0.11 mmol) of the active ester solution were added after 40 minutes and 13 hours, respectively, and the mixture was stirred for another 8 hours. Water (10 ml) was added to the reaction mixture, which was then extracted with ethyl acetate (20 ml+3×10 ml). The combined organic layers were washed with aqueous sodium bicarbonate (2×15 ml), 0.2 N hydrochloric acid (15 ml), and saturated brine (15 ml), dried over sodium sulfate, and concentrated under reduced pressure. The resultant residue was triturated with n-hexane/ethyl acetate (3:1) to give an oxime, (E)-3,4-difluoro-2-(2-fluoro-4-iodo-phenylamino)-N-(2-hydroxy-ethoxy)-5-[(2-propionylamino-ethoxyimino)-methyl]-benzamide (94.6 mg, 84%) as a pale yellow solid.

ESI (LC/MS positive mode) m/z 595 (M+H)

Step B

Synthesis of 3,4-difluoro-2-(2-fluoro-4-iodo-phenylamino)-N-(2-hydroxy-ethoxy)-5-[(2-propionylamino-ethoxyamino)-methyl]-benzamide (Compound C34)

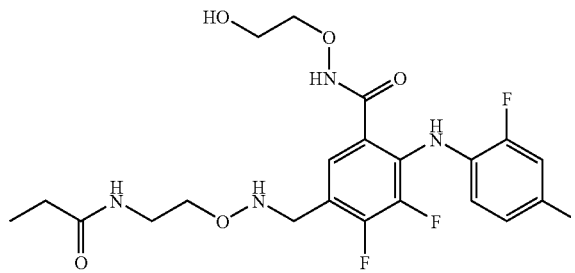

The oxime, (E)-3,4-difluoro-2-(2-fluoro-4-iodo-phenylamino)-N-(2-hydroxy-ethoxy)-5-[(2-propionylamino-ethoxyimino)-methyl]-benzamide (33.0 mg, 51.0 μmol) obtained in Step A was suspended in methylene chloride (1 ml), and dichloroacetic acid (60 ml) and borane-pyridine complex (70 μl) were added thereto at room temperature. The mixture was stirred at room temperature for 2 hours. Water (6 ml) and aqueous sodium bicarbonate (2 ml) were added to the reaction mixture, which was then extracted with methylene chloride (2×10 ml). The combined organic layers were washed with aqueous sodium bicarbonate (5-fold dilution of saturated solution, 8 ml) and saturated brine (8 ml), dried over sodium sulfate, and concentrated under reduced pressure. The resultant residue was purified by silica gel column chromatography (methylene chloride/methanol (40:3)) to give 3,4-difluoro-2-(2-fluoro-4-iodo-phenylamino)-N-(2-hydroxy-ethoxy)-5-[(2-propionylamino-ethoxyamino)-methyl]-benzamide (Compound C-34, 21.6 mg, 71%) as a colorless syrup.

$^{1}$H-NMR (CD$_{3}$OD, 270 MHz) δ(PPM) 1.09 (3H, t, J=7.8 Hz), 2.17 (2H, q, J=7.8 Hz), 3.33 (2H, t, J=5.7 Hz), 3.67 (2H, dd (like t), J=5.1, 5.7 Hz), 3.70 (2H, br. t, J=5.1 Hz), 3.93 (2H, br. t, J=4.1 Hz), 4.07 (2H, s), 6.58 (1H, td, J=8.9, 4.3 Hz), 7.34 (1H, ddd, J=8.4, 1.6, 1.4 Hz), 7.44 (1H, dd, J=10.5, 1.9 Hz), 1H is overlapped with the dd peak at 7.44 ppm.

ESI (LC/MS positive mode) m/z 597 (M+H)

Example 31

3,4-Difluoro-2-(2-fluoro-4-iodo-phenylamino)-N-(2-hydroxy-ethoxy)-5-[(2-isobutyrylamino-ethoxyamino)-methyl]-benzamide (Compound C-35)

Step A

Synthesis of (E)-3,4-difluoro-2-(2-fluoro-4-iodo-phenylamino)-N-(2-hydroxy-ethoxy)-5-[(2-isobutyrylamino-ethoxyimino)-methyl]-benzamide

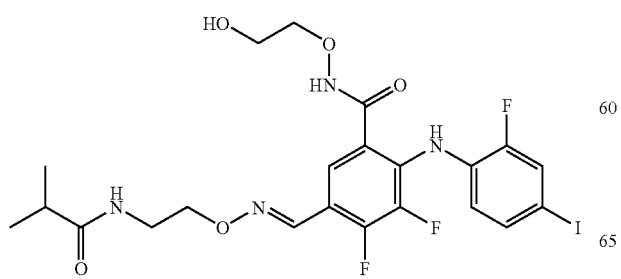

To a solution of isobutyric acid (172 μl, 1.85 mmol) in a mixed solvent of methylene chloride and DMF (3 ml and 1 ml) were added 1-ethyl-3-(3'-dimethylaminopropyl)carbodiimide hydrochloride (352.1 mg, 1.84 mmol) and N-hydroxybenzotriazole (250.0 mg, 1.87 mmol) at room temperature, and the mixture was stirred at room temperature for 30 minutes to give a solution of an active ester of isobutyric acid in methylene chloride—DMF (0.46 M). To a suspension of 5-[(2-amino-ethoxyimino)-methyl]-3,4-difluoro-2-(2-fluoro-4-iodo-phenylamino)-N-(2-hydroxy-ethoxy)-benzamide (106.7 mg, 0.198 mmol) obtained in Step C of Example 29 in DMF (2 ml) were added dimethylaminopyridine (51.2 mg, 0.419 mmol) and the solution of the active ester in methylene chloride (0.46 M, 0.50 ml, 0.23 mmol) obtained above, and the mixture was stirred at room temperature. With monitoring the reaction, 0.20 ml (0.09 mmol) and 0.20 ml (0.09 mmol) of the active ester solution were added after 20 minutes and 13 hours, respectively, and the mixture was stirred for another 8 hours. Water (10 ml) was added to the reaction mixture, which was then extracted with ethyl acetate (20 ml+3×10 ml). The combined organic layers were washed with aqueous sodium bicarbonate (2×10 ml), 0.2 N hydrochloric acid (15 ml), and saturated brine (10 ml), dried over sodium sulfate, and concentrated under reduced pressure. The resultant residue was triturated with n-hexane/ethyl acetate (3:1) to give an oxime, (E)-3,4-difluoro-2-(2-fluoro-4-iodo-phenylamino)-N-(2-hydroxy-ethoxy)-5-[(2-isobutyrylamino-ethoxyimino)-methyl]-benzamide (98.5 mg, 82%) as a pale yellow solid.

ESI (LC/MS positive mode) m/z 609 (M+H)

Step B

Synthesis of 3,4-difluoro-2-(2-fluoro-4-iodo-phenylamino)-N-(2-hydroxy-ethoxy)-5-[(2-isobutyrylamino-ethoxyamino)-methyl]-benzamide (Compound C-35)

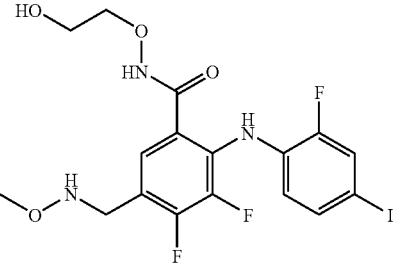

The oxime, (E)-3,4-difluoro-2-(2-fluoro-4-iodo-phenylamino)-N-(2-hydroxy-ethoxy)-5-[(2-isobutyrylamino-ethoxyimino)-methyl]-benzamide (28.8 mg, 47.3 μmol) obtained in Step A was suspended in methylene chloride (1 ml), and dichloroacetic acid (60 ml) and borane-pyridine complex (70 μl) were added thereto at room temperature. The mixture was stirred at room temperature for 2 hours. Water (6 ml) and aqueous sodium bicarbonate (2 ml) were added to the reaction mixture, which was then extracted with methylene chloride (2×10 ml). The combined organic layers were washed with aqueous sodium bicarbonate (5-fold dilution of saturated solution, 8 ml) and saturated brine (8 ml), dried over sodium sulfate, and concentrated under reduced pressure. The resultant residue was purified by silica gel column chromatography (methylene chloride/methanol (40:3)) to give 3,4-difluoro-2-(2-fluoro-4-iodo-phenylamino)-N-(2-hydroxy-ethoxy)-5-[(2-isobutyrylamino-ethoxyamino)-methyl]-benzamide (Compound C-35, 20.5 mg, 71%) as a colorless syrup.

$^1$H-NMR (CD$_3$OD, 270 MHz) δ(PPM) 1.07 (6H, d, J=6.8 Hz), 2.40 (1H, quinted, J=6.8 Hz), 3.34 (2H, t, J=5.4 Hz), 3.67 (2H, t, J=5.4 Hz), 3.70 (2H, br. t, J=4.9 Hz), 3.93 (2H, br. t, J=4.3 Hz), 4.07 (2H, s), 6.58 (1H, td, J=8.6, 4.1 Hz), 7.34 (1H, ddd, J=8.6, 1.9, 1.1 Hz), 7.44 (1H, dd, J=10.8, 1.9 Hz), 1H is overlapped with the dd peak at 7.44 ppm.

ESI (LC/MS positive mode) m/z 611 (M+H)

Example 32

2-(4-Ethynyl-2-fluoro-phenylamino)-3,4-difluoro-N-(2-hydroxy-ethoxy)-5-[(2-hydroxy-2-methyl-propoxyamino)-methyl]-benzamide (Compound C-29)

Step A (E)-2-(4-Ethynyl-2-fluoro-phenylamino)-3,4-difluoro-N-(2-hydroxy-ethoxy)-5-[(2-hydroxy-2-methyl-propoxyimino)-methyl]-benzamide

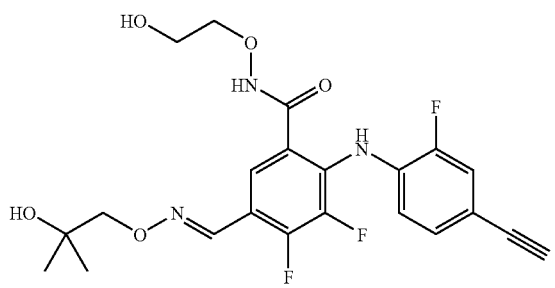

(E)-3,4-difluoro-2-(2-fluoro-4-iodophenylamino)-N-(2-hydroxy-ethoxy)-5-[(2-hydroxy-2-methyl-propoxyimino)-methyl]-benzamide (200 mg, 0.35 mmol), Pd(CH$_3$CN)$_2$Cl$_2$ (4.5 mg, 0.0176 mmol), triphenylphosphine-3,3',3''-trisulfonic acid trisodium salt (25.0 mg, 0.037 mmol), N($^i$Pr)$_2$Et (48.0 mg, 0.37 mmol), trimethylsilyl acetylene (172 mg, 1.76 mmol), and CuI (3.4 mg, 0.0176 mmol) were stirred in MeOH at room temperature for 1 hour, and the solvent was evaporated. The resultant residue was added to THF/H$_2$O containing tetrabutylammonium fluoride (0.35 mmol), and the mixture was stirred for 1 hour. EtOAc was added thereto, and the organic layer was washed with 0.4 N aqueous HCl, dried over Na$_2$SO$_4$, and evaporated. The resultant residue was purified by silica gel chromatography (CH$_2$Cl$_2$/MeOH as a developing solvent) to give a title compound (99 mg).

$^1$H-NMR (CD$_3$OD, 270 MHz) δ(PPM) 1.26 (6H, s), 3.46 (1H, s), 3.71 (2H, m), 3.95 (2H, m), 4.08 (2H, s), 6.85 (1H, m), 7.16 (d, J=8.9 Hz), 7.21 (1H, dd, J=13.9, 1.6 Hz), 7.82 (1H, br. d, J=5.3 Hz), 8.31 (1H, s)

ESI (LC/MS positive mode) m/z 466 (M+H)

Step B 2-(4-Ethynyl-2-fluoro-phenylamino)-3,4-difluoro-N-(2-hydroxy-ethoxy)-5-[(2-hydroxy-2-methyl-propoxyamino)-methyl]-benzamide (Compound C-29)

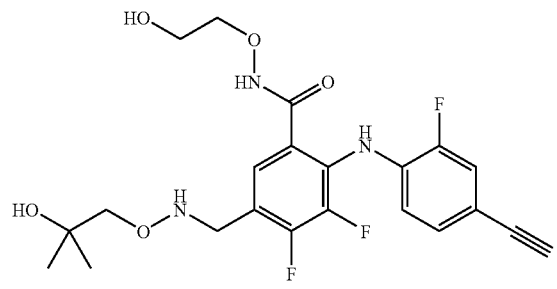

Using (E)-2-(4-ethynyl-2-fluoro-phenylamino)-3,4-difluoro-N-(2-hydroxy-ethoxy)-5-[(2-hydroxy-2-methyl-propoxyimino)-methyl]-benzamide obtained in Step A as a starting material, synthesis was performed according to the procedure described in Step C of Example 24 to give 2-(4-ethynyl-2-fluoro-phenylamino)-3,4-difluoro-N-(2-hydroxy-ethoxy)-5-[(2-hydroxy-2-methyl-propoxyamino)-methyl]-benzamide (Compound C-29).

$^1$H-NMR (DMSO-d$_6$, 400 MHz) δ(PPM) 1.00 (6H, s), 3.53 (2H, br), 3.81 (2H, br), 3.96 (2H, d, J=5.9 Hz), 4.08 (1H, s), 4.40 (1H, br), 4.71 (1H, br), 6.69 (1H, m), 6.97 (1H, t, J=5.9 Hz), 7.13 (1H, d, J=8.8 Hz), 7.30 (1H, d, J=11.6 Hz), 7.49 (1H, d, J=6.8 Hz), 8.66 (1H, br), 11.73 (1H, br). The peak of a methylene group is overlapping with that of H$_2$O peak.

ESI (LC/MS positive mode) m/z 468 (M+H)

Example 33

2-(4-Ethynyl-2-fluoro-phenylamino)-3,4-difluoro-N-(2-hydroxy-ethoxy)-5-[(2-hydroxy-ethoxyamino)-methyl]-benzamide (Compound C-2)

Step A

Synthesis of (E)-2-(4-ethynyl-2-fluoro-phenylamino)-3,4-difluoro-N-(2-hydroxy-ethoxy)-5-[(2-hydroxy-ethoxyimino)-methyl]-benzamide

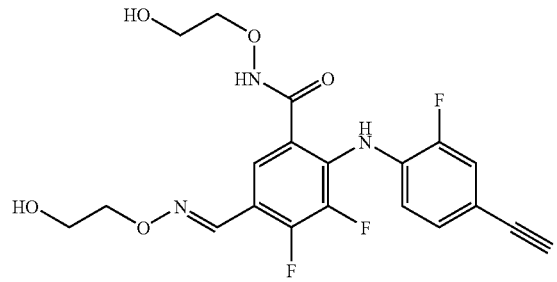

Starting from (E)3,4-difluoro-2-(2-fluoro-4-iodo-phenylamino)-N-(2-hydroxy-ethoxy)-5-[(2-hydroxy-ethoxyimino)-methyl]-benzamide obtained in Step B of Example 6, synthesis was performed according to the procedure described in Step A of Example 32 to give (E)-2-(4-ethynyl-2-fluoro-phenylamino)-3,4-difluoro-N-(2-hydroxy-ethoxy)-5-[(2-hydroxy-ethoxyimino)-methyl]-benzamide.

$^1$H-NMR (CD$_3$OD, 270 MHz) δ(PPM): 3.45 (1H, s), 3.72 (2H, dd, J=4.9, 4.3 Hz), 3.82 (2H, dd, J=5.3, 4.6 Hz), 3.96 (2H, dd, 4.9, 4.3 Hz), 4.27 (2H, t, J=4.9 Hz), 6.85 (1H, td, J=8.6, 4.6 Hz), 7.18 (2H, m), 7.83 (1H, dd, J=7.0, 2.0 Hz), 8.39 (1H, s)

ESI (LC/MS positive mode) m/z 438 (M+H)

Step B

Synthesis of 2-(4-ethynyl-2-fluoro-phenylamino)-3,4-difluoro-N-(2-hydroxy-ethoxy)-5-[(2-hydroxy-ethoxyamino)-methyl]-benzamide (Compound C-2)

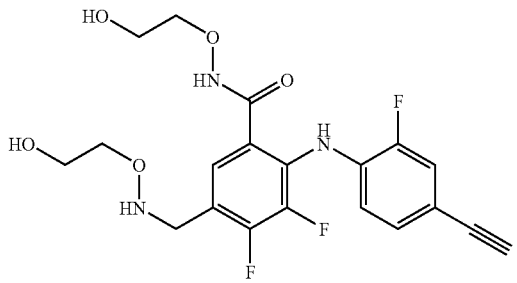

Using (E)-2-(4-ethynyl-2-fluoro-phenylamino)-3,4-difluoro-N-(2-hydroxy-ethoxy)-5-[(2-hydroxy-ethoxyimino)-methyl]-benzamide obtained in Step A, synthesis was performed according to the procedure described in Step C of Example 24 to give 2-(4-ethynyl-2-fluoro-phenylamino)-3,4-difluoro-N-(2-hydroxy-ethoxy)-5-[(2-hydroxy-ethoxyamino)-methyl]-benzamide (Compound C-2).

$^1$H-NMR (DMSO-d$_6$, 400 MHz) δ(PPM) 3.46 (2H, t, J=4.7 Hz), 3.55 (4H, m), 3.82 (2H, t, J=4.7 Hz), 3.96 (2H, d, J=5.8 Hz), 4.08 (1H, s), 4.53 (1H, br), 4.71 (1H, br), 6.70 (1H, m), 6.85 (1H, t, J=5.8 Hz), 7.13 (1H, d, J=8.3 Hz), 7.30 (1H, dd, J=12.0 Hz, 2.0 Hz), 7.49 (1H, d, J=6.3 Hz), 8.66 (1H, br), 11.72 (1H, br).

ESI (LC/MS positive mode) m/z 440 (M+H)

Example 34

3,4-Difluoro-2-(2-fluoro-4-iodo-phenylamino)-5-(2-hydroxy-1,1-dimethyl-ethoxymethyl)-N-(2-hydroxy-ethoxy)-benzamide (Compound B-19)

Step A

Synthesis of 2-methyl-propane-1,2-diol

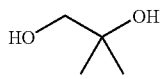

2-Methyl-propane-1,2-diol is a known compound (CAS No. 558-43-0), and may be prepared by one of the method described in the following literatures:

Zh. Obshch. Khim. 7, 1319 (1937),

Chem. Zentralbl. 109, 561 (1938),

Meml. Poudres, 28, 263 (1938), and

Chem. Zentralbl. 110, 2398 (1939).

Practically, the title compound was prepared by the following procedure.

To a suspension of lithium aluminum hydride (321.3 mg, 8.47 mmol) in THF (5 ml) was added dropwise a solution of 2-hydroxy-2-methyl-propionic acid methyl ester (commercially available, 1.0 g, 8.47 mmol) in THF (3 ml), and the mixture was stirred at room temperature for 4 hours. Water (0.70 ml) was added to the reaction mixture, which was stirred for additional 10 minutes. The resultant mixture was filtered through a mixed bed of celite powder and sodium sulfate powder. The filtrate was concentrated under reduced pressure, and the residue was diluted with THF, dried over sodium sulfate, and concentrated under reduced pressure to give 2-methyl-propane-1,2-diol (659.7 mg, 86%) as an oily crude product.

$^1$H-NMR (DMSO-d$_6$, 270 MHz) δ(PPM) 1.03 (6H, s), 3.13 (2H, d, J=5.6 Hz), 4.10 (1H, s), 4.50 (1H, t, J=5.9 Hz).

Step B

Synthesis of 3,4-difluoro-2-(2-fluoro-4-iodo-phenylamino)-5-(2-hydroxy-1,1-dimethyl-ethoxymethyl)-N-(2-hydroxy-ethoxy)-benzamide (Compound B-19)

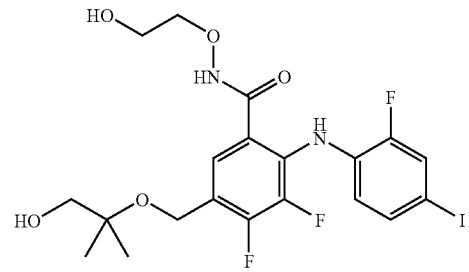

Using 3,4-difluoro-2-(2-fluoro-4-iodo-phenylamino)-5,formyl-N-(2-hydroxy-ethoxy)-benzamide obtained in Step F of Example 1 as a starting material, and 2-methyl-propane-1,2-diol obtained in Step A instead of ethylene glycol used as a reagent in Step G of Example 1, synthesis similar to that in Step G of Example 1 was performed. The resultant cyclic acetal was subjected to reduction condition similar to that in Step H of Example 1 to give the title compound.

$^1$H-NMR (DMSO-d$_6$, 270 MHz) δ(PPM) 1.18 (6H, s), 3.35 (2H, overlapped with H$_2$O peak in DMSO, singlet after addition of D$_2$O), 3.37 (2H, s), 3.56 (2H, dd, J=4.9, 4.6 Hz), 3.83 (2H, dd, J=4.9, 4.6 Hz), 4.50 (2H, s), 4.69 (1H, t, J=5.6 Hz, disappeared after addition of D$_2$O), 4.70 (1H, br. s, disappeared after addition of D$_2$O), 6.60 (1H, td, J=8.7, 4.1 Hz), 7.36 (1H, br. d, J=8.4 Hz), 7.46 (1H, br. d, J=6.6 Hz), 7.57 (1H, dd, J=10.9, 1.8 Hz), 8.61 (1H, br. s, disappeared after addition of D$_2$O), 11.80 (1H, br. s, disappeared after addition of D$_2$O).

ESI (LC/MS positive mode) m/z 569 (M+H)

Example 35

Synthesis of 3,4-difluoro-2-(2-fluoro-4-iodo-phenylamino)-N-(2-hydroxy-ethoxy)-5-(2-methanesulfonyl-ethoxymethyl)-benzamide (Compound B-12)

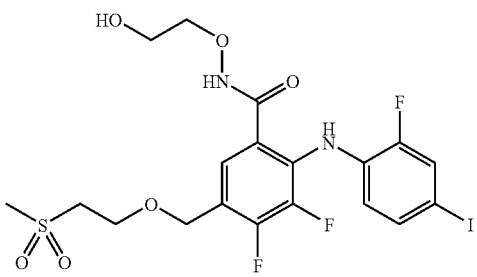

To a suspension of 3,4-difluoro-2-(2-fluoro-4-iodo-phenylamino)-5-formyl-N-(2-hydroxy-ethoxy)-benzamide (52 mg, 0.108 mmol) obtained in Step F of Example 1 in methylene chloride (anhydrous, 5 mL) were added copper trifluoromethanesulfonate (20 mg, 0.005 mmol), methanesulfonylethanol (200 µL), and triethylsilane (500 µL, 3.13 mmol) under a nitrogen atmosphere, and the mixture was stirred thoroughly for a whole day and night. After completion of the reaction, the reaction mixture was extracted with ethyl acetate, and the organic layer was washed sequentially with 2% aqueous EDTA, water, and saturated brine, dried over anhydrous sodium sulfate, and concentrated under reduced pressure. The resultant residue was purified by preparative TLC (No. 5744, Merck, 5% methanol/methylene chloride as a developing solvent) to give 3,4-difluoro-2-(2-fluoro-4-iodo-phenylamino)-N-(2-hydroxy-ethoxy)-5-(2-methanesulfonyl-ethoxymethyl)-benzamide (13.3 mg, 21%) as a white solid.

$^1$H-NMR (CD$_3$OD, 270 MHz) δ(PPM) 3.02 (3H, s), 3.41 (2H, dd, J=5.4, 5.1 Hz), 3.71 (2H, dd, J=4.8, 4.5 Hz), 3.95 (4H, m), 4.60 (2H, s), 6.63 (1H, td, J=8.9, 4.3 Hz), 7.35 (1H, br. d, J=8.4 Hz), 7.45 (1H, dd, J=10.9, 1.8 Hz), 7.50 (1H, m)

ESI (LC/MS positive mode) m/z 589 (M+H)

Example 36

3,4-Difluoro-2-(2-fluoro-4-iodo-phenylamino)-N-(2-hydroxy-ethoxy)-5-(3-oxo-[1,2]oxazinan-2-ylmethyl)-benzamide (Compound G-1)

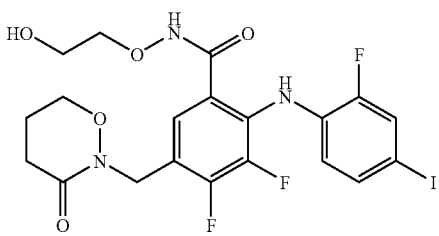

(E)-3,4-Difluoro-2-(2-fluoro-4-iodo-phenylamino)-N-(2-hydroxy-ethoxy)-5-[(3-methylcarbamoyl-propoxyimino)-methyl]-benzamide (8.0 g, 13.5 mmol) obtained in Step C of Example 28 was suspended in methylene chloride (240 ml), and borane-pyridine complex (5.45 ml, 53.8 mmol) and dichloroacetic acid (6.65 ml, 80.8 mmol) were added thereto at room temperature. The reaction mixture was stirred at room temperature for 15 hours, and dichloromethane was removed under reduced pressure with a rotary evaporator. The residue was diluted with 1,2-dichloroethane (240 ml), and the mixture was stirred at 60° C. for 8 hours, and filtered. The residue obtained by concentrating the filtrate was diluted with ethyl acetate (800 ml), and washed sequentially with water (400 ml), saturated aqueous sodium bicarbonate (400 ml), and saturated brine (400 ml). The organic layer was dried over anhydrous sodium sulfate, and concentrated under reduced pressure. The residue was purified by silica gel column chromatography (CH$_2$Cl$_2$/MeOH (25:1)) to give 3,4-difluoro-2-(2-fluoro-4-iodo-phenylamino)-N-(2-hydroxy-ethoxy)-5-(3-oxo-[1,2]oxazinan-2-ylmethyl)-benzamide (Compound G-1, 6.93 g, 91% yield).

This compound may also be obtained as a by-product (18 mg, 35% yield) in a synthesis of 3,4-difluoro-2-(2-fluoro-4-iodo-phenylamino)-N-(2-hydroxy-ethoxy)-5-[(3-methylcarbamoyl-propoxyamino)-methyl]-benzamide (Compound C-21) in Example 28.

$^1$H-NMR (CD$_3$OD, 400 MHz) δ(PPM) 2.10 (2H, quinted, J=6.8 Hz), 2.53 (2H, t, J=6.8 Hz), 3.72 (2H, t, J=4.4 Hz), 3.92 (2H, t, J=4.4 Hz), 4.04 (2H, t, J=6.8 Hz), 4.86 (2H, s), 6.61 (1H, ddd, J=8.8, 8.8, 3.9 Hz), 7.33-7.36 (1H, m), 7.41 (1H, dd, J=7.0, 1.7 Hz), 7.45 (1H, dd, J=10.3, 2.0 Hz)

ESI (LC/MS positive mode) m/z 566 (M+H)

Example 37

3,4-Difluoro-2-(2-fluoro-4-iodo-phenylamino)-N-(2-hydroxy-ethoxy)-5-(3-oxo-isoxazolidin-2-yl methyl)-benzamide (Compound G-2)

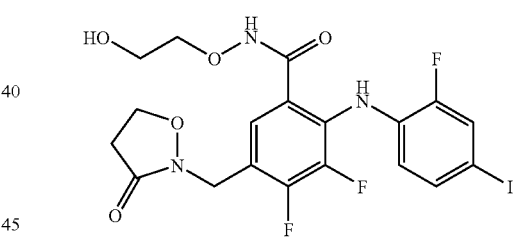

To (E)-3,4-difluoro-2-(2-fluoro-4-iodo-phenylamino)-N-(2-hydroxy-ethoxy)-5-[(2-methylcarbamoyl-ethoxyimino)-methyl]-benzamide (9.60 g, 15.54 mmol) were added sequentially dichloromethane (300 ml) and borane-pyridine complex (11.70 ml, 115.80 mmol) to give a suspension. This mixture was stirred at room temperature, and dichloroacetic acid (9.51 ml, 115.80 mmol) was added dropwise thereto over 10 minutes. After the mixture was stirred at room temperature for 13 hours, dichloromethane was removed under reduced pressure with a rotary evaporator, and the resultant residue was diluted with 1,2-dichloroethane (300 ml). This mixture was stirred at 60° C. for 6 hours, diluted with ethyl acetate, and washed sequentially with 0.1 M aqueous hydrochloric acid, saturated aqueous sodium bicarbonate, and saturated aqueous sodium chloride. The organic layer was dried over anhydrous sodium sulfate, and concentrated under reduced pressure. The residue was purified by silica gel column chromatography to give the title compound (8.28 g, 90% yield).

This compound may also be obtained as a by-product in a synthesis of 3,4-difluoro-2-(2-fluoro-4-iodo-phenylamino)-

N-(2-hydroxy-ethoxy)-5-[(2-methylcarbamoyl-ethoxyamino)-methyl]-benzamide (Compound C-6) in Example 27.

$^{1}$H-NMR (CD$_{3}$OD, 400 MHz) δ(PPM) 2.84 (2H, t, J=8.3 Hz), 3.70 (2H, t, J=4.7 Hz), 3.93 (2H, t, J=4.7 Hz), 4.36 (2H, t, J=8.3 Hz), 4.76 (2H, s), 6.62 (1H, ddd, J=8.8, 8.8, 3.9 Hz), 7.34-7.36 (1H, m), 7.39 (1H, br. d, J=5.4 Hz), 7.45 (1H, dd, J=10.5, 1.7 Hz)

ESI (LC/MS positive mode) m/z 552 (M+H)

Example 38

2-(4-Ethynyl-2-fluoro-phenylamino)-3,4-difluoro-N-(2-hydroxy-ethoxy)-5-(3-oxo-isoxazolidin-2-ylmethyl)-benzamide (Compound G-5)

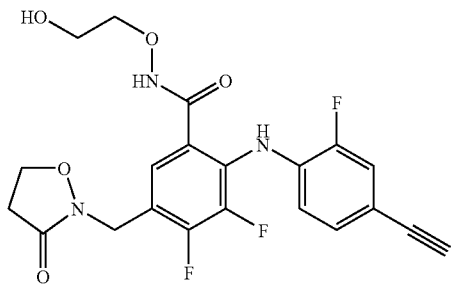

3,4-Difluoro-2-(2-fluoro-4-iodo-phenylamino)-N-(2-hydroxy-ethoxy)-5-(3-oxo-isoxazolidin-2-ylmethyl)-benzamide (36.9 mg, 66.9 μmol) obtained in Example 37, bis(acetonitrile)dichloropalladium (II) (3.5 mg, 13.5 μmol), 3,3',3"-phosphinidine-tris(benzenesulfonic acid) trisodium salt (19.0 mg, 33.4 μmol), and copper iodide (I) (2.6 mg, 13.6 μmol) were suspended in methanol (2.5 ml) under a nitrogen atmosphere. To this suspension, N,N-diisopropylethylamine (14.0 μl, 80.4 μmol) and trimethylsilylacetylene (47.3 μl, 334.7 μmol) were added at room temperature, and the mixture was stirred for 1 hour. The reaction mixture was diluted with methylene chloride (30 ml), and washed with saturated brine (2×15 ml). The organic layer was dried over anhydrous magnesium sulfate, and concentrated under reduced pressure. The resultant residue was dissolved in THF (2 ml). To this solution, tetrabutylammonium fluoride (1.0 M solution in THF, 0.10 ml, 0.10 mmol) was added, and the mixture was stirred for 1 hour, and then concentrated under reduced pressure. The resultant residue was purified by preparative TLC (EtOAc/MeOH (8:1)) to give 2-(4-ethynyl-2-fluoro-phenylamino)-3,4-difluoro-N-(2-hydroxy-ethoxy)-5-(3-oxo-isoxazolidin-2-ylmethyl)-benzamide (Compound G-5, 11.1 mg, 37%) as a brown oil.

$^{1}$H-NMR (CD$_{3}$OD, 270 MHz) δ(PPM) 2.85 (2H, t, J=8.1 Hz), 3.43 (1H, s), 3.70 (2H, t, J=4.6 Hz), 3.93 (2H, t, J=4.6 Hz), 4.36 (2H, t, J=8.1 Hz), 4.78 (2H, s), 6.75 (1H, dt, J=4.6, 8.6 Hz), 7.11-7.17 (1H, m), 7.20 (1H, dd, J=1.8, 11.9 Hz), 7.41 (1H, dd, J=1.8, 7.3 Hz).

ESI (LC/MS positive mode) m/z 450 (M+H)

Example 39

2-(4-Ethynyl-2-fluoro-phenylamino)-3,4-difluoro-N-(2-hydroxy-ethoxy)-5-(3-oxo-[1,2]oxadinan-2-ylmethyl)-benzamide (Compound G-4)

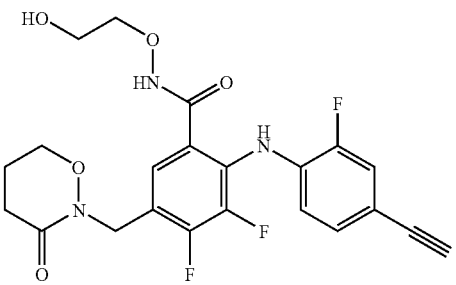

Using 3,4-difluoro-2-(2-fluoro-4-iodo-phenylamino)-N-(2-hydroxy-ethoxy)-5-(3-oxo-[1,2]oxazinan-2-ylmethyl)-benzamide obtained in Example 36, synthesis was performed according to the procedure described in Example 38 to give 2-(4-ethynyl-2-fluoro-phenylamino)-3,4-difluoro-N-(2-hydroxy-ethoxy)-5-(3-oxo-[1,2]oxadinan-2-ylmethyl)-benzamide (Compound G-4).

$^{1}$H-NMR (CD$_{3}$OD, 270 MHz) δ(PPM) 2.11 (2H, quint., J=6.9 Hz), 2.54 (2H, t, J=6.9 Hz), 3.43 (1H, s), 3.70 (2H, t, J=4.5 Hz), 3.93 (2H, t, J=4.5 Hz), 4.05 (2H, t, J=6.9 Hz), 4.87 (2H, s), 6.75 (1H, dt, J=4.6, 8.6 Hz), 7.10-7.17 (1H, m), 7.19 (1H, dd, J=1.9, 11.9 Hz), 7.43 (1H, dd, J=1.9, 7.0 Hz).

ESI (LC/MS positive mode) m/z 464 (M+H)

Example 40

5-(4,4-Dimethyl-3-oxo-isoxazolidin-2-ylmethyl)-3,4-difluoro-2-(2-fluoro-4-iodo-phenylamino)-N-(2-hydroxy-ethoxy)-benzamide (Compound G-3)

Step A

Synthesis of 3-(1,3-dioxo-1,3-dihydro-isoindol-2-yloxy)-2,2-dimethyl-propionic acid methyl ester

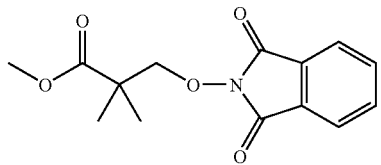

To methyl hydroxypivalate (1.31 g, 9.89 mmol) were added tetrahydrofuran (40 ml), hydroxyphthalimide (3.23 g, 19.78 mmol) and triphenylphosphine (6.48 g, 24.73 mmol). After this solution was cooled to 0° C., diisopropyl azodicarboxylate (4.87 ml, 24.73 mmol) was added dropwise to the solution. While being allowed to warm gradually, the reaction mixture was stirred for 12 hours, and concentrated under reduced pressure. The residue was roughly purified by silica gel column chromatography to give the title compound (922 mg).

$^1$H-NMR (CDCl$_3$, 400 MHz) δ(PPM) 1.35 (6H, s), 3.74 (3H, s), 4.26 (2H, s), 7.27-7.76 (2H, m), 7.81-7.85 (2H, m)

Step B

Synthesis of 3-aminooxy-2,2,N-trimethyl-propionamide

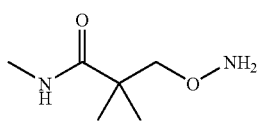

To 3-(1,3-dioxo-1,3-dihydro-isoindol-2-yloxy)-2,2-dimethyl-propionic acid methyl ester (800 mg) obtained in Step A was added a 40% solution of methylamine in methanol (6 ml), and the mixture was stirred at 60° C. for 13 hours. After the reaction mixture was concentrated under reduced pressure, dichloromethane was added to the residue, and insoluble matter was filtered. The filtrate was concentrated, and the residue was purified by silica gel column chromatography to give the title compound (202 mg).

$^1$H-NMR (CD$_3$OD, 400 MHz) δ(PPM) 1.14 (6H, s), 2.71 (3H, s), 3.64 (2H, s)

Step C

Synthesis of 3,4-difluoro-2-(2-fluoro-4-iodo-phenylamino)-N-(2-hydroxy-ethoxy)-[(2-methyl-2-methyl-carbamoyl-propoxyimino)-methyl]-benzamide

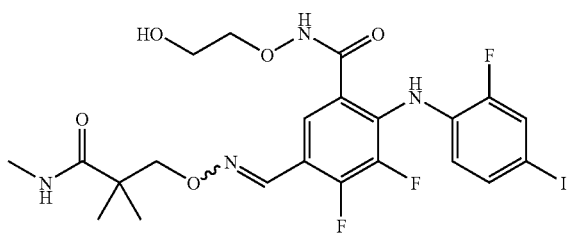

The title compound was synthesized as a mixture of E/Z geometric isomers, using the procedure described in Step C of Example 19, from 3-aminooxy-2,2,N-trimethyl-propionamide obtained in Step B and 3,4-difluoro-2-(2-fluoro-4-iodo-phenylamino)-5-formyl-N-(2-hydroxy-ethoxy-benzamide obtained in Step F of Example 1.

ESI (LC/MS positive mode) m/z 609 (M+H)

Step D 5-(4,4-Dimethyl-3-oxo-isoxazolidin-2-ylmethyl)-3,4-difluoro-2-(2-fluoro-4-iodo-phenylamino)-N-(2-hydroxy-ethoxy)-benzamide (Compound G-3)

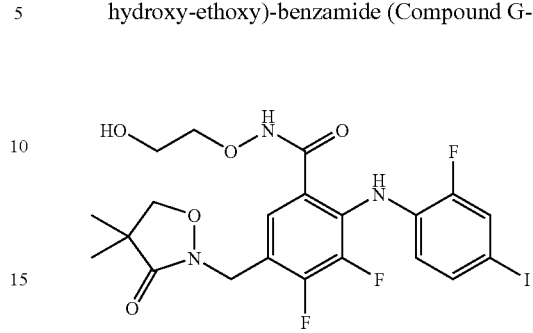

The title compound was synthesized by a similar procedure to that in Example 36 from 3,4-difluoro-2-(2-fluoro-4-iodo-phenylamino)-N-(2-hydroxy-ethoxy)-[(2-methyl-2-methyl-carbamoyl-propoxyimino)-methyl]-benzamide obtained in Step C.

$^1$H-NMR (CD$_3$OD, 400 MHz) δ(PPM) 1.20 (6H, s), 3.70 (2H, t, J=3.7 Hz), 3.92 (2H, t, J=3.7 Hz), 4.07-4.12 (5H, m), 4.77 (2H, s), 6.61-6.65 (1H, m), 7.35 (1H, d, J=8.3 Hz), 7.39 (1H, d, J=7.3 Hz), 7.44 (1H, br. d, J=10.7 Hz)

ESI (LC/MS positive mode) m/z 580 (M+H)

Example 41

5-{[Acetyl-(2-hydroxy-ethoxy)-amino]-methyl}-3,4-difluoro-2-(2-fluoro-4-iodo-phenylamino)-N-(2-hydroxy-ethoxy)-benzamide (Compound F-15)

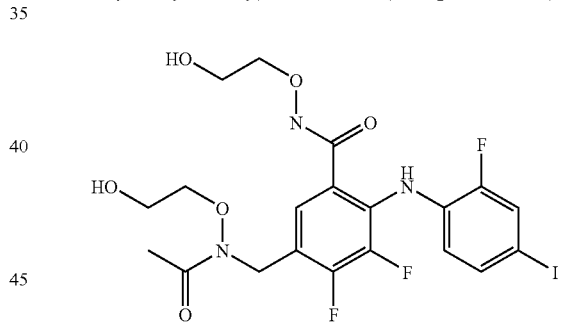

CH$_3$CO$_2$H (300 mg), EDC HCl (958 mg), and HODhbt (816 mg) were mixed in CH$_2$Cl$_2$ (5 mL) for 2 hours to give an active ester solution. A portion of this solution (0.2 mL) was added to a solution of 3,4-difluoro-2-(2-fluoro-4-iodo-phenylamino)-N-(2-hydroxy-ethoxy)-5-[(2-hydroxy-ethoxyamino)-methyl]-benzamide (80 mg) obtained in Example 6 and NEt$_3$ (29 μL) in THF, and the mixture was stirred for 12 hours. The reaction mixture was washed with 0.3 N aqueous HCl and aqueous NaHCO$_3$, and subjected to silica gel chromatography (CH$_2$Cl$_2$/MeOH as a developing solvent) to give the title compound (12.0 mg).

$^1$H-NMR (CD$_3$OD, 400 MHz) δ(PPM) 2.21 (3H, s), 3.69 (2H, t, J=4.5 Hz), 3.73 (2H, t, J=4.5 Hz), 3.92 (2H, t, J=4.5 Hz), 4.03 (2H, t, J=4.5 Hz), 4.91 (2H, s), 6.60 (1H, m), 7.34 (1H, d, J=8.3 Hz), 7.43 (2H, m)

ESI (LC/MS positive mode) m/z 584 (M+H)

In Examples 42 to 53 below, an alkoxyamine as a starting material was acetylated by a similar procedure to that in Example 41 to give the target compound.

Example 42

5-{[Acetyl-(2-hydroxy-ethoxy)-amino]-methyl}-2-(4-ethynyl-2-fluoro-phenylamino)-3,4-difluoro-N-(2-hydroxy-ethoxy)-benzamide (Compound F-25)

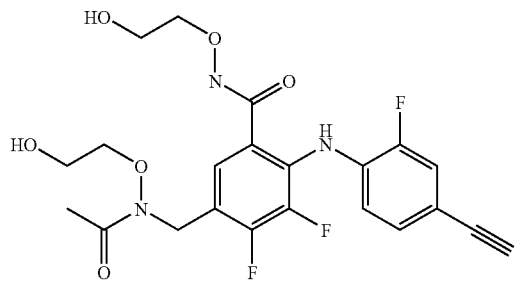

$^1$H-NMR (CD$_3$OD, 400 MHz) δ(PPM) 2.23 (3H, s), 3.42 (1H, s), 3.69 (2H, t, J=4.4 Hz), 3.74 (2H, t, J=4.4 Hz), 3.93 (2H, t, J=4.4 Hz), 4.03 (2H, t, J=4.4 Hz), 4.93 (2H, s), 6.74 (1H, m), 7.13 (1H, d, J=8.3 Hz), 7.18 (1H, dd, J=8.3 Hz, 2.0 Hz), 7.35 (1H, d, J=7.4)

ESI (LC/MS positive mode) m/z 482 (M+H)

Example 43

5-{[Acetyl-(3-hydroxy-propoxy)-amino]-methyl}-3,4-difluoro-2-(2-fluoro-4-iodo-phenylamino)-N-(2-hydroxy-ethoxy)-benzamide (Compound F-16)

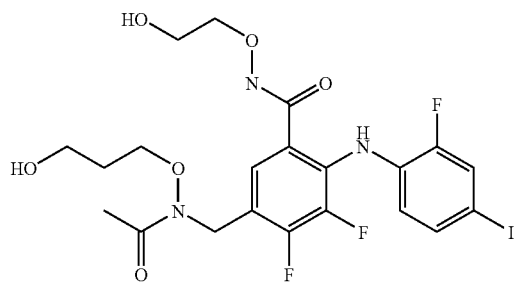

$^1$H-NMR (CD$_3$OD, 400 MHz) δ(PPM) 1.83 (2H, m), 2.21 (3H, s), 3.61 (2H, t, J=6.3 Hz), 3.70 (2H, t, J=4.4), 3.92 (2H, br), 4.05 (2H, t, J=6.3 Hz), 4.90 (2H, s), 6.61 (1H, m), 7.35 (1H, d, J=8.8 Hz), 7.40 (1H, d, J=5.4 Hz), 7.44 (1H, dd, J=10.7 Hz, 1.9 Hz)

ESI (LC/MS positive mode) m/z 598 (M+H)

Example 44

5-{[Acetyl-(2-hydroxy-2-methyl-propoxy)-amino]-methyl}-3,4-difluoro-2-(2-fluoro-4-iodo-phenylamino)-N-(2-hydroxy-ethoxy)-benzamide (Compound F-17)

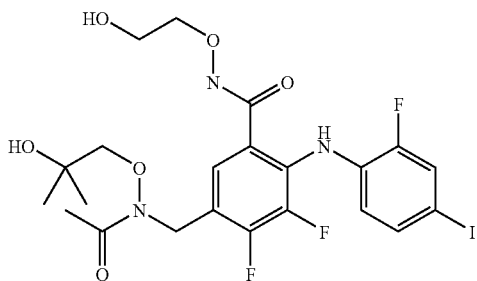

$^1$H-NMR (CD$_3$OD, 400 MHz) δ(PPM) 1.22 (6H, s), 2.20 (3H, s), 3.70 (2H, t, J=4.4 Hz), 3.78 (2H, s), 3.92 (2H, br), 4.91 (2H, s), 6.61 (1H, m), 7.34 (1H, d, J=7.4 Hz), 7.43 (2H, m)

ESI (LC/MS positive mode) m/z 612 (M+H)

Example 45

5-{[Acetyl-(2-hydroxy-2-methyl-propoxy)-amino]-methyl}-2-(4-ethynyl-2-fluoro-phenylamino)-3,4-difluoro-N-(2-hydroxy-ethoxy)-benzamide (Compound F-26)

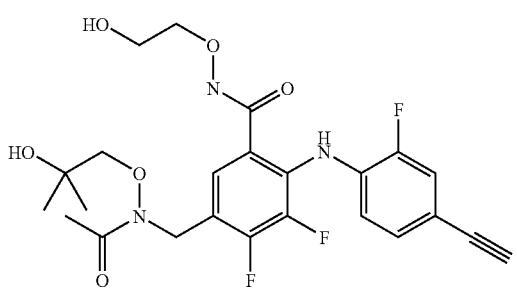

$^1$H-NMR (CD$_3$OD, 400 MHz) δ(PPM) 1.22 (6H, s), 2.21 (3H, s), 3.42 (1H, s), 3.69 (2H, t, J=4.6 Hz), 3.79 (2H, s), 3.92 (2H, t, J=4.6 Hz), 4.92 (2H, s), 6.74 (1H, m), 7.13 (1H, d, J=8.8 Hz), 7.19 (1H, dd, J=11.7 Hz, 2.0 Hz), 7.44 (2H, d, J=6.8 Hz)

ESI (LC/MS positive mode) m/z 510 (M+H)

Example 46

5-[Acetyl-methoxy-amino-methyl]-3,4-difluoro-2-(2-fluoro-4-iodo-phenylamino)-N-(2-hydroxy-ethoxy)-benzamide (Compound F-2)

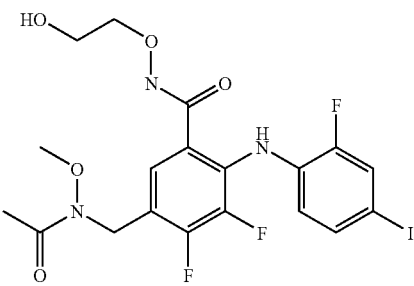

$^1$H-NMR (DMSO-d$_6$, 400 MHz) δ(PPM) 2.10 (3H, s), 3.55 (2H, t, J=4.4 Hz), 3.81 (2H, br), 4.81 (2H, s), 6.63 (1H, m), 7.32 (1H, br), 7.34 (1H, m), 7.56 (1H, dd, J=10.7 Hz, 2.0 Hz), 8.53 (1H, br), 11.85 (1H, br), The peak of CH$_3$(methoxy) was overlapping with that of H$_2$O in solvent.

ESI (LC/MS positive mode) m/z 554 (M+H)

Example 47

5-[(Acetyl-hydroxy-amino)-methyl]-3,4-difluoro-2-(2-fluoro-4-iodo-phenylamino)-N-(2-hydroxy-ethoxy)-benzamide (Compound F-13)

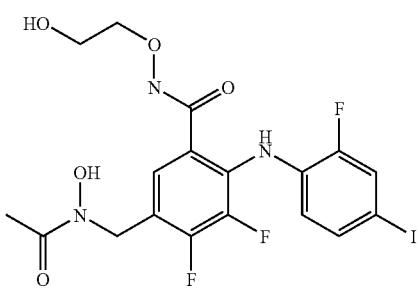

$^1$H-NMR (DMSO-d$_6$, 400 MHz) δ(PPM) 2.01 (3H, s), 3.77 (2H, br), 3.98 (2H, br), 4.71 (2H, s), 6.58 (1H, m), 7.31 (2H, m), 7.53 (1H, d, J=10.8 Hz), 8.50 (1H, br), 9.96 (1H, br), 11.81 (1H, br),

ESI (LC/MS positive mode) m/z 540 (M+H)

Example 48

5-[(Acetoxy-acetyl-amino)-methyl]-3,4-difluoro-2-(2-fluoro-4-iodo-phenylamino)-N-(2-hydroxy-ethoxy)-benzamide (Compound F-14)

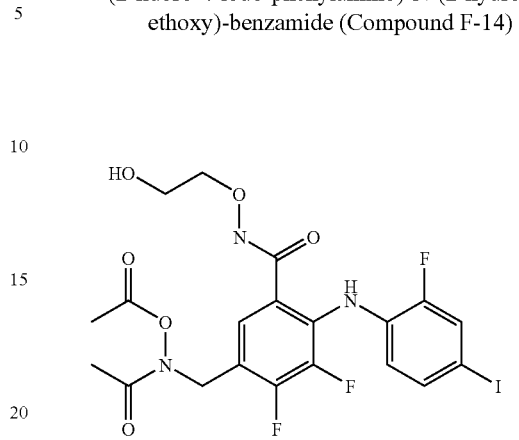

The title compound was obtained as a by-product in the preparation of 5-[(Acetyl-hydroxy-amino)-methyl]-3,4-difluoro-2-(2-fluoro-4-iodo-phenylamino)-N-(2-hydroxy-ethoxy)-benzamide in Example 47.

$^1$H-NMR (DMSO-d$_6$, 400 MHz) δ(PPM) 1.22 (3H, s), 2.17 (3H, s), 3.54 (2H, br), 3.80 (2H, br), 4.85 (2H, s), 6.62 (1H, m), 7.37 (2H, m), 7.56 (1H, d, J=6.8 Hz), 8.64 (1H, br), 11.85 (1H, br),

ESI (LC/MS positive mode) m/z 582 (M+H)

Example 49

5-{[Acetyl-(2-methylsulfanyl-ethoxy)-amino]-methyl}-3,4-difluoro-2-(2-fluoro-4-iodo-phenylamino)-N-(2-hydroxy-ethoxy)-benzamide (Compound F-21)

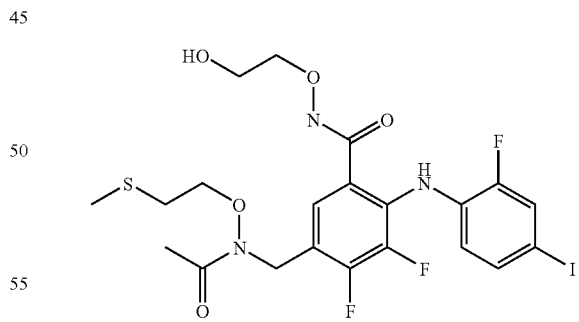

$^1$H-NMR (DMSO-d$_6$, 400 MHz) δ(PPM) 2.04 (3H, s), 2.12 (3H, s), 2.66 (2H, t, J=6.3 Hz), 3.80 (1H, br), 4.02 (2H, m), 4.82 (2H, s), 6.62 (1H, m), 7.34 (2H, d, br, J=8.3 Hz), 7.55 (1H, dd, J=10.7 Hz, 1.7 Hz), 8.52 (1H, s), 11.8 (1H, s). The peaks of two methylene groups are overlapping with that of H$_2$O peak.

ESI (LC/MS positive mode) m/z 614 (M+H)

Example 50

5-{[Acetyl-(3-methylsulfanyl-propoxy)-amino]-methyl}-3,4-difluoro-2-(2-fluoro-4-iodo-phenylamino)-N-(2-hydroxy-ethoxy)-benzamide

Example 52

5-{[Acetyl-(2-propionylamino-ethoxy)-amino]-methyl}-3,4-difluoro-2-(2-fluoro-4-iodo-phenylamino)-N-(2-hydroxy-ethoxy)-benzamide (Compound F-19)

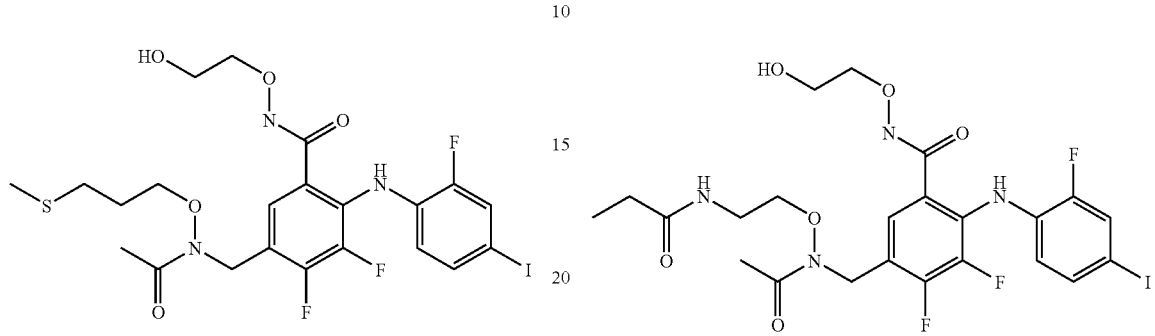

$^1$H-NMR (DMSO-$d_6$, 400 MHz) δ(PPM) 1.75 (2H, m), 2.04 (3H, s), 2.12 (3H, s), 2.66 (2H, t, J=6.3 Hz), 3.80 (2H, br), 4.02 (2H, m), 4.82 (2H, s), 6.62 (1H, m), 7.34 (2H, d, br, J=8.3 Hz), 7.55 (1H, dd, J=10.7 Hz, 1.7 Hz), 8.52 (1H, s), 11.8 (1H, s). A peak of methylene group is overlapping with that of H$_2$O peak.

ESI (LC/MS positive mode) m/z 628 (M+H)

$^1$H-NMR (DMSO-$d_6$, 400 MHz) δ(PPM) 0.94 (3H, t, J=7.7 Hz), 2.04 (2H, d, J=7.7 Hz), 2.07 (3H, s), 3.24 (2H, m), 3.80 (2H, br), 3.89 (2H, t, J=5.0 Hz), 4.79 (2H, s), 6.64 (1H, m), 7.33 (2H, m), 7.55 (1H, dd, J=10.7 Hz, 2.0 Hz), 7.94 (1H, t, J=5.1 Hz), 8.53 (1H, br), 11.85 (1H, br). A peak of methylene group is overlapping with that of H$_2$O peak.

ESI (LC/MS positive mode) m/z 639 (M+H)

Example 51

5-{[Acetyl-(2-acetylamino-ethoxy)-amino]-methyl}-3,4-difluoro-2-(2-fluoro-4-iodo-phenylamino)-N-(2-hydroxy-ethoxy)-benzamide (Compound F-18)

Example 53

5-{[Acetyl-(2-isobutyrylamino-ethoxy)-amino]-methyl}-3,4-difluoro-2-(2-fluoro-4-iodo-phenylamino)-N-(2-hydroxy-ethoxy)-benzamide (Compound F-20)

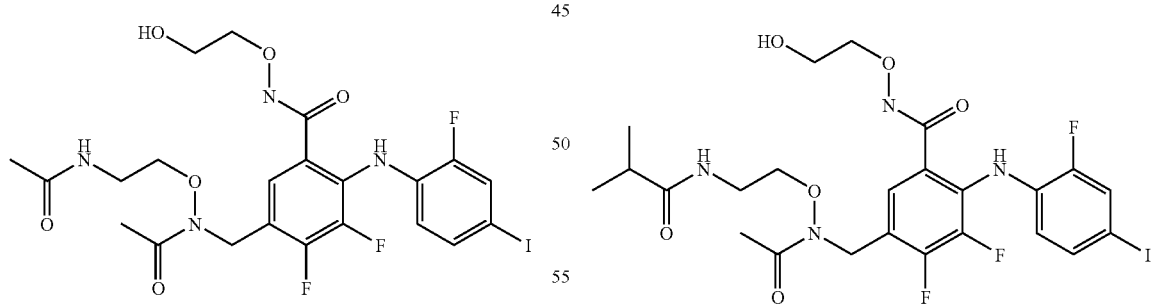

$^1$H-NMR (DMSO-$d_6$, 400 MHz) δ(PPM) 1.76 (3H, s), 2.07 (3H, s), 3.23 (2H, m), 3.80 (2H, br), 3.89 (2H, t, J=5.0 Hz), 4.79 (2H, s), 6.64 (1H, m), 7.33 (2H, m), 7.56 (1H, dd, J=10.7 Hz, 2.0 Hz), 8.00 (1H, t, J=5.6 Hz), 8.53 (1H, br), 11.8 (1H, br). A peak of methylene group is overlapping with that of H$_2$O peak.

ESI (LC/MS positive mode) m/z 625 (M+H)

$^1$H-NMR (DMSO-$d_6$, 400 MHz) δ(PPM) 0.92 (6H, d, J=6.8 Hz), 2.07 (3H, s), 2.30 (1H, hepta, J=6.8 Hz), 3.24 (2H, m), 3.80 (2H, br), 3.90 (2H, t, J=5.0 Hz), 4.79 (2H, s), 6.63 (1H, m), 7.33 (2H, m), 7.55 (1H, dd, J=10.7 Hz, 1.5 Hz), 7.91 (1H, t, J=5.6 Hz), 8.53 (1H, br), 11.84 (1H, br). The peak of a methylene group is overlapping with that of H$_2$O peak.

ESI (LC/MS positive mode) m/z 639 (M+H)

Example 54

3,4-Difluoro-2-(2-fluoro-4-iodo-phenylamino)-N-(2-hydroxy-ethoxy)-5-(3-oxo-[1,4,2]dioxazinan-2-ylmethyl)-benzamide (Compound H-1)

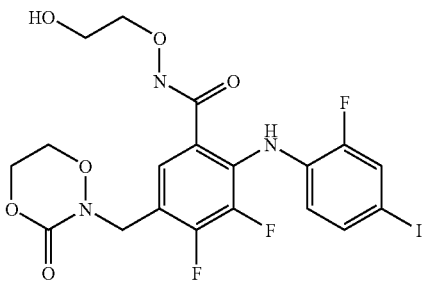

3,4-Difluoro-2-(2-fluoro-4-iodo-phenylamino)-N-(2-hydroxy-ethoxy)-5-[(2-hydroxy-ethoxyamino)-methyl]-benzamide (100 mg, 0.185 mmol) obtained in Example 6, N,N'-disuccinimidyl carbonate (59 mg, 0.231 mmol) and NEt$_3$ (113 mg, 1.12 mmol) were stirred in a mixed solvent of CH$_2$Cl$_2$/THF (1 mL/1 mL) at room temperature for 10 hours. The reaction mixture was purified by silica gel column chromatography (CH$_2$Cl$_2$/MeOH as a developing solvent) to give the title compound (12.5 mg).

$^1$H-NMR (DMSO-d$_6$, 400 MHz) δ(PPM) 3.54 (2H, br), 3.82 (2H, br), 4.16 (2H, t, J=4.4), 4.42 (2H, t, J=4.4 Hz), 4.76 (2H+1H, s+br), 6.65 (1H, m), 7.35 (1H, d, J=8.3 Hz), 7.40 (1H, d, J=6.3 Hz), 7.56 (1H, d, J=10.8 Hz), 8.68 (1H, br), 11.88 (1H, br)

ESI (LC/MS positive mode) m/z 568 (M+H)

Example 55

2-(4-Ethynyl-2-fluoro-phenylamino)-3,4-difluoro-N-(2-hydroxy-ethoxy)-5-(3-oxo-[1,4,2]dioxazinan-2-ylmethyl)-benzamide (Compound H-2)

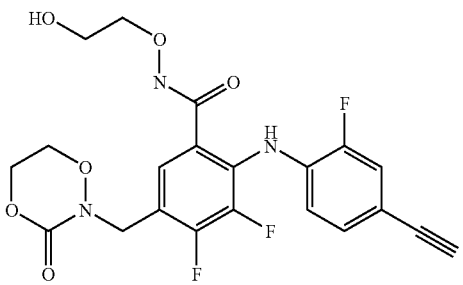

The title compound was synthesized by a similar procedure to that in Example 38 from 3,4-difluoro-2-(2-fluoro-4-iodo-phenylamino)-N-(2-hydroxy-ethoxy)-5-(3-oxo-[1,4,2]dioxazinan-2-ylmethyl)-benzamide obtained in Example 54.

$^1$H-NMR (DMSO-d$_6$, 400 MHz) δ(PPM) 3.54 (2H, br), 3.83 (2H, br), 4.09 (1H, br), 4.17 (2H, br), 4.42 (2H, br), 4.72 (1H, br), 4.78 (2H, br), 6.77 (1H, br), 7.14 (1H, d, J=6.8 Hz), 7.31 (1H, d, J=11.8 Hz), 7.42 (1H, d, J=6.4 Hz), 8.78 (1H, br), 11.87 (1H, br)

ESI (LC/MS positive mode) m/z 466 (M+H)

Example 56

3,4-Difluoro-2-(2-fluoro-4-iodo-phenylamino)-N-(2-hydroxy-ethoxy)-5-{[methoxy-(2-methoxy-acetyl)-amino]-methyl}-benzamide (Compound F-6)

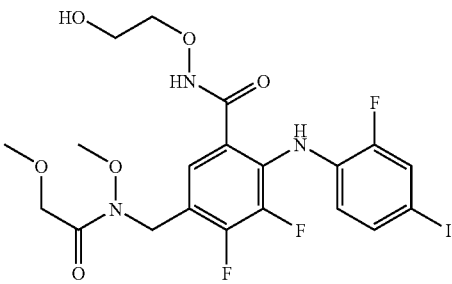

To a solution of methoxyacetic acid (9.0 μl, 0.12 mmol) in methylene chloride (1 ml) were added 3-hydroxy-4-oxo-3,4-dihydro-1,2,3-benzotriazine (18.9 mg, 0.12 mmol) and 1-(3-dimethylaminopropyl)-3-ethylcarbodiimide hydrochloride (22.5 mg, 0.12 mmol), and the mixture was stirred for 3 hours. This solution was added dropwise to a solution of 3,4-difluoro-2-(2-fluoro-4-iodo-phenylamino)-N-(2-hydroxy-ethoxy)-5-(methoxyamino-methyl)-benzamide (50.0 mg, 0.10 mmol) obtained in Example 15 in THF (3 ml), and triethylamine (40.9 μl, 0.29 mmol) was added thereto. The mixture was stirred for 15 hours. The reaction mixture was diluted with ethyl acetate (45 ml), and washed with saturated aqueous ammonium chloride (20 ml), and then with saturated brine (2×20 ml). The organic layer was dried over anhydrous magnesium sulfate, and concentrated under reduced pressure. The resultant residue was purified by preparative TLC (CH$_2$Cl$_2$/MeOH (10:1)) to give 3,4-difluoro-2-(2-fluoro-4-iodo-phenylamino)-N-(2-hydroxy-ethoxy)-5-{[methoxy-(2-methoxy-acetyl)-amino]-methyl}-benzamide (Compound F-6, 19.1 mg, 34%) as a colorless oil.

$^1$H-NMR (CD$_3$OD, 270 MHz) δ(PPM) 3.44 (3H, s), 3.67-3.73 (2H, m), 3.76 (3H, s), 3.89-3.95 (2H, m), 4.30 (2H, s), 4.90 (2H, s), 6.61 (1H, dt, J=4.3, 8.6 Hz), 7.34 (1H, ddd, J=1.1, 1.9, 8.6 Hz), 7.37-7.43 (1H, m), 7.44 (1H, dd, J=1.9, 10.8 Hz).

ESI (LC/MS positive mode) m/z 584 (M+H)

Example 57

3,4-Difluoro-2-(2-fluoro-4-iodo-phenylamino)-5-{[(2-hydroxy-acetyl)-methoxy-amino]-methyl}-N-(2-hydroxy-ethoxy)-benzamide (Compound F-5)

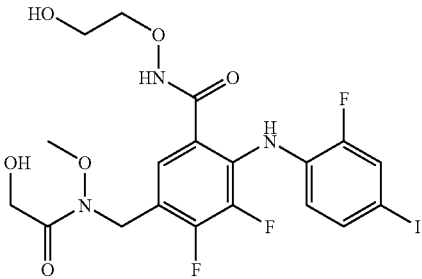

To a solution of acetoxyacetic acid (13.9 mg, 0.12 mmol) in methylene chloride (1 ml) were added 3-hydroxy-4-oxo-3,4-dihydro-1,2,3-benzotriazine (18.9 mg, 0.12 mmol) and 1-(3-dimethylaminopropyl)-3-ethylcarbodiimide hydrochloride (22.5 mg, 0.12 mmol), and the mixture was stirred for 3 hours. This solution was added dropwise to a solution of 3,4-difluoro-2-(2-fluoro-4-iodo-phenylamino)-N-(2-hydroxy-ethoxy)-5-(methoxyamino-methyl)-benzamide (50.0 mg, 0.10 mmol) obtained in Example 15 in THF (2 ml), and triethylamine (40.9 µl, 0.29 mmol) was added thereto. The mixture was stirred for 24 hours. The reaction mixture was diluted with ethyl acetate (45 ml), and washed with saturated aqueous ammonium chloride (20 ml), and then with saturated brine (2×20 ml). The organic layer was dried over anhydrous magnesium sulfate, and concentrated under reduced pressure. The resultant residue was roughly purified by preparative TLC (CH$_2$Cl$_2$/MeOH (10:1)) to give {[2,3-difluoro-4-(2-fluoro-4-iodo-phenylamino)-5-(2-hydroxy-ethoxycarbamoyl)-benzyl]-methoxy-carbamoyl}acetic acid methyl ester (14.0 mg, containing impurities) as a colorless oil. To a solution of the resultant {[2,3-difluoro-4-(2-fluoro-4-iodo-phenylamino)-5-(2-hydroxy-ethoxycarbamoyl)-benzyl]-methoxy-carbamoyl}acetic acid methyl ester (14.0 mg, containing impurities) in methanol (1 ml) was added sodium methoxide (3.0 mg, 0.06 mmol), and the mixture was stirred for 2 hours. The reaction mixture was diluted with saturated ammonium chloride, and extracted with methylene chloride (30 ml and 15 ml). The organic layer was dried over anhydrous magnesium sulfate, and concentrated under reduced pressure. The resultant residue was purified by preparative TLC (CH$_2$Cl$_2$/MeOH (10:1)) to give 3,4-difluoro-2-(2-fluoro-4-iodo-phenylamino)-5-{[(2-hydroxy-acetyl)-methoxy-amino]-methyl}-N-(2-hydroxy-ethoxy)-benzamide (F-5, 5.8 mg, 12% for 2 steps) as a colorless oil.

$^1$H-NMR (CD$_3$OD, 270 MHz) δ(PPM) 3.70 (2H, t, J=4.6 Hz), 3.75 (3H, s), 3.92 (2H, t, J=4.6 Hz), 4.36 (2H, s), 4.90 (2H, s), 6.61 (1H, dt, J=4.3, 8.9 Hz), 7.31-7.37 (1H, m), 7.37-7.43 (1H, m), 7.44 (1H, dd, J=1.9, 10.8 Hz).

ESI (LC/MS positive mode) m/z 570 (M+H)

Example 58

3,4-Difluoro-2-(2-fluoro-4-iodo-phenylamino)-N-(2-hydroxy-ethoxy)-5-[(isobutyryl-methoxy-amino)-methyl]-benzamide (Compound F-4)

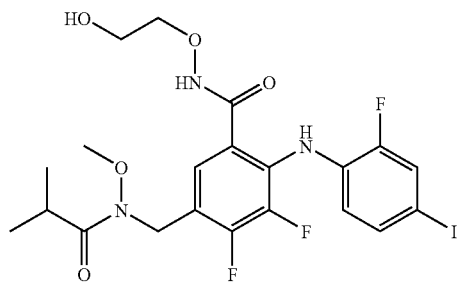

The title compound was prepared by a procedure similar to that in Example 41. Namely, 3,4-difluoro-2-(2-fluoro-4-iodo-phenylamino)-N-(2-hydroxy-ethoxy)-5-(methoxyamino-methyl)-benzamide obtained in Example 15 was reacted with 4-oxo-4H-benzo[d][1,2,3]triazin-3-yl isobutyrate prepared from isobutyric acid to give 3,4-difluoro-2-(2-fluoro-4-iodo-phenylamino)-N-(2-hydroxy-ethoxy)-5-[(isobutyryl-methoxy-amino)-methyl]-benzamide (88.9 mg, 77%).

$^1$H-NMR (DMSO-d$_6$, 270 MHz) δ(PPM) 1.04 (6H, d, J=6.8 Hz), 2.95 (1H, m), 3.00 (3H, s), 3.54 (2H, m), 3.80 (2H, m), 4.75 (1H, br.s), 4.85 (2H, s), 6.63 (1H, td, J=8.6, 3.8 Hz), 7.30 (1H, br. d, J=6.8 Hz), 7.36 (1H, d, J=8.4 Hz), 7.58 (1H, dd, J=10.9, 1.8 Hz), 8.53 (1H, br.s)

ESI (LC/MS positive mode) m/z 582 (M+H)

Example 59

3,4-Difluoro-2-(2-fluoro-4-iodo-phenylamino)-N-(2-hydroxy-ethoxy)-5-[(methoxy-propionyl-amino)-methyl]-benzamide (Compound F-3)

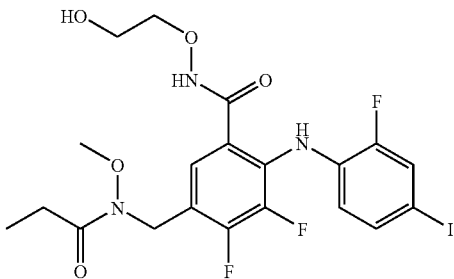

The title compound was prepared by a procedure similar to that in Example 41. Namely, 3,4-difluoro-2-(2-fluoro-4-iodo-phenylamino)-N-(2-hydroxy-ethoxy)-5-(methoxyamino-methyl)-benzamide obtained in Example 15 was reacted with 4-oxo-4H-benzo[d][1,2,3]triazin-3-yl propionate prepared from propionic acid to give 3,4-difluoro-2-(2-fluoro-4-iodo-phenylamino)-N-(2-hydroxy-ethoxy)-5-[(methoxy-propionyl-amino)-methyl]-benzamide (35.0 mg, 31%).

$^1$H-NMR (DMSO-d$_6$, 270 MHz) δ(PPM) 1.02 (3H, t, J=7.5 Hz), 2.45 (2H, q, J=7.5 Hz), 3.31 (3H, s), 3.54 (2H, t, J=4.8 Hz), 3.81 (2H, t, J=4.8 Hz), 4.83 (2H, s), 6.64 (1H, td, J=8.7, 4.3 Hz), 7.32 (1H, br.s), 7.36 (1H, br. d, J=8.4 Hz), 7.57 (1H, dd, J=10.9, 1.8 Hz), 8.62 (1H, br.s)

ESI (LC/MS positive mode) m/z 568 (M+H)

Example 60

5-[(Acetyl-ethoxy-amino)-methyl]-3,4-difluoro-2-(2-fluoro-4-iodo-phenylamino)-N-(2-hydroxy-ethoxy)-benzamide (Compound F-10)

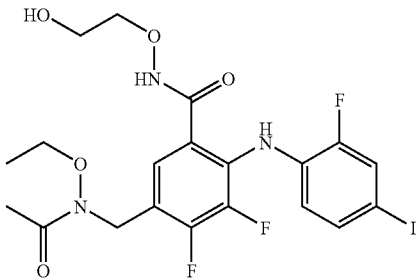

The title compound was prepared by a procedure similar to that in Example 41. Namely, 5-(ethoxyamino-methyl)-3,4-difluoro-2-(2-fluoro-4-iodo-phenylamino)-N-(2-hydroxy-ethoxy)-benzamide obtained in Example 17 was reacted with 4-oxo-4H-benzo[d][1,2,3]triazin-3-yl acetate prepared from acetic acid to give 5-[(acetyl-ethoxy-amino)-methyl]-3,4-difluoro-2-(2-fluoro-4-iodo-phenylamino)-N-(2-hydroxy-ethoxy)-benzamide (19.3 mg, 71%).

$^1$H-NMR (DMSO-d$_6$, 270 MHz) δ(PPM) 1.15 (3H, t, J=6.9 Hz), 2.10 (3H, s), 3.31 (3H, s), 3.55 (2H, m), 3.82 (2H, m), 3.94 (2H, q, J=6.9 Hz), 4.71 (1H, br.s), 4.81 (2H, s), 6.64 (1H, m), 7.34 (1H, m), 7.36 (1H, m), 7.58 (1H, d, J=9.7 Hz), 8.53 (1H, br.s), 11.84 (1H, br.s)

ESI (LC/MS positive mode) m/z 568 (M+H)

Example 61

5-[(Ethoxy-propionyl-amino)-methyl]-3,4-difluoro-2-(2-fluoro-4-iodo-phenylamino)-N-(2-hydroxy-ethoxy)-benzamide (Compound F11)

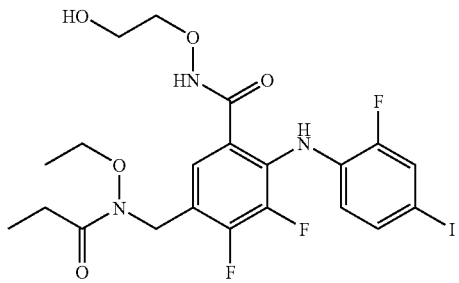

The title compound was prepared by a procedure similar to that in Example 41. Namely, 5-(ethoxyamino-methyl)-3,4-difluoro-2-(2-fluoro-4-iodo-phenylamino)-N-(2-hydroxy-ethoxy)-benzamide obtained in Example 17 was reacted with 4-oxo-4H-benzo[d][1,2,3]triazin-3-yl propionate prepared from propionic acid to give 5-[(ethoxy-propionyl-amino)-methyl]-3,4-difluoro-2-(2-fluoro-4-iodo-phenylamino)-N-(2-hydroxy-ethoxy)-benzamide (17.0 mg, 61%).

$^1$H-NMR (CD$_3$OD, 270 MHz) δ(PPM) 1.12 (3H, t, J=7.4 Hz), 1.24 (3H, t, J=7.1 Hz), 2.53 (2H, q, J=7.4 Hz), 3.67 (2H, m), 3.92 (2H, m), 3.99 (2H, q, J=7.1 Hz), 4.89 (2H, s), 6.61 (1H, td, J=8.7, 4.3 Hz), 7.34 (1H, m), 7.38 (1H, m), 7.44 (1H, dd, J=10.7, 2.0 Hz)

ESI (LC/MS positive mode) m/z 582 (M+H)

Example 62

2-(4-Ethynyl-2-fluoro-phenylamino)-3,4-difluoro-N-(2-hydroxy-ethoxy)-5-[(isobutyryl-methoxy-amino)-methyl]-benzamide (Compound F-9)

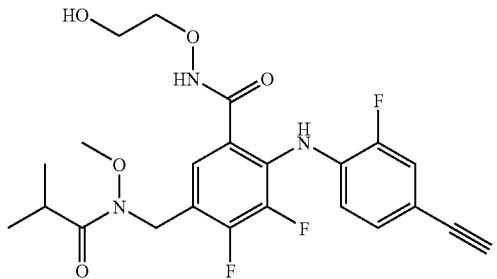

Dichlorobis(triphenylphosphine)-palladium (Aldrich, 4 mg, 0.006 mmol), copper iodide (2.2 mg, 0.012 mmol), and N,N-diisopropylethylamine (30 µL, 0.175 mmol) were added to a solution of 5-[(acetyl-methoxy-amino)-methyl]-3,4-difluoro-2-(2-fluoro-4-iodo-phenylamino)-N-(2-hydroxy-ethoxy)-benzamide (67.78 mg, 0.117 mmol) obtained in Example 58 in tetrahydrofuran (anhydrous, 2.0 mL) under a nitrogen atmosphere. The mixture was stirred thoroughly. After a homogenous solution was obtained, trimethylsilylacetylene (65 µL, 0.466 mmol) was added to the solution, which was stirred at room temperature for a whole day and night.

After completion of the reaction, the solvent was evaporated under reduced pressure, and the yellowish brown oily residue was extracted with ethyl acetate. The organic layer was washed sequentially with 2% aqueous EDTA, water, and saturated brine, dried over anhydrous sodium sulfate, and concentrated under reduced pressure. The resultant residue was purified by silica gel flash chromatography (Mega Bond Elut, Varian, 5% methanol/methylene chloride as an eluent). The resultant 5-[(acetyl-methoxy-amino)-methyl]-3,4-difluoro-2-(2-fluoro-4-trimethylsilanylethynyl-phenylamino)-N-(2-hydroxy-ethoxy)-benzamide was dissolved in tetrahydrofuran (anhydrous, 2.0 mL), and tetra-n-butylammonium fluoride (1 mol/L solution in tetrahydrofuran, 150 µL, 0.150 mmol) was added thereto. The mixture was stirred for 1 day. After completion of the reaction, the solvent was evaporated under reduced pressure, and the yellowish brown oily residue was extracted with ethyl acetate. The organic layer was washed sequentially with diluted (1%) hydrochloric acid, water, and saturated brine, dried over anhydrous sodium sulfate, and concentrated under reduced pressure. The resultant residue was purified by silica gel flash chromatography (Mega Bond Elut, Varian, ethyl acetate as an eluent) to give a yellow solid, which was triturated with 10% ethyl acetate/hexane to give a pale yellow solid (23.6 mg, 42% in 2 steps).

$^1$H-NMR (CD$_3$OD, 270 MHz) δ(PPM) 1.12 (6H, d, J=6.8 Hz), 3.06 (1H, quin., J=6.8 Hz), 3.42 (1H, s), 3.68 (2H, m), 3.78 (3H, s), 3.91 (2H, m), 4.91 (2H, s), 6.73 (1H, td, J=8.7, 4.5 Hz), 7.14 (1H, br. d, J=9.2 Hz), 7.19 (1H, dd, J=11.9, 1.8 Hz), 7.39 (1H, m)

ESI (LC/MS positive mode) m/z 480 (M+H)

Example 63

2-(4-Ethynyl-2-fluoro-phenylamino)-3,4-difluoro-N-(2-hydroxy-ethoxy)-5-[(methoxy-propionyl-amino)-methyl]-benzamide (Compound F-8)

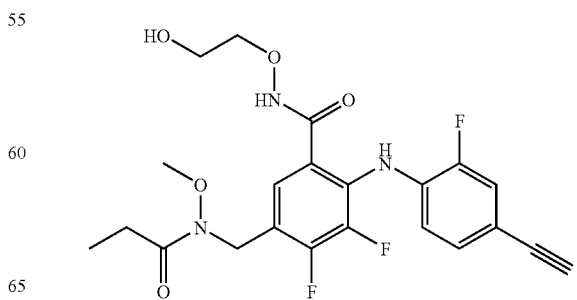

The title compound was synthesized in 2 steps by a procedure similar to that in Example 62 from 3,4-difluoro-2-(2-fluoro-4-iodo-phenylamino)-N-(2-hydroxy-ethoxy)-5-[(methoxy-propionyl-amino)-methyl]-benzamide obtained in Example 59. 6.9 mg (35% in 2 steps).

¹H-NMR (CD₃OD, 270 MHz) δ(PPM) 1.12 (3H, t, J=7.4 Hz), 2.54 (1H, q, J=7.4 Hz), 3.42 (1H, s), 3.70 (2H, m), 3.76 (3H, s), 3.91 (2H, m), 4.90 (2H, s), 6.73 (1H, td, J=8.6, 4.6 Hz), 7.14 (1H, br. d, J=9.1 Hz), 7.19 (1H, dd, J=11.9, 1.8 Hz), 7.39 (1H, br. d, J=5.4 Hz)

ESI (LC/MS positive mode) m/z 466 (M+H)

Example 64

5-[(Acetyl-methoxy-amino)-methyl]-2-(4-ethynyl-2-fluoro-phenylamino)-3,4-difluoro-N-(2-hydroxy-ethoxy)-benzamide (Compound F-7)

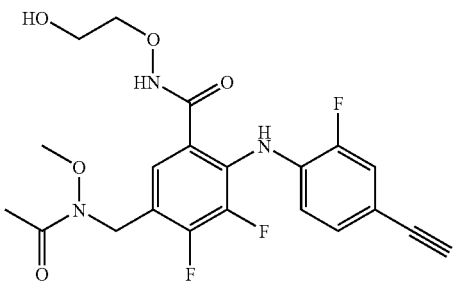

The title compound was synthesized in 2 steps by a procedure similar to that in Example 62 from 5-[(acetyl-methoxy-amino)-methyl]-3,4-difluoro-2-(2-fluoro-4-iodo-phenylamino)-N-(2-hydroxy-ethoxy)-benzamide obtained in Example 46. 191.67 mg (79% in 2 steps).

¹H-NMR (CD₃OD, 270 MHz) δ(PPM) 2.18 (3H, s), 3.42 (1H, s), 3.68 (2H, m), 3.77 (3H, s), 3.92 (2H, m), 4.90 (2H, s), 6.74 (1H, td, J=8.6, 4.3 Hz), 7.13 (1H, br. d, J=9.1 Hz), 7.19 (1H, dd, J=11.9, 1.8 Hz), 7.40 (1H, br. d, J=6.4 Hz)

ESI (LC/MS positive mode) m/z 452 (M+H)

Example 65

5-[(Ethoxy-propionyl-amino)-methyl]-2-(4-ethynyl-2-fluoro-phenylamino)-3,4-difluoro-N-(2-hydroxy-ethoxy)-benzamide (Compound F-24)

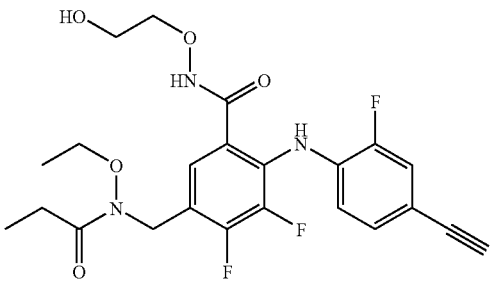

The title compound was synthesized in 2 steps by a procedure similar to that in Example 62 from 5-[(ethoxy-propionyl-amino)-methyl]-3,4-difluoro-2-(2-fluoro-4-iodo-phenylamino)-N-(2-hydroxy-ethoxy)-benzamide obtained in Example 61. 3.5 mg (45% in 2 steps).

¹H-NMR (CD₃OD, 270 MHz) δ(PPM) 1.11 (3H, t, J=7.4 Hz), 1.22 (3H, t, J=7.1 Hz), 2.53 (2H, q, J=7.4 Hz), 3.39 (1H, s), 3.69 (2H, m), 3.94 (2H, m), 3.97 (2H, q, J=7.4 Hz), 4.90 (2H, s), 6.69 (1H, td, J=8.6, 5.4 Hz), 7.12 (1H, br. d, J=8.7 Hz), 7.17 (1H, dd, J=12.0, 1.8 Hz), 7.50 (1H, br. d, J=5.8 Hz)

ESI (LC/MS positive mode) m/z 480 (M+H)

Example 66

5-[(Acetyl-ethoxy-amino)-methyl]-2-(4-ethynyl-2-fluoro-phenylamino)-3,4-difluoro-N-(2-hydroxy-ethoxy)-benzamide (Compound F-23)

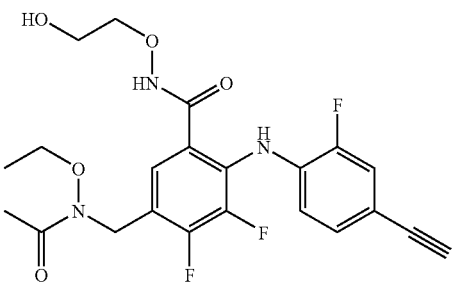

The title compound was synthesized in 2 steps by a procedure similar to that in Example 62 from 5-[(acetyl-ethoxy-amino)-methyl]-3,4-difluoro-2-(2-fluoro-4-iodo-phenylamino)-N-(2-hydroxy-ethoxy)-benzamide obtained in Example 60. 1.8 mg (22%).

¹H-NMR (CD₃OD, 270 MHz) δ(PPM) 1.25 (3H, t, J=7.1 Hz), 2.18 (3H, s), 3.43 (1H, s), 3.63 (2H, m), 3.68 (2H, m), 4.01 (2H, q, J=7.1 Hz), 4.90 (2H, s), 6.74 (1H, td, J=8.6, 4.5 Hz), 7.14 (1H, br. d, J=8.2 Hz), 7.20 (1H, dd, J=11.9, 1.8 Hz), 7.40 (1H, m)

ESI (LC/MS positive mode) m/z 466 (M+H)

Example 67

3,4-Difluoro-2-(2-fluoro-4-iodo-phenylamino)-5-[(formyl-methoxy-amino)-methyl]-N-(2-hydroxy-ethoxy)-benzamide (Compound F-1)

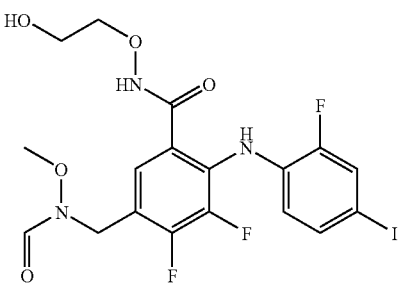

Ethyl formate (0.2 mL) was added to 3,4-difluoro-2-(2-fluoro-4-iodo-phenylamino)-N-(2-hydroxy-ethoxy)-5-(methoxyamino-methyl)-benzamide (Compound C-24, 50 mg, 0.0978 mmol) obtained in Example 15, and the mixture was heated to reflux at 80° C. for 1 hour.

After completion of the reaction, the reaction mixture was concentrated under reduced pressure. The resultant white solid was fractionated by TLC (No. 5715, Merck, 5% methanol/methylene chloride as a developing solvent), and the resultant white solid was further triturated with 10% methylene chloride/hexane to give 3,4-difluoro-2-(2-fluoro-4-iodo-phenylamino)-5-[(formyl-methoxy-amino)-methyl]-N-(2-hydroxy-ethoxy)-benzamide (Compound F-1, 18.2 mg, 35%) as a white solid.

$^1$H-NMR (DMSO-$d_6$, 400 MHz, at 80° C.) δ(PPM) 3.55 (2H, dd, J=5.4, 4.9 Hz), 3.69 (3H, s), 3.84 (2H, dd, J=5.4, 4.9 Hz), 4.77 (2H, s), 6.65 (1H, td, J=8.9, 3.9 Hz), 7.35 (1H, d, J=8.3 Hz), 7.45 (1H, d, J=7.3 Hz), 7.51 (1H, dd, J=11.0, 2.0 Hz), 8.35 (1H, br.s)

ESI (LC/MS positive mode) m/z 540 (M+H)

Example 68

3,4-Difluoro-2-(2-fluoro-4-iodo-phenylamino)-N-(2-hydroxy-ethoxy)-5-(2-oxo-pyrrolidin-1-ylmethyl)-benzamide (Compound H-3)

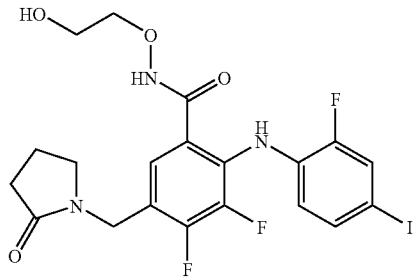

Methyl 4-amino-butyrate hydrochloride (commercially available, 48 mg, 0.312 mmol) and sodium cyanoborohydride (20 mg, 0.312 mmol) were added to a solution of 3,4-difluoro-2-(2-fluoro-4-iodo-phenylamino)-5-formyl-N-(2-hydroxy-ethoxy)-benzamide (50 mg, 0.104 mmol) obtained in Step F of Example 1 in methanol (2.0 mL). The mixture was stirred at room temperature for 18 hours. Then, the reaction vessel was equipped with a reflux condenser, and the mixture was heated at 80° C. for 2 hours. After completion of the reaction, the reaction mixture was extracted with ethyl acetate, and the organic layer was washed sequentially with water and saturated brine, dried over anhydrous sodium sulfate, and concentrated under reduced pressure. The resultant residue was purified by silica gel flash chromatography (Mega Bond Elut, Varian, 5% methanol/methylene chloride as an eluent) to give 3,4-difluoro-2-(2-fluoro-4-iodo-phenylamino)-N-(2-hydroxy-ethoxy)-5-(2-oxo-pyrrolidin-1-ylmethyl)-benzamide (Compound H-3, 26.8 mg, 47%) as a white solid.

$^1$H-NMR (CD$_3$OD, 270 MHz) δ(PPM) 2.06 (2H, m), 2.43 (2H, dd, J=8.4, 7.7 Hz), 3.44 (2H, dd, J=7.1, 6.9 Hz), 3.70 (2H, dd, J=4.8, 4.5 Hz), 3.93 (2H, dd, J=4.9, 4.0 Hz), 4.53 (2H, s), 6.62 (1H, td, J=8.7, 4.3 Hz), 7.32 (1H, m), 7.35 (1H, m), 7.45 (1H, dd, J=10.7, 2.0 Hz)

ESI (LC/MS positive mode) m/z 550 (M+H)

Example 69

3,4-Difluoro-2-(2-fluoro-4-iodo-phenylamino)-N-(2-hydroxy-ethoxy)-5-(2-oxo-piperidin-1-ylmethyl)-benzamide (Compound H-4)

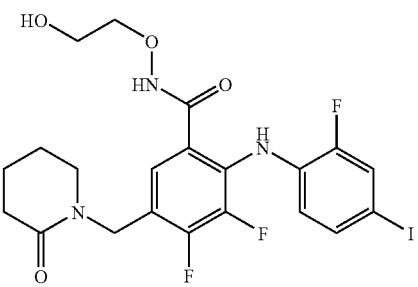

Methyl 5-amino-pentanoate hydrochloride {see J. Org. Chem. (1968) 1581} (128 mg, 0.178 mmol) and sodium cyanoborohydride (45 mg, 0.718 mmol) were added to a solution of 3,4-difluoro-2-(2-fluoro-4-iodo-phenylamino)-5-formyl-N-(2-hydroxy-ethoxy)-benzamide (115 mg, 0.239 mmol) obtained in Step F of Example 1 in tetrahydrofuran (anhydrous, 4.0 mL). The mixture was stirred at room temperature for 1.5 hours. Then, the reaction vessel was equipped with a reflux condenser, and the mixture was heated at 60° C. for 2 days. After completion of the reaction, the reaction mixture was extracted with ethyl acetate, and the organic layer was washed sequentially with water and saturated brine, dried over anhydrous sodium sulfate, and concentrated under reduced pressure. The resultant residue was purified by silica gel flash chromatography (Mega Bond Elut, Varian, 4% methanol/methylene chloride as an eluent) to give 3,4-difluoro-2-(2-fluoro-4-iodo-phenylamino)-N-(2-hydroxy-ethoxy)-5-(2-oxo-piperidin-1-ylmethyl)-benzamide (Compound H-4, 42.7 mg, 37%) as a white solid.

$^1$H-NMR (CD$_3$OD, 270 MHz) δ(PPM) 1.85 (4H, m), 2.42 (2H, m), 3.40 (2H, m) 3.70 (2H, dd, J=4.9, 4.3 Hz), 3.92 (2H, dd, J=4.9, 4.3 Hz), 4.65 (2H, s), 6.56 (1H, td, J=8.9, 4.3 Hz), 7.34 (1H, m), 7.35 (1H, m), 7.45 (1H, dd, J=10.7, 2.0 Hz)

ESI (LC/MS positive mode) m/z 564 (M+H)

Example 70

3,4-Difluoro-2-(2-fluoro-4-iodo-phenylamino)-5-[(2-hydroxy-acetylamino)-methyl]-N-(2-hydroxy-ethoxy)-benzamide (Compound E-5)

Step A

Synthesis of 5-aminomethyl-3,4-difluoro-2-(2-fluoro-4-iodo-phenylamino)-benzoic acid trifluoroacette

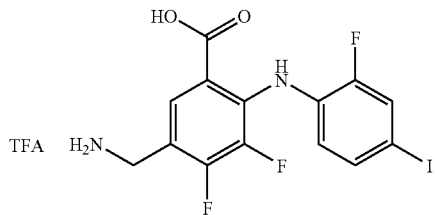

tert-Butyl carbamate (commercially available, 187 mg, 1.602 mmol), trifluoroacetic acid (123 µL, 1.602 mmol), and triethylsilane (255 µL, 1.602 mmol) were added sequentially to a suspension of 3,4-difluoro-2-(2-fluoro-4-iodo-phenylamino)-5-formyl-benzoic acid (225 mg, 0.534 mmol) obtained in Step A of Example 5 in acetonitrile (anhydrous, 20 mL). The mixture was stirred at room temperature for 5 days. After completion of the reaction, the reaction mixture was evaporated under reduced pressure, and the resultant residue was extracted with ethyl acetate. The organic layer was washed sequentially with water and saturated brine, dried over anhydrous sodium sulfate, and evaporated under reduced pressure. The resultant crude product was purified by silica gel flash chromatography (Mega Bond Elut, Varian, 5% methanol/methylene chloride as an eluent) to give 5-(tert-butoxycarbonylamino-methyl)-3,4-difluoro-2-(2-fluoro-4-iodo-phenylamino)-benzoic acid. [LC/MS m/z 523 (M+1)]. Then, trifluoroacetic acid (0.5 mL) was added to a solution of the resultant product in methylene chloride (20 mL), and the mixture was stirred at room temperature for 14 hours. After completion of the reaction, the reaction mixture was evaporated under reduced pressure, and the resultant residue was recrystallized from a mixed solvent of diethyl ether:hexane (1:1) to give 5-aminomethyl-3,4-difluoro-2-(2-fluoro-4-iodo-phenylamino)-benzoic acid trifluoroacetate (285 mg, 99% in 2 steps) as white crystals.

$^1$H-NMR (CD$_3$OD, 270 MHz) δ(PPM) 4.19 (2H, s), 6.84 (1H, td, J=8.6, 4.8 Hz), 7.44 (1H, br. d, J=10.1 Hz), 7.51 (1H, dd, J=10.4, 2.0 Hz), 8.06 (1H, dd, J=7.8, 1.8 Hz) ESI (LC/MS positive mode) m/z 423 (M+H)

Step B

Synthesis of 5-(acryloylamino-methyl)-N-[2-(tert-butyl-dimethyl-silanyloxy)-ethoxy]-3,4-difluoro-2-(2-fluoro-4-iodo-phenylamino)-benzamide

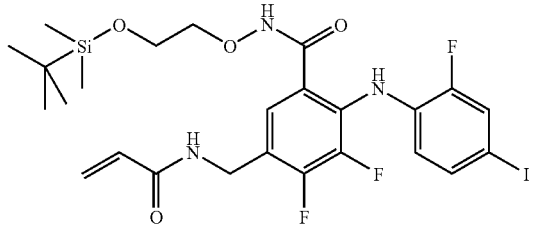

Acryloyl chloride (100 µL, 0.986 mmol) and triethylamine (689 µL, 4.93 mmol) were added to a solution of hydroxypyrrolidine-2,5-dione (commercially available, 227 mg, 1.973 mmol) in methylene chloride (anhydrous, 2 mL), and the mixture was stirred at room temperature for 30 minutes.

5-aminomethyl-3,4-difluoro-2-(2-fluoro-4-iodo-phenylamino)-benzoic acid (150 mg, 0.355 mmol) obtained in Step A was added to this solution, and the mixture was stirred for 1 hour. After completion of the reaction, the reaction mixture was evaporated under reduced pressure, and the resultant residue was extracted with ethyl acetate. The organic layer was washed sequentially with water and saturated brine, dried over anhydrous sodium sulfate, and concentrated under reduced pressure to give 5-(acryloylamino-methyl)-3,4-difluoro-2-(2-fluoro-4-iodo-phenylamino)-benzoic acid as a white solid. This product was confirmed for the structure by LC/MS. LC/MS (positive mode) m/z 477 (M+1). This compound was dissolved in methylene chloride (anhydrous, 10 mL) under argon flow. N,N-diisopropylethylamine (250 µL, 1.42 mmol), O-[2-(tert-butyl-dimethyl-silanyloxy)-ethyl]-hydroxylamine (135 mg, 0.71 mmol), 1-hydroxy-1H-benzotriazole (71 mg, 0.533 mmol), and (3-dimethylamino-propyl)-ethyl-carbodiimide hydrochloride (102 mg, 0.533 mmol) were added sequentially to the solution. The mixture was stirred at room temperature for 20 hours.

After completion of the reaction, the reaction mixture was evaporated under reduced pressure, and the resultant residue was extracted with ethyl acetate. The organic layer was washed sequentially with water and saturated brine, dried over anhydrous sodium sulfate, and evaporated under reduced pressure. The resultant crude product was purified by silica gel flash chromatography (Mega Bond Elut, Varian, 40% ethyl acetate/hexane as an eluent) and preparative TLC (No. 5744, Merck, 40% ethyl acetate/hexane as a developing solvent) to give 5-(acryloylamino-methyl)-N-[2-(tert-butyl-dimethyl-silanyloxy)-ethoxy]-3,4-difluoro-2-(2-fluoro-4-iodo-phenylamino)-benzamide (7.4 mg, 3%) as a waxy solid.

$^1$H-NMR (CDCl$_3$, 270 MHz) δ(PPM) 0.07 (6H, s), 0.09 (9H, s), 3.89 (2H, m), 4.07 (2H, m), 4.51 (2H, d, J=6.1 Hz), 5.71 (2H, dd, J=10.1, 1.5 Hz), 6.12 (1H, dd, J=17.0 Hz, 10.2 Hz), 6.20 (1H, br.s), 6.33 (1H, dd, J=17.0, 1.5 Hz), 6.56 (1H, td, J=8.7, 5.3 Hz), 7.30 (1H, dt, J=8.6, 3.0 Hz), 7.38 (1H, dd, J=10.2, 2.0 Hz), 7.40 (1H, m), 8.57 (1H, br.s)

ESI (LC/MS positive mode) m/z 650 (M+H)

Step C

Synthesis of N-[2-(tert-butyl-dimethyl-silanyloxy)-ethoxy]-3,4-difluoro-2-(2-fluoro-4-iodo-phenylamino)-5-[(2-hydroxy-acetylamino)-methyl]-benzamide

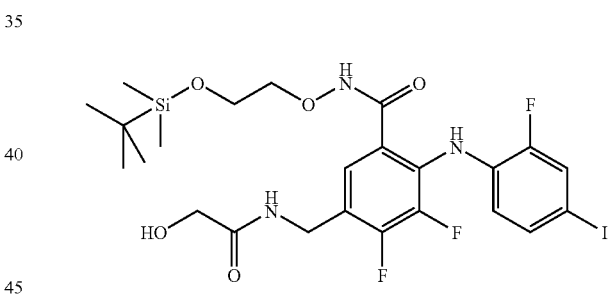

Aqueous osmium tetroxide (4%, 0.1 mL) and sodium metaperiodate (12 mg, 0.056 mmol) were added to a solution of 5-(acryloylamino-methyl)-N-[2-(tert-butyl-dimethyl-silanyloxy)-ethoxy]-3,4-difluoro-2-(2-fluoro-4-iodo-phenylamino)-benzamide (7.3 mg, 0.011 mmol) obtained in Step B in tetrahydrofuran (4 mL) and water (1 mL). The mixture was stirred for 3 hours. After the disappearance of the starting material was confirmed by LC/MS, the reaction mixture was extracted with ethyl acetate. The organic layer was washed sequentially with water and saturated brine, dried over anhydrous sodium sulfate, and concentrated under reduced pressure to give N-[2-(tert-butyl-dimethyl-silanyloxy)-ethoxy]-3, 4-difluoro-2-(2-fluoro-4-iodo-phenylamino)-5-[(2-oxo-acetylamino)-methyl]-benzamide. Subsequently, this was dissolved in methanol (2.0 mL). Sodium borohydride (3 mg, 0.079 mmol) was added to this solution at room temperature, and the mixture was stirred for 1 hour. After completion of the reaction, the reaction mixture was extracted with ethyl acetate, and the organic layer was washed sequentially with water and saturated brine, dried over anhydrous sodium sulfate, and evaporated under reduced pressure. The resultant crude product was purified by silica gel flash chromatography (Mega Bond Elut, Varian, 60% ethyl acetate/hexane as an eluent) to give N-[2-(tert-butyl-dimethyl-silanyloxy)-ethoxy]-3,4-difluoro-2-(2-fluoro-4-iodo-phenylamino)-5-[(2-hydroxy-acetylamino)-methyl]-benzamide (4.34 mg, 60% in 2 steps) as a pale yellow solid.

ESI (LC/MS positive mode) m/z 654 (M+H)

Step D

Synthesis of 3,4-difluoro-2-(2-fluoro-4-iodo-phenylamino)-5-[(2-hydroxy-acetylamino)-methyl]-N-(2-hydroxy-ethoxy)-benzamide (Compound E-5)

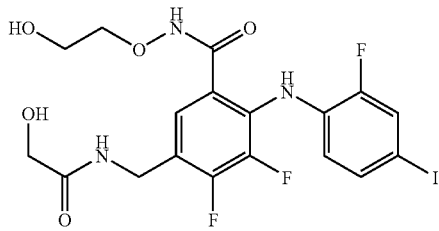

Tetra-n-butylammonium fluoride (1 mol/L solution in tetrahydrofuran, 0.5 mL, 0.500 mmol) was added to a solution of N-[2-(tert-butyl-dimethyl-silanyloxy)-ethoxy]-3,4-difluoro-2-(2-fluoro-4-iodo-phenylamino)-5-[(2-hydroxy-acetylamino)-methyl]-benzamide (4.34 mg, 0.00665 mmol) obtained in Step C in tetrahydrofuran (anhydrous, 1 mL) at room temperature. The mixture was stirred for 1.5 hours. After completion of the reaction, the reaction mixture was extracted with ethyl acetate, and the organic layer was washed sequentially with water and saturated brine, dried over anhydrous sodium sulfate, and evaporated under reduced pressure. The resultant crude product was purified sequentially with silica gel flash chromatography (Mega Bond Elut, Varian, 5% methanol/methylene chloride as an eluent) and preparative TLC (No. 5715, Merck, 7% methanol/methylene chloride as a developing solvent) to give 3,4-difluoro-2-(2-fluoro-4-iodo-phenylamino)-5-[(2-hydroxy-acetylamino)-methyl]-N-(2-hydroxy-ethoxy)-benzamide (Compound E-5, 1.4 mg, 39%) as a white solid.

$^1$H-NMR (CD$_3$OD, 270 MHz) δ(PPM) 3.71 (2H, dd, J=7.4, 4.7 Hz), 3.94 (2H, dd, J=7.4, 4.7 Hz), 4.03 (2H, s), 4.50 (2H, s), 6.55 (1H, td, J=8.6, 5.3 Hz), 7.32 (1H, m), 7.42 (1H, dd, J=10.7, 1.8 Hz), 7.45 (1H, dd, J=5.8, 2.1 Hz)

ESI (LC/MS positive mode) m/z 540 (M+H)

Example 71

3,4-Difluoro-2-(2-fluoro-4-iodo-phenylamino)-N-(2-hydroxy-ethoxy)-5-(2-oxo-tetrahydro-pyrimidin-1-ylmethyl)-benzamide (Compound H-6)

Step A

Synthesis of 5-[(3-amino-propylamino)-methyl]-3,4-difluoro-2-(2-fluoro-4-iodo-phenylamino)-N-(2-hydroxy-ethoxy)-benzamide

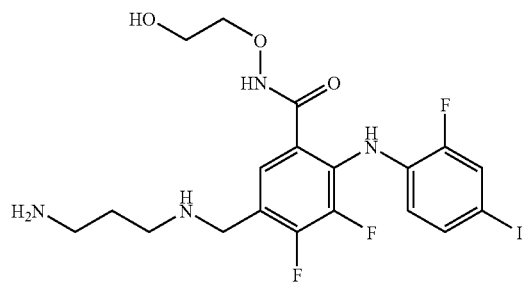

3,4-Difluoro-2-(2-fluoro-4-iodo-phenylamino)-5-formyl-N-(2-hydroxy-ethoxy)-benzamide obtained in Step F of Example 1 was reacted with propane-1,3-diamine in THF. The thus-obtained imine was reduced with sodium borohydride in methanol to give the title compound.

ESI (LC/MS positive mode) m/z 539 (M+H)

Step B

Synthesis of 3,4-difluoro-2-(2-fluoro-4-iodo-phenylamino)-N-(2-hydroxy-ethoxy)-5-(2-oxo-tetrahydro-pyrimidin-1-ylmethyl)-benzamide (Compound H-6)

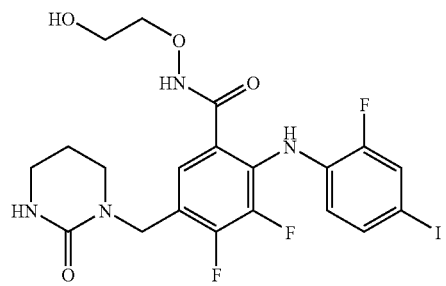

The amine synthesized in Step A (66.4 mg, 0.1233 mmol) was dissolved in THF:CH$_3$CN (1:1 v/v, 3.0 ml). N,N-disuccinimidyl carbonate (47.4 mg, 1.5 eq., 0.1849 mmol) and triethylamine (103.1 μl, 6.0 eq., 0.7398 mmol) were added sequentially to this solution, and the mixture was stirred at room temperature for 20 hours. The solvent was removed under reduced pressure, and the residue was purified by LC/MS to give white crystals (42.6 mg).

$^1$H-NMR (DMSO-d$_6$, 400 MHz) δ(PPM) 1.83 (2H, t, J=5.2 Hz), 3.14 (2H, t, J=5.6 Hz), 3.23 (2H, t, J=5.6 Hz), 3.51-3.58 (2H, m), 3.82 (2H, brt), 4.49 (2H, s), 6.41 (1H, brs), 6.61 (1H, dt, J=3.9, 8.3 Hz), 7.28 (1H, d, J=6.4 Hz), 7.34 (1H, d, J=7.9 Hz), 7.56 (1H, d, J=10.8 Hz), 8.48 (1H, s), 12.0 (1H, s)

ESI (LC/MS positive mode) m/z 565 (M+H)

Example 72

3,4-Difluoro-2-(2-fluoro-4-iodo-phenylamino)-N-(2-hydroxy-ethoxy)-5-(2-oxo-oxazolidin-3-yl methyl)-benzamide (Compound H-5)

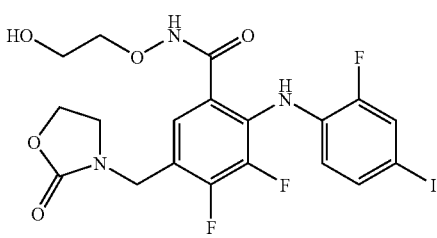

Step A

Synthesis of 3,4-difluoro-2-(2-fluoro-4-iodo-phenylamino)-N-(2-hydroxy-ethoxy)-5-{[(E)-2-hydroxy-ethylimino]-methyl}-benzamide

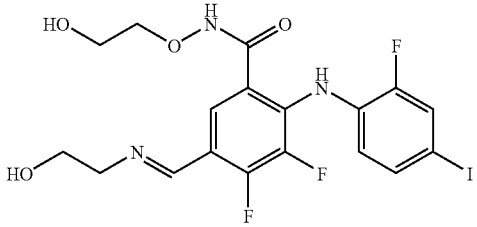

The title compound was synthesized by reacting 3,4-difluoro-2-(2-fluoro-4-iodo-phenylamino)-5-formyl-N-(2-hydroxy-ethoxy)-benzamide obtained in Step F of Example 1 with ethanolamine in THF.

$^1$H-NMR (CD$_3$OD, 400 MHz) δ(PPM) 3.72-3.74 (4H, m), 3.81-3.84 (2H, m), 3.96-3.99 (2H, m), 6.64-6.68 (1H, m), 7.36 (1H, d, J=8.79 Hz), 7.43 (1H, d, J=9.99 Hz), 8.13 (1H, d, J=5.6 Hz), 8.50 (1H, s)

ESI (LC/MS positive mode) m/z 524 (M+H)

Step B

Synthesis of 3,4-difluoro-2-(2-fluoro-4-iodo-phenylamino)-N-(2-hydroxy-ethoxy)-5-[(2-hydroxy-ethylamino)-methyl]-benzamide

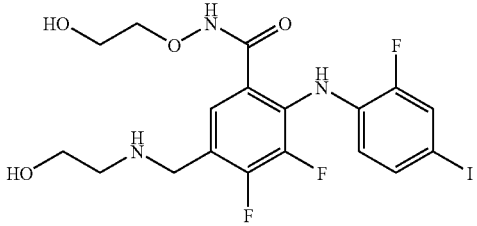

Sodium borohydride was added to a solution of the imine, 3,4-difluoro-2-(2-fluoro-4-iodo-phenylamino)-N-(2-hydroxy-ethoxy)-5-{[(E)-2-hydroxy-ethylimino]-methyl}-benzamide obtained in Step A in MeOH at 0° C. While being allowed to warm gradually, the mixture was stirred overnight. The solvent was removed under reduced pressure, and the residue was purified with a silica gel column (CH$_2$Cl$_2$:MeOH (4:1 to 2:1)) to give the title compound as a white solid.

$^1$H-NMR (CD$_3$OD, 400 MHz) δ(PPM) 2.80 (2H, t, J=5.38 Hz), 3.69-3.72 (4H, m), 3.92-3.95 (4H, m), 6.59 (1H, dt, J=3.9, 8.3 Hz), 7.34 (1H, d, J=10.3 Hz), 7.44 (1H, dd, J=1.95, 10.3 Hz), 7.49 (1H, d, J=7.3 Hz)

ESI (LC/MS positive mode) m/z 526 (M+H)

Step B'

An Alternative to Step B 3,4-Difluoro-2-(2-fluoro-4-iodo-phenylamino)-N-(2-hydroxy-ethoxy)-5-[(2-hydroxy-ethylamino)-methyl]-benzamide obtained in Step B can be prepared in 1 step by reductive amination of 3,4-difluoro-2-(2-fluoro-4-iodo-phenylamino)-5-formyl-N-(2-hydroxy-ethoxy)-benzamide obtained in Step F of Example 1. Namely, 2-aminoethanol (0.070 ml), acetic acid (0.080 ml), and sodium cyanoborohydride (44 mg) were added to a solution of an aldehyde, 3,4-difluoro-2-(2-fluoro-4-iodo-phenylamino)-5-formyl-N-(2-hydroxy-ethoxy)-benzamide (65.7 mg, 0.136 mmol) in methanol (2 ml) at room temperature. The mixture was stirred overnight. Water (6 ml), saturated brine (3 ml), and aqueous sodium bicarbonate (2 ml) were added, and the reaction mixture was extracted with ethyl acetate (2×10 ml). The combined organic layers were washed with saturated brine (10 ml), dried over anhydrous sodium sulfate, and concentrated under reduced pressure. The residue was triturated with ethyl acetate/n-hexane (2:1) to give 3,4-difluoro-2-(2-fluoro-4-iodo-phenylamino)-N-(2-hydroxy-ethoxy)-5-[(2-hydroxy-ethylamino)-methyl]-benzamide (60.4 mg, 84%) as a colorless solid.

Step C 3,4-Difluoro-2-(2-fluoro-4-iodo-phenylamino)-N-(2-hydroxy-ethoxy)-5-(2-oxo-oxazolidin-3-yl methyl)-benzamide (Compound H-5)

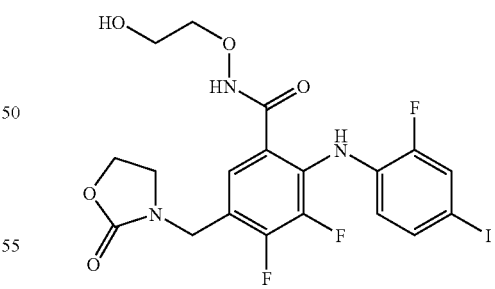

Using 3,4-difluoro-2-(2-fluoro-4-iodo-phenylamino)-N-(2-hydroxy-ethoxy)-5-[(2-hydroxy-ethylamino)-methyl]-benzamide obtained in Step B (or Step B') as a starting material, synthesis was performed according to the procedure described in Step B of Example 27 to give 3,4-difluoro-2-(2-fluoro-4-iodo-phenylamino)-N-(2-hydroxy-ethoxy)-5-(2-oxo-oxazolidin-3-ylmethyl)-benzamide (Compound H-5).

$^1$H-NMR (DMSO-d$_6$, 400 MHz) δ(PPM) 3.49-3.59 (4H, m), 3.83-3.85 (2H, m), 4.28-4.32 (2H, m), 4.42 (2H, s), 6.87

(1H, td, J=8.8, 3.9 Hz), 7.36 (1H, d, J=7.9 Hz), 7.46 (1H, d, J=8.4 Hz), 7.57 (1H, dd, J=1.9, 10.8 Hz), 8.76 (1H, s), 12.3 (1H, s)

ESI (LC/MS positive mode) m/z 552 (M+H)

Example 73

5-(2,3-Dioxo-morpholin-4-ylmethyl)-3,4-difluoro-2-(2-fluoro-4-iodo-phenylamino)-N-(2-hydroxy-ethoxy)-benzamide (Compound H-7)

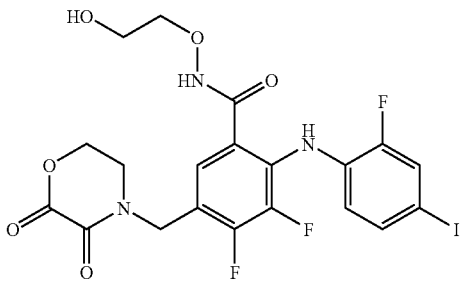

4-Dimethylaminopyridine (12.1 mg) and dibenzotriazol-1-yl oxalate (9.2 mg, 27.4 μmol) were added to a solution of 3,4-difluoro-2-(2-fluoro-4-iodo-phenylamino)-N-(2-hydroxy-ethoxy)-5-[(2-hydroxy-ethylamino)-methyl]-benzamide (15.9 mg, 30.2 μmol) obtained in Step B (or Step B') of Example 72 in anhydrous N,N-dimethylformamide (1.5 ml) at room temperature. The mixture was stirred at room temperature for 2 hours. Water (6 ml) and 1 N hydrochloric acid (0.5 ml) were added, and the reaction mixture was extracted with ethyl acetate (2×10 ml). The combined organic layers were washed with saturated brine (8 ml), dried over anhydrous sodium sulfate, and concentrated under reduced pressure. The residue was purified with a preparative silica gel plate (No. 5744, Merck, $CH_2Cl_2$/MeOH (10:1) as a developing solvent) to give 5-(2,3-dioxo-morpholin-4-ylmethyl)-3,4-difluoro-2-(2-fluoro-4-iodo-phenylamino)-N-(2-hydroxy-ethoxy)-benzamide (Compound H-7, 1.0 mg, 6% yield).

$^1$H-NMR (DMSO-$d_6$, 270 MHz) δ(PPM) 3.57 (2H, br.s), 3.70 (2H, t, J=6.1 Hz), 3.86 (2H, t, J=4.9 Hz), 4.55 (2H, t, J=5.4 Hz), 4.66 (2H, s), 6.67 (1H, td, J=J=8.4, 4.3 Hz), 7.32-7.40 (2H, m), 7.59 (1H, dd, J=10.8, 1.4 Hz).

ESI (LC/MS positive mode) m/z 580 (M+H)

Example 74

5-{[Acetyl-(2-hydroxy-ethyl)-amino]-methyl}-3,4-difluoro-2-(2-fluoro-4-iodo-phenylamino)-N-(2-hydroxy-ethoxy)-benzamide (Compound E-6)

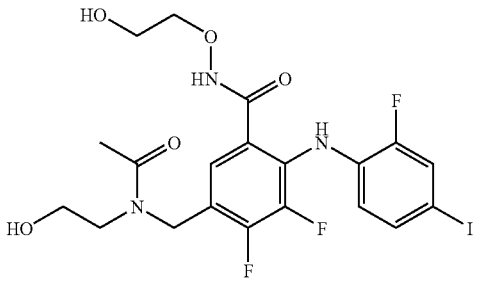

Using 3,4-difluoro-2-(2-fluoro-4-iodo-phenylamino)-N-(2-hydroxy-ethoxy)-5-[(2-hydroxy-ethylamino)-methyl]-benzamide obtained in Step B (or Step B') of Example 72 as a starting material, synthesis was performed according to the procedure described in Example 41 to give 5-{[acetyl-(2-hydroxy-ethyl)-amino]-methyl}-3,4-difluoro-2-(2-fluoro-4-iodo-phenylamino)-N-(2-hydroxy-ethoxy)-benzamide (Compound E-6).

$^1$H-NMR (DMSO-$d_6$, 270 MHz) δ(PPM) 2.07 (3H×⅓, s), 2.12 (3H×⅔, s), 3.47-3.56 (4H, m), 3.83 (2H, t, J=4.5 Hz), 4.58 (2H×⅔, s), 4.69 (2H×⅓, s), 6.61 (1H, td, J=8.9, 4.3 Hz), 7.24 (1H, d, J=7.4 Hz), 7.35 (1H, d, J=8.6 Hz), 7.57 (1H, d, J=7.6 Hz),

ESI (LC/MS positive mode) m/z 568 (M+H)

Test Example 1

Measurement of MEK Inhibitory Activity

MEK inhibitory activities were measured for Compounds B-1, B-2, B-6, B-9, B-12, C-1, C-6; C-7, C-8, C-10, C-13, C-24, C-28, C-31, F-1, F-2, F-3, F-4, F-5, F-6, F-7, F-8, F-9, G-1, G-2, G-3, G-4, and G-5 obtained in the Examples, and the following known compounds, P (WO02/06213, Example 9), Q (WO02/06213, Example 39), and R (WO99/01426, Example 95).

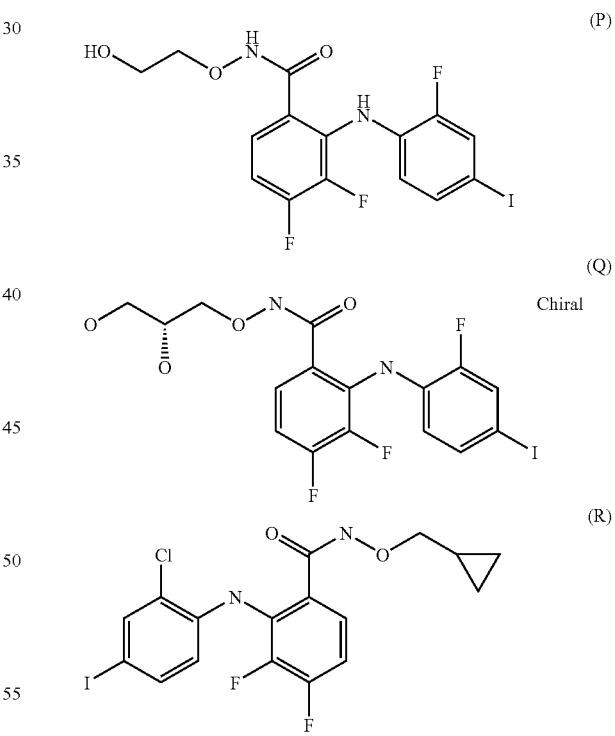

Compound P was prepared according to the description (Example 9) of WO02/06213. Compound Q was prepared according to the description (Example 39) of WO02/06213. Compound R was prepared according to the description (Example 95) of WO99/01426.

For the measurement of MEK inhibitory activities, an assay system was constructed so that phosphorylation of MBP (Myelin Basic Protein) could occur in proportion to the MEK kinase activity, with adjusting the amount of the enzyme and the like, according to the method of Raf-1 Kinase Cascade Assay Kit (cat. 17-172, Upstate Biotechnology Inc., New York, USA).

[$\gamma^{33}$P] ATP (Amersham Biosciences) was used as a radioisotope.

The amount of the $^{33}$P-labelled MBP was measured using Microbeta 1450 (PerkinElmer Inc., Massachusetts, USA), and 50% inhibitory concentration (IC50) was calculated.

Results are shown in Table 2.

Test Example 2

Measurement of Growth Inhibitory Activity Against Cancer Cells

Growth inhibitory activities against cancer cells based on MEK inhibitory activities were measured for Compounds B-1, B-2, B-6, B-9, B-12, C-1, C-6, C-7, C-8, C-10, C-13, C-24, C-28, C-31, F-1, F-2, F-3, F-4, F-5, F-6, F-7, F-8, F-9, G-1, G-2, G-3, G-4, and G-5 obtained in the Examples, and the known compounds, P, Q, and R shown above.

The growth inhibitory activities against cancer cells were measured using Cell Counting Kit-8 (Dojindo Laboratories).

Human colon cancer cell line HT-29 obtained from American Type Culture Collection (Virginia, USA) and human non-small cell lung carcinoma cell line QG56 obtained from Immuno-Biological Laboratories Co., Ltd. were plated onto 96-well culture plate at a density of 2000 cells/well, a designated concentration of MEK inhibitor was added, and the cells were incubated for 4 days.

On the 4th day of culture, a solution of Cell Counting Kit-8 was added, and absorbance (measurement wavelength: 450 nm; reference wavelength: 615 nm) was measured according to the protocol attached to the kit, and 50% inhibitory concentration (IC50) was calculated.

Results are shown in Table 2.

Test Example 3

Measurement of Stability Against Mouse Liver Microsome

A variety of metabolic enzymes exist in the liver, and play a key role in the foreign substance detoxication. Many enzymes involved in drug metabolism (e.g., cytochrome P450) are localized in the endoplasmic reticulum in the cells, and are collected in the microsome fraction during preparation from the cells. The stability in liver microsome is used universally as a simple measure for evaluation of drug metabolism.

There is a correlation between in vitro intrinsic clearance calculated from the stability in human liver microsome and human in vivo clearance (Ito K. et al. Annu. Rev. Pharmacol. Toxicol. 1998, 38: 461-99, Naritomi Y et al. Drug Metab. Dispos. 2001, 29:1316-24, Yuichi Sugiyama et al., Pharmacokinetics—Understanding by exercises, Nanzando).

Clearance is an important parameter that determines a blood concentration. The better the drug stability in liver microsome is, the smaller the clearance is and the higher the blood concentration is. A drug having a good stability in liver microsome can achieve a certain blood concentration with a lower dose, compared to a drug having a poor stability.

Compounds B-1, B-2, B-6, B-9, B-12, C-1, C-2, C-6, C-7, C-10, C-24, C-28, C-29, C-31, C-34, C-35, F-1, F-2, F-5, F-7, G-1, G-2, G-3, G-4, and G-5 obtained in the Examples, and the known compounds, P, Q, and R shown above were incubated with mouse liver microsome (1 mg protein/mL) in 50 mM phosphate buffer (pH 7.4) containing 5 mM $MgCl_2$ and 2 mM NADPH (the reduced form of nicotinamide adenine dinucleotide phosphate) at 37° C. for 1 hour. After the enzyme reaction was terminated with the addition of a three-fold volume of acetonitrile, the reaction mixture was centrifuged at 1500 rpm for 10 minutes, and the resultant supernatant was used as a test sample to measure the stability in human liver microsome by quantitating the compound in the sample using HPLC/MS.

Table 3 shows the stability of the test compounds in mouse liver microsome. When a test compound has a longer half-life, the compound is metabolically very stable, and can produce a high blood concentration.

Test Example 4

Measurement of Water Solubility

Biopharmaceutical Classification System (BCS) is widely used to scientifically classify oral formulations in regard to membrane permeability and solubility. Drugs having good membrane permeability and good solubility are classified into Class 1, and guaranteed that they are absorbed almost perfectly after oral administration, and that the variability among individuals is small (Lenneras H. et al. J. Pharm. Pharmacol. 2005, 57: 273-85, Kasim N A et al. Mol. Pharmaceutics 2004, 1: 85-96).

Excessive amount of each of Compounds B-1, B-2, B-6, B-9, B-12, C-1, C-2, C-6, C-7, C-10, C-24, C-28, C-29, C-31, C-34, C-35, F-1, F-2, F-5, F-7, G-1, G-2, G-3, G-4, and G-5 obtained in the Examples, and the known compounds, P, Q, and R shown above was added to a glass vessel, to which 50 mM phosphate buffer (pH 6.5) was added. The vessel was sealed, sonicated at room temperature (20° C.) for 10 minutes, and agitated on an agitator for 2 hours. After dissolution equilibrium was achieved, the reaction mixture was filtered through a membrane filter, and the solute concentration in the filtrate was determined by HPLC.

Results are shown in Table 3.

Test Example 5

Measurement of Tumor Growth Suppressive Activity

A mouse model carrying human cancer was used to measure tumor growth suppressive activity of Compounds B-1, C-1, C-10, C-13, F-1, F-2, F-5, G-1, G-2, G-3, G-4, and H-3 obtained in the Examples, and the known compound, Q shown above.

Human colon cancer cell line HT-29 (obtained from American Type Culture Collection) was inoculated subcutaneously to BALB/c nu/nu mice. The test compound was dissolved in the vehicle (10% Cremophor, 10% ethanol, and 80% distilled water for injection), and orally given to the mice once a day for 14 consecutive days after the average tumor volume (0.5× long diameter×short diameter$^2$) reached to about 200 mm$^3$. One day after the last administration, the tumor volume was measured, and the tumor growth suppression rate, (1-tumor volume increase in the group received the test compound/tumor volume increase in the group received the vehicle)×100, of each of the test compounds was determined compared to the group received the vehicle. The higher value (%) indicates the stronger tumor suppressive activity.

Results of the tumor growth suppression rate at maximum tolerance dose (MTD) are shown in Table 4.

Table 4 shows very high tumor growth suppression rates of the compounds of this invention, indicating that they have very strong effect of tumor regression, compared to control compound Q, which has the tumor growth suppression rate of 66-82%.

Test Example 6

Anti-Type II Collagen Antibody-Induced Arthritis in Mice

Suppressive effects of compounds B-1 and G-2 obtained in Examples on arthritis development were determined using anti-Type II collagen antibody (anti-CII)-induced arthritis (J Immunol. 2002 Aug. 1; 169(3):1459-66).

Anti-CII (10 mg/mL of antibody cocktail for arthritis, code No. 62200, Chondrex) was administered intravenously at 1 mg/body/100 µL to BALB/c mice (female mice of 5 weeks old were purchased from Charles River Japan, Inc., and used at 5 animals per group after 1 week acclimation), and after 3 days, LPS (lipopolysaccharide) solution (0111:B4 250 µg/mL, code No. 62200, Chondrex) was administered intraperitoneally at 25 µg/0.1 mL/body. The test compounds were dissolved in the vehicle (10% Cremophor, 10% ethanol, and 80% distilled water for injection), and orally administered 1 hour before, 1, 2, 4-8, and 11 days after LPS administration (once a day, 1 mg/kg).

Arthritis score was evaluated with the full score 4 points per limb, and 16 points per animal. Score indicates as follows:

0.5: erythema is observed at 1 joint;

1: erythema is observed at 2 joints. Or reddening of the upper surface of the paws is observed, but swelling is not observed;

2: Slight swelling is observed;

3: Moderate swelling is observed on the upper surface of the paws;

4: Severe swelling is observed on the upper surface of the paws and digits.

In the group received the vehicle, arthritis developed the day after LPS administration. On the other hand, arthritis development was strongly suppressed in both groups received B-1 and G-2. Results of suppressive effect on arthritis development (arthritis score; mean+/−standard deviation) are shown in FIG. 1. FIG. 1 shows that the present compounds are effective anti-arthritis drugs.

TABLE 2

| Compound No. | Structure | MEK inhibitory activity IC50 (µM) | Growth inhibitory activity against cancer cells | |
|---|---|---|---|---|
| | | | HT29 IC50 (µM) | QG56 IC50 (µM) |
| B-1 | [structure] | 0.021 | 0.016 | 0.02 |
| B-2 | [structure] | 0.032 | 0.0405 | 0.0388 |
| B-6 | [structure] | 0.023 | 0.01 | 0.034 |
| B-9 | [structure] | 0.015 | 0.029 | 0.138 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| B-12 | 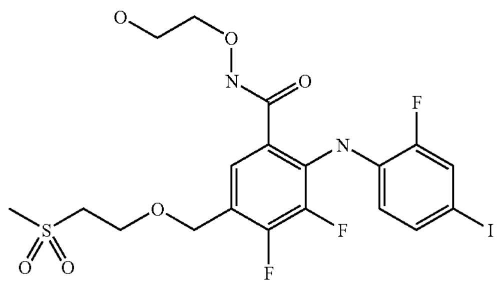 | 0.031 | 0.0062 | 0.028 |
| C-1 | 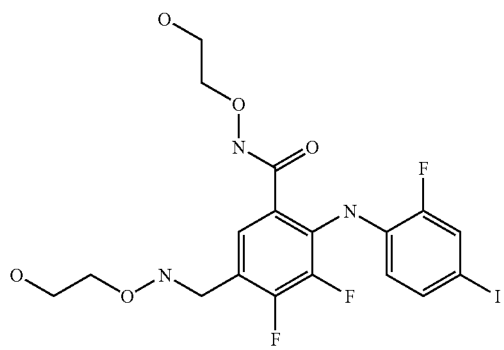 | 0.019 | 0.029 | 0.094 |
| C-6 | 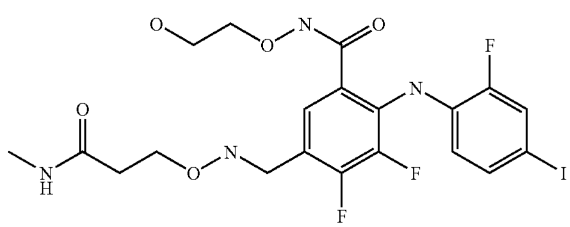 | 0.049 | 0.031 | 0.154 |
| C-7 | 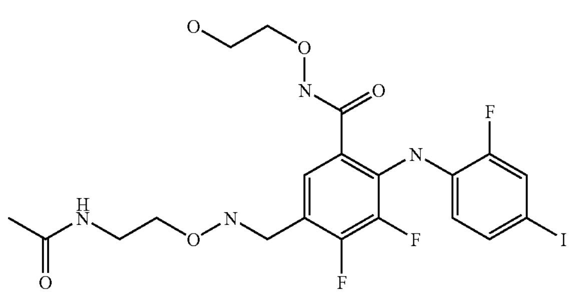 | 0.14 | 0.028 | 0.084 |
| C-8 | 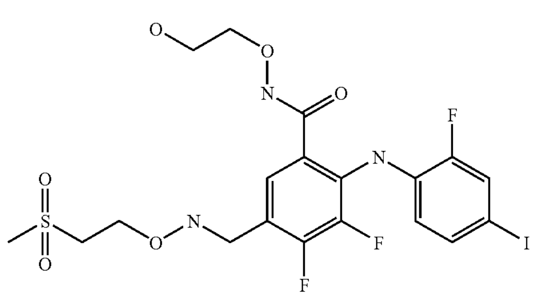 | 0.032 | 0.0086 | 0.023 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| C-10 | 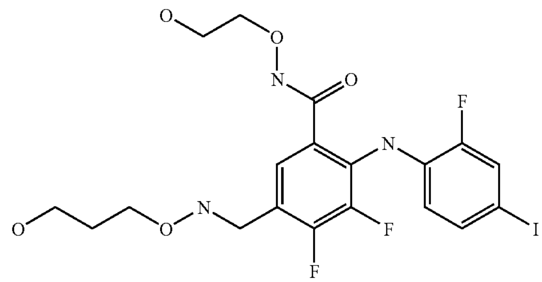 | 0.019 | 0.04 | 0.092 |
| C-13 | 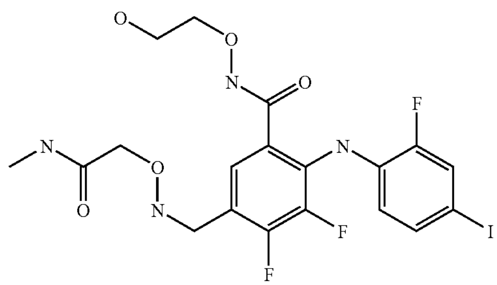 | 0.028 | 0.0059 | 0.012 |
| C-24 | 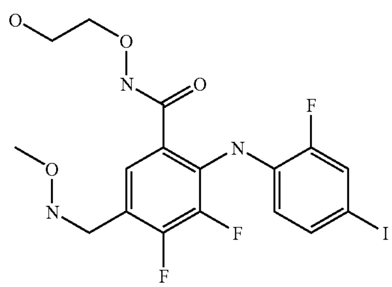 | 0.068 | 0.014 | 0.041 |
| C-28 | 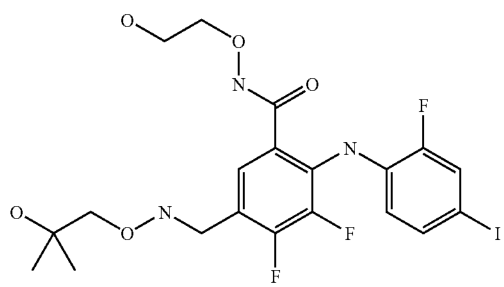 | 0.068 | 0.059 | 0.221 |
| C-31 | 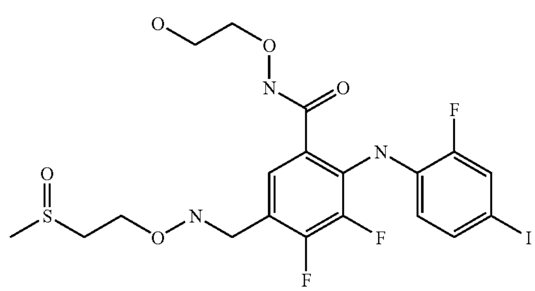 | 0.012 | 0.0083 | 0.022 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| F-1 | 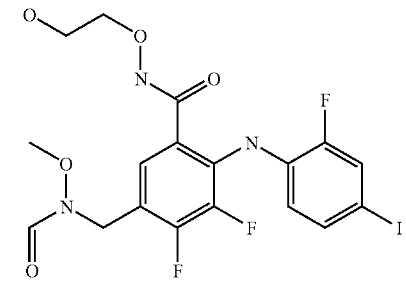 | 0.035 | 0.0026 | 0.02 |
| F-2 | 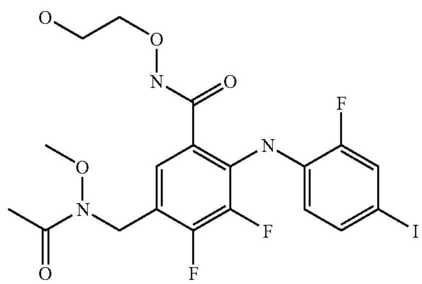 | 0.0086 | 0.0033 | 0.017 |
| F-3 | 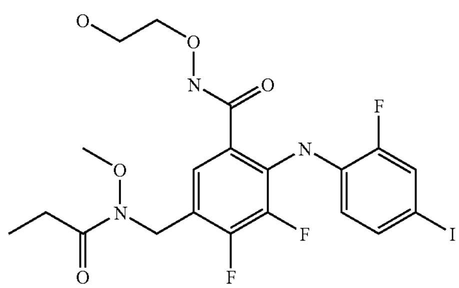 | 0.029 | 0.0073 | 0.01 |
| F-4 | 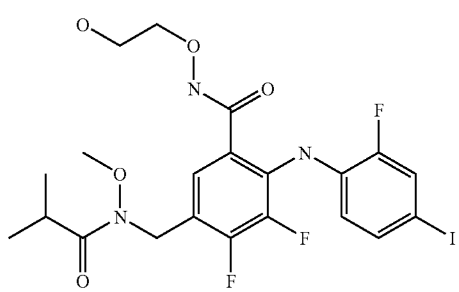 | 0.035 | 0.01032 | 0.02155 |
| F-5 | 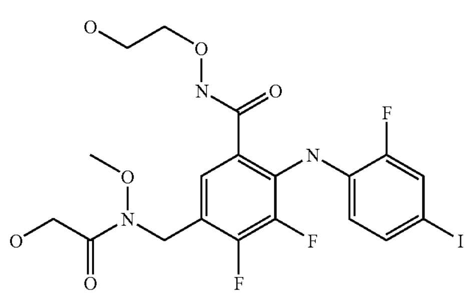 | 0.043 | 0.0048 | 0.0051 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| F-6 | 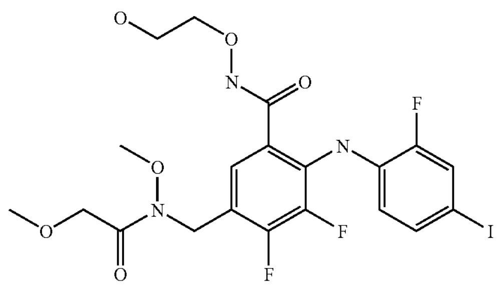 | 0.028 | 0.0046 | 0.0046 |
| F-7 | 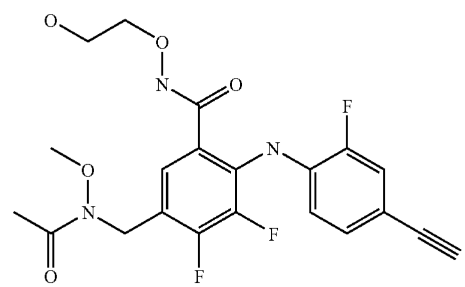 | 0.048 | 0.0074 | 0.0092 |
| F-8 | 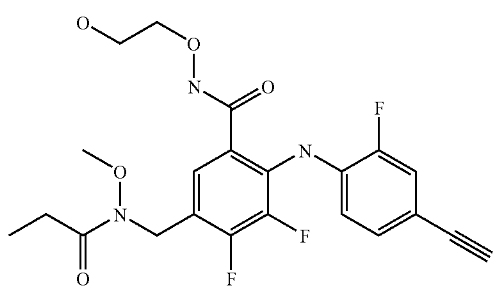 | 0.065 | 0.012 | 0.017 |
| F-9 | 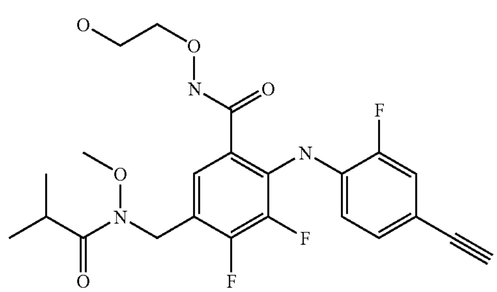 | 0.07 | 0.011 | 0.02 |
| G-1 | 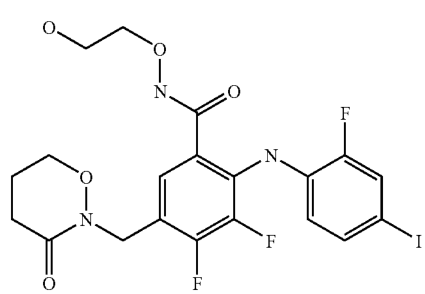 | 0.0088 | 0.0015 | 0.021 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| G-2 | 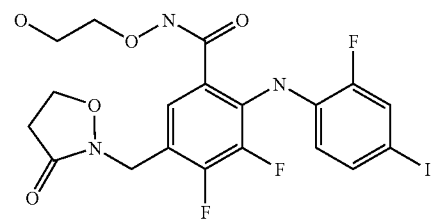 | 0.0072 | 0.0034 | 0.0086 |
| G-3 | 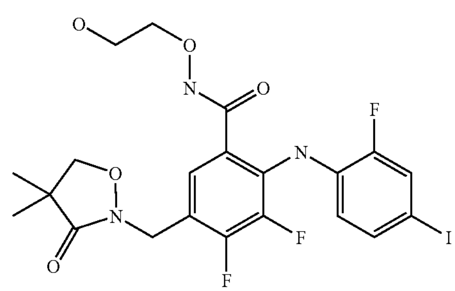 | 0.037 | 0.0051 | 0.038 |
| G-4 | 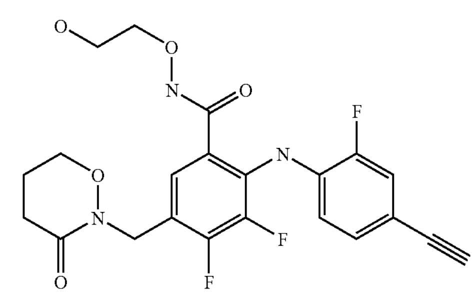 | 0.056 | 0.0057 | 0.021 |
| G-5 | 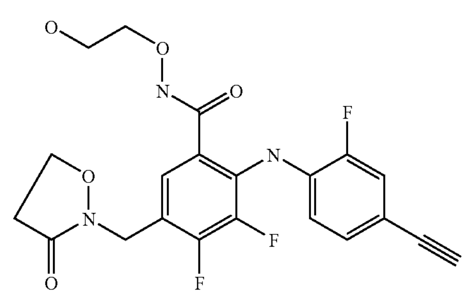 | 0.04 | 0.016 | 0.058 |
| P | 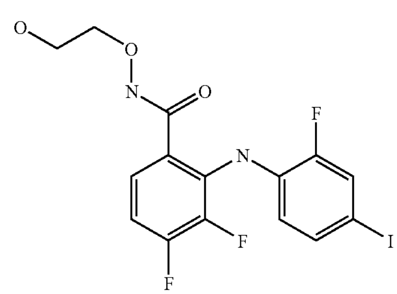 | 0.002 | 0.0059 | 0.017 |

TABLE 2-continued

| Compound No. | Structure | MEK inhibitory activity IC50 (μM) | Growth inhibitory activity against cancer cells | |
|---|---|---|---|---|
| | | | HT29 IC50 (μM) | QG56 IC50 (μM) |
| Q | (structure, Chiral) | 0.0052 | 0.005 | 0.01 |
| R | (structure) | 0.13 | 0.1 | 0.13 |

TABLE 3

| Compound No. | Structure | Water solubility (μM) | Stability against mouse liver microsome T1/2 (min) |
|---|---|---|---|
| B-1 | (structure) | 728 | >360 |
| B-2 | (structure) | 811 | >360 |
| B-6 | (structure) | 519 | >360 |
| B-9 | (structure) | 958 | >360 |

TABLE 3-continued

| Compound No. | Structure | Water solubility (μM) | Stability against mouse liver microsome T1/2 (min) |
|---|---|---|---|
| B-12 | 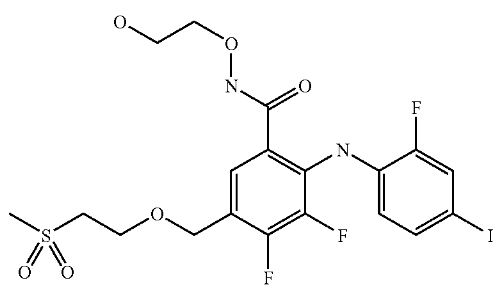 | 159 | >360 |
| C-1 | 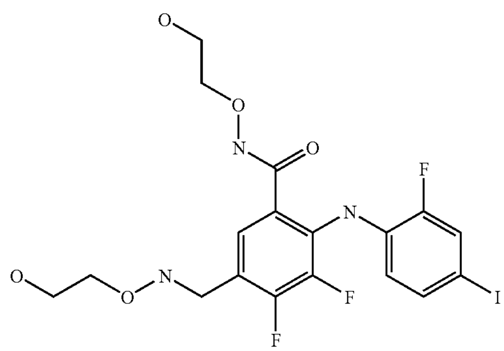 | 606 | 129 |
| C-2 | 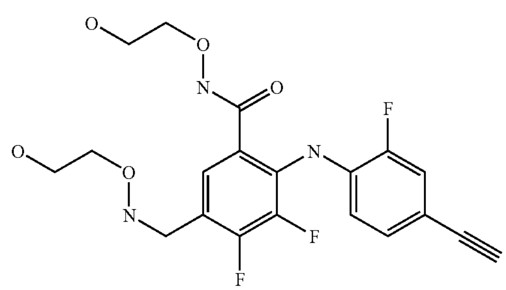 | 2913 | >360 |
| C-6 | 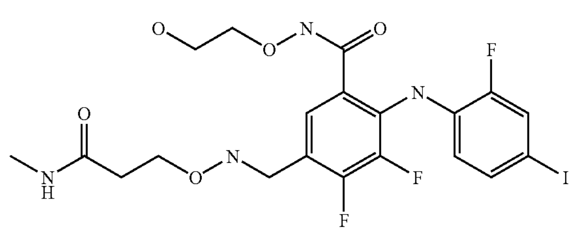 | 291 | >360 |
| C-7 | 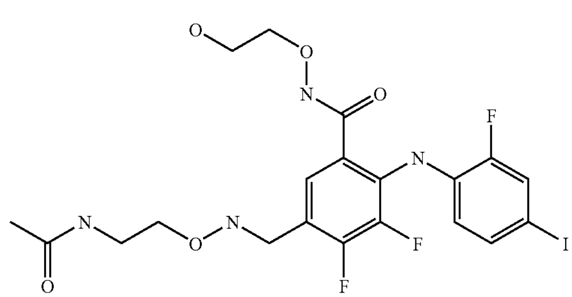 | 582 | 128 |

TABLE 3-continued
| Compound No. | Structure | Water solubility (μM) | Stability against mouse liver microsome T1/2 (min) |
|---|---|---|---|
| C-10 | 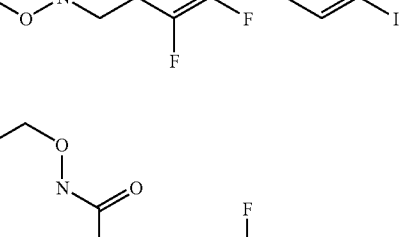 | 557 | 114 |
| C-24 | 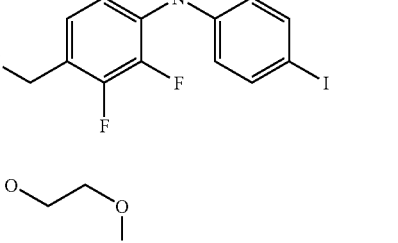 | 455 | 59 |
| C-28 | 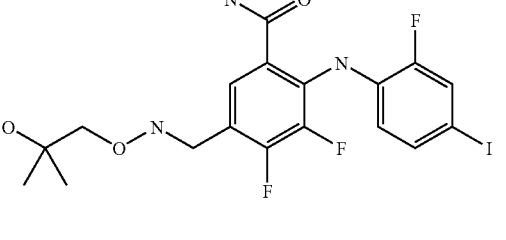 | 206 | >360 |
| C-29 | 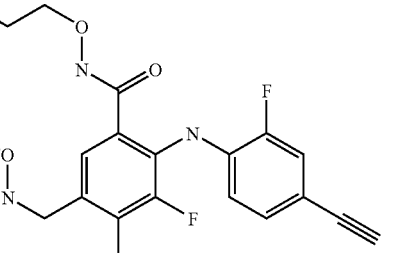 | 237 | >360 |
| C-31 | 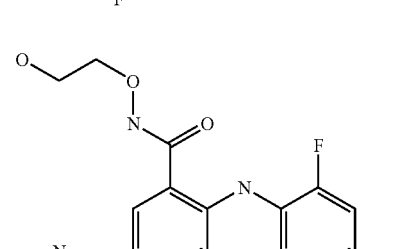 | 613 | >360 |

TABLE 3-continued
| Compound No. | Structure | Water solubility (μM) | Stability against mouse liver microsome T1/2 (min) |
|---|---|---|---|
| C-34 | 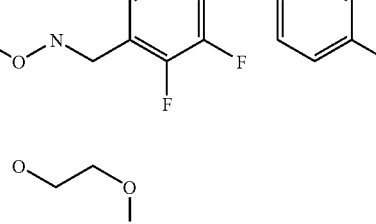 | 427 | 238 |
| C-35 | 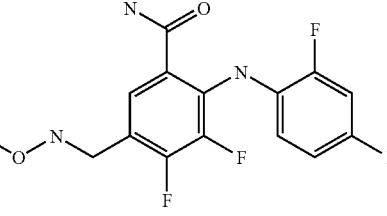 | 219 | >360 |
| F-1 | 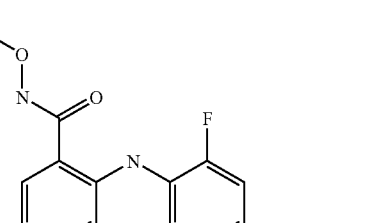 | 457 | 169 |
| F-2 | 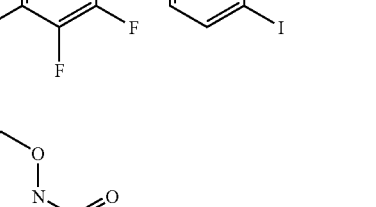 | 118 | 36 |
| F-5 | 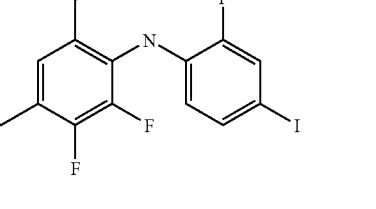 | 509 | 52 |

TABLE 3-continued

| Compound No. | Structure | Water solubility (μM) | Stability against mouse liver microsome T1/2 (min) |
|---|---|---|---|
| F-7 | 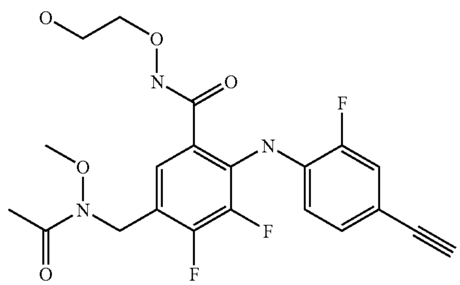 | 550 | 41 |
| G-1 | 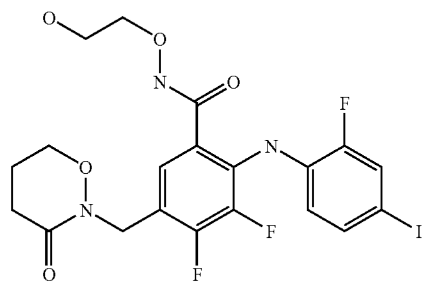 | 88 | >360 |
| G-2 | 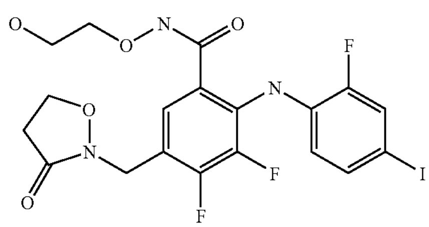 | 216 | >360 |
| G-3 | 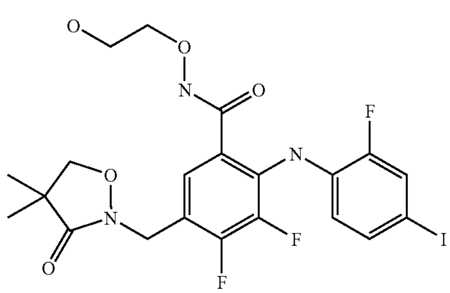 | 39 | >360 |
| G-4 | 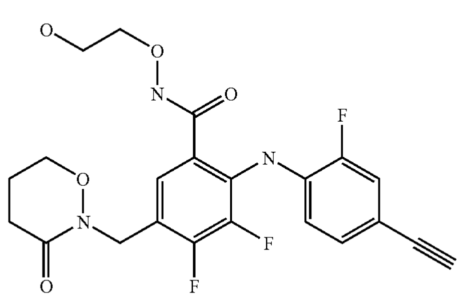 | 344 | >360 |

TABLE 3-continued

| Compound No. | Structure | Water solubility (μM) | Stability against mouse liver microsome T1/2 (min) |
|---|---|---|---|
| G-5 | 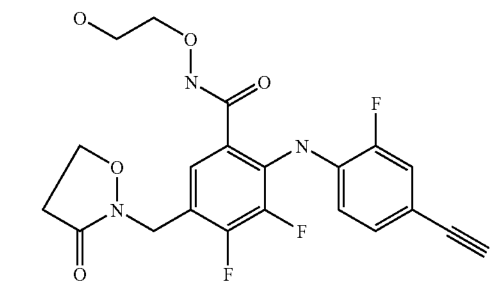 | 95 | >360 |
| P | 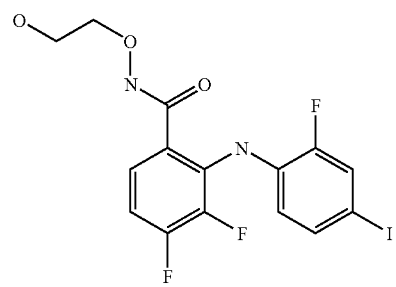 | <32 | 8 |
| Q | 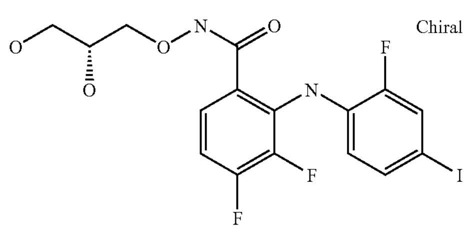 | 645 | 29 |
| R | 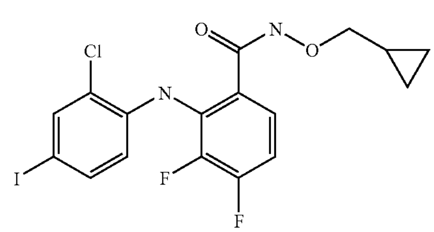 | <<2 | 11 |

TABLE 4

| Compound No. | Structure | Tumor growth suppression rate at maximum tolerance dose (MTD) 1 day after last administration |
|---|---|---|
| B-1 | 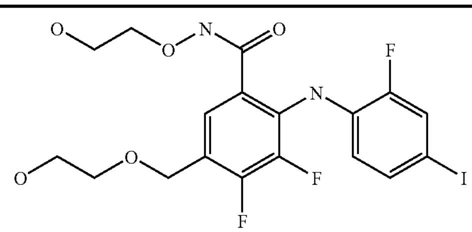 | 96% |

TABLE 4-continued

| Compound No. | Structure | Tumor growth suppression rate at maximum tolerance dose (MTD) 1 day after last administration |
| --- | --- | --- |
| C-1 | 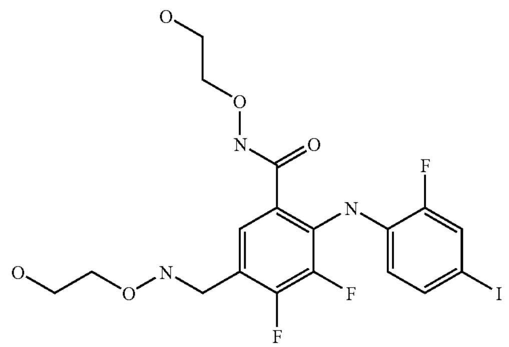 | 93% |
| C-10 | 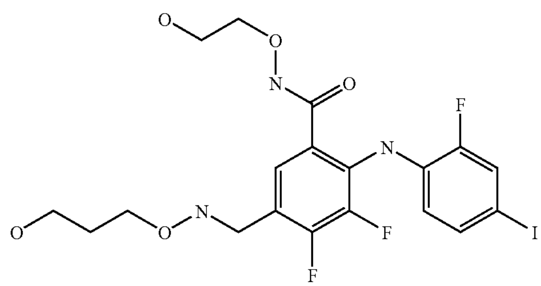 | 107% |
| C-13 | 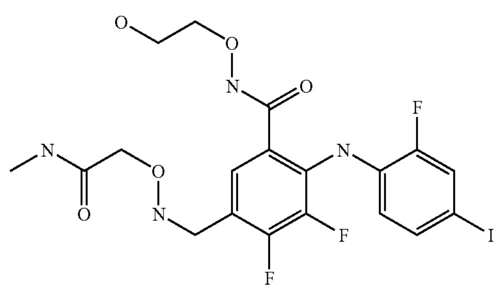 | 97% |
| F-1 | 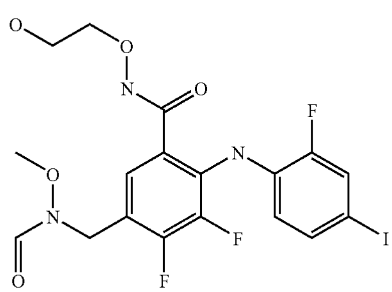 | 101% |
| F-2 | 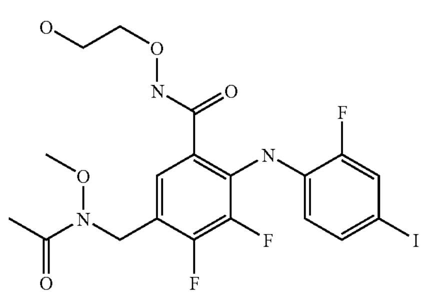 | 113% |

TABLE 4-continued

| Compound No. | Structure | Tumor growth suppression rate at maximum tolerance dose (MTD) 1 day after last administration |
|---|---|---|
| F-5 | 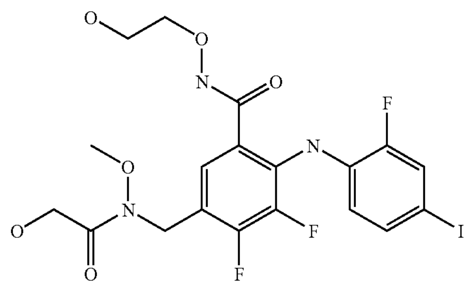 | 99% |
| G-1 | 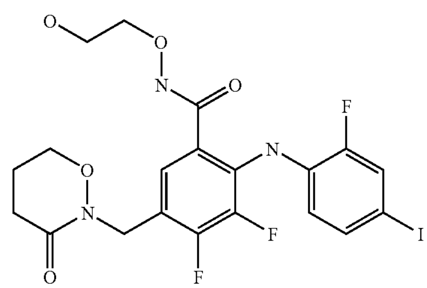 | 124% |
| G-2 | 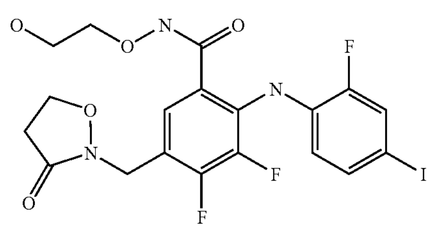 | 105% |
| G-3 | 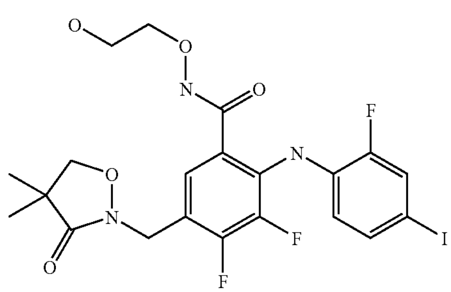 | 104% |
| G-4 | 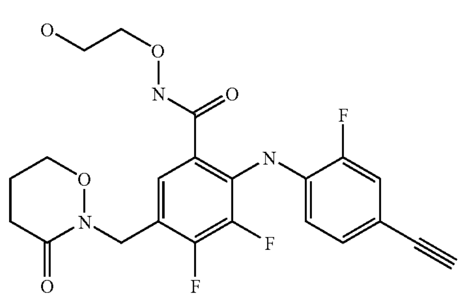 | 112% |

TABLE 4-continued

| Compound No. | Structure | Tumor growth suppression rate at maximum tolerance dose (MTD) 1 day after last administration |
|---|---|---|
| H-3 | 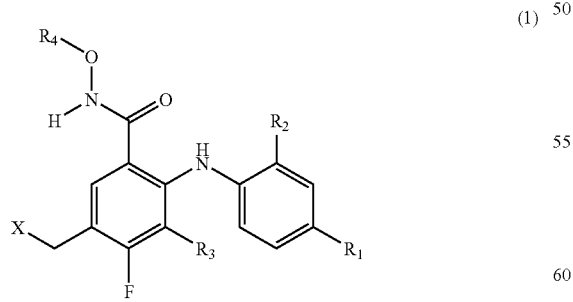 | 107% |
| Q | 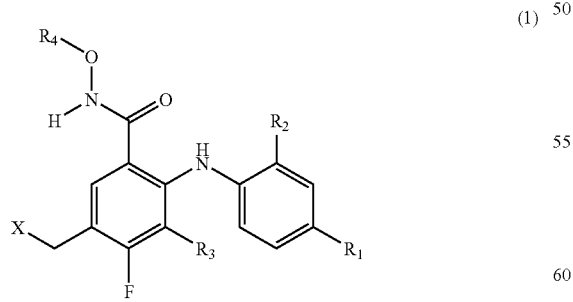 | 66%~82% |

Test Examples 1-3 described above were performed according to "Development of pharmaceuticals, Vol. 15, "Physicochemical property of formulation", edited by Koichiro Miyajima, Professor of Kyoto University, pages 45 to 48", and Test Example 4 described above was performed according to "2.2 Method for measuring solubility, 2.2.1 Equilibrium method, a. Stirring method, Hirokawa Publishing Co."

INDUSTRIAL APPLICABILITY

The compounds according to the present invention and the pharmaceutically acceptable salts thereof have a MEK inhibitory effect, a cell growth inhibitory effect, are excellent in stability in vivo and solubility in water, and are useful as preventing agents or therapeutic agents for proliferative diseases, e.g., cancers and joint diseases with inflammation.

The invention claimed is:

1. A compound represented by the following formula (1), or a pharmaceutically acceptable salt thereof, (1)

wherein
$R_1$ represents a halogen atom, an alkenyl group, or an alkynyl group;
$R_2$ represents a halogen atom or an alkyl group; the alkyl group is optionally substituted by a hydroxyl group;
$R_3$ represents a hydrogen atom or a halogen atom;
$R_4$ represents a hydrogen atom, an alkyl group, an alkenyl group, or an alkynyl group; the alkyl group, the alkenyl group, and the alkynyl group optionally have one to three substituents selected from the group consisting of —ORa, —NRaRb, —NRaCORb, a heterocyclic group, and a heteroaryl group; the heterocyclic group and the heteroaryl group optionally have one to three substituents selected from the group consisting of a $C_{1-5}$ alkyl group, —ORa, and —NRaRb;
X represents a group represented by the following formula (i):

wherein
Y represents —O—, —NR$_8$O—, —ONR$_8$—, —NR$_8$CO—, or —NR$_8$SO$_2$—;
Z represents a $C_{1-8}$ alkylene chain which is optionally substituted by one to three groups represented by W';
where $R_8$ represents a hydrogen atom, an alkyl group, —ORa, or —COR$_9$; and the alkyl group is optionally substituted by a halogen atom, —ORa, or —NRaRb;
$R_9$ represents a hydrogen atom, an alkyl group, or —ORa; and the alkyl group is optionally substituted by a halogen atom, —ORa, or —NRaRb;
$R_8$ and $R_9$ are optionally linked to the alkylene chain of Z or form a heterocyclic group through a linkage to the substituent represented by Ra or Rb of W,
or alternatively,
X represents a group represented by the following formula (ii):

wherein

Y$_1$ and Y$_2$, which may be the same or different, each represent a single bond, —CO—, —COO—, —O—, —OCO—, —NRa—, or —SO$_2$—;

Z' represents a C$_{1-5}$ alkylene chain which is optionally substituted by one to three groups represented by W';

in the above formulae (i) and (ii),

W and W', which may be the same or different, each represent a C$_{1-5}$ alkyl group, a halogen atom, an oxo group, —ORa, —COORa, —COOCORa, —CO-halogen atom, —OCORa, —CONRaRb, —SRa, —SORa, —SO$_2$Ra, —NRaRb, —NRaCORb, —NRaSO$_2$Rb, —SO$_2$NRaRb, a heterocyclic group, or a heteroaryl group; the heterocyclic group and the heteroaryl group optionally have a substituent selected from the group consisting of a C$_{1-5}$ alkyl group, —ORa, and —NRaRb; the alkyl group is optionally substituted by a hydroxyl group, a C$_{1-5}$ alkoxy group, or an amino group;

the above substituents except the oxo group and the halogen atom are optionally linked to each other to form a cycloalkyl group or a heterocyclic group; the cycloalkyl group or the heterocyclic group optionally has a substituent selected from the group consisting of —ORa, —NRaRb, and a C$_{1-5}$ alkyl group that is optionally substituted with ORa;

Ra and Rb, which may be the same or different, each represent a hydrogen atom or a C$_{1-5}$ alkyl group; the alkyl group is optionally substituted by one to three groups selected from the group consisting of a hydroxyl group, a C$_{1-5}$ alkoxy group, and an amino group;

provided that, when X is the group represented by the above formula (i) and Y is not —O—, W is a hydrogen atom or any of the groups assigned to W defined above.

2. The compound according to claim 1, or a pharmaceutically acceptable salt thereof, wherein X represents the group —Y—Z—W of the formula (i) and Z represents a C$_{1-5}$ alkylene chain, wherein the alkylene chain optionally has one to three substituents selected from the group consisting of a C$_{1-5}$ alkyl group, a halogen atom, —ORa, —NRaRb, and an oxo group;

the above substituents except the oxo group and the halogen atom are optionally linked to each other to form a cycloalkyl group or a heterocyclic group; the cycloalkyl group or the heterocyclic group optionally has a substituent selected from the group consisting of —ORa, —NRaRb, and a C$_{1-5}$ alkyl group that is optionally substituted with —ORa;

Ra and Rb, which may be the same or different, each represent a hydrogen atom or a C$_{1-5}$ alkyl group; and the alkyl group is optionally substituted by a hydroxyl group, a C$_{1-5}$ alkoxy group, or an amino group.

3. The compound according to claim 1, or a pharmaceutically acceptable salt thereof, wherein X represents the group —Y—Z—W of the formula (i), wherein the alkylene chain of Z is any one of the groups represented by the following formulae:

—CH$_2$—, —(CH$_2$)$_2$—, —(CH$_2$)$_3$—, —(CH$_2$)$_4$—, —CH$_2$CH(Me)—, —CH$_2$C(Me)$_2$-, —C(Me)$_2$CH$_2$—, —(CH$_2$)$_2$CH(Me)—, —(CH$_2$)$_2$C(Me)$_2$-, —CH(Me)(CH$_2$)$_2$—, —C(Me)$_2$(CH$_2$)$_2$—, —CH$_2$CH(Me)CH$_2$—, —CH$_2$C(Me)$_2$CH$_2$—, —CH$_2$C(CH$_2$CH$_2$)CH$_2$—, —CO—, —CH$_2$CO—, —COCH$_2$—, —(CH$_2$)$_2$CO—, —CO(CH$_2$)$_2$—, —CHOH—, —CH$_2$CH(OH)—, —CH(OH)CH$_2$—, —CH$_2$CH(OH)CH$_2$—, —CH(OH)CH$_2$CH$_2$—, and —CH$_2$CH$_2$CH(OH)—.

4. The compound according to claim 1, or a pharmaceutically acceptable salt thereof, wherein X represents —Y—Z—W of the formula (i), wherein R$_8$ represents a hydrogen atom, a hydroxyl group, a C$_{1-5}$ alkyl group, or —COR$_9$;

R$_9$ represents a hydrogen atom, a hydroxyl group, a C$_{1-5}$ alkyl group, or a C$_{1-5}$ alkoxy group; and the alkyl group and the alkoxy group represented by R$_8$ and R$_9$ are optionally substituted by one to three hydroxyl groups at arbitrary positions of the hydrocarbon moiety.

5. The compound according to claim 1, or a pharmaceutically acceptable salt thereof, wherein X represents —Y—Z—W of the formula (i), wherein R$_8$ represents a hydrogen atom, a hydroxyl group, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a formyl group, an acetyl group, a 2-methoxyacetyl group, a 2-ethoxyacetyl group, a 2-hydroxyacetyl group, a propionyl group, a 2-methylpropionyl group, a 2-methoxypropionyl group, a 2-ethoxypropionyl group, a 2-hydroxypropionyl group, a 3-methoxypropionyl group, a 3-ethoxypropionyl group, a 3-hydroxypropionyl group, a methoxy group, an ethoxy group, an n-propyloxy group, an i-propyloxy group, a hydroxymethyl group, or a 2-hydroxyethyl group.

6. The compound according to claim 1, or a pharmaceutically acceptable salt thereof, wherein X represents —Y—Z—W of the formula (i), wherein Y represents —O—, —NHO—, —N(COCH$_3$)O—, —N(COCH$_2$OH)O—, —N(COCH$_2$CH$_3$)O—, —N(COCH(OH)CH$_3$)O—, —N(COCH$_2$CH$_2$OH)O—, —N(COCH(OH)CH$_2$OH)O—, —N(COCH$_2$CH$_2$CH$_3$)O—, —N(COCH$_2$CH$_2$OH)O—, —N(COCH(OH)CH$_2$CH$_3$)O—, —N(COCH$_2$CH(OH)CH$_3$)O—, —NHCO—, or —NHSO$_2$—.

7. The compound according to claim 1, or a pharmaceutically acceptable salt thereof, wherein X represents a group represented by the formula (ii) and X is any one of the groups represented by the following formulae:

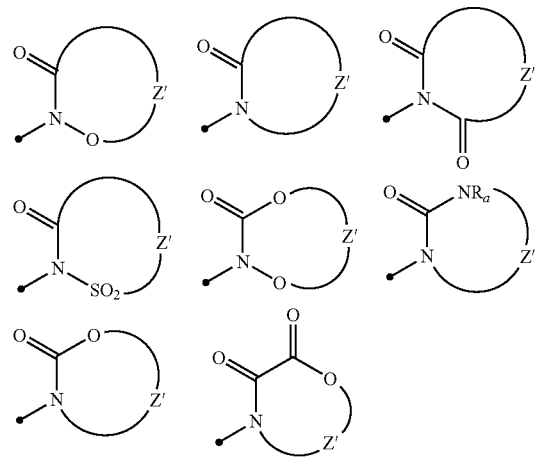

wherein Z' represents a C$_{1-5}$ alkylene chain which is optionally substituted by one to three groups represented by W';

W' represents a C$_{1-5}$ alkyl group, a halogen atom, an oxo group, —ORa, —CONRaRb, —SRa, —SORa, —SO₂Ra, —NRaRb, —NRaCORb, —NRaSO₂Rb, —SO₂NRaRb, a heterocyclic group, or a heteroaryl group;

the heterocyclic group and the heteroaryl group optionally have substituents selected from the group consisting of a $C_{1-5}$ alkyl group, —ORa, and —NRaRb; the alkyl group is optionally substituted by a hydroxyl group, a $C_{1-5}$ alkoxy group, or an amino group;

the above substituents except the oxo group and the halogen atom are optionally linked to each other to form a cycloalkyl group or a heterocyclic group; the cycloalkyl group or the heterocyclic group optionally has a substituent selected from the group consisting of —ORa, —NRaRb, and a $C_{1-5}$ alkyl group that is optionally substituted with —ORa;

Ra and Rb, which may be the same or different, each represent a hydrogen atom or a $C_{1-5}$ alkyl group; and the alkyl group is optionally substituted by a hydroxyl group, a $C_{1-5}$ alkoxy group, or an amino group.

8. The compound according to claim 1, or a pharmaceutically acceptable salt thereof wherein X represents the group represented by the formula (ii), wherein W' represents any one of the groups represented by the formulae:

-Me, -Et, -n-Pr, -i-Pr, —CH₂OH, —CH₂CH₂OH, —CH(OH)CH₃, —OH, —OMe, —OEt, —OCH₂OH, —O(CH₂)₂OH, —O(i-Pr), —O(n-Pr), —CONH₂, —CONHMe, —CONHEt, —CONH(n-Pr), —CONH(i-Pr), —CONMe₂, —CON(Et)Me, —SO₂Me, —SOMe, —SMe, —NH₂, —NHMe, —NHCH₂OH, —NH(CH₂)₂OH, —N(Me)CH₂CH₂OH, —NHEt, —NMe₂, —N(Et)Me, —NHCOMe, —NMeCOMe, —NHCOEt, —NHCO(n-Pr), and —NHCO(i-Pr).

9. The compound according to claim 1, or a pharmaceutically acceptable salt thereof, wherein X represents the group represented by the formula (ii), wherein the alkylene chain of Z' is any one of the groups represented by the following formulae:

—CH₂—, —(CH₂)₂—, —(CH₂)₃—, —(CH₂)₄—, —CH₂CH(Me)—, —CH₂C(Me)₂-, —C(Me)₂CH₂—, —(CH₂)₂CH(Me)—, —(CH₂)₂C(Me)₂-, —CH(Me)(CH₂)₂—, —C(Me)₂(CH₂)₂—, —CH₂CH(Me)CH₂—, —CH₂C(Me)₂CH₂—, —CHOH—, —CH₂CH(OH)—, —CH(OH)CH₂—, —CH₂CH(OH)CH₂—, —CH(OH)CH₂CH₂—, —CH₂CH₂CH(OH)—, —CO—, —CH₂CO—, —COCH₂—, —(CH₂)₂CO—, —CO(CH₂)₂—, and —CH₂CH(OH)CH₂—.

10. The compound according to claim 1, or a pharmaceutically acceptable salt thereof, wherein X represents the group represented by the formula (ii) and X is any one of the groups represented by the following formulae:

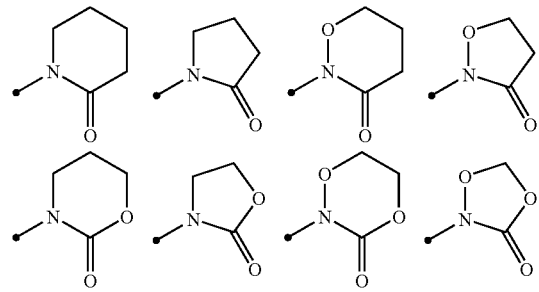

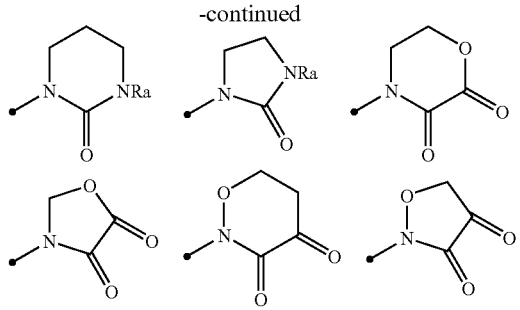

wherein the alkylene chain is optionally substituted at arbitrary positions by one to three substituents selected from the group consisting of a $C_{1-5}$ alkyl group, a halogen atom, —ORa, —NRaRb, and an oxo group; Ra and Rb, which may be the same or different, each represent a hydrogen atom or a $C_{1-5}$ alkyl group; and the alkyl group is optionally substituted by a hydroxyl group, a $C_{1-5}$ alkoxy group, or an amino group.

11. The compound according to claim 1, or a pharmaceutically acceptable salt thereof, wherein X represents the group represented by the following formula (iii) or (iv):

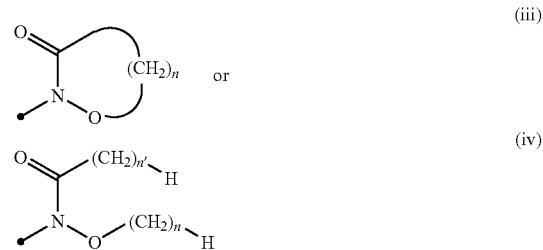

wherein n represents an integer ranging from 1 to 5 and n' represents an integer ranging from 0 to 5; the repeated units represented by —(CH₂)n- or —(CH₂)n'- in the formulae optionally are substituted at arbitrary positions in the hydrocarbon moiety by one to three substituents selected from the group consisting of a $C_{1-5}$ alkyl group, a halogen atom, —ORa, —NRaRb, and an oxo group; Ra and Rb, which may be the same or different, each represent a hydrogen atom or a $C_{1-5}$ alkyl group; and the alkyl group is optionally substituted by a hydroxyl group, a $C_{1-5}$ alkoxy group, or an amino group.

12. The compound according to claim 1, or a pharmaceutically acceptable salt thereof, wherein X represents a group selected from the group consisting of a 2-hydroxyethoxy group, a 3-hydroxy-2-dimethylpropoxy group, a 3-hydroxypropoxy group, a 2-carbamoylethoxy group, a 2-methylcarbamoylethoxy group, a 2-methanesulfonyl-ethoxy group, a 2-acetylamino-ethoxy group, a 2-hydroxyethoxyamino group, a 3-hydroxypropionylamino group, a 2-hydroxyethanesulfonamide group, a 1-hydroxymethyl-cyclopropylmethoxy group, a 2,3-dihydroxy-propoxy group, a 1H-imidazol-2-ylmethoxy group, a 2-methylcarbamoylethoxyamino group, a 2-acetylamino-ethoxyamino group, a 2-methanesulfonyl-ethoxyamino group, a 1H-imidazol-2-ylmethoxyamino group, a 3-hydroxypropoxyamino group, a hydroxyethoxy)-ethoxy group, a 2-methylaminoethoxy group, a 2-(2-hydroxyethylamino)-ethoxy group, a 2-morpholin-4-yl-ethoxy group, a 2-(4-hydroxy-piperidin-1-yl)-ethoxy group, a 2-methylamino-ethoxyamino group, a 2,3- dihydroxy-propoxyamino group, a formyl-methoxyamino group, an acetyl-methoxyamino group, a methoxy-propionylamino group, an isobutyryl-methoxy-amino group, a (2-hydroxy-acetyl)-methoxyamino group, a methoxy-(2-methoxy-acetyl)-amino group, an acetyl-ethoxy-amino group, an ethoxy-propionyl-amino group, an acetyl-isopropoxy-amino group, an acetylhydroxyamino group, an acetoxy-acetylamino group, an acetyl-(2-hydroxy-ethoxy)-amino group, an acetyl-(3-hydroxy-propoxy)-amino group, an acetyl-(2-hydroxy-2-methyl-propoxy)-amino group, an acetyl-(2-acetylamino-ethoxy)-amino group, an acetyl-(2-propionylamino-ethoxy)-amino group, an acetyl-(2-isobutyrylamino-ethoxy)-amino group, an acetyl-(2-methylsulfanyl-ethoxy)-amino group, an acetyl-(3-methylsulfanyl-propoxy)-amino group, a 2-hydroxy-1,1-dimethyl-ethoxy group, a methylcarbamoylmethoxyamino group, an ethylcarbamoylmethoxyamino group, a propylcarbamoylmethoxyamino group, an isopropylcarbamoyl-methoxyamino group, a dimethylcarbamoylmethoxyamino group, a 2-ethylcarbamoyl-ethoxyamino group, a 2-propylcarbamoyl-ethoxyamino group, a 2-isopropylcarbamoyl-ethoxyamino group, a 3-methylcarbamoyl-propoxyamino group, a 2-methoxycarbonyl-ethoxyamino group, a methoxyamino group, a methoxy-methyl-amino group, an ethoxyamino group, an isopropoxyamino group, a 2-hydroxy-2-methyl-propoxyamino group, a 2-methylsulfanyl-ethoxyamino group, a 2-methanesulfinyl-ethoxyamino group, a 3-methylsulfanyl-propoxyamino group, a 3-methanesulfinyl-propoxyamino group, a 2-propionylamino-ethoxyamino group, a 2-isobutyrylamino-ethoxyamino group, a 2-hydroxy-acetylamino group, and an acetyl-(2-hydroxy-ethyl)-amino group.

13. The compound according to claim 1, or a pharmaceutically acceptable salt thereof, wherein X represents a group selected from the group consisting of a 3-oxo-[1,2]oxazinan-2-yl group, a 3-oxo-isoxazolidin-2-yl group, a 4,4-dimethyl-3-oxo-isoxazolidin-2-yl group, a 4-hydroxy-3-oxo-[1,2]oxazinan-2-yl group, a 3-oxo-[1,4,2]dioxazinan-2-yl group, a 2-oxo-pyrrolidin-1-yl group, a 2-oxo-piperidin-1-yl group, a 2-oxo-oxazolidin-3-yl group, a 2-oxo-tetrahydro-pyrimidin-1-yl group, and a 2,3-dioxo-morpholin-4-yl group.

14. The compound according to claim 1, or a pharmaceutically acceptable salt thereof, wherein $R_1$ represents an iodine atom, a bromine atom, a vinyl group, or an ethynyl group.

15. The compound according to claim 1, or a pharmaceutically acceptable salt thereof, wherein $R_1$ represents an iodine atom or an ethynyl group.

16. The compound according to claim 1, or a pharmaceutically acceptable salt thereof, wherein $R_2$ represents a chlorine atom, a fluorine atom, a methyl group, or a hydroxymethyl group.

17. The compound according to claim 1, or a pharmaceutically acceptable salt thereof, wherein $R_2$ represents a fluorine atom.

18. The compound according to claim 1, or a pharmaceutically acceptable salt thereof, wherein $R_3$ represents a fluorine atom.

19. The compound according to claim 1, or a pharmaceutically acceptable salt thereof, wherein $R_4$ represents a $C_{1-5}$ alkyl group substituted by one to three hydroxyl groups.

20. The compound according to claim 1, or a pharmaceutically acceptable salt thereof, wherein $R_4$ represents a group selected from the group consisting of the groups represented by the following formulae:

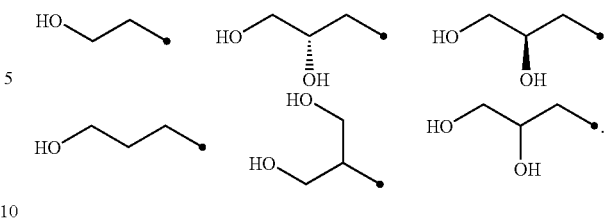

21. The compound according to claim 1, or a pharmaceutically acceptable salt thereof, wherein Ra and Rb, which may be the same or different, each represent a group selected from the group consisting of a hydrogen atom, a methyl group, an ethyl group, an n-propyl group, an i-propyl group, an n-butyl group, an i-butyl group, a t-butyl group, a sec-butyl group, a 1,1-dimethylpropyl group, a 2,2-dimethylpropyl group, a 1,2-dimethylpropyl group, a pentyl group, a hydroxymethyl group, a 1-hydroxyethyl group, a 1-hydroxy-1-methylethyl group, a 2-hydroxy-1-methylethyl group, a 2-hydroxy-1,1-dimethylethyl group, a 2-hydroxyethyl group, a 1-hydroxypropyl group, a 2-hydroxypropyl group, and a 3-hydroxypropyl group.

22. The compound according to claim 1, or a pharmaceutically acceptable salt thereof, wherein X represents —Y—Z—W of the formula (i), wherein W and W', which may be the same or different, each represent a group selected from the group consisting of —OH, —OMe, —OEt, —OCH$_2$OH, —O(CH$_2$)$_2$OH, —O(i-Pr), —O(n-Pr), —COOH, —COOMe, —COOEt, —COOCOMe, —COCl, —CONH$_2$, —CONHMe, —CONHEt, —CONH(n-Pr), —CONH(i-Pr), —CONMe$_2$, —CON(Et)Me, —SO$_2$Me, —SOMe, —SMe, —NH$_2$, —NHMe, —NHCH$_2$OH, —NH(CH$_2$)$_2$OH, —N(Me)CH$_2$CH$_2$OH, —NHEt, —NMe$_2$, —N(Et)Me, —NHCOMe, —NMeCOMe, —NHCOEt, —NHCO(n-Pr), and —NHCO(i-Pr); and W may be a hydrogen atom when Y is not —O—.

23. The compound according to claim 1, or a pharmaceutically acceptable salt thereof, wherein the compound represented by the above formula (1) is any one selected from the group consisting of:

(1) B-1

3,4-difluoro-2-(2-fluoro-4-iodo-phenylamino)-N-(2-hydroxy-ethoxy)-5(2-hydroxy-ethoxymethyl)-benzamide, (2) B-2

2-(4-ethynyl-2-fluoro-phenylamino)-3,4-difluoro-N-(2-hydroxy-ethoxy)-5-(2-hydroxy-ethoxymethyl)-benzamide, (3) B-3

N-(2,3-dihydroxy-propoxy)-3,4-difluoro-2-(2-fluoro-4-iodo-phenylamino)-5-(2-hydroxy-ethoxymethyl)-benzamide, (4) B-4

2-(2-chloro-4-iodo-phenylamino)-3,4-difluoro-N-(2-hydroxy-ethoxy)-5-(2-hydroxy-ethoxymethyl)-benzamide, (5) B-5

3,4-difluoro-2-(2-fluoro-4-vinyl-phenylamino)-N-(2-hydroxy-ethoxy)-5-(2-hydroxy-ethoxymethyl)-benzamide, (6) B-6

3,4-difluoro-2-(2-fluoro-4-iodo-phenylamino)-N-(2-hydroxy-ethoxy)-5-(3-hydroxypropoxymethyl)-benzamide, (7) B-7
3,4-difluoro-2-(2-fluoro-4-iodo-phenylamino)-5-(3-hydroxy-2,2-dimethyl-propoxymethyl)-N-(2-hydroxy-ethoxy)-benzamide, (8) B-8
3,4-difluoro-2-(2-fluoro-4-iodo-phenylamino)-N-(2-hydroxy-ethoxy)-5-(1-hydroxymethyl-cyclopropylmethoxymethyl)-benzamide, (9) B-9
5-(2,3-dihydroxy-propoxymethyl)-3,4-difluoro-2-(2-fluoro-4-iodo-phenylamino)-N-(2-hydroxy-ethoxy)-benzamide,

(10) B-10
3,4-difluoro-2-(2-fluoro-4-iodo-phenylamino)-N-(2-hydroxy-ethoxy)-5-(2-methylcarbamoyl-ethoxymethyl)-benzamide,

(11) B-11
5-(2-acetylamino-ethoxymethyl)-3,4-difluoro-2-(2-fluoro-4-iodo-phenylamino)-N-(2-hydroxy-ethoxy)-benzamide,

(12) B-12
3,4-difluoro-2-(2-fluoro-4-iodo-phenylamino)-N-(2-hydroxy-ethoxy)-5-(2-methanesulfonyl-ethoxymethyl)-benzamide,

(13) B-13
3,4-difluoro-2-(2-fluoro-4-iodo-phenylamino)-N-(2-hydroxy-ethoxy)-5-(1H-imidazol-2-yl methoxymethyl)-benzamide,

(14) B-14
3,4-difluoro-2-(2-fluoro-4-iodo-phenylamino)-N-(2-hydroxy-ethoxy)-5-[2-(2-hydroxy-ethoxy)-ethoxymethyl]-benzamide,

(15) B-15
3,4-difluoro-2-(2-fluoro-4-iodo-phenylamino)-N-(2-hydroxy-ethoxy)-5-(2-methylamino-ethoxymethyl)-benzamide,

(16) B-16
3,4-difluoro-2-(2-fluoro-4-iodo-phenylamino)-N-(2-hydroxy-ethoxy)-5-[2-(2-hydroxy-ethylamino)-ethoxymethyl]-benzamide,

(17) B-17
3,4-difluoro-2-(2-fluoro-4-iodo-phenylamino)-N-(2-hydroxy-ethoxy)-5-(2-morpholin-4-yl-ethoxymethyl)-benzamide,

(18) B-18
3,4-difluoro-2-(2-fluoro-4-iodo-phenylamino)-N-(2-hydroxy-ethoxy)-5-[2-(4-hydroxy-piperidin-1-yl)-ethoxymethyl]-benzamide, and

(19) B-19
3,4-difluoro-2-(2-fluoro-4-iodo-phenylamino)-5-(2-hydroxy-1,1-dimethyl-ethoxymethyl)-N-(2-hydroxy-ethoxy)-benzamide.

24. The compound according to claim 1, or a pharmaceutically acceptable salt thereof, wherein the compound represented by the above formula (1) is any one selected from the group consisting of:

(1) C-1
3,4-difluoro-2-(2-fluoro-4-iodo-phenylamino)-N-(2-hydroxy-ethoxy)-5-[(2-hydroxy-ethoxyamino)-methyl]-benzamide, (2) C-2
2-(4-ethynyl-2-fluoro-phenylamino)-3,4-difluoro-N-(2-hydroxy-ethoxy)-5-[(2-hydroxy-ethoxyamino)-methyl]-benzamide, (3) C-3
N-(2,3-dihydroxy-propoxy)-3,4-difluoro-2-(2-fluoro-4-iodo-phenylamino)-5-[(2-hydroxy-ethoxyamino)-methyl]-benzamide, (4) C-4
2-(2-chloro-4-iodo-phenylamino)-3,4-difluoro-N-(2-hydroxy-ethoxy)-5-[(2-hydroxy ethoxyamino)-methyl]-benzamide, (5) C-5
3,4-difluoro-2-(2-fluoro-4-vinyl-phenylamino)-N-(2-hydroxy-ethoxy)-5-[(2-hydroxy-ethoxyamino)-methyl]-benzamide, (6) C-6
3,4-difluoro-2-(2-fluoro-4-iodo-phenylamino)-N-(2-hydroxy-ethoxy)-5-[(2-methylcarbamoyl-ethoxyamino)-methyl]-benzamide, (7) C-7
5-[(2-acetylamino-ethoxyamino)-methyl]-3,4-difluoro-2-(2-fluoro-4-iodo-phenylamino)-N-(2-hydroxy-ethoxy)-benzamide, (8) C-8
3,4-difluoro-2-(2-fluoro-4-iodo-phenylamino)-N-(2-hydroxy-ethoxy)-5-[(2-methanesulfonyl-ethoxyamino)-methyl]-benzamide, (9) C-9
3,4-difluoro-2-(2-fluoro-4-iodo-phenylamino)-N-(2-hydroxy-ethoxy)-5-[(1H-imidazol-2-ylmethoxyamino)-methyl]-benzamide,

(10) C-10
3,4-difluoro-2-(2-fluoro-4-iodo-phenylamino)-N-(2-hydroxy-ethoxy)-5-[(3-hydroxy-propoxyamino)-methyl]-benzamide,

(11) C-11
3,4-difluoro-2-(2-fluoro-4-iodo-phenylamino)-N-(2-hydroxy-ethoxy)-5-[(2-methylamino-ethoxyamino)-methyl]-benzamide,

(12) C-12
5-[(2,3-dihydroxy-propoxyamino)-methyl]-3,4-difluoro-2-(2-fluoro-4-iodo-phenylamino)-N-(2-hydroxy-ethoxy)-benzamide,

(13) C-13
3,4-difluoro-2-(2-fluoro-4-iodo-phenylamino)-N-(2-hydroxy-ethoxy)-5-(methylcarbamoylmethoxyamino-methyl)-benzamide,

(14) C-14
5-(ethylcarbamoylmethoxyamino-methyl)-3,4-difluoro-2-(2-fluoro-4-iodo-phenylamino)-N-(2-hydroxy-ethoxy)-benzamide,

(15) C-15
3,4-difluoro-2-(2-fluoro-4-iodo-phenylamino)-N-(2-hydroxy-ethoxy)-5-(propylcarbamoylmethoxyamino-methyl)-benzamide,

(16) C-16
3,4-difluoro-2-(2-fluoro-4-iodo-phenylamino)-N-(2-hydroxy-ethoxy)-5-[(isopropylcarbamoyl-methoxyamino)-methyl]-benzamide,

(17) C-17
5-(dimethylcarbamoylmethoxyamino-methyl)-3,4-difluoro-2-(2-fluoro-4-iodo-phenylamino)-N-(2-hydroxy-ethoxy)-benzamide,

(18) C-18
5-[(2-ethylcarbamoyl-ethoxyamino)-methyl]-3,4-difluoro-2-(2-fluoro-4-iodo-phenylamino)-N-(2-hydroxy-ethoxy)-benzamide,

(19) C-19
5-[(2-propylcarbamoyl-ethoxyamino)-methyl]-3,4-difluoro-2-(2-fluoro-4-iodo-phenylamino)-N-(2-hydroxyethoxy)-benzamide,
(20) C-20
5-[(2-isopropylcarbamoyl-ethoxyamino)-methyl]-3,4-difluoro-2-(2-fluoro-4-iodo-phenylamino)-N-(2-hydroxyethoxy)-benzamide,
(21) C-21
3,4-difluoro-2-(2-fluoro-4-iodo-phenylamino)-N-(2-hydroxy-ethoxy)-5-[(3-methylcarbamoyl-propoxyamino)-methyl]-benzamide,
(22) C-22
3-[N-[2,3-difluoro-4-(2-fluoro-4-iodo-phenylamino)-5-(2-hydroxyethoxycarbamoyl)benzyl]aminooxy]propionic acid methyl ester,
(24) C-24
3,4-difluoro-2-(2-fluoro-4-iodo-phenylamino)-N-(2-hydroxy-ethoxy)-5-(methoxyamino-methyl)-benzamide,
(25) C-25
3,4-difluoro-2-(2-fluoro-4-iodo-phenylamino)-N-(2-hydroxy-ethoxy)-5-[(methoxy-methyl-amino)-methyl]-benzamide,
(26) C-26
5-(ethoxyamino-methyl)-3,4-difluoro-2-(2-fluoro-4-iodo-phenylamino)-N-(2-hydroxy-ethoxy)-benzamide,
(27) C-27
3,4-difluoro-2-(2-fluoro-4-iodo-phenylamino)-N-(2-hydroxy-ethoxy)-5-(isopropoxyamino-methyl)-benzamide,
(28) C-28
3,4-difluoro-2-(2-fluoro-4-iodo-phenylamino)-N-(2-hydroxy-ethoxy)5-[(2-hydroxy-2-methyl-propoxyamino)-methyl]-benzamide,
(29) C-29
2-(4-ethynyl-2-fluoro-phenylamino)-3,4-difluoro-N-(2-hydroxy-ethoxy)5-[(2-hydroxy-2-methyl-propoxyamino)-methyl]-benzamide,
(30) C-30
3,4-difluoro-2-(2-fluoro-4-iodo-phenylamino)-N-(2-hydroxy-ethoxy)-5-[(2-methylsulfanyl-ethoxyamino)-methyl]-benzamide,
(31) C-31
3,4-difluoro-2-(2-fluoro-4-iodo-phenylamino)-N-(2-hydroxy-ethoxy)-5-[(2-methanesulfinyl-ethoxyamino)-methyl]-benzamide,
(32) C-32
3,4-difluoro-2-(2-fluoro-4-iodo-phenylamino)-N-(2-hydroxy-ethoxy)-5-[(3-methylsulfanyl-propoxyamino)-methyl]-benzamide,
(33) C-33
3,4-difluoro-2-(2-fluoro-4-iodo-phenylamino)-N-(2-hydroxy-ethoxy)-5-[(3-methanesulfinyl-propoxyamino)-methyl]-benzamide,
(34) C-34
3,4-difluoro-2-(2-fluoro-4-iodo-phenylamino)-N-(2-hydroxy-ethoxy)-5-[(2-propionylamino-ethoxyamino)-methyl]-benzamide, and
(35) C-35
3,4-difluoro-2-(2-fluoro-4-iodo-phenylamino)-N-(2-hydroxy-ethoxy)-5-[(2-isobutyrylamino-ethoxyamino)-methyl]-benzamide.

25. The compound according to claim 1, or a pharmaceutically acceptable salt thereof, wherein the compound represented by the above formula (1) is any one selected from the group consisting of:

(1) E-1
3,4-difluoro-2-(2-fluoro-4-iodo-phenylamino)-N-(2-hydroxy-ethoxy)-5-[(3-hydroxy-propionylamino)-methyl]-benzamide
(2) E-2
2-(4-ethynyl-2-fluoro-phenylamino)-3,4-difluoro-N-(2-hydroxy-ethoxy)-5-[(3-hydroxy-propionylamino)-methyl]-benzamide
(3) E-3
3,4-difluoro-2-(2-fluoro-4-iodo-phenylamino)-5-[(2-hydroxy-ethanesulfonylamino)-methyl]-N-(2-hydroxy-ethoxy)-benzamide,
(4) E-4
2-(4-ethynyl-2-fluoro-phenylamino)-3,4-difluoro-5-[(2-hydroxy-ethanesulfonylamino)-methyl]-N-(2-hydroxy-ethoxy)-benzamide,
(5) E-5
3,4-difluoro-2-(2-fluoro-4-iodo-phenylamino)-5-[(2-hydroxy-acetylamino)methyl]-N-(2-hydroxy-ethoxy)-benzamide, and
(6) E-6
5-{[acetyl-(2-hydroxy-ethyl)-amino]-methyl}-3,4-difluoro-2-(2-fluoro-4-iodo-phenylamino)-N-(2-hydroxy-ethoxy)-benzamide.

26. The compound according to claim 1, or a pharmaceutically acceptable salt thereof, wherein the compound represented by the above formula (1) is any one selected from the group consisting of:

(1) F-1
3,4-difluoro-2-(2-fluoro-4-iodo-phenylamino)-5-[(formyl-methoxy-amino)-methyl]-N-(2-hydroxy-ethoxy)-benzamide,
(2) F-2
5-[acetyl-methoxy-amino-methyl]-3,4-difluoro-2-(2-fluoro-4-iodo-phenylamino)-N-(2-hydroxy-ethoxy)-benzamide,
(3) F-3
3,4-difluoro-2-(2-fluoro-4-iodo-phenylamino)-N-(2-hydroxy-ethoxy)-5-[(methoxy-propionyl-amino)-methyl]-benzamide,
(4) F-4
3,4-difluoro-2-(2-fluoro-4-iodo-phenylamino)-N-(2-hydroxy-ethoxy)-5-[(isobutyryl-methoxy-amino)-methyl]-benzamide,
(5) F-5
3,4-difluoro-2-(2-fluoro-4-iodo-phenylamino)-5-{[(2-hydroxy-acetyl)-methoxy-amino]-methyl}-N-(2-hydroxy-ethoxy)-benzamide,
(6) F-6
3,4-difluoro-2-(2-fluoro-4-iodo-phenylamino)-N-(2-hydroxy-ethoxy)-5-{[methoxy-(2-methoxy-acetyl)-amino]-methyl}-benzamide,
(7) F-7
5-[(acetyl-methoxy-amino)-methyl]-2-(4-ethynyl-2-fluoro-phenylamino)-3,4-difluoro-N-(2-hydroxy-ethoxy)-benzamide,
(8) F-8
2-(4-ethynyl-2-fluoro-phenylamino)-3,4-difluoro-N-(2-hydroxy-ethoxy)-5-[(methoxy-propionyl-amino)-methyl]-benzamide,
(9) F-9
2-(4-ethynyl-2-fluoro-phenylamino)-3,4-difluoro-N-(2-hydroxy-ethoxy)-5-[(isobutyryl-methoxy-amino)-methyl]-benzamide,

(10) F-10
5-[(acetyl-ethoxy-amino)-methyl]-3,4-difluoro-2-(2-fluoro-4-iodo-phenylamino)-N-(2-hydroxy-ethoxy)-benzamide,
(11) F-11
5-[(ethoxy-propionyl-amino)-methyl]-3,4-difluoro-2-(2-fluoro-4-iodo-phenylamino)-N-(2-hydroxy-ethoxy)-benzamide,
(12) F-12
5-[(acetyl-isopropoxy-amino)-methyl]-3,4-difluoro-2-(2-fluoro-4-iodo-phenylamino)-N-(2-hydroxy-ethoxy)-benzamide,
(13) F-13
5-[(acetyl-hydroxy-amino)-methyl]-3,4-difluoro-2-(2-fluoro-4-iodo-phenylamino)-N-(2-hydroxy-ethoxy)-benzamide,
(14) F-14
5-[(acetoxy-acetyl-amino)-methyl]-3,4-difluoro-2-(2-fluoro-4-iodo-phenylamino)-N-(2-hydroxy-ethoxy)-benzamide,
(15) F-15
5-{[acetyl-(2-hydroxy-ethoxy)-amino]-methyl}-3,4-difluoro-2-(2-fluoro-4-iodo-phenylamino)-N-(2-hydroxy-ethoxy)-benzamide,
(16) F-16
5-{[acetyl-(3-hydroxy-propoxy)-amino]-methyl}-3,4-difluoro-2-(2-fluoro-4-iodo-phenylamino)-N-(2-hydroxy-ethoxy)-benzamide,
(17) F-17
5-{[acetyl-(2-hydroxy-2-methyl-propoxy)-amino]-methyl}-3,4-difluoro-2-(2-fluoro-4-iodo-phenylamino)-N-(2-hydroxy-ethoxy)-benzamide,
(18) F-18
5-{[acetyl-(2-acetylamino-ethoxy)-amino]-methyl}-3,4-difluoro-2-(2-fluoro-4-iodo-phenylamino)-N-(2-hydroxy-ethoxy)-benzamide,
(19) F-19
5-{[acetyl-(2-propionylamino-ethoxy)-amino]-methyl}-3,4-difluoro-2-(2-fluoro-4-iodo-phenylamino)-N-(2-hydroxy-ethoxy)-benzamide,
(20) F-20
5-{[acetyl-(2-isobutyrylamino-ethoxy)-amino]-methyl}-3,4-difluoro-2-(2-fluoro-4-iodo-phenylamino)-N-(2-hydroxy-ethoxy)-benzamide,
(21) F-21
5-{[acetyl-(2-methylsulfanyl-ethoxy)-amino]-methyl}-3,4-difluoro-2-(2-fluoro-4-iodo-phenylamino)-N-(2-hydroxy-ethoxy)-benzamide,
(22) F-22
5-{[acetyl-(3-methylsulfanyl-propoxy)-amino]-methyl}-3,4-difluoro-2-(2-fluoro-4-iodo-phenylamino)-N-(2-hydroxy-ethoxy)-benzamide,
(23) F-23
5-[(acetyl-ethoxy-amino)-methyl]-2-(4-ethynyl-2-fluoro-phenylamino)-3,4-difluoro-N-(2-hydroxy-ethoxy)-benzamide,
(24) F-24
5-[(ethoxy-propionyl-amino)-methyl]-2-(4-ethynyl-2-fluoro-phenylamino)-3,4-difluoro-N-(2-hydroxy-ethoxy)-benzamide,
(25) F-25
5-{[acetyl-(2-hydroxy-ethoxy)-amino]-methyl)-2-(4-ethynyl-2-fluoro-phenylamino)-3,4-difluoro-N-(2-hydroxy-ethoxy)-benzamide, and
(26) F-26
5-{[acetyl-(2-hydroxy-2-methyl-propoxy)-amino]-methyl)-2-(4-ethynyl-2-fluoro-phenylamino)-3,4-difluoro-N-(2-hydroxy-ethoxy)-benzamide.

27. The compound according to claim 1, or a pharmaceutically acceptable salt thereof, wherein the compound represented by the above formula (1) is any one selected from the group consisting of:
(1) G-1
3,4-difluoro-2-(2-fluoro-4-iodo-phenylamino)-N(2-hydroxyethoxy)-5-(3-oxo-[1,2]oxazinan-2-ylmethyl)-benzamide,
(2) G-2
3,4-difluoro-2-(2-fluoro-4-iodo-phenylamino)-N-(2-hydroxyethoxy)-5-(3-oxo-isoxazolidin-2-ylmethyl)-benzamide,
(3) G-3
5-(4,4-dimethyl-3-oxo-isoxazolidin-2-ylmethyl)-3,4-difluoro-2-(2-fluoro-4-iodo-phenylamino)-N-(2-hydroxyethoxy)-benzamide,
(4) G-4
2-(4-ethynyl-2-fluoro-phenylamino)-3,4-difluoro-N-(2-hydroxy-ethoxy)-5-(3-oxo-[1,2]oxazinan-2-ylmethyl)-benzamide,
(5) G-5
2-(4-ethynyl-2-fluoro-phenylamino)-3,4-difluoro-N-(2-hydroxy-ethoxy)-5-(3-oxo-isoxazolidin-2-ylmethyl)-benzamide,
(6) G-6
N-(2,3-dihydroxy-propoxy)-3,4-difluoro-2-(2-fluoro-4-iodo-phenylamino)-5-(3-oxo-[1,2]oxazinan-2-ylmethyl)-benzamide,
(7) G-7
N-(2,3-dihydroxy-propoxy)-3,4-difluoro-2-(2-fluoro-4-iodo-phenylamino)-5-(3-oxo-isoxazolidin-2-ylmethyl)-benzamide, and
(8) G-8
3,4-difluoro-2-(2-fluoro-4-iodo-phenylamino)-N-(2-hydroxy-ethoxy)-5-(4-hydroxy-3-oxo-[1,2]oxazinan-2-ylmethyl)-benzamide.

28. The compound according to claim 1, or a pharmaceutically acceptable salt thereof, wherein the compound represented by the above formula (1) is any one selected from the group consisting of:
(1) H-1
3,4-difluoro-2-(2-fluoro-4-iodo-phenylamino)-N-(2-hydroxy-ethoxy)-5-(3-oxo-[1,4,2]dioxazinan-2-ylmethyl)-benzamide,
(2) H-2
2-(4-ethynyl-2-fluoro-phenylamino)-3,4-difluoro-N-(2-hydroxy-ethoxy)-5-(3-oxo-[1,4,2]dioxazinan-2-ylmethyl)-benzamide,
(3) H-3
3,4-difluoro-2-(2-fluoro-4-iodo-phenylamino)-N-(2-hydroxy-ethoxy)-5-(2-oxo-pyrrolidin-1-ylmethyl)-benzamide,
(4) H-4
3,4-difluoro-2-(2-fluoro-4-iodo-phenylamino)-N-(2-hydroxy-ethoxy)-5-(2-oxo-piperidin-1-ylmethyl)-benzamide,
(5) H-5
3,4-difluoro-2-(2-fluoro-4-iodo-phenylamino)-N-(2-hydroxy-ethoxy)-5-(2-oxo-oxazolidin-3-ylmethyl)-benzamide, (6) H-6 3,4-difluoro-2-(2-fluoro-4-iodo-phenylamino)-N-(2-hydroxy-ethoxy)-5-(2-oxo-tetrahydro-pyrimidin-1-ylmethyl)-benzamide, and (7) H-7 5-(2,3-dioxo-morpholin-4-ylmethyl)-3,4-difluoro-2-(2-fluoro-4-iodo-phenylamino)-N-(2-hydroxy-ethoxy)-benzamide.

29. A pharmaceutical composition comprising as an active ingredient the compound according to claim 1 or a pharmaceutically acceptable salt thereof.

30. An MEK inhibitor comprising as an active ingredient the compound according to claim 1 or a pharmaceutically acceptable salt thereof.

* * * * *